United States Patent [19]
Göschke et al.

[11] Patent Number: 5,646,143
[45] Date of Patent: Jul. 8, 1997

[54] δ-AMINO-γ-HYDROXY-ω-ARYL-ALKANOIC ACID AMIDES

[75] Inventors: Richard Göschke, Bottmingen, Switzerland; Jürgen Klaus Maibaum, Weil-Haltingen, Germany; Walter Schilling, Himmelried; Stefan Stutz, Basel, both of Switzerland; Pascal Rigollier, Sierentz, France; Yasuchika Yamaguchi, Basel, Switzerland; Nissim Claude Cohen, Village-Neuf, France; Peter Herold, Arlesheim, Switzerland

[73] Assignee: Ciba-Geigy Corporation, Tarrytown, N.Y.

[21] Appl. No.: 687,277

[22] Filed: Jul. 25, 1996

Related U.S. Application Data

[62] Division of Ser. No. 416,242, Apr. 4, 1995, Pat. No. 5,559,111.

[30] Foreign Application Priority Data

Apr. 18, 1994 [CH] Switzerland ............... 1169/94

[51] Int. Cl.⁶ .............. A61K 31/335; A61K 31/535; C07D 317/64; C07D 413/12
[52] U.S. Cl. .............. 514/233.8; 544/148; 549/362; 549/441; 554/55
[58] Field of Search .............. 544/148; 549/362, 549/441; 514/233.8

[56] References Cited

U.S. PATENT DOCUMENTS 4,937,360  6/1990  Liu et al. ............... 549/441

FOREIGN PATENT DOCUMENTS 0212903  3/1987  European Pat. Off. .

OTHER PUBLICATIONS

Plummer et al., Biorganic and Medicinal Chemistry Letters, 3(10):2119–2124 (1993).
Hanessian et al., Biorganic and Medicinal Chemistry Letters, 4(14):1696–1702 (1994).

*Primary Examiner*—Robert W. Ramsuer
*Attorney, Agent, or Firm*—Gregory D. Ferraro

[57] ABSTRACT

δ-Amino-γ-hydroxy-ω-aryl-alkanoic acid amides of formula I

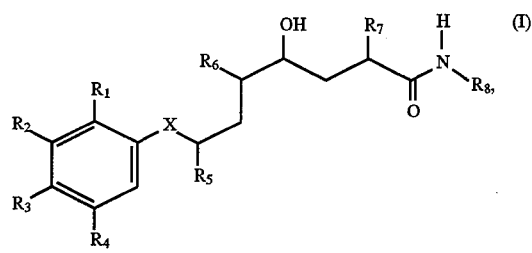

10 Claims, No Drawings

δ-AMINO-γ-HYDROXY-ω-ARYL-ALKANOIC ACID AMIDES

This is a divisional application of U.S. application Ser. No. 08/416,242 filed Apr. 4, 1995 now U.S. Pat. No. 5,559,111.

The invention relates to novel δ-amino-γ-hydroxy-ω-aryl-alkanoic acid amides of formula I

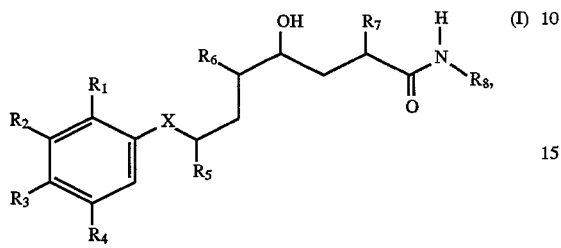

wherein $R_1$ is hydrogen, hydroxy, lower alkoxy, cycloalkoxy, lower alkoxy-lower alkoxy or free or esterified or amidated carboxy-lower alkoxy, $R_2$ is hydrogen, lower alkyl, cycloalkyl, lower alkoxy-lower alkyl, lower alkoxy-lower alkoxy-lower alkyl, cycloalkoxy-lower alkyl, hydroxy, optionally lower alkanoylated, halogenated or sulfonylated hydroxy-lower alkoxy; amino-lower alkyl that is unsubstituted or substituted by lower alkyl, by lower alkanoyl and/or by lower alkoxycarbonyl; optionally hydrogenated heteroaryl-lower alkyl; amino-lower alkoxy that is substituted by lower alkyl, by lower alkanoyl and/or by lower alkoxycarbonyl; oxo-lower alkoxy, lower alkoxy, cycloalkoxy, lower alkenyloxy, cycloalkoxy-lower alkoxy, lower alkoxy-lower alkoxy, lower alkoxy-lower alkenyl, lower alkenyloxy-lower alkoxy, lower alkoxy-lower alkenyloxy, lower alkenyloxy-lower alkyl, lower alkanoyl-lower alkoxy, optionally S-oxidised lower alkylthio-lower alkoxy, lower alkylthio-(hydroxy)-lower alkoxy, aryl-lower alkoxy, optionally hydrogenated hetero-aryl-lower alkoxy, cyano-lower alkoxy, free or esterified or amidated carboxy-lower alkoxy or free or esterified or amidated carboxy-lower alkyl, $R_3$ is optionally halogenated lower alkyl, lower alkoxy-lower alkyl, cycloalkoxy-lower alkyl, hydroxy-lower alkyl, optionally S-oxidised lower alkylthio-lower alkyl, optionally hydrogenated heteroarylthio-lower alkyl, optionally hydrogenated heteroaryl-lower alkyl; amino-lower alkyl that is unsubstituted or N-mono- or N,N-di-lower alkylated, N-lower alkanoylated or N-lower alkanesulfonylated or N,N-disubstituted by lower alkylene, by unsubstituted or N'-lower alkylated or N'-lower alkanoylated aza-lower alkylene, by oxa-lower alkylene or by optionally S-oxidised thia-lower alkylene; cyano-lower alkyl, free or esterified or amidated carboxy-lower alkyl, cycloalkyl, aryl, hydroxy, lower alkoxy, cycloalkoxy, lower alkoxy-lower alkoxy, cycloalkoxy-lower alkoxy, hydroxy-lower alkoxy, aryl-lower alkoxy, optionally halogenated lower alkoxy, optionally S-oxidised lower alkylthio-lower alkoxy, optionally hydrogenated heteroaryl-lower alkoxy, optionally hydrogenated heteroarylthio-lower alkoxy; amino-lower alkoxy that is unsubstituted or N-mono- or N,N-di-lower alkylated, N-lower alkanoylated or N-lower alkanesulfonylated or substituted by lower alkylene, by unsubstituted or N'-lower alkylated or N'-lower alkanoylated aza-lower alkylene, by oxa-lower alkylene or by optionally S-oxidised thia-lower alkylene; cyano-lower alkoxy or free or esterified or amidated carboxy-lower alkoxy, or together with R4 is lower alkylenedioxy or a fused-on benzo or cyclohexeno ring, $R_4$ together with $R_3$ is lower alkylenedioxy or a fused-on benzo or cyclohexeno ring, or is hydrogen, lower alkyl, hydroxy, lower alkoxy or cycloalkoxy, X is methylene or hydroxymethylene, $R_5$ is lower alkyl or cycloalkyl, $R_6$ is unsubstituted or N-mono- or N,N-di-lower alkylated or N-lower alkanoylated amino, $R_7$ is lower alkyl, lower alkenyl, cycloalkyl or aryl-lower alkyl, and $R_8$ is lower alkyl, cycloalkyl, free or aliphatically esterified or etherified hydroxy-lower alkyl; amino-lower alkyl that is unsubstituted or N-lower alkanoylated or N-mono- or N,N-di-lower alkylated or N,N-disubstituted by lower alkylene, by hydroxy-, lower alkoxy- or lower alkanoyloxy-lower alkylene, by unsubstituted or N'-lower alkanoylated or N'-lower alkylated aza-lower alkylene, by oxa-lower alkylene or by optionally S-oxidised thia-lower alkylene; free or esterified or amidated carboxy-lower alkyl, free or esterified or amidated dicarboxy-lower alkyl, free or esterified or amidated carboxy-(hydroxy)-lower alkyl, free or esterified or amidated carboxycycloalkyl-lower alkyl, cyano-lower alkyl, lower alkanesulfonyl-lower alkyl, unsubstituted or N-mono- or N,N-di-lower alkylated thiocarbamoyl-lower alkyl, unsubstituted or N-mono- or N,N-di-lower alkylated sulfamoyl-lower alkyl, or a heteroaryl radical bonded via a carbon atom and optionally hydrogenated and/or oxo-substituted, or lower alkyl substituted by a heteroaryl radical bonded via a carbon atom and optionally hydrogenated and/or oxo-substituted, and to the salts thereof, to processes for the preparation of the compounds according to the invention, to pharmaceutical compositions containing them, and to their use as medicinal active ingredients.

Aryl and aryl in aryl-lower alkoxy, aryl-lower alkyl and the like is, for example, phenyl or naphthyl that is unsubstituted or mono-, di- or tri-substituted by lower alkyl, lower alkoxy, hydroxy, lower alkylamino, di-lower alkylamino, halogen and/or by trifluoromethyl.

Cycloalkoxy and cycloalkoxy in cycloalkoxy-lower alkoxy is, for example, 3- to 8-membered, preferably 3-, 5- or 6-membered, cycloalkoxy, such as cyclopropyloxy, cyclopentyloxy, cyclohexyloxy, also cyclobutyloxy, cycloheptyloxy or cyclooctyloxy.

Cycloalkyl is, for example, 3- to 8-membered, preferably 3-, 5- or 6-membered, cycloalkyl, such as cyclopropyl, cyclopentyl, cyclohexyl, also cyclobutyl, cycloheptyl or cyclooctyl.

Free or esterified or amidated carboxy-lower alkoxy is, for example, carboxy-lower alkoxy, lower alkoxycarbonyl-lower alkoxy, carbamyl-lower alkoxy or N-mono- or N,N-di-lower alkylcarbamoyl-lower alkoxy.

Optionally lower alkanoylated, halogenated or sulfonylated hydroxy-lower alkoxy is, for example, lower alkanoyloxy-lower alkyl, hydroxy-lower alkoxy, halo-(hydroxy)-lower alkoxy or lower alkanesulfonyl-(hydroxy)-lower alkoxy.

Amino-lower alkyl that is unsubstituted or substituted by lower alkyl, lower alkanoyl and/or by lower alkoxycarbonyl is, for example, amino-lower alkyl, lower alkylamino-lower alkyl, di-lower alkylamino-lower alkyl, lower alkanoylamino-lower alkyl or lower alkoxycarbonylamino-lower alkyl.

Amino-lower alkoxy that is unsubstituted or substituted by lower alkyl, lower alkanoyl and/or by lower alkoxycarbonyl is, for example, amino-lower alkoxy, lower alkylamino-lower alkoxy, di-lower alkylamino-lower alkoxy, lower alkanoylamino-lower alkoxy or lower alkoxycarbonylamino-lower alkoxy.

Optionally S-oxidised lower alkylthio-lower alkoxy is, for example, lower alkylthio-lower alkoxy or lower alkanesulfonyl-lower alkoxy.

Optionally hydrogenated heteroaryl-lower alkoxy is, for example, optionally partially hydrogenated or N-oxidised pyridyl-lower alkoxy, thiazolyl-lower alkoxy or especially morpholino-lower alkoxy.

Optionally hydrogenated heteroarylthio-lower alkoxy is, for example, optionally partially or fully hydrogenated heteroarylthio-lower alkoxy, such as thiazolylthio-lower alkoxy or thiazolinylthio-lower alkoxy, imidazolylthio-lower alkoxy, optionally N-oxidised pyridylthio-lower alkoxy or pyrimidinylthio-lower alkoxy.

Free or esterified or amidated carboxy-lower alkyl is, for example, carboxy-lower alkyl, lower alkoxycarbonyl-lower alkyl, carbamoyl-lower alkyl or N-mono- or N,N-di-lower alkylcarbamoyl-lower alkyl.

Optionally halogenated lower alkyl is, for example, lower alkyl or polyhalo-lower alkyl.

Optionally halogenated lower alkoxy is, for example, lower alkoxy or polyhalo-lower alkoxy.

Optionally S-oxidised lower alkylthio-lower alkyl is, for example, lower alkylthio-lower alkyl or lower alkanesulfonyl-lower alkyl.

Optionally S-oxidised lower alkylthio-lower alkoxy is, for example, lower alkylthio-lower alkoxy or lower alkanesulfonyl-lower alkoxy.

Optionally hydrogenated heteroaryl-lower alkyl is, for example, optionally partially hydrogenated or N-oxidised pyridyl-lower alkyl.

Optionally hydrogenated heteroarylthio-lower alkyl is, for example, thiazolylthio-lower alkyl or thiazolinylthio-lower alkyl, imidazolylthio-lower alkyl, optionally N-oxidised pyridylthio-lower alkyl or pyrimidinylthio-lower alkyl.

Amino-lower alkyl that is unsubstituted or N-mono- or N,N-di-lower alkylated, N-lower alkanoylated or N-lower alkanesulfonylated or N,N-disubstituted by lower alkylene, by unsubstituted or N'-lower alkylated or N'-lower alkanoylated aza-lower alkylene, by oxa-lower alkylene or by optionally S-oxidised thia-lower alkylene is, for example, amino-lower alkyl, lower alkylamino-lower alkyl, all-lower alkylamino-lower alkyl, lower alkanoylamino-lower alkyl, lower alkanesulfonylamino-lower alkyl, polyhalo-lower alkanesulfonylamino-lower alkyl, pyrrolidino-lower alkyl, piperidino-lower alkyl, piperazino-, N'-lower alkylpiperazino- or N'-lower alkanoylpiperazino-lower alkyl, morpholino-lower alkyl, thiomorpholino-, S-oxothiomorpholino- or S,S-dioxothiomorpholino-lower alkyl.

Optionally S-oxidised lower alkylthio-lower alkoxy is, for example, lower alkylthio-lower alkoxy or lower alkanesulfonyl-lower alkoxy.

Amino-lower alkoxy that is unsubstituted or N-mono- or N,N-di-lower alkylated, N-lower alkanoylated or N-lower alkanesulfonylated or N,N-disubstituted by lower alkylene, by unsubstituted or N'-lower alkylated or N'-lower alkanoy-lated aza-lower alkylene, by oxa-lower alkylene or by optionally S-oxidised thia-lower alkylene is, for example, amino-lower alkoxy, lower alkylamino-lower alkoxy, all-lower alkylamino-lower alkoxy, lower alkanoylamino-lower alkoxy, lower alkanesulfonylamino-lower alkoxy, polyhalo-lower alkanesulfonylamino-lower alkoxy, pyrrolidino-lower alkoxy, piperidino-lower alkoxy, piperazino-, N'-lower alkylpiperazino- or N'-lower alkanoylpiperazino-lower alkoxy, morpholino-lower alkoxy, thiomorpholino-, S-oxothiomorpholino- or S,S-dioxothio-morpholino-lower alkoxy.

Unsubstituted or N-mono- or N,N-di-lower alkylated or N-lower alkanoylated amino is, for example, amino, lower alkylamino, di-lower alkylamino or lower alkanoylamino.

Free or aliphatically esterified or etherified hydroxy-lower alkyl is, for example, hydroxy-lower alkyl, lower alkanoyloxy-lower alkyl, lower alkoxy-lower alkyl or lower alkenyloxy-lower alkyl.

Amino-lower alkyl that is unsubstituted or N-lower alkanoylated, N-mono- or N,N-di-lower alkylated or N,N-disubstituted by lower alkylene, by hydroxy-, lower alkoxy- or lower alkanoyloxy-lower alkylene, by unsubstituted or N'-lower alkanoylated aza-lower alkylene, by oxa-lower alkylene or by optionally S-oxidised thia-lower alkylene is, for example, amino-lower alkyl, lower alkanoylamino-lower alkyl, N-mono- or N,N-di-lower alkylamino-lower alkyl, optionally hydroxylated or lower alkoxylated piperidino-lower alkyl, such as piperidino-lower alkyl, hydroxypiperidino-lower alkyl or lower alkoxypiperidino-lower alkyl, piperazino-, N'-lower alkylpiperazino- or N'-lower alkanoylpiperazino-lower alkyl, unsubstituted or lower alkylated morpholino-lower alkyl, such as morpholino-lower alkyl or dimethylmorpholino-lower alkyl, or optionally S-oxidised thio-morpholino-lower alkyl, such as thiomorpholino-lower alkyl or S,S-dioxothiomorpholino-lower alkyl.

Free or esterified or amidated dicarboxy-lower alkyl is, for example, dicarboxy-lower alkyl, di-l-lower alkoxycarbonyl-lower alkyl, dicarbamoyl-lower alkyl or di-(N-mono- or N,N-di-lower alkylcarbamoyl)-lower alkyl.

Free or esterified or amidated carboxy-(hydroxy)-lower alkyl is, for example, carboxy-(hydroxy)-lower alkyl, lower alkoxycarbonyl-(hydroxy)-lower alkyl or carbamoyl-(hydroxy)-lower alkyl.

Free or esterified or amidated carboxycycloalkyl-lower alkyl is, for example, 5- or 6-membered carboxycycloalkyl-lower alkyl, lower alkoxycarbonylcycloalkyl-lower alkyl, carbamoylcycloalkyl-lower alkyl, or N-mono- or N,N-di-lower alkylcarbamoylcyclo-alkyl-lower alkyl.

Unsubstituted or N-mono- or N,N-di-lower alkylated sulfamoyl-lower alkyl is, for example, sulfamoyl-lower alkyl, lower alkylsulfamoyl-lower alkyl or all-lower alkylsulfamoyl-lower alkyl.

Unsubstituted or N-mono- or N,N-di-lower alkylated thiocarbamoyl-lower alkyl is, for example, thiocarbamoyl-lower alkyl, lower alkylthiocarbamoyl-lower alkyl or di-lower alkylthiocarbamoyl-lower alkyl, such as N,N-dimethylthiocarbamoylmethyl.

Heteroaryl that is optionally oxo-substituted, bonded via a carbon atom and optionally hydrogenated, and such a heteroaryl in a lower alkyl that is substituted by heteroaryl radicals that are optionally oxo-substituted, bonded via a carbon atom and optionally hydrogenated, contains as optionally hydrogenated heteroaryl radical, for example, an optionally partially hydrogenated and/or benzo-fused 5-membered aza-, diaza-, triaza-, oxadiaza- or tetraaza-aryl radical or a 6-membered aza- or diaza-aryl radical, and as lower alkyl radical, for example, $C_1$–$C_7$alkyl, preferably $C_1$–$C_4$alkyl, and is, for example, pyrrolidinyl-lower alkyl, e.g. oxopyrrolidinyl-$C_1$–$C_4$alkyl, imidazolyl-lower alkyl, e.g. imidazol-4-yl-$C_1$–$C_4$alkyl, benzimidazolyl-lower alkyl, e.g. benzimidazol-2-yl-$C_1$–$C_4$alkyl, oxodiazolyl-lower alkyl, e.g. 1,2,4-oxadiazol-5-yl-$C_1$–$C_4$alkyl, pyridyl-lower alkyl, e.g. pyridin-2-yl-$C_1$–$C_4$alkyl, oxopiperidinyl-$C_1$–$C_4$alkyl, dioxopiperidinyl-$C_1$–$C_4$alkyl, oxo-thiazolyl-$C_1$–$C_4$alkyl, oxo-oxazolinyl-$C_1$–$C_4$alkyl or quinolinyl-lower alkyl, e.g. quinolin-2-yl-$C_1$–$C_4$, also morpholinocarbonyl-lower alkyl or unsubstituted or N-lower alkanoylated piperidyl-lower alkyl.

Hereinbefore and hereinafter, lower radicals and compounds are to be understood as being, for example, those having up to and including 7, preferably up to and including 4, carbon atoms.

5- or 6-Membered carboxycycloalkyl-lower alkyl, lower alkoxycarbonylcycloalkyl-lower alkyl, carbamoylcycloalkyl-lower alkyl, N-mono- or N,N-di-lower alkylcarbamoylcycloalkyl-lower alkyl is, for example, ω-(1-carboxycycloalkyl)-$C_1$–$C_4$alkyl, ω-(1-lower alkoxycarbonylcycloalkyl)-$C_1$–$C_4$alkyl, ω-(1-carbamoylcycloalkyl)-$C_1$–$C_4$alkyl, ω-(1-lower alkylcarbamoylcycloalkyl)-$C_1$–$C_4$alkyl or ω-(1-di-lower alkylcarbamoylcycloalkyl)-$C_1$–$C_4$alkyl, wherein cycloalkyl is, for example, cyclopentyl or cyclohexyl, lower alkoxycarbonyl is, for example, $C_1$–$C_4$alkoxycarbonyl, such as methoxy- or ethoxy-carbonyl, lower alkylcarbamoyl is, for example, $C_1$–$C_4$alkylcarbamoyl, such as methylcarbamoyl, di-lower alkylcarbamoyl is, for example, di-$C_1$–$C_4$alkylcarbamoyl, such as dimethylcarbamoyl, and lower alkyl is, for example, $C_1$–$C_4$alkyl, such as methyl, ethyl, propyl or butyl, especially (1-carboxycyclopentyl)methyl.

5- or 6-Membered cycloalkoxy-lower alkoxy is, for example, cyclopentyloxy- or cyclohexyloxy-$C_1$–$C_4$alkoxy, such as cyclopentyloxy- or cyclohexyloxy-methoxy, 2-cyclopentyloxy- or 2-cyclohexyloxy-ethoxy, 2- or 3-cyclopentyloxy- or 2- or 3-cyclohexyloxy-propyloxy or 4-cyclopentyloxy- or 4-cyclohexyloxy-butyloxy, especially cyclopentyloxy- or cyclohexyloxy-methoxy.

5- or 6-Membered cycloalkoxy-lower alkyl is, for example, cyclopentyloxy- or cyclohexyloxy-$C_1$–$C_4$alkyl, such as cyclopentyloxy- or cyclohexyloxy-methyl, 2-cyclopentyloxy or 2-cyclohexyloxy-ethyl, 2- or 3-cyclopentyloxy- or 2- or 3-cyclohexyloxy-propyl, 2-cyclopentyloxy- or 2-cyclohexyloxy-2-methyl-propyl, 2-cyclopentyloxy- or 2-cyclohexyloxy-2-ethyl-butyl or 4-cyclopentyloxy- or 4-cyclohexyloxy-butyl, especially cyclopentyloxy- or cyclohexyloxy-methyl.

Amino-lower alkoxy is, for example, amino-$C_1$–$C_4$alkoxy, such as 2-aminoethoxy or 5-aminopentyloxy, also 3-aminopropyloxy or 4-aminobutyloxy.

Amino-lower alkyl is, for example, amino-$C_1$–$C_4$alkyl, such as 2-aminoethyl, 3-aminopropyl or 4-aminobutyl.

Carbamoyl-(hydroxy)-lower alkyl is, for example, carbamoyl-$C_1$–$C_7$(hydroxy)alkyl, such as 1-carbamoyl-2-hydroxyethyl.

Carbamoyl-lower alkoxy is, for example, carbamoyl-$C_1$–$C_4$alkoxy, such as carbamoylmethoxy, 2-carbamoylethoxy, 3-carbamoylpropyloxy or 4-carbamoylbutyloxy, especially carbamoylmethoxy.

Carbamoyl-lower alkyl is, for example, carbamoyl-$C_1$–$C_7$alkyl, such as carbamoylmethyl, 2-carbamoylethyl, 3-carbamoylpropyl, 2-(3-carbamoyl)propyl, 2-carbamoylpropyl, 3-(1-carbamoyl)propyl, 2-(2-carbamoyl)propyl, 2-(carbamoyl-2-methyl)propyl, 4-carbamoylbutyl, 1-carbamoylbutyl, 1-(1-carbamoyl-2-methyl)butyl or 3-(4-carbamoyl-2-methyl)butyl.

Carboxy-(hydroxy)-lower alkyl is, for example, carboxy-$C_1$–$C_7$(hydroxy)alkyl, such as 1-carboxy-2-hydroxy-ethyl.

Carboxy-lower alkoxy is, for example, carboxy-$C_1$–$C_4$alkoxy, such as carboxymethoxy, 2-carboxyethoxy, 2- or 3-carboxypropyloxy or 4-carboxybutyloxy, especially carboxymethoxy.

Carboxy-lower alkyl is, for example, carboxy-$C_1$–$C_4$alkyl, such as carboxymethyl, 2-carboxyethyl, 2- or 3-carboxypropyl, 2-carboxy-2-methyl-propyl, 2-carboxy-2-ethyl-butyl or 4-carboxybutyl, especially carboxymethyl.

Cyano-lower alkoxy is, for example, cyano-$C_1$–$C_4$alkoxy, such as cyanomethoxy, 2-cyanoethoxy, 2- or 3-cyanopropyloxy or 4-cyanobutyloxy, especially cyanomethoxy.

Cyano-lower alkyl is, for example, cyano-$C_1$–$C_4$alkyl, such as cyanomethyl, 2-cyanoethyl, 2- or 3-cyanopropyl, 2-cyano-2-methyl-propyl, 2-cyano-2-ethyl-butyl or 4-cyanobutyl, especially cyanomethyl.

Di-(N-mono- or N,N-di-lower alkylcarbamoyl)-lower alkyl is, for example, di-(N-mono- or N,N-di-$C_1$–$C_4$alkylcarbamoyl)-$C_1$–$C_4$alkyl, such as 1,2-di-(N-mono- or N,N-di-$C_1$–$C_4$alkylcarbamoyl)ethyl or 1,3-di-(N-mono- or N,N-di-$C_1$–$C_4$alkylcarbamoyl)propyl.

Dicarbamoyl-lower alkyl is, for example, dicarbamoyl-$C_1$–$C_4$alkyl, such as 1,2-dicarbamoylethyl or 1,3-dicarbamoylpropyl.

Dicarboxy-lower alkyl is, for example, dicarboxy-$C_1$–$C_4$alkyl, such as 1,2-dicarboxyethyl or 1,3-dicarboxypropyl.

Dimethylmorpholino-lower alkoxy can be N-oxidised and is, for example, 2,6-dimethyl-morpholino- or 3,5-dimethylmorpholino-$C_1$–$C_4$alkoxy, such as 2,6-dimethylmorpholino- or 3,5-dimethylmorpholino-methoxy, 2-(2,6-dimethylmorpholino- or 3,5-dimethylmorpholino)-ethoxy, 3-(2,6-dimethylmorpholino- or 3,5-dimethylmorpholino)-propyloxy, 2-(2,6-dimethylmorpholino- or 3,5-dimethylmorpholino-3-methyl)propyloxy, or 1- or 2-[4-(2,6-dimethylmorpholino- or 3,5-dimethylmorpholino)]-butyloxy.

Dimethylmorpholino-lower alkyl can be N-oxidised and is, for example, 2,6-dimethyl-morpholino- or 3,5-dimethylmorpholino-$C_1$–$C_4$alkyl, such as 2,6-dimethylmorpholino- or 3,5-dimethylmorpholino-methoxy, 2-(2,6-dimethylmorpholino- or 3,5-dimethylmorpho-lino)-ethoxy, 3-(2,6-dimethylmorpholino- or 3,5-dimethylmorpholino)-propyl, 2-(2,6-di-methylmorpholino- or 3,5-dimethylmorpholino-3-methyl)-propyl, or 1- or 2-[4-(2,6-di- methylmorpholino- or 3,5-dimethylmorpholino)]-butyl.

Di-lower alkoxycarbonyl-lower alkyl is, for example, di-lower alkoxycarbonyl-$C_1$–$C_4$alkyl, such as 1,2-dimethoxycarbonylethyl, 1,3-dimethoxycarbonylpropyl, 1,2-dimethoxycarbonylethyl or 1,3-dimethoxycarbonylpropyl.

Di-lower alkylamino is, for example, di-$C_1$–$C_4$alkylamino, such as dimethylamino, N-methyl-N-ethylamino, diethylamino, N-methyl-N-propylamino or N-butyl-N-methyl-amino.

Di-lower alkylamino-lower alkoxy is, for example, N,N-di-$C_1$–$C_4$alkylamino-$C_1$–$C_4$alkoxy, such as 2-dimethylaminoethoxy, 3-dimethylaminopropyloxy, 4-dimethylaminobutyloxy, 2-diethylaminoethoxy, 2-(N-methyl-N-ethyl-amino)ethoxy or 2-(N-butyl-N-methyl-amino)ethoxy.

Di-lower alkylamino-lower alkyl is, for example, N,N-di-$C_1$–$C_4$alkylamino-$C_1$–$C_4$alkyl, such as 2-dimethylaminoethyl, 3-dimethylaminopropyl, 4-dimethylaminobutyl, 2-diethylaminoethyl, 2-(N-methyl-N-ethyl-amino)ethyl or 2-(N-butyl-N-methyl-amino)ethyl.

Di-lower alkylcarbamoyl-lower alkoxy is, for example, N,N-di-$C_1$-$C_4$alkylcarbamoyl-$C_1$-$C_4$alkoxy, such as methyl- or dimethyl-carbamoyl-$C_1$-$C_4$alkoxy, such as N-methyl-, N-butyl- or N,N-dimethyl-carbamoylmethoxy, 2-(N-methylcarbamoyl)ethoxy, 2-(N-butyl-carbamoyl)ethoxy, 2-(N,N-dimethylcarbamoyl)ethoxy, 3-(N-methylcarbamoyl)propyloxy, 3-(N-butylcarbamoyl)propyloxy, 3-(N,N-dimethylcarbamoyl)propyloxy or 4-(N-methyl-carbamoyl)butyloxy, 4-(N-butylcarbamoyl)butyloxy or 4-(N,N-dimethylcarbamoyl)butyl-oxy, especially N-methyl-, N-butyl- or N,N-dimethyl-carbamoylmethoxy.

Di-lower alkylcarbamoyl-lower alkyl is, for example, N,N-di-$C_1$-$C_4$alkylcarbamoyl-$C_1$-$C_4$alkyl, such as 2-dimethylcarbamoylethyl, 3-dimethylcarbamoylpropyl, 2-dimethylcarbamoylpropyl, 2-(dimethylcarbamoyl-2-methyl)propyl or 2-(1-dimethylcarbamoyl-3-methyl)butyl.

Di-lower alkylsulfamoyl-lower alkyl is, for example, N,N-di-$C_1$-$C_4$alkylsulfamoyl-$C_1$-$C_4$alkyl, N,N-dimethylsulfamoyl-$C_1$-$C_4$alkyl, such as N,N-dimethylsulfamoylmethyl, 2-(N,N-dimethylcarbamoyl)ethyl, 3-(N,N-dimethylcarbamoyl)propyl or 4-(N,N-dimethylcarbamoyl)butyl, especially N,N-dimethylcarbamoylmethyl.

Unsubstituted or N-lower alkanoylated piperidyl-lower alkyl is, for example, 1-$C_1$-$C_7$-lower alkanoylpiperidin-4-yl-$C_1$-$C_4$alkyl, such as 1-acetylpiperidinylmethyl or 2-(1-acetylpiperidinyl)ethyl.

Optionally partially hydrogenated or N-oxidised pyridyl-lower alkoxy is, for example, optionally partially hydrogenated pyridyl- or N-oxidopyridyl-$C_1$-$C_4$alkoxy, such as pyridyl- or N-oxidopyridyl-methoxy, 2-pyridylethoxy, 2- or 3-pyridylpropyloxy or 4-pyridylbutyloxy, especially 3- or 4-pyridylmethoxy.

Optionally partially hydrogenated or N-oxidised pyridyl-lower alkyl is, for example, optionally partially hydrogenated pyridyl- or N-oxidopyridyl-$C_1$-$C_4$alkyl, such as pyridyl- or N-oxidopyridyl-methyl, 2-pyridylethyl, 2- or 3-pyridylpropyl or 4-pyridylbutyl, especially 3- or 4-pyridylmethyl.

Halo-(hydroxy)-lower alkoxy is, for example, halo-$C_2$-$C_7$(hydroxy)alkoxy, especially halo-$C_2$-$C_4$(hydroxy)alkoxy, such as 3-halo-, such as 3-chloro-2-hydroxy-propyloxy.

Hydroxy-lower alkoxy is, for example, hydroxy-C2-$C_7$alkoxy, especially hydroxy-$C_1$-$C_4$alkoxy, such as 2-hydroxybutyloxy, 3-hydroxypropyloxy or 4-hydroxybutyloxy.

Hydroxy-lower alkyl is, for example, hydroxy-$C_2$-$C_7$alkyl, especially hydroxy-C2-$C_4$alkyl, such as 2-hydroxyethyl, 3-hydroxypropyl or 4-hydroxybutyl.

Hydroxypiperidino-lower alkyl is, for example, 3- or 4-hydroxypiperidino-$C_1$-$C_4$alkoxy, such as 3- or 4-hydroxypiperidinomethyl, 2-(3- or 4-hydroxypiperidino)ethoxy, 3-(3- or 4-hydroxypiperidino)propyloxy or 4-(3- or 4-hydroxypiperidino)butyloxy.

Imidazolyl-lower alkyl is, for example, imidazolyl-$C_1$-$C_4$alkyl, such as imidazol-4-yl-methyl, 2-(imidazol-4-yl)ethyl, 3-(imidazol-4-yl)propyl or 4-(imidazol-4-yl)butyl.

Imidazolyl-lower alkoxy is, for example, imidazolyl-$C_1$-$C_4$alkoxy, such as imidazol-4-yl-methoxy, 2-(imidazol-4-yl)ethoxy, 3-(imidazol-4-yl)propyloxy or 4-(imidazol-4-yl)butyl-oxy.

Imidazolyl-lower alkyl is, for example, imidazolyl-$C_1$-$C_4$alkyl, such as imidazol-4-yl-methyl, 2-(imidazol-4-yl)ethyl, 3-(imidazol-4-yl)propyl or 4-(imidazol-4-yl)butyl.

Morpholinocarbonyl-lower alkyl is, for example, morpholinocarbonyl-$C_1$-$C_4$alkyl, such as 1-morpholinocarbonylethyl, 3-morpholinocarbonylpropyl, or 1-(morpholinocarbonyl-2-methyl)propyl.

Morpholino-lower alkoxy can be N-oxidised and is, for example, morpholino-$C_1$-$C_4$alkoxy, such as 1-morpholinoethoxy, 3-morpholinopropyloxy, or 1-(morpholino-2-methyl)propyloxy.

Morpholino-lower alkyl can be N-oxidised and is, for example, morpholino-$C_1$-$C_4$alkyl, such as morpholinomethyl, 2-morpholinoethyl, 3-morpholinopropyl or 1- or 2-(4-morpho-lino)butyl.

Lower alkanoyl is, for example, $C_1$-$C_7$alkanoyl, especially C2-C6alkanoyl, such as acetyl, propionyl, butyryl, isobutyryl or pivaloyl.

Lower alkanoylamino is, for example, N-$C_1$-$C_7$alkanoylamino, such as acetylamino or pivaloylamino.

Lower alkanoylamino is, for example, N-$C_1$-$C_7$alkanoylamino, such as acetylamino or pivaloylamino.

Lower alkanoylamino-lower alkyl is, for example, N-$C_1$-$C_4$alkanoylamino-$C_1$-$C_4$alkyl, such as 2-acetoxyaminoethyl.

Lower alkanoylamino-lower alkyl is, for example, N-$C_1$-$C_4$alkanoylamino-$C_1$-$C_4$alkyl, such as 2-acetoxyaminoethyl.

Lower alkanoyl-lower alkoxy (oxo-lower alkoxy) carries the lower alkanoyl group in a position higher than the α-position and is, for example, $C_1$-$C_7$alkanoyl-$C_1$-$C_4$alkoxy, such as 4-acetylbutoxy.

Lower alkanoyloxy-lower alkyl carries the lower alkanoyloxy group in a position higher than the α-position and is, for example, $C_1$-$C_7$alkanoyloxy-$C_1$-$C_4$alkyl, such as 4-acetoxybutyl.

Lower alkanesulfonyl-(hydroxy)-lower alkoxy is, for example, $C_1$-$C_7$alkanesulfonyl-$C_1$-$C_4$(hydroxy)alkoxy, such as 3-methanesulfonyl-2-hydroxy-propyloxy.

Lower alkanesulfonyl-lower alkoxy is, for example, $C_1$-$C_7$alkanesulfonyl-$C_1$—$C_4$alkoxy, such as methanesulfonylmethoxy or 3-methanesulfonyl-2-hydroxy-propyloxy.

Lower alkanesulfonylamino-lower alkoxy is, for example, $C_1$-$C_7$alkanesulfonylamino-$C_1$-$C_4$alkoxy, such as ethanesulfonylaminomethoxy, 2-ethanesulfonylaminoethoxy, 3-ethanesulfonylaminopropyloxy or 3-(1,1-dimethylethanesulfonylamino)propyloxy.

Lower alkanesulfonylamino-lower alkyl is, for example, $C_1$-$C_7$alkanesulfonylamino-$C_1$-$C_4$alkyl, such as ethanesulfonylaminomethyl, 2-ethanesulfonylaminoethyl, 3-ethanesulfonylaminopropyl or 3-(1,1-dimethylethanesulfonylamino)propyl.

Lower alkanesulfonyl-lower alkyl is, for example, $C_1$-$C_7$alkanesulfonyl-$C_1$-$C_4$alkyl, such as ethanesulfonylmethyl, 2-ethanesulfonylethyl, 3-ethanesulfonylpropyl or 3-(1,1-di-methylethanesulfonyl)propyl.

Lower alkenyl is, for example, $C_1$-$C_7$alkenyl, such as vinyl or allyl.

Lower alkenyloxy is, for example, $C_1$-$C_7$alkenyloxy, such as allyloxy.

Lower alkenyloxy-lower alkoxy is, for example, $C_1$-$C_7$alkenyloxy-$C_1$-$C_4$alkoxy, such as allyloxymethoxy.

Lower alkenyloxy-lower alkyl is, for example, $C_1$-$C_7$alkenyloxy-$C_1$-$C_4$alkyl, such as allyloxymethyl.

Lower alkoxy is, for example, $C_1$-$C_7$alkoxy, preferably $C_1$-$C_5$alkoxy, such as methoxy, ethoxy, propyloxy, isopropyloxy, butyloxy, isobutyloxy, secondary butyloxy, tertiary butyloxy, pentyloxy or a hexyloxy or heptyloxy group.

Lower alkoxycarbonyl is, for example, $C_1$–$C_7$alkoxycarbonyl, preferably $C_1$–$C_5$alkoxycarbonyl, such as methoxycarbonyl, ethoxycarbonyl, propyloxycarbonyl, isopropyloxycarbonyl, butyloxycarbonyl, isobutyloxycarbonyl, secondary butyloxycarbonyl, tertiary butyloxy, pentyloxycarbonyl or a hexyloxycarbonyl or heptyloxycarbonyl group.

Lower alkoxycarbonyl-(hydroxy)-lower alkyl is, for example, $C_1$–$C_4$alkoxycarbonyl-$C_1$–$C_7$(hydroxy)alkyl, such as 1-methoxycarbonyl- or 1-ethoxycarbonyl-2-hydroxyethyl.

Lower alkoxycarbonylamino-lower alkoxy is, for example, $C_1$–$C_7$alkoxycarbonylamino-$C_2$–$C_7$alkoxy, preferably $C_2$–$C_5$alkoxycarbonylamino-$C_2$–$C_7$alkoxy, such as methoxycarbonylamino-$C_2$–$C_7$alkoxy, ethoxycarbonylamino-$C_2$–$C_7$alkoxy, propyloxycarbonylamino-$C_2$–$C_7$alkoxy, isopropyloxycarbonylamino-$C_1$–$C_7$alkoxy, butyloxycarbonylamino-$C_2$–$C_7$alkoxy, isobutyloxycarbonylamino-$C_2$–$C_7$alkoxy, secondary butyloxycarbonylamino-$C_2$–$C_7$alkoxy or tertiary butyloxyamino-$C_2$–$C_7$alkoxy, wherein $C_2$–$C_7$alkoxy is, for example, methoxy, ethoxy, propyloxy, butyloxy, pentyloxy or hexyloxy.

Lower alkoxycarbonylamino-lower alkyl is, for example, $C_1$–$C_7$alkoxycarbonylamino-$C_2$–$C_7$alkyl, preferably $C_2$–$C_5$alkoxycarbonylamino-$C_2$–$C_7$alkyl, such as methoxycarbonylamino-$C_2$–$C_7$alkyl, ethoxycarbonylamino-$C_2$–$C_7$alkyl, propyloxycarbonylamino-$C_2$–$C_7$alkyl, isopropyloxycarbonylamino-$C_2$–$C_7$alkyl, butyloxycarbonylamino-$C_2$–$C_7$alkyl, isobutyloxycarbonylamino-$C_2$–$C_7$alkyl, secondary butyloxycarbonylamino-$C_1$–$C_7$alkyl or tertiary butyloxyamino-$C_2$–$C_7$alkyl, wherein $C_2$–$C_7$alkyl is, for example, methyl, ethyl, propyl, butyl, pentyl or hexyl.

Lower alkoxycarbonyl-lower alkoxy is, for example, $C_1$–$C_4$alkoxycarbonyl-$C_1$–$C_4$alkoxy, such as methoxycarbonyl- or ethoxycarbonyl-methoxy, 2-methoxycarbonyl- or 2-ethoxycarbonyl-ethoxy, 2- or 3-methoxycarbonyl- or 2- or 3-ethoxycarbonyl-propyloxy or 4-methoxycarbonyl- or 4-ethoxycarbonyl-butyloxy, especially methoxycarbonyl- or ethoxycarbonyl-methoxy or 3-methoxycarbonyl- or 3-ethoxycarbonyl-propyloxy.

Lower alkoxycarbonyl-lower alkyl is, for example, $C_1$-$C_1$–$C_4$alkoxycarbonyl-$C_1$–$C_4$alkyl, such as methoxycarbonyl- or ethoxycarbonyl-methoxy, 2-methoxycarbonyl- or 2-ethoxycarbonyl-ethoxy, 3-methoxycarbonyl- or 3-ethoxycarbonyl-propyloxy or 4-ethoxy-carbonylbutyloxy.

Lower alkoxy-lower alkenyl is, for example, $C_1$–$C_4$alkoxy-$C_2$–$C_4$alkenyl, such as 4-methoxybut-2-enyl.

Lower alkoxy-lower alkoxy is, for example, $C_1$–$C_4$alkoxy-$C_2$–$C_4$alkoxy, such as 2-methoxy-, 2-ethoxy- or 2-propyloxy-ethoxy, 3-methoxy- or 3-ethoxy-propyloxy or 4-methoxybutyloxy, especially 3-methoxypropyloxy or 4-methoxybutyloxy.

Lower alkoxy-lower alkoxy-lower alkyl is, for example, $C_1$–$C_4$alkoxy-$C_1$–$C_4$alkoxy-$C_1$–$C_4$alkyl, such as 2-methoxy-, 2-ethoxy- or 2-propyloxy-ethoxymethyl, 2-(2-methoxy-2-ethoxy- or 2-propyloxy-ethoxy)ethyl, 3-(3-methoxy- or 3-ethoxy-propyloxy)propyl or 4-(2-methoxybutyloxy)butyl, especially 2-(3-methoxypropyloxy)ethyl or 2-(4-methoxybutyloxy)ethyl.

Lower alkoxy-lower alkyl is, for example, $C_1$–$C_4$alkoxy-$C_1$–$C_4$alkyl, such as ethoxymethyl, propyloxymethyl, butyloxymethyl, 2-methoxy-, 2-ethoxy- or 2-propyloxy-ethyl, 3-methoxy- or 3-ethoxy-propyl or 4-methoxybutyl, especially 3-methoxypropyl or 4-methoxybutyl.

Lower alkoxypiperidino-lower alkyl is, for example, piperidino-, hydroxypiperidino- or lower alkoxypiperidino-$C_1$–$C_4$alkyl, such as piperidinomethyl, 4-hydroxypiperidinomethyl or 4-$C_1$–$C_4$alkoxy-, such as 4-methoxy-piperidinomethyl.

Lower alkoxypiperidino-lower alkyl is, for example, $C_1$–$C_4$alkoxypiperidino-$C_1$–$C_4$alkyl, such as 4-$C_1$–$C_4$alkoxy-piperidinomethyl, especially 4-methoxypiperidinomethyl.

Lower alkyl may be straight-chained or branched and/or bridged and is, for example, corresponding $C_1$–$C_7$alkyl, such as methyl, ethyl, propyl, isopropyl, butyl, isobutyl, secondary butyl or tertiary butyl, or a pentyl, hexyl or heptyl group. Lower alkyl $R_2$ or $R_3$ is especially $C_2$–$C_7$alkyl, lower alkyl $R_5$ or $R_7$ is especially branched $C_3$–$C_7$alkyl and lower alkyl $R_8$ or $R_3$ is, for example, straight-chained, branched or bridged $C_3$–$C_7$alkyl.

Lower alkylamino is, for example, $C_1$–$C_4$alkylamino, such as methylamino, ethylamino, propylamino, butylamino, isobutylamino, secondary butylamino or tertiary butylamino.

Lower alkylamino-lower alkoxy is, for example, $C_1$–$C_4$alkylamino-$C_1$–$C_4$alkoxy, such as propylaminomethoxy, 2-methylamino-, 2-ethylamino-, 2-propylamino- or 2-butylaminoethoxy, 3-ethylamino- or 3-propylamino-propyloxy or 4-methylaminobutoxy.

Lower alkylamino-lower alkyl is, for example, $C_1$–$C_4$alkylamino-$C_1$–$C_4$alkyl, such as propylaminomethyl, 2-methylamino-, 2-ethylamino-, 2-propylamino- or 2-butylaminoethyl, 3-ethylamino- or 3-propylamino-propyl or 4-methylaminobutyl.

Lower alkylcarbamoyl-lower alkoxy is, for example, N-$C_1$–$C_7$alkylcarbamoyl-$C_1$–$C_4$alkoxy, such as methyl- or dimethyl-carbamoyl-$C_1$–$C_4$alkoxy, e.g. methylcarbamoylmethoxy, 2-methylcarbamoylethoxy or 3-methylcarbamoylpropyloxy.

Lower alkylenedioxy is, for example, methylenedioxy or ethylenedioxy, but can also be 1,3- or 1,2-propylenedioxy.

Lower alkylsulfamoyl-lower alkyl is, for example, N-$C_1$–$C_7$alkylsulfamoyl-$C_1$–$C_4$alkyl, such as N-methyl-, N-ethyl-, N-propyl- or N-butyl-sulfamoyl-$C_1$–$C_4$alkyl, such as N-methyl-, N-ethyl-, N-propyl- or N-butyl-sulfamoylmethyl, 2-(N-methylsulfamoyl)ethyl, 2-(N-butylsulfamoyl)ethyl, 3-(N-methylsulfamoyl)propyl, 3-(N-butylsulfamoyl)propyl, or 4-(N-methylsulfamoyl)butyl, 4-(N-butylsulfamoyl)butyl or 4-(N,N-dimethylsulfamoyl)-butyl, especially N-methyl-, N-butyl- or N,N-dimethyl-sulfamoylmethyl.

Lower alkylthio-(hydroxy)-lower alkoxy is, for example, N-$C_1$–$C_4$alkylthio-$C_1$–$C_4$(hydroxy)alkoxy, such as 2-hydroxy-3-methylthiopropyloxy.

Oxazolyl-lower alkyl is, for example, oxazolyl-$C_1$–$C_4$alkyl, such as 2-(1,2,4-oxadiazol-5-yl)ethyl, 3-(1,2,4-oxadiazol-5-yl)propyl or 4-(1,2,4-oxadiazol-5-yl)butyl.

Lower alkylthio-lower alkoxy is, for example, N-$C_1$–$C_4$alkylthio-$C_1$–$C_4$alkoxy, such as methylthio-$C_1$–$C_4$alkoxy, e.g. methylthiomethoxy, 2-methylthioethoxy or 3-methylthiopropyloxy.

Lower alkylthio-lower alkyl is, for example, N-$C_1$–$C_4$alkylthio-$C_1$–$C_4$alkyl, such as methylthio-$C_1$–$C_4$alkyl, e.g. methylthiomethyl, 2-methylthioethyl or 3-methylthiopropyl.

N'-Lower alkanoylpiperazino-lower alkoxy is, for example, N'-lower alkanoylpiperazino-$C_1$–$C_4$alkoxy, such as 4-acetylpiperazinomethoxy.

N'-Lower alkanoylpiperazino-lower alkyl is, for example, N'-$C_2$–$C_7$-lower alkanoylpiperazino-$C_1$–$C_4$alkyl, such as 4-acetylpiperazinomethyl.

N'-Lower alkylpiperazino-lower alkyl is, for example, N'-$C_1$–$C_4$alkylpiperazino-$C_1$–$C_4$alkyl, such as 4-methylpiperazinomethyl.

Oxo-lower alkoxy is, for example, oxo-$C_1$–$C_4$alkoxy, such as 3,3-dimethyl-2-oxo-butyloxy.

Piperazino-lower alkyl is, for example, piperazino-$C_1$–$C_4$alkyl, such as piperazinomethyl, 2-piperazinoethyl or 3-piperazinopropyl.

Piperidino-lower alkoxy is, for example, piperidino-$C_1$–$C_4$alkoxy, such as piperidinomethoxy, 2-piperidinoethoxy or 3-piperidinopropyloxy.

Piperidino-lower alkyl is, for example, piperidino-$C_1$–$C_4$alkyl, such as piperidinomethyl, 2-piperidinoethyl or 3-piperidinopropyl.

Polyhalo-lower alkanesulfonylamino-lower alkoxy is, for example, trifluoro-$C_1$–$C_7$alkanesulfonyl-$C_1$–$C_4$alkoxy, such as trifluoromethanesulfonylaminobutyloxy.

Polyhalo-lower alkanesulfonylamino-lower alkyl is, for example, trifluoro-$C_1$–$C_7$ alkane-sulfonyl-$C_1$–$C_4$alkyl, such as trifluoromethanesulfonylaminobutyl.

Pyrimidinyl-lower alkoxy is, for example, pyrimidinyl-$C_1$–$C_4$alkoxy, such as pyrimidinylmethoxy, 2-pyrimidinylethoxy or 3-pyrimidinylpropyloxy.

Pyrimidinyl-lower alkyl is, for example, pyrimidinyl-$C_1$–$C_4$alkyl, such as pyrimidinylmethyl, 2-pyrimidinylethyl or 3-pyrimidinylpropyl.

Pyrrolidino-lower alkoxy is, for example, pyrrolidino-$C_2$–$C_4$alkoxy, such as 2-pyrrolidinoethoxy or 3-pyrrolidinopropyloxy.

Pyrrolidino-lower alkyl is, for example, pyrrolidino-$C_1$–$C_4$alkyl, such as pyrrolidinomethyl, 2-pyrrolidinoethyl or 3-pyrrolidinopropyl.

S,S-Dioxothiomorpholino-lower alkyl is, for example, S,S-dioxothiomorpholino-$C_1$–$C_4$alkyl, such as S,S-dioxothiomorpholinomethyl or 2-(S,S-dioxo)thiomorpholinoethyl.

S-Oxothiomorpholino-lower alkyl is, for example, S-oxothiomorpholino-$C_1$–$C_4$alkyl, such as S-oxothiomorpholinomethyl or 2-(S-oxo)thiomorpholinoethyl.

Sulfamoyl-lower alkyl is, for example, sulfamoyl-$C_1$–$C_4$alkyl, such as sulfamoyl-$C_1$–$C_4$alkyl, such as sulfamoylmethyl, 2-sulfamoylethyl, 3-sulfamoylpropyl or 4-sulfamoylbutyl.

Tetrazolyl-lower alkyl is, for example, tetrazolyl-$C_1$–$C_4$alkyl, such as tetrazol-5-ylmethyl, 2-(tetrazol-5-yl)ethyl, 3-(tetrazol-5-yl)propyl or 4-(tetrazol-4-yl)butyl.

Thiazolinyl-lower alkoxy is, for example, thiazolinyl-$C_1$–$C_4$alkoxy, such as thiazolinyl-methoxy, 2-thiazolinylmethoxy or 3-thiazolinylpropyloxy.

Thiazolinyl-lower alkyl is, for example, thiazolinyl-$C_1$–$C_4$alkyl, such as thiazolinylmethyl, 2-thiazolinylethyl or 3-thiazolinylpropyl.

Thiazolyl-lower alkoxy is, for example, thiazolyl-$C_1$–$C_4$alkoxy, such as thiazolylmethoxy, 2-thiazolylethoxy or 3-thiazolylpropyloxy.

Thiazolyl-lower alkyl is, for example, thiazolyl-$C_1$–$C_4$alkyl, such as thiazolylmethyl, 2-thiazolylethyl or 3-thiazolylpropyl.

Thiomorpholino-lower alkyl or S,S-dioxothiomorpholino-lower alkyl is, for example, thiomorpholino-$C_1$–$C_4$alkyl, such as -methyl or -ethyl, or S,S-dioxothiomorpholino-$C_1$–$C_4$alkyl, such as -methyl or -ethyl.

Depending on whether asymmetric carbon atoms are present, the compounds of the invention can be present as mixtures of isomers, especially as racemates, or in the form of pure isomers, especially optical antipodes.

Salts of compounds having salt-forming groups are especially acid addition salts, salts with bases or, where several salt-forming groups are present, can also be mixed salts or internal salts.

Salts are especially the pharmaceutically acceptable or non-toxic salts of compounds of formula I.

Such salts are formed, for example, by compounds of formula I having an acid group, for example a carboxy group or a sulfo group, and are, for example, salts thereof with suitable bases, such as non- toxic metal salts derived from metals of groups Ia, Ib, IIa and IIb of the Periodic Table of the Elements, for example alkali metal salts, especially lithium, sodium or potassium salts, or alkaline earth metal salts, for example magnesium or calcium salts, also zinc salts or ammonium salts, as well as salts formed with organic amines, such as unsubstituted or hydroxy-substituted mono-, di- or tri-alkylamines, especially mono-, di- or tri-lower alkylamines, or with quaternary ammonium bases, for example with methyl-, ethyl-, diethyl- or triethyl-amine, mono-, bis- or tris-(2-hydroxy-lower alkyl)-amines, such as ethanol-, diethanol- or triethanol-amine, tris-(hydroxymethyl)-methylamine or 2-hydroxy-tert-butylamines, N,N-di-lower alkyl-N-(hydroxy-lower alkyl)-amines, such as N,N-dimethyl-N-(2-hydroxyethyl)-amine, or N-methyl-D-glucamine, or quaternary ammonium hydroxides, such as tetrabutylammonium hydroxide. The compounds of formula I having a basic group, for example an amino group, can form acid addition salts, for example with suitable inorganic acids, for example hydrohalic acids, such as hydrochloric acid or hydrobromic acid, or sulfuric acid with replacement of one or both protons, phosphoric acid with replacement of one or more protons, e.g. orthophosphoric acid or metaphosphoric acid, or pyrophosphoric acid with replacement of one or more protons, or with organic carboxylic, sulfonic, sulfo or phosphonic acids or N-substituted sulfamic acids, for example acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, as well as with amino acids, such as the α-amino acids mentioned hereinbefore, and with methanesulfonic acid, ethanesulfonic acid, 2-hydroxyethanesulfonic acid, ethane-1,2-disulfonic acid, benzenesulfonic acid, 4-toluenesulfonic acid, naphthalene-2-sulfonic acid, 2- or 3-phosphoglycerate, glucose-6-phosphate, or N-cyclohexylsulfamic acid (forming cyclamates) or with other acidic organic compounds, such as ascorbic acid. Compounds of formula I having acid and basic groups can also form internal salts.

For isolation and purification purposes it is also possible to use pharmaceutically unacceptable salts.

The compounds of the present invention have enzyme-inhibiting properties. In particular, they inhibit the action of the natural enzyme renin. The latter passes from the kidneys into the blood where it effects the cleavage of angiotensinogen, releasing the decapeptide angiotensin I which is then cleaved in the lungs, the kidneys and other organs to form the octapeptide angiotensinogen II. The octapeptide increases blood pressure both directly by arterial vasoconstriction and indirectly by liberating from the adrenal glands the sodium-ion-retaining hormone aldosterone, accompanied by an increase in extracellular fluid volume.

That increase can be attributed to the action of angiotensin II. Inhibitors of the enzymatic activity of renin bring about a reduction in the formation of angiotensin I. As a result a smaller amount of angiotensin II is produced. The reduced concentration of that active peptide hormone is the direct cause of the hypotensive effect of renin inhibitors.

The action of renin inhibitors is demonstrated inter alia experimentally by means of in vitro tests, the reduction in the formation of angiotensin I being measured in various systems (human plasma, purified human renin together with synthetic or natural renin substrate). Inter alia the following in vitro test is used: an extract of human renin from the kidney (0.5 mGU [milli-Goldblatt units]/ml) is incubated for one hour at 37° C. and pH 7.2 in 1-molar aqueous 2-N-(tris-hydroxymethylmethyl)amino-ethanesulfonic acid buffer solution with 23 μg/ml of synthetic renin substrate, the tetradecapeptide H-Asp-Arg-Val-Tyr-Ile-His-ProPhe-His-Leu-Leu-Val-Tyr-Ser-OH. The amount of angiotensin I formed is determined by radioimmunoassay. Each of the inhibitors according to the invention is added to the incubation mixture at different concentrations. The $IC_{50}$ is defined as the concentration of a particular inhibitor that reduces the formation of angiotensin I by 50%. In the in vitro systems the compounds of the present invention exhibit inhibiting activities at minimum concentrations of from approximately $10^{-6}$ to approximately $10^{10}$ mol/l.

In animals deficient in salt, renin inhibitors bring about a reduction in blood pressure. Human renin differs from the renin of other species. In order to test inhibitors of human renin, primates (marmosets, *Callithrix jacchus*) are used, because human renin and primate renin are substantially homologous in the enzymatically active region. Inter alia the following in vivo test is used: the test compounds are tested on normotensive marmosets of both sexes having a body weight of approximately 350 g that are conscious, allowed to move freely and in their normal cages. The blood pressure and heart rate are measured via a catheter in the descending aorta and recorded radiometrically. The endogenous release of renin is stimulated by the combination of a 1-week low-salt diet and a single intramuscular injection of furosemide (5-(aminosulfonyl)-4-chloro-2-[(2-furanylmethyl) amino]benzoic acid) (5 mg/kg). 16 hours after the injection of furosemide the test compounds are administered either directly into the femoral artery using an injection cannula or, in the form of a suspension or solution, via an oesophageal tube into the stomach, and their action on the blood pressure and heart rate are evaluated. In the in vivo test described, the compounds of the present invention have hypotensive action at doses of from approximately 0.003 to approximately 0.3 mg/kg i.v. and at doses of from approximately 0.31 to approximately 30 mg/kg p.o.

The compounds of the present invention also have the property of regulating, especially reducing, intra-ocular pressure.

The extent of the reduction in intra-ocular pressure after administration of a pharmaceutical active ingredient of formula (I) according to the present invention can be determined, for example, in animals, for example rabbits or monkeys. Two typical experimental procedures that illustrate the present invention, but are not intended to limit it in any way, are described hereinafter.

The in vivo test on a rabbit of the "Fauve de Bourgogne" type to determine the intra-ocular-pressure-reducing activity of topically applied compositions can be designed, for example, as follows. The intra-ocular pressure (IOP) is measured using an aplanation tonometer both before the experiment and at regular intervals of time. After a local anaesthetic has been administered, the suitably formulated test compound is applied topically in a precisely defined concentration (e.g. 0.000001–5% by weight) to one eye of the animal in question. The contralateral eye is treated, for example, with physiological saline. The measured values thus obtained are evaluated statistically.

The in vivo tests on monkeys of the species *Macaca Fascicularis* to determine the intra-ocular-pressure-reducing activity of topically applied compositions can be carried out, for example, as follows. The suitably formulated test compound is applied in a precisely defined concentration (e.g. 0.000001–5% by weight) to one eye of each monkey. The other eye of the monkey is treated correspondingly, for example with physiological saline. Before the start of the test the animals are anaesthetised with intramuscular injections of, for example, ketamine. At regular intervals of time, the intra-ocular pressure (IOP) is measured. The test is carried out and evaluated in accordance with the rules of "good laboratory practice" (GLP).

The compounds of the present invention can be used in the treatment of hypertension, congestive heart failure, cardiac hypertrophy, cardiac fibrosis, cardiomyopathy post-infraction, complications resulting from diabetes, such as nephropathy, vasculopathy and neuropathy, diseases of the coronary vessels, restenosis following angioplasty, raised intra-ocular pressure, glaucoma, abnormal vascular growth, hyperaldosteronism, anxiety states and cognitive disorders.

The groups of compounds mentioned below are not to be regarded as exclusive; rather, for example in order to replace general definitions with more specific definitions, parts of those groups of compounds can be interchanged or exchanged for the definitions given above, or omitted, as appropriate.

The invention relates especially to compounds of formula I wherein $R_1$ is hydrogen, hydroxy, lower alkoxy, cycloalkoxy, lower alkoxy-lower alkoxy, carboxy-lower alkoxy, lower alkoxycarbonyl-lower alkoxy, carbamoyl-lower alkoxy or N-mono- or N,N-di-lower alkylcarbamoyl-lower alkoxy, $R_2$ is hydrogen, lower alkyl, cycloalkyl, lower alkoxy-lower alkyl, lower alkoxy-lower alkoxy-lower alkyl, cycloalkoxy-lower alkyl, hydroxy, lower alkanoyloxy-lower alkyl, hydroxy-lower alkoxy, halo-(hydroxy)-lower alkoxy, lower alkanesulfonyl-(hydroxy)-lower alkoxy, amino-lower alkyl, lower alkylamino-lower alkyl, di-lower alkylamino-lower alkyl, lower alkanoylamino-lower alkyl, lower alkoxycarbonylamino-lower alkyl, amino-lower alkoxy, lower alkylamino-lower alkoxy, di-lower alkylamino-lower alkoxy, lower alkanoylamino-lower alkoxy, lower alkoxycarbonylamino-lower alkoxy, oxo-lower alkoxy, lower alkoxy, cycloalkoxy, lower alkenyloxy, cycloalkoxy-lower alkoxy, lower alkoxy-lower alkoxy, lower alkoxy-lower alkenyl, lower alkenyloxy-lower alkoxy, lower alkoxy-lower alkenyloxy, lower alkenyloxy-lower alkyl, lower alkanoyl-lower alkoxy, lower alkylthio-lower alkoxy, lower alkanesulfonyl-lower alkoxy, lower alkylthio-(hydroxy)-lower alkoxy, aryl-lower alkoxy, thiazolylthio-lower alkoxy or thiazolinylthio-lower alkoxy, imidazolylthio-lower alkoxy, optionally N-oxidised pyridylthio-lower alkoxy, pyrimidinylthio-lower alkoxy, cyano-lower alkoxy, lower alkoxycarbonyl-lower alkoxy, carbamoyl-lower alkoxy, N-mono- or N,N-di-lower alkylcarbamoyl-lower alkoxy, carboxy-lower alkyl, lower alkoxycarbonyl-lower alkyl, carbamoyl-lower alkyl or N-mono- or N,N-di-lower alkylcarbamoyl-lower alkyl, $R_3$ is lower alkyl, polyhalo-lower alkyl, lower alkoxy-lower alkyl, cycloalkoxy-lower alkyl, hydroxy-lower alkyl, lower alkylthio-lower alkyl, lower alkanesulfonyl-lower alkyl, optionally partially hydrogenated or N-oxidised pyridyl-lower alkyl, thiazolylthio-lower alkyl or thiazolinylthio-lower alkyl, imidazolylthio-lower alkyl, optionally N-oxidised pyridylthio-lower alkyl, pyrimidinylthio-lower alkyl, aminolower alkyl, lower alkylamino-lower alkyl, all-lower alkylamino-lower alkyl, lower alkanoylamino-lower alkyl, lower alkanesulfonylamino-lower alkyl, polyhalo-lower alkanesulfonylamino-lower alkyl, pyrrolidino-lower alkyl, piperidino-lower alkyl, piperazino-, N'-lower alkylpiperazino- or N'-lower alkanoylpiperazino-lower alkyl, morpholino-lower alkyl, thiomorpholino-, S-oxothiomorpholino- or S,S-dioxothiomorpholino-lower alkyl, cyano-lower alkyl, carboxy-lower alkyl, lower alkoxycarbonyl-lower carbonyl-lower alkyl, carbamoyl-lower alkyl, N-mono- or N,N-di-lower alkylcarbamoyl-lower alkyl, cycloalkyl; phenyl or naphthyl that is unsubstituted or mono-, di- or tri-substituted by lower alkyl, lower alkoxy, hydroxy, lower alkylamino, di-lower alkylamino, halogen and/or by trifluoromethyl; hydroxy, lower alkoxy, cycloalkoxy, lower alkoxy-lower alkoxy, cycloalkoxy-lower alkoxy, hydroxy-lower alkoxy; phenyl-lower alkoxy or naphthyl-lower alkoxy that is unsubstituted or mono-,di- or tri-substituted by lower alkyl, lower alkoxy, hydroxy, lower alkylamino, di-lower alkylamino, halogen and/or by trifluoromethyl; lower alkoxy, polyhalo-lower alkoxy, lower alkylthio-lower alkoxy, lower alkanesulfonyl-lower alkoxy, optionally hydrogenated heteroaryl-lower alkoxy, optionally partially or fully hydrogenated heteroarylthio-lower alkoxy, such as thiazolylthio-lower alkoxy or thiazolinylthio-lower alkoxy, imidazolylthio-lower alkoxy, optionally N-oxidised pyridylthio-lower alkoxy, pyrimidinylthio-lower alkoxy, amino-lower alkoxy, lower alkylamino-lower alkoxy, di-lower alkylamino-lower alkoxy, lower alkanoylamino-lower alkoxy, lower alkanesulfonylamino-lower alkoxy, polyhalo-lower alkanesulfonylamino-lower alkoxy, pyrrolidino-lower alkoxy, piperidino-lower alkoxy, piperazino-, N'-lower alkylpiperazino- or N'-lower alkanoylpiperazino-lower alkoxy, morpholino-lower alkoxy, thiomorpholino-, S-oxothiomorpholino- or S,S-dioxothiomorpholino-lower alkoxy, cyano-lower alkoxy, carboxy-lower alkoxy, lower alkoxycarbonyl-lower alkoxy, carbamoyl-lower alkoxy or N-mono- or N,N-di-lower alkylcarbamoyl-lower alkoxy or together with $R_4$ is lower alkylenedioxy or a fused-on benzo or cyclohexeno ring, $R_4$ together with $R_3$ is lower alkylenedioxy or a fused-on benzo or cyclohexeno ring, or is hydrogen, lower alkyl, hydroxy, lower alkoxy or cycloalkoxy, X is methylene or hydroxymethylene, $R_5$ is lower alkyl or cycloalkyl, $R_6$ is amino, lower alkylamino, di-lower alkylamino or lower alkanoylamino, $R_7$ is lower alkyl, lower alkenyl, cycloalkyl, or phenyl- or naphthyl-lower alkyl that is unsubstituted or mono-, di- or tri-substituted by lower alkyl, lower alkoxy, hydroxy, lower alkylamino, di-lower alkylamino, halogen and/or by trifluoromethyl, and $R_8$ is lower alkyl, cycloalkyl, hydroxy-lower alkyl, lower alkanoyloxy-lower alkyl, lower alkoxy-lower alkyl or lower alkenyloxy-lower alkyl, amino-lower alkyl, lower alkanoylamino-lower alkyl, N-mono- or N,N-di-lower alkylamino-lower alkyl, optionally hydroxylated or lower alkoxylated piperidino-lower alkyl, such as piperidino-lower alkyl, hydroxypiperidino-lower alkyl or lower alkoxypiperidino-lower alkyl, piperazino-, N'-lower alkylpiperazino- or N'-lower alkanoylpiperazino-lower alkyl, unsubstituted or lower alkylated morpholino-lower alkyl, such as morpholino-lower alkyl or dimethylmorpholino-lower alkyl, or optionally S-oxidised thiomorpholino-lower alkyl, such as thiomorpholino-lower alkyl, S,S-dioxothiomorpholino-lower alkyl, carboxy-lower alkyl, lower alkoxycarbonyl-lower alkyl, carbamoyl-lower alkyl, N-mono- or N,N-di-lower alkylcarbamoyl-lower alkyl, dicarboxy-lower alkyl, di-lower alkoxycarbonyl-lower alkyl, dicarbamoyl-lower alkyl, di-(N-mono- or N,N-di-lower alkylcarbamoyl)-lower alkyl, carboxy-(hydroxy)-lower alkyl, lower alkoxycarbonyl-(hydroxy)-lower alkyl or carbamoyl-(hydroxy)-lower alkyl, cyano-lower alkyl, lower alkanesulfonyl-lower alkyl, sulfamoyl-lower alkyl, lower alkyl-sulfamoyl lower alkyl, di-lower alkylsulfamoyl-lower alkyl, thiocarbamoyl-lower alkyl, lower alkylthiocarbamoyl-lower alkyl, di-lower alkylthiocarbamoyl-lower alkyl, pyrrolidinyl, imidazolyl, benzimidazolyl, oxadiazolyl, pyridyl, oxopiperidinyl, quinolinyl, unsubstituted or N-lower alkanoylated piperidyl or pyrrolidinyl, imidazol-yl-lower alkyl, benzimidazolyl-lower alkyl, oxadiazolyl-lower alkyl, pyridyl-lower alkyl, unsubstituted or N-lower alkanoylated piperidyl-lower alkyl or pyrrolidinyl-lower alkyl, oxopiperidinyl-lower alkyl, quinolinyl-lower alkyl, morpholinocarbamoyl-lower alkyl or unsubstituted or N-lower alkanoylated piperidyl-lower alkyl, and the salts thereof.

The invention relates especially to compounds of formula I wherein $R_1$ is hydrogen, $R_2$ is lower alkyl, lower alkoxy-lower alkyl, lower alkoxy-lower alkoxy, lower alkoxy-lower alkoxy-lower alkyl; phenyl-lower alkoxy that is unsubstituted or substituted by lower alkyl, lower alkoxy, hydroxy, halogen, nitro and/or by amino; optionally N-oxidised pyridyl-lower alkoxy, lower alkylthio-lower alkoxy, lower alkanesulfonyl-lower alkoxy, lower alkanoyl-lower alkoxy, optionally N-oxidised pyridyl-lower alkoxy, cyano-lower alkoxy, carboxy-lower alkoxy, lower alkoxycarbonyl-lower alkoxy, carbamoyl-lower alkoxy, lower alkylcarbamoyl-lower alkoxy or di-lower alkylcarbamoyl-lower alkoxy, $R_3$ is hydrogen, lower alkyl, hydroxy, lower alkoxy or polyhalo-lower alkoxy or together with $R_4$ is lower alkylenedioxy, $R_4$ is hydrogen or together with $R_3$ is lower alkylidenedioxy, X is methylene or hydroxymethylene, $R_5$ is lower alkyl or cycloalkyl, $R_6$ is amino, lower alkylamino, di-lower alkylamino or lower alkanoylamino, $R_7$ is lower alkyl, and $R_8$ is lower alkyl, hydroxy-lower alkyl, lower alkanoyl-lower alkyl, lower alkoxy-lower alkyl, lower alkenyloxy-lower alkyl, amino-lower alkyl, lower alkanoylamino-lower alkyl, such as 2-(C₁-C₄alkanoylamino)-2-methyl-propyl, such as 2-acetylamino-2-methyl-propyl or 2-formylamino-2-methyl-propyl, N-mono- or N,N-di-lower alkylamino-lower alkyl, piperidino-lower alkyl, hydroxypiperidino-lower alkyl, lower alkoxypiperidino-lower alkyl, morpholino-lower alkyl, dimethylmorpholino-lower alkyl, thiomorpholino-lower alkyl, S,S-dioxothiomorpholino-lower alkyl, carboxy-lower alkyl, lower alkoxycarbonyl-lower alkyl, carbamoyl-lower alkyl, N-mono- or N,N-di-lower alkylcarbamoyl-lower alkyl, carboxy-(hydroxy)-lower alkyl, lower alkoxycarbonyl-(hydroxy)-lower alkyl, carbamoyl-(hydroxy)-lower alkyl, 5- or 6-membered carboxycycloalkyl-lower alkyl, 5- or 6-membered lower alkoxycarbonylcycloalkyl-lower alkyl, 5- or 6-membered carbamoylcycloalkyl-lower alkyl, 5- or 6-membered N-mono- or N,N-di-lower alkylcarbamoylcycloalkyl-lower alkyl, cyano-lower alkyl, lower alkanesulfonyl-lower alkyl, sulfamoyl-lower alkyl, lower alkylsulfamoyl-lower alkyl, or di-lower alkylsulfamoyl-lower alkyl, imidazolyl-lower alkyl, oxopyrrolidinyl-lower alkyl, benzimidazolyl-lower alkyl, oxadiazolyl-lower alkyl, pyridyl-lower alkyl, oxopiperidinyl-lower alkyl or quinolinyl-lower alkyl, piperidin-4-yl-lower alkyl or 1-C₁-C₇lower alkanoylpiperidin-4-yl-lower alkyl, and the salts thereof.

The invention relates above all to compounds of formula I wherein $R_1$ and $R_4$ are hydrogen, $R_2$ is $C_1-C_4$alkoxy-$C_1-C_4$alkoxy, such as 3-methoxypropyloxy, or $C_1-C_4$alkoxy-$C_1-C_4$alkyl, such as 4-methoxybutyl, $R_3$ is $C_1-C_4$alkyl, such as isopropyl or tert-butyl, or $C_1-C_4$alkoxy, such as methoxy, $R_6$ is amino, X is methylene, $R_5$ and $R_7$ are branched $C_1-C_4$alkyl, such as isopropyl, and $R_8$ is carbamoyl-$C_1-C_4$alkyl, such as 2- or 3-carbamoylpropyl, 2-(3-carbamoyl)propyl or 1-(2-carbamoyl-2-methyl)propyl, N-C₁-C₄alkylcarbamoyl-C₁-C₄alkyl, such as 3-(N-methylcarbamoyl)propyl, 1-(N-methylcarbamoyl)prop-2-yl, 2-(N-methylcarbamoyl)alkane-1-yl, especially 2(R)-(N-methylcarbamoyl)prop-1-yl, N,N-di-C₁-C₄alkylcarbamoyl-C₁-C₄alkyl, such as N,N-dimethylcarbamoylmethyl or 2-(N,N-dimethylcarbamoyl)ethyl, 3-(N,N-dimethylcarbamoyl)propyl, morpholino-C₁-C₄alkyl, such as 2-morpholinoethyl, 3-morpholinopropyl or 1-(2-morpholino-2-methyl)propyl, thiomorpholino-C₁-C₄alkyl, such as 2-thiomorpholinoethyl, 4-(1-C₁-C₄alkanoylpiperidyl)-C₁₋₄alkyl, such as 2-[4-(1-acetyl)piperidinyl]ethyl, 2-oxopyrrolidinyl-C₁-C₄alkyl, such as 2-oxopyrrolidin-5(S)-ylmethyl or 2-oxopyrrolidin-5(R)-ylmethyl, and the salts thereof.

Especially effective are those compounds of formula I wherein at least one, for example one, two, or preferably all four, of the asymmetric carbon atoms of the main chain have the stereochemical configuration shown in formula Ia

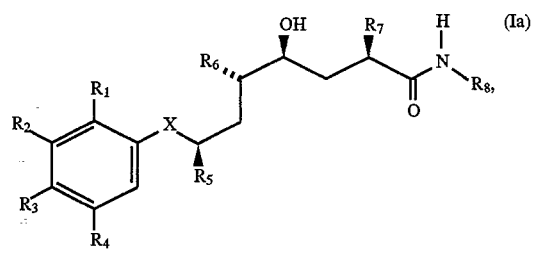

the variables each being as defined above, and the pharmaceutically acceptable salts thereof.

Accordingly, the invention relates preferably to compounds of formula I wherein at least one, for example one, two, or preferably all four, of the asymmetric carbon atoms of the main chain have the stereochemical configuration shown in formula Ia.

The invention relates very especially to those of the above-defined compounds of formulae I and Ia that are described as being preferred wherein X is methylene.

The invention relates specifically to the compounds of formula I mentioned in the Examples and to the salts thereof, especially the pharmaceutically acceptable salts thereof.

The process according to the invention for the preparation of compounds of formula I comprises a) reacting a compound of formula II

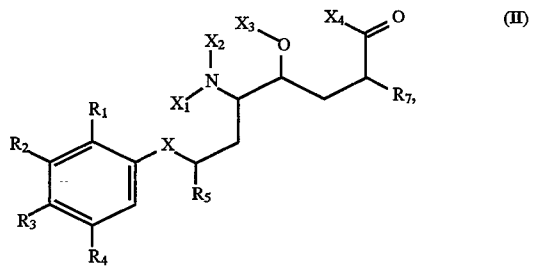

wherein $X_1$ is lower alkyl, lower alkanoyl or an amino-protecting group, $X_2$ is hydrogen or together with $X_3$ is a bivalent protecting group, $X_3$ is hydrogen or a hydroxy-protecting group or together with $X_2$ is a bivalent protecting group or together with $X_4$ is a direct bond, $X_4$ is free or reactively etherified or esterified hydroxy or together with $X_3$ is a direct bond, and $R_1, R_2, R_3, R_4, X, R_5, R_6$ and $R_7$ are as defined for formula I, with an amine of formula III $$H_2N—R_8 \qquad (III),$$

wherein $R_8$ has one of the meanings given for formula I, with the formation of an amide bond, and removing any protecting groups present, or b) in a carboxylic acid amide of formula IV

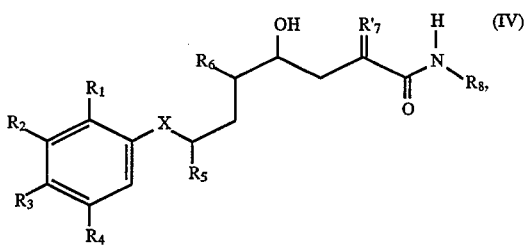

wherein $R_1$, $R_2$, $R_3$, $R_4$, X, $R_5$, $R_6$, $R_7$ and $R_8$ are as defined for formula I and $R'_7$ is a lower alkylidene or aryl-lower alkylidene group corresponding to the lower alkyl or aryl-lower alkyl group $R_7$, free functional groups being present, if desired, in protected form, or in a salt thereof, reducing the group $R'_7$ to $R_7$ by treatment with a hydrogenating agent, or c) for the preparation of compounds of formula I wherein $R_6$ is amino, in a 5-azidocarboxylic acid derivative of formula V

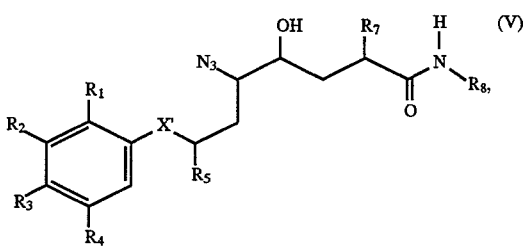

wherein $R_1$, $R_2$, $R_3$, $R_4$, $R_5$, $R_7$ and $R_8$ are as defined for formula I, X' is methylene or free or esterified or etherified hydroxymethyl, and free functional groups are present, if desired, in protected form, or in a salt thereof, reducing the azido group to amino, if desired with the freeing of hydroxymethyl X or the reduction of X' to methylene X, and removing any protecting groups present, and, if desired, converting a compound of formula I having at least one salt-forming group obtainable by one of the above-mentioned processes a) to c) into its salt, or converting an obtainable salt into the free compound or into a different salt and/or separating mixtures of isomers that may be obtainable and/or converting a compound of formula I according to the invention into a different compound of formula I according to the invention.

Functional groups in starting materials the reaction of which is to be avoided, especially carboxy, amino, hydroxy and mercapto groups, can be protected by suitable protecting groups (conventional protecting groups) which are customarily used in the synthesis of peptide compounds, and also in the synthesis of cephalosporins and penicillins as well as nucleic acid derivatives and sugars. Those protecting groups may already be present in the precursors and are intended to protect the functional groups in question against undesired secondary reactions, such as acylation, etherification, esterification, oxidation, solvolysis, etc. In certain cases the protecting groups can additionally cause the reactions to proceed selectively, for example stereoselectively. It is characteristic of protecting groups that they can be removed easily, i.e. without undesired secondary reactions taking place, for example by solvolysis, reduction, photolysis, and also enzymatically, for example under physiological conditions. Protecting groups may also be present in the end products, however. Compounds of formula I having protected functional groups may have greater metabolic stability or pharmacodynamic properties that are better in some other way than the corresponding compounds having free functional groups.

The protection of functional groups by such protecting groups, the protecting groups themselves and the reactions for their removal are described, for example, in standard works such as J. F. W. McOmie, "Protective Groups in Organic Chemistry", Plenum Press, London and New York 1973, in Th. W. Greene, "Protective Groups in Organic Synthesis", Wiley, New York 1981, in "The Peptides", Volume 3 (E. Gross and J. Meienhofer, eds.), Academic Press, London and New York 1981, in "Methoden der organischen Chemie", Houben-Weyl, 4th edition, Volume 15/I, Georg Thieme Verlag, Stuttgart 1974, in H.-D. Jakubke and H. Jescheit, "Aminosäuren, Peptide, Proteine" ("Amino acids, peptides, proteins"), Verlag Chemie, Weinheim, Deerfield Beach and Basle 1982, and in Jochen Lehmann, "Chemie der Kohlenhydrate: Monosaccharide und Derivate" ("The Chemistry of Carbohydrates: monosaccharides and derivatives"), Georg Thieme Verlag, Stuttgart 1974.

Process Variant a)(Formation of the Amide Bond):

Amino-protecting groups $X_1$ are, for example, acyl groups other than lower alkanoyl, also arylmethyl, lower alkylthio, 2-acyl-lower alk-1-enyl or silyl. The group $X_1$-N ($X_2$)- can also be in the form of an azido group.

Acyl groups other than lower alkanoyl are, for example, halo-lower alkanoyl, for example 2-haloacetyl, such as 2-chloro-, 2-bromo-, 2-iodo-, 2,2,2-trifluoro- or 2,2,2-trichloro-acetyl, unsubstituted or substituted, for example halo-, lower alkoxy- or nitro-substituted, benzoyl, for example benzoyl, 4-chlorobenzoyl, 4-methoxybenzoyl or 4-nitrobenzoyl, or lower alkoxycarbonyl that is branched in the 1-position of the lower alkyl radical or suitably substituted in the 1- or 2-position, for example tertiary lower alkoxycarbonyl, such as tert-butoxycarbonyl, arylmethoxycarbonyl having one or two aryl radicals which are phenyl that is unsubstituted or mono- or poly-substituted, for example, by lower alkyl, for example tertiary lower alkyl, such as tertiary butyl, lower alkoxy, such as methoxy, hydroxy, halogen, such as chlorine, and/or by nitro, for example benzyloxycarbonyl, unsubstituted or substituted benzyloxycarbonyl, such as 4-nitrobenzyloxycarbonyl, diphenylmethoxycarbonyl, fluorenylmethoxycarbonyl or substituted diphenylmethoxycarbonyl, such as di(4-methoxyphenyl)methoxycarbonyl, aroylmethoxycarbonyl wherein the aroyl group is preferably benzoyl that is unsubstituted or substituted, for example, by halogen, such as bromine, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, 2-(trisubstituted silyl)-lower alkoxycarbonyl, for example 2-trilower alkylsilyl-lower alkoxycarbonyl, for example 2-trimethylsilylethoxycarbonyl or 2-(di-n-butyl-methylsilyl)-ethoxycarbonyl, or triarylsilyl-lower alkoxycarbonyl, for example 2-triphenylsilylethoxycarbonyl.

In a 2-acyl-lower alk-1-enyl radical that can be used as an amino-protecting group, acyl is, for example, the corresponding radical of a lower alkanecarboxylic acid, of a benzoic acid that is unsubstituted or substituted, for example, by lower alkyl, such as methyl or tertiary butyl, lower alkoxy, such as methoxy, halogen, such as chlorine, and/or by nitro, or especially of a carbonic acid semiester, such as a carbonic acid lower alkyl semiester. Corresponding protecting groups are especially 1-lower alkanoyl-prop- 1-en-2-yl, for example 1-acetyl-prop-1-en-2-yl, or lower alkoxycarbonyl-prop-1-en-2-yl, for example 1-ethoxycarbonyl-prop-1-en-2-yl.

A silylamino group is, for example, a tri-lower alkylsilylamino group, for example trimethylsilylamino. The silicon atom of the silylamino group can also be substituted by only two lower alkyl groups, for example methyl groups, and by the amino group or carboxy group of a second molecule of formula I. Compounds having such protecting groups can be prepared, for example, using dimethylchlorosilane as silylating agent.

An amino group can also be protected by conversion into the protonated form; suitable corresponding anions are especially those of strong inorganic acids, such as sulfuric acid, phosphoric acid or hydrohalic acids, for example the chlorine or bromine anion, or of organic sulfonic acids, such as p- toluenesulfonic acid.

Preferred amino-protecting groups $X_1$ are acyl radicals of carbonic acid semiesters, such as lower alkoxycarbonyl, especially tert-butyloxycarbonyl or fluorenylmethoxycarbonyl, unsubstituted or lower alkyl-, lower alkoxy-, nitro- and/or halo-substituted α-phenyl- or α,α-diphenyl-lower alkoxycarbonyl, such as benzyloxycarbonyl, p-nitrobenzyloxycarbonyl or diphenylmethoxycarbonyl, or 2-halo-lower alkoxycarbonyl, e.g. 2,2,2-trichloroethoxycarbonyl, also trityl or formyl.

Hydroxy-protecting groups $X_3$ are, for example, acyl groups, for example lower alkanoyl that is substituted by halogen, such as chlorine, for example 2,2-dichloroacetyl, or especially acyl radicals of a carbonic acid semiester mentioned for protected amino groups. A preferred hydroxy-protecting group is, for example, 2,2,2-trichloroethoxycarbonyl, 4-nitrobenzyloxycarbonyl, diphenylmethoxycarbonyl or trityl. A further suitable hydroxy-protecting group $X_3$ is tri-lower alkylsilyl, for example trimethylsilyl, triisopropylsilyl or dimethyl-tert-butylsilyl, a readily removable etherifying group, for example an alkyl group, such as tertiary lower alkyl, for example tertiary butyl, an oxa- or a thiaaliphatic or -cycloaliphatic, especially 2-oxa- or 2-thiaaliphatic or -cycloaliphatic, hydrocarbon radical, for example 1-lower alkoxy-lower alkyl or 1-lower alkylthio-lower alkyl, for example methoxymethyl, 1-methoxyethyl, 1-ethoxyethyl, methylthiomethyl, 1-methylthioethyl or 1-ethylthioethyl, or 2-oxa- or 2-thia-cycloalkyl having from 5 to 7 ring atoms, for example 2-tetrahydrofuryl or 2-tetrahydropyranyl, or a corresponding thia analogue, and also 1-phenyl-lower alkyl, for example benzyl, diphenylmethyl or trityl, wherein the phenyl radicals can be substituted, for example, by halogen, for example chlorine, lower alkoxy, for example methoxy, and/or by nitro.

Bivalent protecting groups formed by $X_2$ and $X_3$ together are, for example, methylene groups substituted by one or two alkyl radicals and are accordingly unsubstituted or substituted alkylidene, such as lower alkylidene, for example isopropylidene, cycloalkylidene, such as cyclohexylidene, also carbonyl or benzylidene.

If $X_4$ is reactively etherified or esterified hydroxy, the terminal group —(=O)—$X_4$ is a reactively functionally modified carboxylic acid function and is, for example, in the form of an activated ester or anhydride. The reactive acid derivatives can also be formed in situ.

Such activated esters of compounds of formula II are especially esters unsaturated at the linking carbon atom of the esterifying radical, for example of the vinyl ester type, such as vinyl esters (obtainable, for example, by transesterification of a corresponding ester with vinyl acetate; activated vinyl ester method), carbamoyl esters (obtainable, for example, by treatment of the corresponding acid with an isoxazolium reagent; 1,2-oxazolium or Woodward method), or 1-lower alkoxyvinyl esters (obtainable, for example, by treatment of the corresponding acid with a lower alkoxyacetylene; ethoxyacetylene method), or esters of the amidino type, such as N,N'-disubstituted amidino esters (obtainable, for example, by treatment of the corresponding acid with a suitable N,N'-disubstituted carbodiimide, for example N,N'-dicyclohexylcarbodiimide; carbodiimide method), or N,N-disubstituted amidino esters (obtainable, for example, by treatment of the corresponding acid with an N,N-disubstituted cyanamide; cyanamide method), suitable aryl esters, especially phenyl esters suitably substituted by electron-attracting substituents (obtainable, for example, by treatment of the corresponding acid with a suitably substituted phenol, for example 4-nitrophenol, 4-methylsulfonylphenol, 2,4,5-trichlorophenol, 2,3,4,5,6-pentachlorophenol or 4-phenyldiazophenol, in the presence of a condensation agent, such as N,N'-dicyclohexylcarbodiimide; activated aryl esters method), cyanomethyl esters (obtainable, for example, by treatment of the corresponding acid with chloroacetonitrile in the presence of a base; cyanomethyl esters method), thioesters, especially unsubstituted or substituted, for example nitro-substituted, phenylthio esters (obtainable, for example, by treatment of the corresponding acid with unsubstituted or substituted, for example nitro-substituted, thiophenols, inter alia by the anhydride or carbodiimide method; activated thiol esters method), or especially amino or amido esters (obtainable, for example, by treatment of the corresponding acid with an N-hydroxyamino or N-hydroxyamido compound, for example N-hydroxysuccinimide, N-hydroxypiperidine, N-hydroxyphthalimide, N-hydroxy-5-norbornene-2,3-dicarboxylic acid imide, 1-hydroxybenzotriazole or 3-hydroxy-3,4-dihydro-1,2,3-benzotriazin-4-one, for example by the anhydride or carbodiimide method; activated N-hydroxy esters method). Internal esters, for example γ-lactones, can also be used.

Anhydrides of acids of formula II may be symmetric or preferably mixed anhydrides of those acids, for example anhydrides with inorganic acids, such as acid halides, especially acid chlorides (obtainable, for example, by treatment of the corresponding acid with thionyl chloride, phosphorus pentachloride or oxalyl chloride; acid chloride method), azides (obtainable, for example, from a corresponding acid ester via the corresponding hydrazide and treatment thereof with nitrous acid; azide method), anhydrides with carbonic acid semiesters, for example carbonic acid lower alkyl semiesters (obtainable, for example, by treatment of the corresponding acid with chloroformic acid lower alkyl esters or with a 1-lower alkoxycarbonyl-2-lower alkoxy-1,2-dihydroquinoline; mixed O-alkylcarbonic acid anhydrides method), or anhydrides with dihalogenated, especially dichlorinated, phosphoric acid (obtainable, for example, by treatment of the corresponding acid with phosphorus oxychloride; phosphorus oxychloride method), anhydrides with other phosphoric acid derivatives (for example those obtainable with phenyl-N-phenylphosphoramidochloridate) or with phosphorous acid derivatives, or anhydrides with organic acids, such as mixed anhydrides with organic carboxylic acids (obtainable, for example, by treatment of the corresponding acid with an unsubstituted or substituted lower alkane- or phenyl-lower alkane-carboxylic acid halide, for example phenylacetic acid chloride, pivalic acid chloride or trifluoroacetic acid chloride; mixed carboxylic acid anhydrides method) or with organic sulfonic acids (obtainable, for example, by treatment of a salt, such as an alkali metal salt, of the corresponding acid with a suitable organic sulfonic acid halide, such as a lower alkane- or aryl-, for example methane- or p- toluene-sulfonic acid chloride; mixed sulfonic acid anhydrides method) and symmetric anhydrides (obtainable, for example, by condensation of the corresponding acid in the presence of a carbodiimide or 1-diethylaminopropyne; symmetric anhydrides method).

Preferred starting materials of formula II are compounds of formulae IIa, IIb and IIc

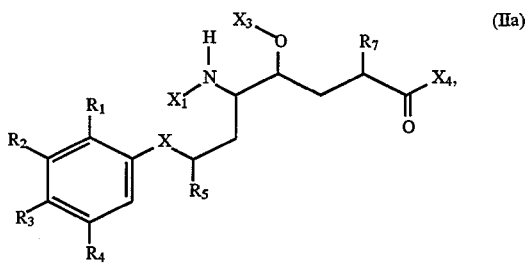

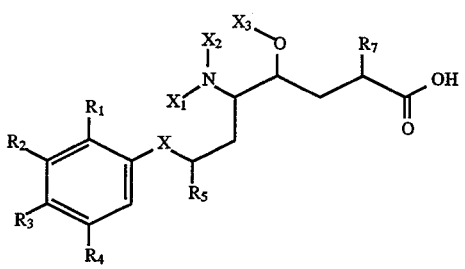

and

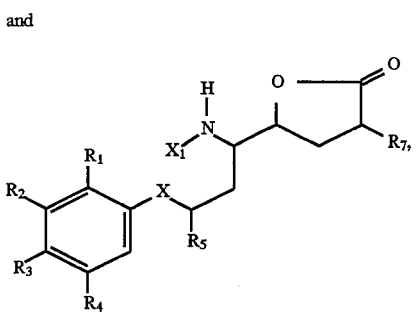

wherein $X_1$ is an amino-protecting group, especially tert-butyloxycarbonyl, $X_2$ together with $X_3$ is a bivalent protecting group, especially lower alkylidene, such as isopropylidene, and $X_3$ in formula IIa is hydrogen or tri-lower alkylsilyl, especially tert-butyl(dimethyl)silyl, or in formula IIb, together with $X_2$, is a bivalent protecting group, especially lower alkylidene, such as isopropylidene, and $X_4$ is hydroxy, lower alkoxy or halogen, such as chlorine.

As mentioned, derivatives of carboxylic acids that are used as acylating agents may also be formed in situ. For example, N,N'-disubstituted amidino esters may be formed in situ by reacting a mixture of the acid used as acylating agent and the starting material of formula III in the presence of a suitable N,N'-disubstituted carbodiimide, for example N,N'-cyclohexylcarbodiimide. In addition, amino or amido esters of the acids used as acylating agents may be formed in the presence of the starting material of formula III to be acylated, by reacting a mixture of the corresponding acid and amino starting materials in the presence of an N,N'-disubstituted carbodiimide, for example N,N'-dicyclohexylcarbodiimide, and of an N-hydroxyamine or N-hydroxyamide, for example N-hydroxysuccinimide, where appropriate in the presence of a suitable base, for example 4-dimethylamino-pyridine.

The condensation to form an amide bond can be carried out in a manner known per se, for example as described in standard works, such as Houben-Weyl, "Methoden der organischen Chemie", 4th edition, Volume 15/II (1974), Volume IX (1955), Volume E 11 (1985), Georg Thieme Verlag, Stuttgart, "The Peptides" (E. Gross and J. Meienhofer, eds.), Volumes 1 and 2, Academic Press, London and New York, 1979/1980, or M. Bodansky, "Principles of Peptide Synthesis", Springer-Verlag, Berlin 1984.

The condensation of a free carboxylic acid with the corresponding amine can be carried out preferably in the presence of one of the customary condensation agents. Customary condensation agents are, for example, carbodiimides, for example diethyl-, dipropyl-,N-ethyl-N'-(3-dimethylaminopropyl)-carbodiimide or especially dicyclohexylcarbodiimide, also suitable carbonyl compounds, for example carbonyldiimidazole, 1,2-oxazolium compounds, for example 2-ethyl-5-phenyl-1,2-oxazolium-3'-sulfonate and 2-tert-butyl-5-methylisoxazolium perchlorate, or a suitable acylamino compound, for example 2-ethoxy-1-ethoxycarbonyl-1,2-dihydroquinoline, also activated phosphoric acid derivatives, for example diphenylphosphoryl azide, diethylphosphoryl cyanide, phenyl-N-phenylphosphoroamidochloridate, bis(2-oxo-3-oxazolidinyl)phosphinic acid chloride or 1-benzotriazolyloxy-tris(dimethylamino)phosphonium hexafluorophosphate.

If desired, an organic base may be added, for example a tri-lower alkylamine having bulky radicals, for example ethyldiisopropylamine, and/or a heterocyclic base, for example pyridine, N-methylmorpholine or preferably 4-dimethylaminopyridine.

The condensation of activated esters, reactive anhydrides or reactive cyclic amides with the corresponding amines is customarily carried out in the presence of an organic base, for example simple tri-lower alkylamines, for example triethylamine or tributylamine, or one of the above-mentioned organic bases. If desired, a condensation agent may additionally be used, for example as described for free carboxylic acids.

The condensation of acid anhydrides with amines can be effected, for example, in the presence of inorganic carbonates, for example ammonium or alkali metal carbonates or hydrogen carbonates, such as sodium or potassium carbonate or hydrogen carbonate (usually together with a sulfate).

Carboxylic acid chlorides, for example the chlorocarbonic acid derivatives derived from the acid of formula II, are condensed with the corresponding amines preferably in the presence of an organic amine, for example the above-mentioned tri-lower alkylamines or heterocyclic bases, where appropriate in the presence of a hydrogen sulfate.

The condensation is preferably carried out in an inert, aprotic, preferably anhydrous, solvent or solvent mixture, for example in a carboxylic acid amide, for example formamide or dimethylformamide, a halogenated hydrocarbon, for example methylene chloride, carbon tetrachloride or chlorobenzene, a ketone, for example acetone, a cyclic ether, for example tetrahydrofuran, an ester, for example ethyl acetate, or a nitrile, for example acetonitrile, or in a mixture thereof, as appropriate at reduced or elevated temperature, for example in a temperature range of from approximately −40° C. to approximately +100° C., preferably from approximately −10° C. to approximately +50° C., and in the case where arylsulfonyl esters are used also at approximately from +100° C. to +200° C., and without an inert gas or under an inert gas atmosphere, for example a nitrogen or argon atmosphere.

Aqueous, for example alcoholic, solvents, for example ethanol, or aromatic solvents, for example benzene or toluene, may also be used. When alkali metal hydroxides are present as bases, acetone can also be added where appropriate.

The condensation can also be carried out in accordance with the technique known as solid-phase synthesis which originates from R. Merrifield and is described, for example, in Angew. Chem. 97, 801–812 (1985), Naturwissenschaften 71, 252–258 (1984) or in R. A. Houghten, Proc. Natl. Acad. Sci. USA 82, 5131–5135 (1985).

A preferred variant of that process is carried out by reacting, as the activated ester, an internal ester (γ-lactone) derived from the carboxylic acid of formula I and having the formula IIc

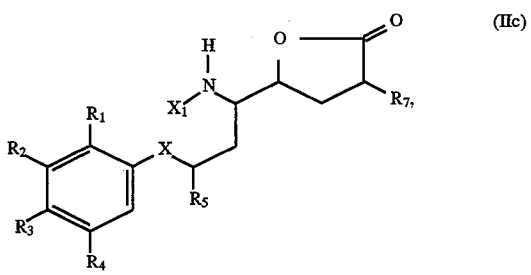

wherein X is methylene, with the compound of formula III, free functional groups present in the reactants, with the exception of the groups participating in the reaction, being if desired, as stated above, in protected form and any protecting groups being removed as described above. The opening of the lactone ring with the formation of the amide bond is carried out under the conditions described above, optionally in the presence of a suitable catalyst. In particular, a γ-lactone IIc may be reacted with a primary amine III without a solvent or in the presence of a polar solvent, for example a lower alcohol, such as methanol or ethanol, a polar ether, such as tetrahydrofuran or dioxane, a nitrile, such as acetonitrile, an amide, such as dimethylformamide, N,N-dimethylacetamide, N-methylpyrrolidone or hexamethylphosphoric acid triamide, a urea, for example N,N'-dimethyl-N,N'-propylenylurea, a lower alkoxy-lower alkanol, for example diethylene glycol monomethyl ether, in dimethyl sulfoxide or in a mixture of the mentioned solvents or in a mixture of one or more of the mentioned solvents with water, at temperatures of from room temperature to 150° C., preferably approximately from 20° C. to 100° C., and in the presence of a catalyst, such as 2-hydroxypyridine and/or triethylamine, the comments made above applying in respect of the protecting groups.

In another preferred variant of that process the starting material used is a compound of formula IIb wherein X is methylene, which is reacted with the reactant of formula III in the presence of a cyanophosphonic acid diester, for example cyanophosphonic acid diethyl ester, and a tertiary organic amine, such as a tri-lower alkylamine, for example trimethylamine, and in a polar solvent, for example a nitrile, such as acetonitrile, an amide, such as dimethylformamide, N,N-dimethylacetamide, N-methylpyrrolidone or hexamethylphosphoric acid triamide, a urea, for example N,N'-dimethyl-N,N'-propylenylurea, a lower alkoxy-lower alkanol, for example diethylene glycol monomethyl ether, in dimethyl sulfoxide or in a mixture of the mentioned solvents or in a mixture of one or more of the mentioned solvents with water, at temperatures of from −30° C. to 100° C., preferably from 20° C. to 80° C., the comments made above applying in respect of the protecting groups.

Starting materials of formula II can be prepared, for example, by reacting a compound of formula VI

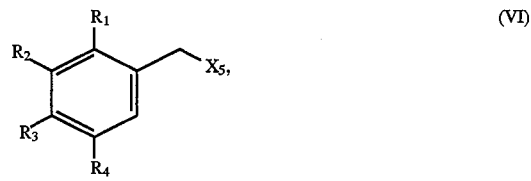

wherein $X_5$ is free or reactively esterified hydroxy, especially halogen, such as bromine, with a compound of formula VII

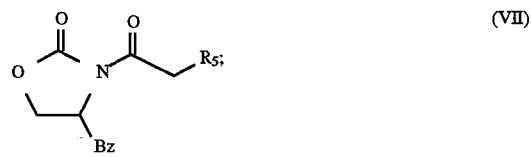

in the resulting compound of formula VIII

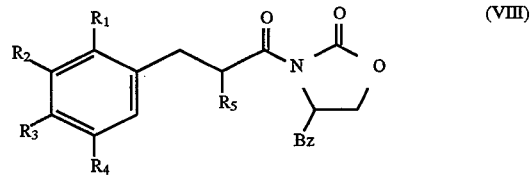

hydrolysing the 4-benzyl-2-oxo-oxazolidin-1-ylcarbonyl group selectively to carboxy, for example by means of lithium hydroxide/hydrogen peroxide; reducing the carboxy group to hydroxymethyl, for example by means of sodium borohydride/iodine in tetrahydrofuran; halogenating the hydroxymethyl group, for example with N-bromosuccinimide/triphenylphosphine in dichloromethane, and reacting the reaction product of formula IX

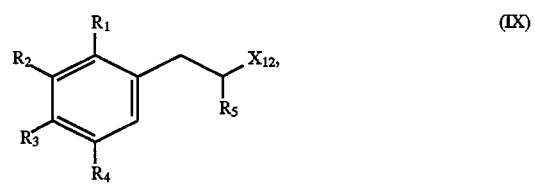

wherein $X_{12}$ is halomethyl, with a compound of formula X

wherein $R_{10}$ and $R_{11}$ are identical or different lower alkoxy groups; hydrolysing the resulting compound of formula XI

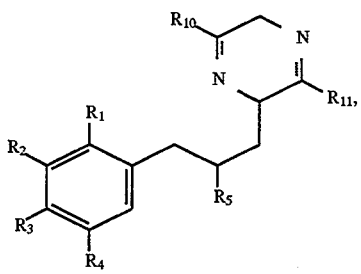

wherein $R_1$, $R_2$, $R_3$, $R_4$ and $R_5$ are as defined above and $R_{10}$ and $R_{11}$ are identical or different lower alkoxy groups; protecting the resulting compound of formula XII

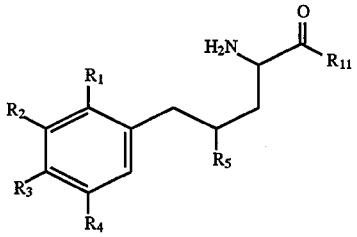

at the amino group by an amino-protecting group $X_1$ and, if desired, reacting the resulting compound of formula XIII

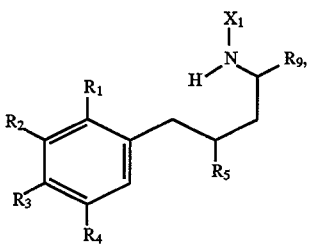

wherein $R_9$ is formyl, with a compound of formula XIV

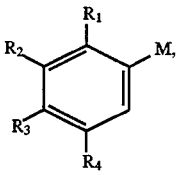

wherein M is a metallic, especially an alkaline earth metallic, radical, for example a group of the formula Mg-Hal (Hal=halogen, especially bromine), in customary manner, for example in an ethereal solvent, such as tetrahydrofuran, with cooling, for example in a temperature range of approximately from −80° to 0°; if desired temporarily protecting the resulting compound of formula XV

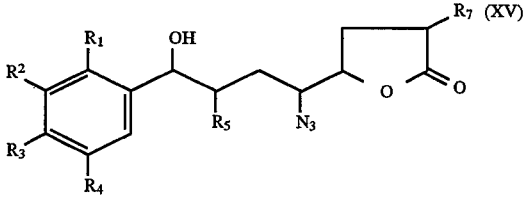

at the hydroxy group, for example by reaction with a lower alkanoic acid anhydride, especially isobutyric acid anhydride, in the presence of dimethylaminopyridine in dichloromethane; in the resulting compound of formula XVI

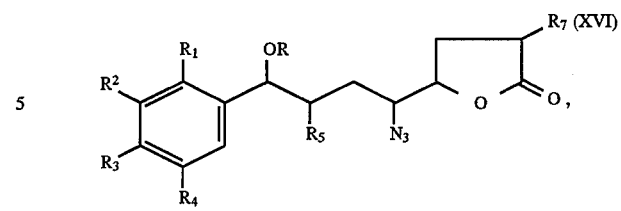

wherein R is hydrogen or a hydroxy-protecting group, such as especially isobutyryl, reducing the azido group to amino, for example by catalytic hydrogenation using palladium-on-carbon, it being possible, if desired, for the group —OR to be replaced reductively by hydrogen, and optionally introducing the protecting group $X_1$.

For the preparation of compounds of formula IIa, a compound of formula IIc can be hydrolysed in customary manner with the lactone ring being opened, for example by treatment with lithium hydroxide in a water-containing solvent, for example in DME/water, optionally the hydroxy-protecting group $X_3$ can be introduced and, if desired, the terminal carboxy group can be reactively modified.

Starting materials of formula IIb are obtained, for example, by reacting a compound of formula XIII wherein $R_9$ is formyl with a compound of formula XVII

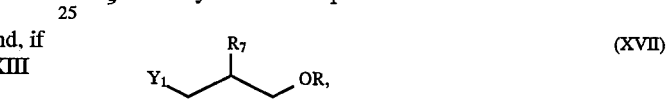

wherein $Y_1$ is a metallic, especially an alkaline earth metallic, radical, for example of the formula -MgHal wherein Hal is bromine, chlorine or iodine, and OR is etherified hydroxy, such as unsubstituted or substituted benzyloxy, to form the corresponding compound of formula XVIII

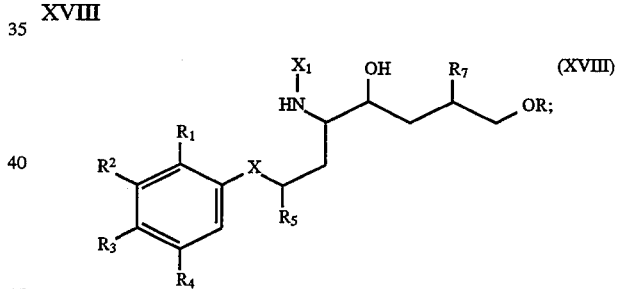

protecting that compound at the amino and hydroxy groups, for example by a bivalent protecting group -$X_2$-$X_3$-, Such as lower alkylidene, especially isopropylidene; in the compound of formula XIX thus protected

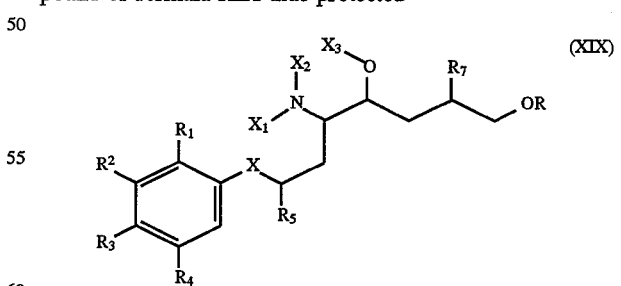

freeing the terminal hydroxy group reductively and converting the terminal hydroxymethyl group into formyl, for example by treatment with N-methylmorpholine-N-oxide and tetrabutylmmonium perruthenate in chloroform, and oxidising the resulting aldehyde to the acid in customary manner, for example by treatment with potassium permanganate, or oxidising the resulting terminal alcohol directly to the acid by suitable measures, for example by treatment with sodium iodate/ruthenium chloride, and in each case, if desired, reactively modifying the carboxy function.

Process Variant b) (Reduction of Lower alkylidene or aryl-lower alkylidene R'₇ to Lower alkyl or aryl-lower alkyl R₇).

In a starting material of formula IV, functional groups that are not to participate in the reaction are protected by suitable protecting groups mentioned under a).

Hydrogenation agents suitable for the hydrogenation of the olefinic double bond are those which under the reaction conditions of the process reduce the double bond selectively or more rapidly than the amide bonds present in compounds of formula IV.

Especially suitable are hydrogenation agents such as hydrogen in the presence of suitable catalysts.

Catalysts suitable for hydrogenation are metals, for example nickel, iron, cobalt or ruthenium, or noble metals or their oxides, such as palladium or rhodium or their oxides, optionally supported on a suitable carrier, such as barium sulfate, aluminium oxide or active carbon, or in the form of skeleton catalysts, for example Raney nickel, but especially homogeneous or heterogeneous metal- or noble metal-ligand complexes, more especially those which produce the configuration at the carbon atom carrying the group R₄ desired in each particular case.

Such catalysts are especially complexes of ruthenium or ruthenium salts, such as Ru(II) halides, such as RuCl₂, Ru₂Cl₂ or RuHCl, optionally halogenated Ru(II) lower alkanoylates, such as Ru(OAc)₂ or Ru(OOC—CF₃)₂, with (S)-bis(2,2'-diphenylphosphino)-1,1'-bi-naphthyl (S-BINAP) or derivatives thereof which contain instead of phenyl substituted phenyl radicals, such as p-tolyl or p-methoxyphenyl, and also ruthenium complexes with (S)-bis(2,2'-diphenylphosphino)-5,5'-dimethyl-diphenyl and the like. Hydrogenation with complexes of that type is preferably carried out in alcohols, such as lower alkanols, or alkyl halides, such as methylene chloride, in a pressure range of approximately from 1 to 100 bar, preferably from 20 to 30 bar, and in a temperature range of approximately from 10° to 80° C., preferably from 15° to 25° C.

Other solvents customarily used for catalytic hydrogenation are polar organic or inorganic solvents, for example water, alcohols, esters, dioxane, glacial acetic acid or mixtures of those solvents. The hydrogenation is carried out at temperatures of from 0° C. to 250° C., preferably from room temperature to about 100° C. and at hydrogen pressures of from 1 to 200 bar. Hydrogenation methods will be found, for example, in "Organikum, organischchemisches Grundpraktikum", 17th revised edition, VEB Deutscher Verlag der Wissenschaften, Berlin 1988.

Carboxylic acid amides of formula IV are obtained, for example, by condensing an aldehyde of formula XIII

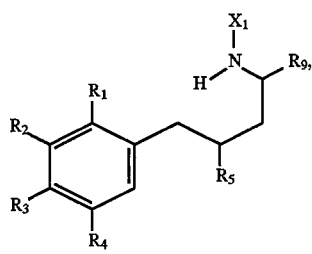

wherein R₉ is formyl, in customary manner with a suitable metallated amide compound, for example obtainable by reaction of a compound of formula XX

with butyllithium and chlorotitanium triisopropyl oxide.

Process Variant c) (Reduction of the Azido Group):

In stating materials of formula V, functional groups that are not to participate in the reaction are protected by one of the protecting groups mentioned under Process a).

Reducing agents suitable for the reduction of the azido group are those which under the reaction conditions of the process reduce an optionally functionalised hydroxy group or azido group selectively or more rapidly than the amide groups present in compounds of formula I.

The reduction is preferably carried out with hydrogen in the presence of suitable heavy metal catalysts, for example Raney nickel or platinum or palladium catalysts, for example platinum or palladium on active carbon.

Intermediates of formula V can be prepared, for example, by reacting E-1,4-dibromobut-2-ene first with a compound of formula VII

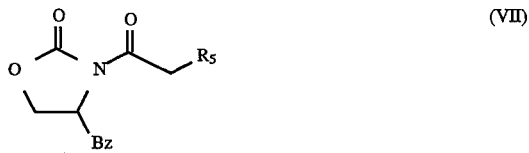

and then with a compound of formula XXI

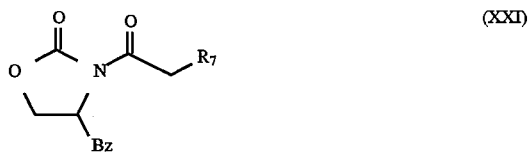

to form the corresponding compound of formula XXII

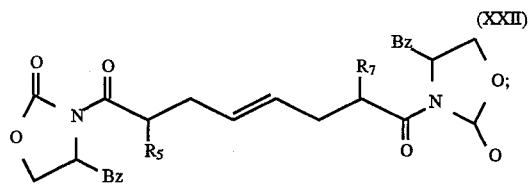

converting that compound, for example by treatment with a customary halogenating agent, such as elemental halogen, especially bromine or iodine, or preferably with an N-halo-succinimide, especially N-bromosuccinimide, in 1,2-dimethoxyethane (DME), into the corresponding compound of formula XXIII

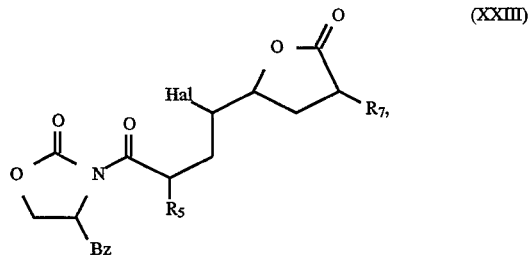

wherein Hal is halogen; separating the desired isomer in respect of R₅ and R₇ and in that isomer replacing the halogen atom by azido, for example by treatment with tetrabenzylammonium azide in toluene, and in the resulting compound of formula XXIV

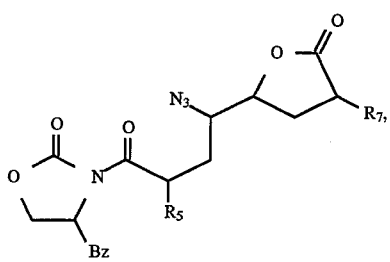
(XXIV)

wherein $R_5$ and $R_7$ are as defined above and Bz is benzyl, hydrolysing the 4-benzyl-2-oxo-oxazolidin-1-ylcarbonyl group selectively to carboxy, for example by treatment with an alkali metal hydroxide in the presence of a basic hydrolysing agent, especially lithium hydroxide in the presence of hydrogen peroxide; re-closing, using an acid catalyst, a lactone ring which may have been opened; in the resulting compound of formula XXV

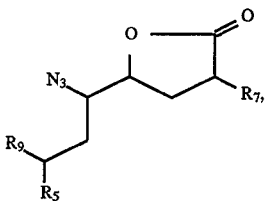
(XXV)

wherein $R_9$ is carboxy, converting the carboxy group into formyl, for example by conversion into the acid chloride by means of oxalyl chloride and subsequent reduction of the chlorocarbonyl group, for example with sodium tri-tert-butyloxyaluminium hydride in tetrahydrofuran; reacting the resulting compound of formula XXV wherein $R_9$ is then formyl with a compound of formula XIV

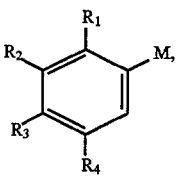
(XIV)

wherein M is a metallic, especially an alkaline earth metallic, radical, for example a group of the formula Mg-Hal (Hal=halogen, especially bromine), in customary manner, for example in an ethereal solvent, such as tetrahydrofuran, with cooling, for example in a temperature range of approximately from −80° to 0° C.; if desired etherifying or, especially, esterifying the resulting compound of formula XV

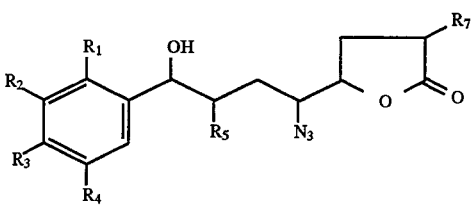
(XV)

at the hydroxy group, for example temporarily protecting the hydroxy group by reaction with a lower alkanoic acid anhydride, especially isobutyric acid anhydride, in the presence of dimethylaminopyridine in dichloromethane; reacting the resulting compound of formula XVI

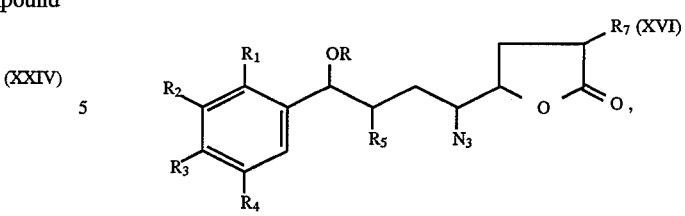
(XVI)

wherein the group —OR is a free or esterified or etherified hydroxy group, with R preferably being a hydroxy-protecting group, such as especially isobutyryl, in customary manner, for example as indicated under Process variant a), with an amine of formula III $$H_2N-R_8 \quad (III),$$

wherein $R_8$ has one of the meanings given under formula I, and, if desired, freeing hydroxymethyl from the group —OR or replacing the group —OR reductively by hydrogen.

The removal of protecting groups that are not constituents of the desired end product of formula I, for example carboxy-, amino-, hydroxy- and/or mercapto-protecting groups, which may be carried out subsequent to the process variants described above, is effected in a manner known per se, for example by means of solvolysis, especially hydrolysis, alcoholysis or acidolysis, or by means of reduction, especially hydrogenolysis or chemical reduction, as well as photolysis, as appropriate stepwise or simultaneously, it being possible also to use enzymatic methods. The removal of the protecting groups is described, for example, in the standard works mentioned hereinabove in the section relating to protecting groups.

For example, protected carboxy, for example tertiary lower alkoxycarbonyl, lower alkoxycarbonyl substituted in the 2-position by a trisubstituted silyl group or in the 1-position by lower alkoxy or by lower alkylthio, or unsubstituted or substituted diphenylmethoxycarbonyl can be converted into free carboxy by treatment with a suitable acid, such as formic acid or trifluoroacetic acid, where appropriate with the addition of a nucleophilic compound, such as phenol or anisole. Unsubstituted or substituted benzyloxycarbonyl can be freed, for example, by means of hydrogenolysis, i.e. by treatment with hydrogen in the presence of a metal hydrogenation catalyst, such as a palladium catalyst. In addition, suitably substituted benzyloxycarbonyl, such as 4-nitrobenzyloxycarbonyl, can be converted into free carboxy also by reduction, for example by treatment with an alkali metal dithionite, such as sodium dithionite, or with a reducing metal, for example zinc, or a reducing metal salt, such as a chromium(II) salt, for example chromium(II) chloride, customarily in the presence of a hydrogen-yielding agent that, together with the metal, is capable of producing nascent hydrogen, such as an acid, especially a suitable carboxylic acid, such as an unsubstituted or substituted, for example hydroxy-substituted, lower alkanecarboxylic acid, for example acetic acid, formic acid, glycolic acid, diphenylglycolic acid, lactic acid, mandelic acid, 4-chloromandelic acid or tartaric acid, or in the presence of an alcohol or thiol, water preferably being added. By treatment with a reducing metal or metal salt, as described above, 2-halo-lower alkoxycarbonyl (where appropriate after conversion of a 2-bromo-lower alkoxycarbonyl group into a corresponding 2-iodo-lower alkoxycarbonyl group) or aroylmethoxycarbonyl can also be converted into free carboxy. Aroylmethoxycarbonyl can be cleaved also by treatment with a nucleophilic, preferably salt-forming, reagent, such as sodium thiophenolate or sodium iodide. 2-(Tri-substituted silyl)-lower alkoxycarbonyl, such as 2-tri-lower alkylsilyl-lower alkoxycarbonyl, can be converted into free carboxy also by treatment with a salt of hydrofluoric acid that yields the fluoride anion, such as an alkali metal fluoride, for example sodium or potassium fluoride, where appropriate in the presence of a macrocyclic polyether ("crown ether"), or with a fluoride of an organic quaternary base, such as tetra-lower alkylammonium fluoride or tri-lower alkylarylammonium fluoride, for example tetraethylammonium fluoride or tetrabutylammonium fluoride, in the presence of an aprotic, polar solvent, such as dimethyl sulfoxide or N,N-dimethylacetamide. Carboxy protected in the form of organic silyloxycarbonyl, such as tri-lower alkylsilyloxycarbonyl, for example trimethylsilyloxycarbonyl, can be freed in customary manner by solvolysis, for example by treatment with water, an alcohol or an acid, or, furthermore, a fluoride, as described above. Esterified carboxy can also be freed enzymatically, for example by means of esterases or suitable peptidases.

A protected amino group is freed in a manner known per se and, according to the nature of the protecting groups, in various ways, preferably by solvolysis or reduction. 2-Halo-lower alkoxycarbonylamino (where appropriate after conversion of a 2-bromo-lower alkoxycarbonylamino group into a 2-iodo-lower alkoxycarbonylamino group), aroylmethoxycarbonylamino or 4-nitrobenzyloxycarbonylamino can be cleaved, for example, by treatment with a suitable reducing agent, such as zinc in the presence of a suitable carboxylic acid, such as aqueous acetic acid. Aroylmethoxycarbonylamino can be cleaved also by treatment with a nucleophilic, preferably salt-forming, reagent, such as sodium thiophenolate, and 4-nitrobenzyloxycarbonylamino also by treatment with an alkali metal tert-lower dithionite, for example sodium dithionite. Unsubstituted or substituted diphenylmethoxycarbonylamino, alkoxycarbonylamino or 2-(tri-substituted silyl)-lower alkoxycarbonylamino, such as 2-tri-lower alkylsilyl-lower alkoxycarbonylamino, can be cleaved by treatment with a suitable acid, for example formic or trifluoroacetic acid; unsubstituted or substituted benzyloxycarbonylamino can be cleaved, for example, by means of hydrogenolysis, i.e. by treatment with hydrogen in the presence of a suitable hydrogenation catalyst, such as a palladium catalyst; unsubstituted or substituted triarylmethylamino or formylamino can be cleaved, for example, by treatment with an acid, such as a mineral acid, for example hydrochloric acid, or an organic acid, for example formic, acetic or trifluoroacetic acid, where appropriate in the presence of water; and an amino group protected in the form of silylamino can be freed, for example, by means of hydrolysis or alcoholysis. An amino group protected by 2-haloacetyl, for example 2-chloroacetyl, can be freed by treatment with thiourea in the presence of a base, or with a thiolate salt, such as an alkali metal thiolate of thiourea, and subsequent solvolysis, such as alcoholysis or hydrolysis, of the resulting condensation product. An amino group protected by 2-(tri-substituted silyl)-lower alkoxycarbonyl, such as 2-tri-lower alkylsilyl-lower alkoxycarbonyl, can be converted into the free amino group also by treatment with a salt of hydrofluoric acid that yields fluoride anions, as indicated above in connection with the freeing of a correspondingly protected carboxy group. Likewise, silyl, such as trimethylsilyl, bonded directly to a hetero atom, such as nitrogen, can be removed using fluoride ions.

Amino protected in the form of an azido group is converted into free amino, for example, by reduction, for example by catalytic hydrogenation with hydrogen in the presence of a hydrogenation catalyst, such as platinum oxide, palladium or Raney nickel, by reduction using mercapto compounds, such as dithiothreitol or mercaptoethanol, or by treatment with zinc in the presence of an acid, such as acetic acid. The catalytic hydrogenation is preferably carried out in an inert solvent, such as a halogenated hydrocarbon, for example methylene chloride, or in water or in a mixture of water and an organic solvent, such as an alcohol or dioxane, at approximately from 20° C. to 25° C., or with cooling or heating.

A hydroxy or mercapto group protected by a suitable acyl group, by a tri-lower alkylsilyl group or by unsubstituted or substituted 1-phenyl-lower alkyl is freed analogously to a correspondingly protected amino group. A hydroxy or mercapto group protected by 2,2-dichloroacetyl is freed, for example, by basic hydrolysis, and a hydroxy or mercapto group protected by tertiary lower alkyl or by a 2-oxa- or 2-thia-aliphatic or -cycloaliphatic hydrocarbon radical is removed by acidolysis, for example by treatment with a mineral acid or a strong carboxylic acid, for example trifluoroacetic acid. Mercapto protected by pyridyldiphenylmethyl can be freed, for example, using mercury(II) salts at pH 2–6 or by zinc/acetic acid or by electrolytic reduction; acetamidomethyl and isobutyrylamidomethyl can be removed, for example, by reaction with mercury(II) salts at pH 2–6; 2-chloroacetamidomethyl can be removed, for example, using 1-piperidinothiocarboxamide; and S-ethylthio, S-tert-butylthio and S-sulfo can be cleaved, for example, by thiolysis with thiophenol, thioglycolic acid, sodium thiophenolate or 1,4-dithiothreitol. Two hydroxy groups or an adjacent amino and hydroxy group which are protected together by means of a bivalent protecting group, preferably, for example, by a methylene group mono- or di-substituted by lower alkyl, such as lower alkylidene, for example isopropylidene, cycloalkylidene, for example cyclohexylidene, or benzylidene, can be freed by acid solvolysis, especially in the presence of a mineral acid or a strong organic acid. 2-Halo-lower alkoxycarbonyl is also removed using the above-mentioned reducing agents, for example a reducing metal, such as zinc, reducing metal salts, such as chromium(II) salts, or using sulfur compounds, for example sodium dithionite or preferably sodium sulfide and carbon disulfide.

When several protected functional groups are present, if desired the protecting groups may be so selected that more than one such group can be removed simultaneously, for example by acidolysis, such as by treatment with trifluoroacetic acid, or with hydrogen and a hydrogenation catalyst, such as a palladium-on-carbon catalyst. Conversely, the groups may also be so selected that they are not all removed simultaneously, but rather they are removed in a desired sequence or only some of them are removed.

In each of the processes mentioned above, the starting compounds may also be used in the form of salts, provided that the reaction conditions allow it.

Compounds of formula I obtainable in accordance with the process can be converted into different compounds of formula I in customary manner.

For example, in a compound of formula I obtainable in accordance with the process, hydroxymethyl X can be reduced reductively to methylene, for example by catalytic hydrogenation in the presence of palladium-on-carbon.

Futhermore, in a compound of formula I obtainable in accordance with the process, a carboxy group in free or reactive form may be esterified or amidated or an esterified or amidated carboxy group may be converted into a free carboxy group.

For the esterification or amidation of a carboxy group in a compound of formula I, if desired the free acid can be used or the free acid can be converted into one of the above-mentioned reactive derivatives and reacted with an alcohol, with ammonia, or with a primary or secondary amine, or, in the case of esterification, the free acid or a reactive salt, for example the caesium salt, can be reacted with a reactive derivative of an alcohol. For example the caesium salt of a carboxylic acid can be reacted with a halide or sulfonic acid ester corresponding to the alcohol. The esterification of the carboxy group can also be carried out with other customary alkylating agents, for example with diazomethane, Meerwein salts or 1-substituted 3-aryltriazenes.

For the conversion of an esterified or amidated carboxy group into the free carboxy group it is possible to use one of the methods described above for the removal of carboxy-protecting groups or, if desired, alkaline hydrolysis in accordance with the reaction conditions mentioned in Organikum, 17th edition, VEB Deutscher Verlag der Wissenschaften, Berlin 1988.

In a compound of formula I obtainable in accordance with the process, an esterified carboxy group can be converted into an unsubstituted or substituted carboxamide group by aminolysis with ammonia or with a primary or secondary amine, optionally in the presence of a suitable condensation agent or catalyst. The aminolysis can be carded out in accordance with the reaction conditions mentioned for such reactions in Organikum, 15th edition, VEB Deutscher Verlag der Wissenschaften, Berlin (East) 1976.

A free amino group present in a compound of formula I obtainable in accordance with the process can be acylated or alkylated, for example to introduce a radical $R_6$ other than hydrogen. The acylation and the alkylation can be carried out in accordance with one of the methods mentioned for protecting groups or according to one of the processes mentioned in Organikum, 17th edition, VEB Deutscher Verlag der Wissenschaften, Berlin (East) 1988.

Furthermore, a free hydroxy group present in a compound of formula I obtainable in accordance with the process, for example as a constituent of the radical $R_8$, can be acylated. The acylation can be carried out with acylating reagents in accordance with one of the methods mentioned for protecting groups or according to one of the processes mentioned in Organikum, 17th edition, VEB Deutscher Verlag der Wissenschaften, Berlin (East) 1988.

In a compound of formula I obtainable in accordance with the process it is also possible to obtain from a sulfide the corresponding sulfoxide or sulfone, that is to say to oxidise a thio group to a sulfinyl or sulfonyl group or a sulfinyl group to sulfonyl, and also to oxidise thiomorpholino to S-oxy- or S,S-dioxy-thiomorpholino.

The oxidation to the sulfone can be carried out with most of the customary oxidising agents. It is especially preferable to use oxidising agents that oxidise the thio group or the sulfide sulfur selectively in the presence of other functional groups, for example amino or hydroxy groups, of the compound of formula I in question, for example aromatic or aliphatic peroxycarboxylic acids, for example peroxybenzoic acid, monoperphthalic acid, m-chloroperbenzoic acid, peracetic acid, performic acid or trifluoroperacetic acid. The oxidation with peroxycarboxylic acids is carried out in suitable solvents customarily used for that purpose, for example chlorinated hydrocarbons, for example methylene chloride or chloroform, ethers, such as diethyl ether, esters, such as ethyl acetate or the like, at temperatures of from −78° C. to room temperature, for example from −20° C. to +10° C., preferably about 0° C. The peroxycarboxylic acid can also be formed in situ, for example with hydrogen peroxide in acetic acid or formic acid that optionally contains acetic anhydride, for example with 30% or 90% hydrogen peroxide in acetic acid/acetic anhydride. Other peroxo compounds are also suitable, for example potassium peroxomonosulfate in lower alkanol/water mixtures, for example methanol/water or ethanol/water, or in aqueous acetic acid at temperatures of from −70° C. to +30° C., for example from −20° C. to room temperature, and also sodium metaperiodate in methanol or methanol/water mixtures at temperatures of from 0° C. to 50° C., for example about room temperature. If stoichiometric amounts of the mentioned oxidising agents are used it is also possible to obtain the corresponding sulfoxides.

If desired, it is possible by reduction of a sulfonyl group or a sulfone radical in an obtainable compound of formula I to obtain the corresponding thio compound or the corresponding sulfide, for example with diisobutylaluminium hydride in ether or tetrahydrofuran.

In compounds of formula I it is also possible to replace hydroxy $R_1$, $R_2$, $R_3$ and/or $R_4$ by one of the etherified hydroxy groups mentioned under formula I by reacting the corresponding compound of formula I wherein $R_1$, $R_2$, $R_3$ and/or $R_4$ is hydroxy in customary manner, for example in the presence of a basic condensation agent, with a compound of the formula(e) $R'_1$-Y, $R'_2$-Y, $R'_3$-Y and/or $R'_4$-Y wherein $R'_1$ is lower alkyl or free or esterified or amidated carboxy-lower alkyl, $R'_2$ is lower alkyl, lower alkoxy-lower alkyl, lower alkoxy-lower alkoxy-lower alkyl, cycloalkoxy-lower alkyl, optionally lower alkanoylated, halogenated or sulfonylated hydroxy-lower alkyl, oxo-lower alkyl, lower alkyl, lower alkenyl, cycloalkoxy-lower alkyl, lower alkoxy-lower alkyl, lower alkoxy-lower alkenyl, lower alkenyloxy-lower alkyl, lower alkenyloxy-lower alkyl, lower alkenyloxy-lower alkyl, lower alkanoyl-lower alkyl, optionally S-oxidised lower alkyl-thio-lower alkyl, lower alkylthio-(hydroxy)-lower alkyl, aryl-lower alkyl, optionally hydrogenated heteroaryl-lower alkyl, optionally hydrogenated heteroarylthio-lower alkyl, cyano-lower alkyl or free or esterified or amidated carboxy-lower alkyl, $R'_3$ is lower alkyl, lower alkoxy-lower alkyl, hydroxy-lower alkyl, aryl-lower alkyl, halogenated lower alkyl, cyano-lower alkyl or free or esterified or amidated carboxy-lower alkyl, and $R'_4$ is lower alkyl, and Y is reactive esterified hydroxy, especially hydroxy esterified by a mineral acid, by sulfuric acid or by an organic sulfonic acid, such as halogen, preferably chlorine, bromine or iodine, groups of the formula O—SO$_2$—O—R'$_A$, or lower alkanesulfonyloxy or unsubstituted or substituted benzenesulfonyloxy, especially methane-, ethane-, benzene-, p-toluene- or p-bromobenzene-sulfonyl. The reaction is, as mentioned, preferably carried out in the presence of a basic condensation agent, such as an alkali metal carbonate, for example potassium carbonate, in an inert solvent, such as a lower alkanol, such as methanol, ethanol, butanol, tert-butanol or especially amyl alcohol, advantageously at elevated temperature, for example in a temperature range of approximately from 40° to 140° C., if necessary with removal of the resulting water of reaction by distillation, for example by azeotropic distillation.

It is also possible for salts of compounds of formula I obtainable in accordance with the process to be converted in a manner known per se into the free compounds, for example by treatment with a base, such as an alkali metal hydroxide, a metal carbonate or metal hydrogen carbonate, or ammonia, or another of the salt-forming bases mentioned at the beginning, or with an acid, such as a mineral acid, for example with hydrochloric acid, or another of the salt-forming acids mentioned at the beginning.

Resulting salts can be converted into different salts in a manner known per se: acid addition salts, for example, by treatment with a suitable metal salt, such as a sodium, barium or silver salt, of a different acid in a suitable solvent in which an inorganic salt being formed is insoluble and is therefore eliminated from the reaction equilibrium, and basic salts by freeing of the free acid and conversion into a salt again.

The compounds of formula I, including their salts, may also be obtained in the form of hydrates or may include the solvent used for crystallisation.

As a result of the close relationship between the novel compounds in free form and in the form of their salts, hereinabove and hereinbelow any reference to the free compounds and their salts is to be understood as including also the corresponding salts and free compounds, respectively, as appropriate and expedient.

Stereoisomeric mixtures, that is to say mixtures of diastereoisomers and/or enantiomers, such as, for example, racemic mixtures, can be separated into the corresponding isomers in a manner known per se by suitable separating processes. For example, mixtures of diastereoisomers can be separated into the individual diastereoisomers by fractional crystallisation, chromatography, solvent partition etc. Racemates can be separated from one another, after conversion of the optical antipodes into diastereoisomers, for example by reaction with optically active compounds, for example optically active acids or bases, by chromatography on column materials charged with optically active compounds or by enzymatic methods, for example by selective reaction of only one of the two enantiomers. This separation can be carried out either at the stage of one of the starting materials or with the compounds of formula I themselves.

In a compound of formula I the configuration at individual chirality centres can be selectively reversed. For example, the configuration of asymmetric carbon atoms that carry nucleophilic substituents, such as amino or hydroxy, can be reversed by second order nucleophilic substitution, optionally after conversion of the bonded nucleophilic substituent into a suitable nucleofugal leaving group and reaction with a reagent introducing the original substituent, or the configuration at carbon atoms having hydroxy groups can be reversed by oxidation and reduction, analogously to European Patent Application EP-A-0 236 734.

Also advantageous is the reactive functional modification of the hydroxy group and the subsequent replacement thereof by hydroxy with the configuration being reversed. For that purpose, the amino and hydroxy groups shown in formula I are bridged by a bivalent group, especially carbonyl, there being obtained a compound of formula XXVI

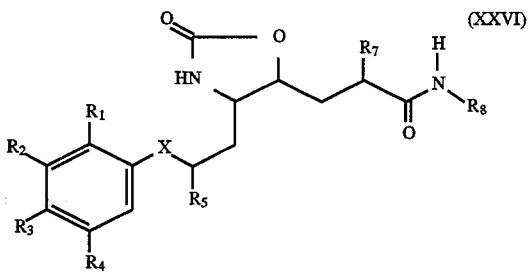

which can be cleaved again by treatment with thionyl chloride with the configuration being reversed.

The invention relates also to those forms of the process in which a compound obtainable as intermediate at any stage is used as starting material and the remaining steps are carried out or the process is interrupted at any stage or a starting material is formed under the reaction conditions or is used in the form of a reactive derivative or salt, or a compound obtainable in accordance with the process of the invention is formed under the process conditions and further processed in situ. It is preferable to use those starting materials which result in the compounds described above as being very preferred or very especially preferred.

The invention relates also to novel starting materials, which have been developed specifically for the preparation of the compounds according to the invention, especially the group of starting materials resulting in the compounds of formula I described at the beginning as being preferred, to processes for their preparation and to their use as intermediates.

This relates to compounds of formula II which, as mentioned, are suitable as intermediates for the preparation of compounds of formula I.

The invention relates accordingly also to compounds of formula II

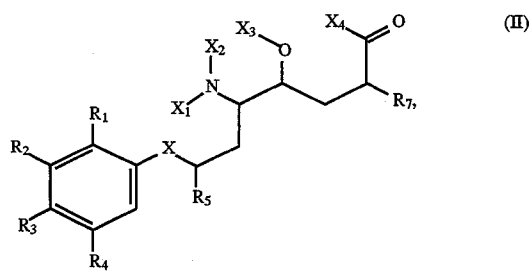

wherein $R_1$ is hydrogen, hydroxy, lower alkoxy, cycloalkoxy, lower alkoxy-lower alkoxy or free or esterified or amidated carboxy-lower alkoxy, $R_2$ is hydrogen, lower alkyl, cycloalkyl, lower alkoxy-lower alkyl, lower alkoxy-lower alkoxy-lower alkyl, cycloalkoxy-lower alkyl, hydroxy, optionally lower alkanoylated, halogenated or sulfonylated hydroxy-lower alkoxy; amino-lower alkyl that is unsubstituted or substituted by lower alkyl-, by lower alkanoyl- and/or by lower alkoxycarbonyl; amino-lower alkoxy that is substituted by lower alkyl, by lower alkanoyl and/or by lower alkoxycarbonyl; oxo-lower alkoxy, lower alkoxy, cycloalkoxy, lower alkenyloxy, cycloalkoxy-lower alkoxy, lower alkoxy-lower alkoxy, lower alkoxy-lower alkenyl, lower alkenyloxy-lower alkoxy, lower alkoxy-lower alkoxy, lower alkenyloxy-lower alkyl, lower alkanoyl-lower alkoxy, optionally S-oxidised lower alkylthio-lower alkoxy, lower alkylthio-(hydroxy)-lower alkoxy, aryl-lower alkoxy, cyano-lower alkoxy, free or esterified or amidated carboxy-lower alkoxy or free or esterified or amidated carboxy-lower alkyl, $R_3$ is optionally halogenated lower alkyl, lower alkoxy-lower alkyl, cycloalkoxy-lower alkyl, hydroxy-lower alkyl, optionally S-oxidised lower alkylthio-lower alkyl, optionally hydrogenated heteroaryl-lower alkyl, optionally hydrogenated heteroarylthio-lower alkyl; amino-lower alkyl that is unsubstituted or N-mono- or N,N-di-lower alkylated, N-lower alkanoylated or N-lower alkanesulfonylated or N,N-disubstituted by lower alkylene, by unsubstituted or N'-lower alkylated or N'-lower alkanoylated aza-lower alkylene, by oxa-lower alkylene or by optionally S-oxidised thia-lower alkylene; cyano-lower alkyl, free or esterified or amidated carboxy-lower alkyl, cycloalkyl, aryl, hydroxy, lower alkoxy, cycloalkoxy, lower alkoxy-lower alkoxy, cycloalkoxy-lower alkoxy, hydroxy-lower alkoxy, aryl-lower alkoxy, optionally halogenated lower alkoxy, optionally S-oxidised lower alkylthio-lower alkoxy, optionally hydrogenated heteroaryl-lower alkoxy, optionally hydrogenated heteroaryl-thio-lower alkoxy; amino-lower alkoxy that is unsubstituted or N-mono- or N,N-di-lower alkylated, N-lower alkanoylated or N-lower alkanesulfonylated or substituted by lower alkylene, by unsubstituted or N'-lower alkylated or N'-lower alkanoylated aza-lower alkylene, by oxa-lower alkylene or by optionally S-oxidised thia-lower alkylene; cyano-lower alkoxy or free or esterified or amidated carboxy-lower alkoxy, or together with $R_4$ is lower alkylenedioxy or a fused-on benzo or cyclohexeno ring, $R_4$ together with $R_3$ is lower alkylenedioxy or a fused-on benzo or cyclohexeno ring, or is hydrogen, hydroxy or lower alkoxy, X is methylene or hydroxymethylene, $R_5$ is lower alkyl or cycloalkyl, $R_7$ is lower alkyl or aryl-lower alkyl, $X_1$ is an amino-protecting group, $X_2$ is hydrogen or together with $X_3$ is a bivalent protecting group, $X_3$ is hydrogen, a hydroxy-protecting group or together with $X_2$ is a bivalent protecting group or together with $X_4$ is a direct bond, and $X_4$ is free or reactively etherified or esterified hydroxy or together with $X_3$ is a direct bond, and to the salts thereof, to processes for the preparation thereof and to the use thereof as intermediates for the preparation of medicinal active ingredients, especially of formula I.

In the compounds of formula II prepared according to the invention the variables $R_1$, $R_2$, $R_3$, $R_4$, X, $R_5$ and $R_7$ are preferably as defined for formula I, and the variables $X_1$, $X_2$, $X_3$ and $X_4$ are preferably as defined for formula II.

The invention relates especially to compounds of formula II wherein $R_1$ is hydrogen, hydroxy, lower alkoxy, cycloalkoxy, lower alkoxy-lower alkoxy, carboxy-lower alkoxy, lower alkoxycarbonyl-lower alkoxy, carbamoyl-lower alkoxy or N-mono- or N,N-di-lower alkylcarbamoyl-lower alkoxy, $R_2$ is hydrogen, lower alkyl, cycloalkyl, lower alkoxy-lower alkyl, lower alkoxy-lower alkoxy-lower alkyl, cycloalkoxy-lower alkyl, hydroxy, lower alkanoyloxy-lower alkyl, hydroxy-lower alkoxy, halo-(hydroxy)-lower alkoxy, lower alkanesulfonyl-(hydroxy)-lower alkoxy, amino-lower alkyl, lower alkylamino-lower alkyl, di-lower alkylamino-lower alkyl, lower alkanoylamino-lower alkyl, lower alkoxycarbonyl-amino-lower alkyl, amino-lower alkoxy, lower alkylamino-lower alkoxy, di-lower alkylamino-lower alkoxy, lower alkanoylamino-lower alkoxy, lower alkoxycarbonyl-amino-lower alkoxy, oxo-lower alkoxy, lower alkoxy, cycloalkoxy, lower alkenyloxy, cycloalkoxy-lower alkoxy, lower alkoxy-lower alkoxy, lower alkoxy-lower alkenyl, lower alkenyloxy-lower alkoxy, lower alkoxy-lower alkoxy, lower alkenyloxy-lower alkyl, lower alkanoyl-lower alkoxy, lower alkylthio-lower alkoxy, lower alkanesulfonyl-lower alkoxy, lower alkylthio-(hydroxy)-lower alkoxy, aryl-lower alkoxy, thiazolylthio-lower alkoxy or thiazolinylthio-lower alkoxy, imidazolylthio-lower alkoxy, optionally N-oxidised pyridylthio-lower alkoxy, pyrimidinylthio-lower alkoxy, cyano-lower alkoxy, lower alkoxycarbonyl-lower alkoxy, casbamoyl-lower alkoxy, N-mono- or N,N-di-lower alkylcarbamoyl-lower alkoxy, carboxy-lower alkyl, lower alkoxycarbonyl-lower alkyl, carbamoyl-lower alkyl or N-mono- or N,N-di-lower alkylcarbamoyl-lower alkyl, $R_3$ is lower alkyl, polyhalo-lower alkyl, lower alkoxy-lower alkyl, cycloalkoxy-lower alkyl, hydroxy-lower alkyl, lower alkylthio-lower alkyl, lower alkanesulfonyl-lower alkyl, optionally partially hydrogenated or N-oxidised pyridyl-lower alkyl, thiazolylthio-lower alkyl or thiazolinylthio-lower alkyl, imidazolylthio-lower alkyl, optionally N-oxidised pyridylthio-lower alkyl, pyrimidinylthio-lower alkyl, amino-lower alkyl, lower alkylamino-lower alkyl, di-lower alkylamino-lower alkyl, lower alkanoylamino-lower alkyl, lower alkanesulfonylamino-lower alkyl, polyhalo-lower alkanesulfonylamino-lower alkyl, pyrrolidino-lower alkyl, piperidino-lower alkyl, piperazino-, N'-lower alkylpiperazino- or N'-lower alkanoylpiperazino-lower alkyl, morpholino-lower alkyl, thiomorpholino-, S-oxothiomorpholino- or S,S-dioxothiomorpholino-lower alkyl, cyano-lower alkyl, carboxy-lower alkyl, lower alkoxycarbonyl-lower alkyl, carbamoyl-lower alkyl, N-mono- or N,N-di-lower alkylcarbamoyl-lower alkyl, cycloalkyl; phenyl or naphthyl that is unsubstituted or mono-, di- or tri-substituted by lower alkyl, lower alkoxy, hydroxy, lower alkylamino, di-lower alkylamino, halogen and/or by trifluoromethyl; hydroxy, lower alkoxy, cycloalkoxy, lower alkoxy-lower alkoxy, cycloalkoxy-lower alkoxy, hydroxy-lower alkoxy; phenyl-lower alkoxy or naphthyl-lower alkoxy that is unsubstituted or mono-, di- or tri-substituted by lower alkyl, lower alkoxy, hydroxy, lower alkylamino, di-lower alkylamino, halogen and/or by trifluoromethyl; lower alkoxy, polyhalo-lower alkoxy, lower alkylthio-lower alkoxy, lower alkanesulfonyl-lower alkoxy, optionally hydrogenated heteroaryl-lower alkoxy, optionally partially or fully hydrogenated heteroarylthio-lower alkoxy, such as thiazolylthio-lower alkoxy or thiazolinylthio-lower alkoxy, imidazolylthio-lower alkoxy, optionally N-oxidised pyridylthio-lower alkoxy, pyrimidinylthio-lower alkoxy, amino-lower alkoxy, lower alkylamino-lower alkoxy, all-lower alkylamino-lower alkoxy, lower alkanoylamino-lower alkoxy, lower alkanesulfonylamino-lower alkoxy, polyhalo-lower alkanesulfonylamino-lower alkoxy, pyrrolidino-lower alkoxy, piperidino-lower alkoxy, piperazino-, N'-lower alkylpiperazino- or N'-lower alkanoylpiperazino-lower alkoxy, morpholino-lower alkoxy, thiomorpholino-, S-oxothiomorpholino- or S,S-dioxothiomorpholino-lower alkoxy, cyano-lower alkoxy, carboxy-lower alkoxy, lower alkoxycarbonyl-lower alkoxy, carbamoyl-lower alkoxy or N-mono- or N,N-di-lower alkylcarbamoyl-lower alkoxy, or together with $R_4$ is lower alkylenedioxy or a fused-on benzo or cyclohexeno ring, $R_4$ together with $R_3$ is lower alkylenedioxy or a fused-on benzo or cyclohexeno ring, or is hydrogen, hydroxy or lower alkoxy, X is methylene or hydroxymethylene, $R_5$ is lower alkyl or cycloalkyl, $R_7$ is lower alkyl, or phenyl-lower alkyl that is unsubstituted or substituted by lower alkyl, lower alkoxy, hydroxy, halogen, nitro and/or by amino, $X_1$ is lower alkoxycarbonyl, or α-phenyl- or α,α-diphenyl-lower alkoxycarbonyl that is unsubstituted or substituted by lower alkyl, lower alkoxy, nitro and/or by halogen, or is 2-halo-lower alkoxycarbonyl, $X_2$ is hydrogen or together with $X_3$ is carbonyl or lower alkylidene, $X_3$ is hydrogen, tri-lower alkylsilyl or together with $X_2$ is carbonyl or lower alkylidene or together with $X_4$ is a direct bond, and $X_4$ is lower alkoxy, phenyl-lower alkoxy or hydroxy or together with $X_3$ is a direct bond, and the salts thereof, The invention relates more especially to compounds of formula II wherein $R_1$ is hydrogen, $R_2$ is lower alkyl, lower alkoxy-lower alkyl, lower alkoxy-lower alkoxy, lower alkoxy-lower alkoxy-lower alkyl; phenyl-lower alkoxy that is unsubstituted or substituted by lower alkyl, lower alkoxy, hydroxy, halogen, nitro and/or by amino; optionally N-oxidised pyridyl-lower alkoxy, lower alkylthio-lower alkoxy, lower alkanesulfonyl-lower alkoxy, lower alkanoyl-lower alkoxy, optionally N-oxidised pyridyl-lower alkoxy, cyano-lower alkoxy, carboxy-lower alkoxy, lower alkoxycarbonyl-lower alkoxy, carbamoyl-lower alkoxy, lower alkylcarbamoyl-lower alkoxy or di-lower alkylcarbamoyl-lower alkoxy, $R_3$ is hydrogen, lower alkyl, hydroxy, lower alkoxy or polyhalo-lower alkoxy or together with $R_4$ is lower alkylenedioxy, X is methylene or hydroxymethylene, $R_5$ is lower alkyl or cycloalkyl, $R_7$ is lower alkyl, $X_1$ is lower alkoxycarbonyl, or α-phenyl-lower alkoxycarbonyl that is unsubstituted or substituted by lower alkyl, lower alkoxy, nitro and/or by halogen, $X_2$ is hydrogen or together with $X_3$ is lower alkylidene, $X_3$ is hydrogen or together with $X_2$ is lower alkylidene or together with $X_4$ is a direct bond, and $X_4$ is hydroxy or together with $X_3$ is a direct bond, and the salts thereof.

The invention relates especially to compounds of formula II wherein at least one, for example one, two or preferably all, of the asymmetric carbon atoms of the main chain have the stereochemical configuration shown in formula IId

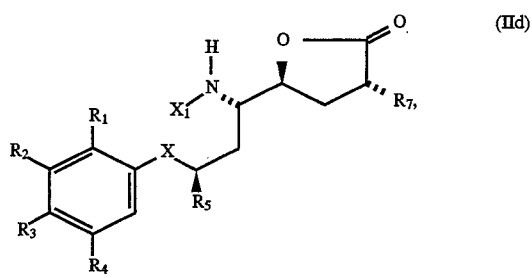

the variables each being as defined above, and the salts thereof.

The invention relates very especially to compounds of formula IId wherein $R_1$ and $R_4$ are hydrogen, $R_2$ is $C_1-C_4$alkoxy-$C_1-C_4$alkoxy, such as 3-methoxypropyloxy, or $C_1-C_4$alkoxy-$C_1-C_4$-alkyl, such as 3-methoxybutyl, $R_3$ is $C_1-C_4$alkyl, such as isopropyl or tert-butyl, or $C_1-C_4$alkoxy, such as methoxy, X is methylene, $R_5$ and $R_7$ are branched $C_1-C_4$alkyl, such as isopropyl, and $X_1$ is $C_1-C_7$alkoxycarbonyl, such as tert-butoxycarbonyl, and the salts thereof.

The invention relates specifically to the compounds of formulae II and IId mentioned in the Examples and the salts thereof.

The process according to the invention for the preparation of compounds of formula II is as follows:

d) for the preparation of compounds of formula IIc, in a compound of formula XVI

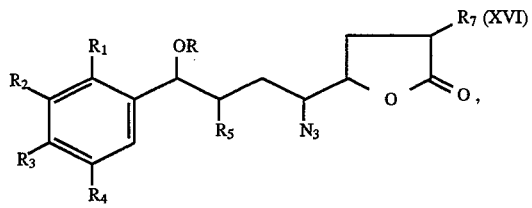

wherein

R is a hydroxy-protecting group, the azido group is reduced to amino and, if desired, hydroxy is freed from the group —OR or the group —OR is replaced reductively by hydrogen, and the protecting group $X_1$ is introduced, and e) for the preparation of compounds of formula IIa, a compound of formula IIc is hydrolysed in customary manner, the hydroxy-protecting group $X_3$ is introduced and, if desired, the terminal carboxy group is reactively modified, or f) for the preparation of compounds of formula IIb, in a compound of formula XIX

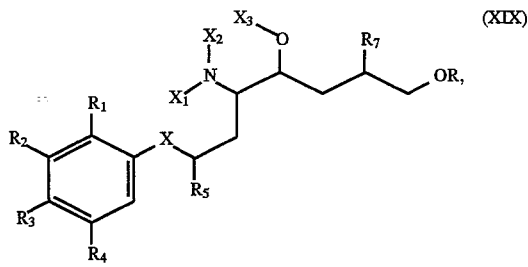

the terminal hydroxy group is freed reductively and the terminal hydroxymethyl group is first converted into formyl in customary manner, for example as indicated under Process variant a), and the formyl group formed is oxidised to the acid in customary manner or the terminal hydroxy group is oxidised directly to the acid, and, if desired, the carboxy function is reactively modified, if necessary any protecting groups present are removed and, if desired, the compound obtainable in accordance with the process is converted into a salt or a salt obtainable in accordance with the process is converted into the free compound or into a different salt and/or mixtures of isomers that may be obtainable are separated.

The starting materials of formulae XVI and XIX are prepared, for example, as indicated under Process variant a).

Compounds of formula II obtainable in accordance with the process can be converted into different compounds of formula II in customary manner.

For example, in a compound of formula II obtainable in accordance with the process, hydroxymethyl X can be reduced reductively to methylene, for example by catalytic hydrogenation in the presence of palladium-on-carbon.

Furthermore, in a compound of formula II obtainable in accordance with the process, a carboxy group in free or reactive form may be esterified or amidated or an esterified or amidated carboxy group may be converted into a free carboxy group.

For the esterification or amidation of a carboxy group in a compound of formula II, if desired the free acid can be used or the free acid can be converted into one of the above-mentioned reactive derivatives and reacted with an alcohol, with ammonia, or with a primary or secondary amine, or in the case of esterification, the free acid or a reactive salt, for example the caesium salt, can be reacted with a reactive derivative of an alcohol. For example the caesium salt of a carboxylic acid can be reacted with a halide or sulfonic acid ester corresponding to the alcohol. The esterification of the carboxy group can also be carried out using other customary alkylating agents, for example with diazomethane, Meerwein salts or 1-substituted 3-aryltriazenes.

For the conversion of an esterified or amidated carboxy group into the free carboxy group it is possible to use one of the methods described above for the removal of carboxy-protecting groups or, if desired, alkaline hydrolysis in accordance with the reaction conditions mentioned in Organikum, 17th edition, VEB Deutscher Verlag der Wissenschaften, Berlin 1988.

In compounds of formula II it is also possible to replace hydroxy $R_1$, $R_2$, $R_3$ and/or $R_4$ by one of the etherified hydroxy groups mentioned under formula II by reacting the corresponding compound of formula II wherein $R_1$, $R_2$, $R_3$ and/or $R_4$ is hydroxy in customary manner, for example in the presence of a basic condensation agent, with a compound of the formula(e) $R'_1$-Y, $R'_2$-Y, $R'_3$-Y and/or $R'_4$-Y wherein $R'_1$ is lower alkyl or free or esterified or amidated carboxy-lower alkyl, $R'_2$ is lower alkyl, lower alkoxy-lower alkyl, lower alkoxy-lower alkoxy-lower alkyl, cycloalkoxy-lower alkyl, optionally lower alkanoylated, halogenated or sulfonylated hydroxy-lower alkyl, oxo-lower alkyl, lower alkyl, lower alkenyl, cycloalkoxy-lower alkyl, lower alkoxy-lower alkyl, lower alkoxy-lower alkenyl, lower alkenyloxy-lower alkyl, lower alkenyloxy-lower alkyl, lower alkenyloxy-lower alkyl, lower alkanoyl-lower alkyl, optionally S-oxidised lower alkylthio-lower alkyl, lower alkylthio-(hydroxy)-lower alkyl, aryl-lower alkyl, optionally hydrogenated heteroaryl-lower alkyl, optionally hydrogenated heteroarylthio-lower alkyl, cyano-lower alkyl or free or esterified or amidated carboxy-lower alkyl, $R'_3$ is lower alkyl, lower alkoxy-lower alkyl, hydroxy-lower alkyl, aryl-lower alkyl, halogenated lower alkyl, cyano-lower alkyl or free or esterified or amidated carboxy-lower alkyl, and $R'_4$, is lower alkyl, and Y is reactive esterified hydroxy, especially hydroxy esterified by a mineral acid, by sulfuric acid or by an organic sulfonic acid, such as halogen, preferably chlorine, bromine or iodine, groups of the formula O—SO$_2$—O—$R'_A$, or lower alkanesulfonyloxy or unsubstituted or substituted benzenesulfonyloxy, especially methane-, ethane-, benzene-, p-toluene- or p-bromobenzene-sulfonyl. The reaction is, as mentioned, preferably carried out in the presence of a basic condensation agent, such as an alkali metal carbonate, for example potassium carbonate, in an inert solvent, such as a lower alkanol, such as methanol, ethanol, butanol, ten-butanol or especially amyl alcohol, advantageously at elevated temperature, for example in a temperature range of approximately from 40° to 140° C., if necessary with removal of the resulting water of reaction by distillation, for example by azeotropic distillation.

It is also possible for salts of compounds of formula II obtainable in accordance with the process to be converted in a manner known per se into the free compounds, for example by treatment with a base, such as an alkali metal hydroxide, a metal carbonate or metal hydrogen carbonate, or ammonia, or another of the salt-forming bases mentioned at the beginning, or with an acid, such as a mineral acid, for example with hydrochloric acid, or another of the salt-forming acids mentioned at the beginning.

Resulting salts can be convened into different salts in a manner known per se: acid addition salts, for example, by treatment with a suitable metal salt, such as a sodium, barium or silver salt, of a different acid in a suitable solvent in which an inorganic salt being formed is insoluble and is therefore eliminated from the reaction equilibrium, and basic salts by freeing of the free acid and conversion into a salt again.

The compounds of formula II, including their salts, may also be obtained in the form of hydrates or may include the solvent used for crystallisation.

As a result of the close relationship between the novel compounds in free form and in the form of their salts, hereinabove and hereinbelow any reference to the free compounds and their salts is to be understood as including also the corresponding salts and free compounds, respectively, as appropriate and expedient.

The invention relates also to pharmaceutical compositions comprising compounds of formula I.

The pharmacologically acceptable compounds of the present invention may be used, for example, in the preparation of pharmaceutical compositions that comprise an effective amount of the active ingredient together or in admixture with a significant amount of inorganic or organic, solid or liquid, pharmaceutically acceptable carders.

The pharmaceutical compositions according to the invention are compositions for enteral, such as nasal, rectal or oral, or parenteral, such as intramuscular or intravenous, administration to warm-blooded animals (human beings and animals) that comprise an effective dose of the pharmacological active ingredient alone or together with a significant amount of a pharmaceutically acceptable carrier. The dose of the active ingredient depends on the species of warm-blooded animal, body weight, age and individual condition, individual pharmacokinetic data, the disease to be treated and the mode of administration.

The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, dragées, tablets or capsules.

The pharmaceutical compositions of the present invention are prepared in a manner known per se, for example by means of conventional dissolving, lyophilising, mixing, granulating or confectioning processes.

Solutions of the active ingredient, and also suspensions, and especially isotonic aqueous solutions or suspensions, are preferably used, it being possible, for example in the case of lyophilised compositions that comprise the active ingredient alone or together with a carrier, for example mannitol, for such solutions or suspensions to be made up prior to use. The pharmaceutical compositions may be sterilised and/or may comprise excipients, for example preservatives, stabilisers, wetting agents and/or emulsifiers, solubilisers, salts for regulating the osmotic pressure and/or buffers, and are prepared in a manner known per se, for example by means of conventional dissolving or lyophilising processes. The said solutions or suspensions may comprise viscosity-increasing substances, such as sodium carboxymethylcellulose, carboxymethylcellulose, dextran, polyvinylpyrrolidone or gelatin.

Suspensions in oil comprise as the oil component the vegetable, synthetic or semi-synthetic oils customary for injection purposes. There may be mentioned as such especially liquid fatty acid esters that contain as the acid component a long-chained fatty acid having from 8 to 22, especially from 12 to 22, carbon atoms, for example lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brassidic acid or linoleic acid, if desired with the addition of antioxidants, for example vitamin E, β-carotene or 3,5-di-tert-butyl-4-hydroxytoluene. The alcohol component of those fatty acid esters has a maximum of 6 carbon atoms and is a mono- or poly-hydric, for example a mono-, di- or tri-hydric, alcohol, for example methanol, ethanol, propanol, butanol or pentanol or the isomers thereof, but especially glycol and glycerol. The following examples of fatty acid esters are therefore to be mentioned: ethyl oleate, isopropyl myristate, isopropyl palmitate, "Labrafil M 2375" (polyoxyethylene glycerol trioleate, Gattefossé, Paris), "Miglyol 812" (triglyceride of saturated fatty acids with a chain length of $C_8$ to $C_{12}$, Chemische Werke Witten/Ruhr, Germany), but especially vegetable oils, such as cottonseed oil, almond oil, olive oil, castor oil, sesame oil, soybean oil and more especially groundnut oil.

The injection compositions are prepared in customary manner under sterile conditions; the same applies also to introducing the compositions into ampoules or vials and sealing the containers.

Pharmaceutical compositions for oral administration can be obtained by combining the active ingredient with solid carders, if desired granulating a resulting mixture, and processing the mixture, if desired or necessary, after the addition of appropriate excipients, into tablets, dragé cores or capsules. They can also be incorporated into plastics carriers that allow the active ingredients to diffuse or be released in measured amounts.

Suitable carders are especially fillers, such as sugars, for example lactose, saccharose, mannitol or sorbitol, cellulose preparations and/or calcium phosphates, for example tricalcium phosphate or calcium hydrogen phosphate, and also binders, such as starch pastes using, for example, corn, wheat, rice or potato starch, gelatin, tragacanth, methylcellulose, hydroxypropylmethylcellulose, sodium carboxymethylcellulose and/or polyvinylpyrrolidone, and/or, if desired, disintegrators, such as the above-mentioned starches, also carboxymethyl starch, crosslinked polyvinylpyrrolidone, agar, alginic acid or a salt thereof, such as sodium alginate. Excipients are especially flow conditioners and lubricants, for example silicic acid, talc, stearic acid or salts thereof, such as magnesium or calcium stearate, and/or polyethylene glycol. Dragée cores are provided with suitable, optionally enteric, coatings, there being used, inter alia, concentrated sugar solutions which may comprise gum arabic, talc, polyvinylpyrrolidone, polyethylene glycol and/or titanium dioxide, or coating solutions in suitable organic solvents, or, for the preparation of enteric coatings, solutions of suitable cellulose preparations, such as ethylcellulose phthalate or hydroxypropylmethylcellulose phthalate. Capsules are dry-filled capsules made of gelatin and also soft, sealed capsules made of gelatin and a plasticiser, such as glycerol or sorbitol. The dry-filled capsules may comprise the active ingredient in the form of granules, for example with fillers, such as lactose, binders, such as starches, and/or glidants, such as talc or magnesium stearate, and if desired with stabilisers. In soft capsules the active ingredient is preferably dissolved or suspended in suitable oily excipients, such as fatty oils, paraffin oil or liquid polyethylene glycols, it likewise being possible for stabilisers and/or antibacterial agents to be added. Dyes or pigments may be added to the tablets or dragée coatings or to the capsule casings, for example for identification purposes or to indicate different doses of active ingredient.

The invention relates also to the use of compounds of formula I in the treatment of disorders responsive to the inhibition of renin, such as those mentioned at the beginning, especially hypertension and/or glaucoma.

The doses to be administered to warm-blooded animals, for example human beings, of, for example, approximately 70 kg body weight, especially the doses effective in the inhibition of the enzyme renin, in lowering blood pressure and/or in improving the symptoms of glaucoma, are from approximately 3 mg to approximately 3 g, preferably from approximately 10 mg to approximately 1 g, for example approximately from 20 mg to 200 mg, per person per day, divided preferably into 1 to 4 single doses which may, for example, be of the same size. Usually, children receive about half of the adult dose. The dose necessary for each individual can be monitored, for example by measuring the serum concentration of the active ingredient, and adjusted to an optimum level.

The following Examples serve to illustrate the invention; temperatures are given in degrees Celsius, pressures in mbar.

| | |
|---|---|
| HPLC - column dimensions: | 250 × 4.6 mm |
| HPLC - column packing: | Nucleosil® 5C$_{18}$ |
| HPLC - eluants: | A) water + 0.1% by vol. trifluoroacetic acid<br>B) acetonitrile + 0.1% by vol. trifluoroacetic acid |
| HPLC - gradient 0: | 20–100% B in 20 minutes + 8 minutes 100% B |
| HPLC - gradient I: | linear in 60 minutes from 30% by vol. B + 70% by vol. A to 90% by vol. B + 10% by vol. A |

The abbreviation "$R_f(A)$" means, for example, that the $R_f$ value was determined in solvent system A. The quantity ratio of solvents to one another is always given in parts by volume.

The same abbreviations are used for indicating the eluant systems for flash chromatography and medium pressure chromatography.

Mass-spectroscopic measurements are obtained either by conventional MS or in accordance with the "Fast-Atom-Bombardment" (FAB-MS) method. In the former case the mass data relate to the unprotonated molecule ion $(M)^+$ or the protonated molecule ion $(M+H)^+$.

The short names and abbreviations used have the following meanings:

| | |
|---|---|
| $C_{18}$-Nucleosil® | brand name for reversed phase column material for HPLC charged with octadecyl radicals (Nucleosil® 5$C_{18}$, Macherey & Nagel, FRG) |
| pFAB-MS | Fast-Atom-Bombardment mass spectroscopy |
| FC | flash chromatography |
| HPLC | high performance liquid chromatography |
| Hyflo® | brand name for filter aids (Fluka, Buchs, Switzerland) |
| IR | infrared spectroscopy |
| b.p. | at the pressure indicated in torr |
| ml | millilitres |
| MS | mass spectroscopy |
| $R_f$ | ratio of the migration of a substance to the distance of the eluant front from the starting point in TLC |
| $R_t$ | retention time of a substance in HPLC (in minutes) |
| m.p. | melting point (temperature). |

EXAMPLE 1

2(R,S)-Methyl-4(S)-hydroxy-5(S)-amino-7(S)-isopropyl-8-(p-tert-butyl-phenyl)-octanoic acid (N-butyl)amide hydrochloride 111 mg of N-tert-butoxycarbonyl-2(R,S)-methyl-4(S)-hydroxy-5(S)-amino-7(S)-iso-propyl-8-(p-tert-butybphenyl)-octanoic acid (N-butyl)amide are dissolved in 2 ml of 4N hydrochloric acid in dioxane at 0° C. and then stirred for 60 minutes at 20° C. The reaction mixture is concentrated by evaporation under reduced pressure and the residue is purified by means of FC (50 g of silica gel, dichloromethane/methanol=9:1). The title compound is obtained in the form of a diastereoisomeric mixture: $R_f$(dichloromethane/methanol=9:1)=0.20; $R_t(I)$=36.6 and 37.5 minutes; FAB-MS $(M+H)^+$=419.

The starting materials are prepared as follows:

a) N-Tert-butoxycarbonyl-2(R,S)-methyl-4(S)-hydroxy-5(S)-amino-7(S)-isopropyl-8-(p-tert-butyl-phenyl)-octanoic acid (N-butyl)amide 150 mg of N-tert-butoxycarbonyl-2-methylene-4(S)-hydroxy-5(S)-amino-7(S)-isopropyl-8-(p-tert-butyl-phenyl)-octanoic acid (N-butyl)amide (diastereoisomer I) are hydrogenated in the presence of 150 mg of 10% Pd/C in 20 ml of tetrahydrofuran for 2 hours at room temperature and under normal pressure. The reaction mixture is filtered and concentrated by evaporation. The residue is purified by means of FC (50 g of silica gel, dichloromethane/diethyl ether=8:2). The title compound is obtained in the form of a diastereoisomeric mixture: $R_f$(dichloromethane/diethyl ether=8:2)=0.18.

b) N-Tert-butoxycarbonyl-2-methylene-4(S)-hydroxy-5(S)-amino-7(S)-isopropyl-8-(p-tert-butyl-phenyl)-octanoic acid (N-butyl)amide 695 mg of methacrylic acid butylamide are dissolved in 30 ml of tetrahydrofuran and, at -75° C., 6.2 ml of 1.6M n-butyllithium in hexane are added thereto. The reaction mixture is stirred for 30 minutes at 0° C. and then, at -75° C., 9.8 ml of 1M chlorotitanium triisopropoxide in hexane are added thereto. The mixture is stirred for a further 15 minutes at -75° C. and then, at the same temperature, a solution of 924 mg of 2(S)-tert-butoxy-carbonyl-amino-4(S)-isopropyl-5-(p-tert-butyl-phenyl)-pentanal in 10 ml of tetrahydrofuran furan is added dropwise thereto. The reaction mixture is then stirred further for 15 minutes at -75° C. and for 70 minutes at 0° C. and then, in succession, 15 ml of 10% aqueous citric acid solution, water and diethyl ether are added thereto. The product is extracted repeatedly with diethyl ether. The diastereoisomeric mixture is separated by FC (700 g of silica gel, eluant: dichloromethane/diethyl ether=9:1). The title compound is obtained: diastereoisomer I: $R_f$(dichloromethane/diethyl ether=9:1)=0.21; diastereoisomer II: $R_f$(dichloromethane/diethyl ether=9:1)=0.14.

c) 2(S)-Tert-butoxycarbonylamino-4(S)-isopropyl-5-(p-tert-butyl-phenyl)-pentanal At -75° C., 4.2 ml of 1.2M diisobutylaluminium hydride solution in toluene are slowly added dropwise to a solution of 1 g of 2(S)-tert-butoxycarbonylamino-4(S)-isopropyl-5-(p-tert-butyl-phenyl)-pentanoic acid methyl ester in 20 ml of toluene. The reaction mixture is then stirred for a further 30 minutes at -70° C., 10 ml of methanol are added, the mixture is poured onto a mixture of ice and 10 ml of 1N hydrochloric acid, and extraction is carried out with ethyl acetate. The title compound is obtained: $R_f$(dichloromethane)=0.35.

d) 2(S)-Tert-butoxycarbonylamino-4(S)-isopropyl-5-(p-tert-butyl-phenyl)-pentanoic acid methyl ester To a solution of 2.6 g of 2(S)-amino-4(S)-isopropyl-5-(p-tert-butyl-phenyl)7pentanoic acid methyl ester in 50 ml of dichloromethane there are added dropwise at 0° C. 2 ml of ethyldiisopropylamine and then a solution of 2.4 g of di-tert-butyl dicarbonate in 10 ml of dichloromethane. The reaction mixture is stirred for 16 hours at room temperature and then concentrated by evaporation. The title compound is obtained by FC (240 g of silica gel, eluant: dichloromethane): $R_f$(dichloromethane)=0.50.

e) 2(S)-Amino-4(S)-isopropyl-5-(p-tert-butyl-phenyl)-pentanoic acid methyl ester With stirring at room temperature, 36 ml of 1N hydrochloric acid are added to a solution of 3.55 g of 2(R)-isopropyl-5(S)-[2(S)-isopropyl-3-(p-tert-butylphenyl)-propyl]-2,5-di-hydro-3,6-dimethoxy-pyrazine in 36 ml of acetonitrile and the mixture is then stirred for a further 3 hours. The reaction solution is then poured onto a mixture of 45 ml of saturated $NaHCO_3$ solution and ice and the suspension is extracted with dichloromethane. The extracts are concentrated by evaporation and purified by FC (700 g of silica gel, eluant: dichloromethane/methanol/$NH_3$=200:10:1), yielding the title compound: $R_f$(dichloromethane/methanol/conc. ammonia=200:10:1)=0.70.

f) 2(R)-Isopropyl-5(S)-[2(S)-isopropyl-3-(p-tert-butylphenyl)-propyl]-2,5-dihydro-3,6-dimethoxypyrazine To a solution of 2.6 ml of 2(R)-2,5-dihydro-3,6-dimethoxy-2-isopropyl-pyrazine in 30 ml of tetrahydrofuran there are added dropwise, with stirring at -70° C., 8.2 ml of 1.6M butyllithium solution in hexane and, after a further 15 minutes' stirring, a solution of 2.8 g of 1-bromo-2(R)-isopropyl-3-(p-tert-butyl-phenyl)-propane in 10 ml of tetrahydrofuran. The reaction mixture is stirred further for 2 hours at -70° C. and for 3 hours at -25° C., is left to stand for 20 hours at -10° C. and is then concentrated by evaporation. Saturated ammonium chloride solution and water are added to the residue and extraction is carried out with diethyl ether. The extracts are concentrated by evaporation and purified by FC (200 g of silica gel, eluant: dichloromethane/hexane=1:1). The title compound is obtained: $R_f$(dichloromethane/hexane=1:1)=0.30.

g) 1-Bromo-2(R)-isopropyl-3-(p-tert-butyl-phenyl)-propane

To a solution of 2.3 g of 2(R)-isopropyl-3-(p-tert-butyl-phenyl)-propanol in 50 ml of dichloromethane there are added, with stirring at 0° C., 3.15 g of triphenylphosphine and then, in portions, 2.14 g of N-bromosuccinimide. The reaction mixture is subsequently stirred for 16 hours at room temperature and is then concentrated by evaporation. The residue is purified by FC (100 g of silica gel, eluant: dichloromethane/hexane=1:1). The title compound is obtained: $R_f$(hexane)=0.49.

h) 2(R)-Isopropyl-3-(p-tert-butyl-phenyl)-propanol

With stirring at 0° C., a solution of 8.63 g of 3-[2(R)-isopropyl-3-(p-tert-butyl-phenyl)-propanoyl]-4(R)-benzyl-oxazolidin-2-one in 40 ml of tetrahydrofuran is added dropwise to a suspension of 2.41 g of LiAlH$_4$ in 160 ml of tetrahydrofuran. The reaction mixture is stirred for a further 4 hours at 0° C. and then, at 0° C., 5 ml of ethyl acetate, 30 ml of a mixture of tetrahydrofuran/water=1:1 and then 80 ml of 2N sulfuric acid are added in succession thereto. The suspension is extracted with ethyl acetate and the extracts are concentrated by evaporation and purified by FC (700 g of silica gel, eluant: dichloromethane). The title compound is obtained: R$_f$(dichloromethane)=0.34; m.p.=49°–51° C.

i) 3-[2(R)-isopropyl-3(p-tert-butyl-phenyl)-propionyl]-4(R)-benzyl-oxazolidin-2-one 30 ml of tetrahydrofuran are added to a solution of 31 ml of 1M lithium hexamethyldisilazide and the mixture is stirred at −70° C. A solution of 3-isovaleroyl-4(R)-benzyloxazolidin-2-one in 20 ml of tetrahydrofuran is then added dropwise thereto and the reaction mixture is stirred for a further 1 hour at −70° C. A solution of 9.6 g of p-tert-butyl-benzyl bromide in 20 ml of tetrahydrofuran is then added dropwise thereto and the reaction mixture is stirred for a further 1 hour at −25° C. and then for 4 hours at 0° C. 6 ml of saturated ammonium chloride solution are then added to the reaction mixture, which is freed of tetrahydrofuran by means of concentration and then subjected to extraction with diethyl ether. The extract is concentrated by evaporation and the residue is purified by FC (700 g of silica gel, eluant: dichloromethane/hexane=1:1), yielding the title compound: R$_f$(dichloromethane/hexane=1:1)=0.30; m.p.=123.5°–124° C.

EXAMPLE 2

2(R,S)-Methyl-4(S)-hydroxy-5(S)-amino-7(S)-ethyl-8-(p-tert-butyl-phenyl)-octanoic acid (N-butyl) amide hydrochloride Analogously to Example 1, the title compound is prepared starting from N-tert-butoxy-carbonyl-2(R,S)-methyl-4(S)-hydroxy-5(S)-amino-7(S)-ethyl-8-(p-tert-butyl-phenyl)-octanoic acid (N-butyl)amide and is purified by FC (20 g of silica gel, eluant: dichloromethane/methanol=95:5). Title compound: R$_f$(dichloromethane/methanol=95:5)=0.09; R$_t$(I)=43.31 minutes; FAB-MS (M+H)$^+$=405.

The starting material is prepared analogously to Example 1, except that in step i) instead of 3-isovaleroyl-4(R)-benzyl-oxazolidin-2-one there is used 3-butyroyl-4(R)-benzyl-oxazolidin-2-one.

EXAMPLE 3

2(R,S)-Methyl-4(S)-hydroxy-5(S)-amino-7(S)-methyl-8-biphenyl-octanoic acid (N-butyl)amide hydrochloride Analogously to Example 1, the title compound is prepared starting from 100 mg of N-tert-butoxycarbonyl-2(R,S)-methyl-4(S)-hydroxy-5(S)-amino-7(S)-methyl-8-biphenyloctanoic acid (N-butyl)amide and is purified by FC (50 g of silica gel, eluant: dichloromethane/methanol=9:1). This yields the pure title compound: R$_f$(dichloromethane/methanol=9:1)=0.11; R$_t$(I)=29 minutes; FAB-MS (M+H)$^+$=411.

The starting material is obtained analogously to Example 1, except that in step i) instead of 3-isovaleroyl-4(R)-benzyl-oxazolidin-2-one there is used 3-propionyl-4(R)-benzyl-oxazolidin-2-one and instead of p-tert-butyl-benzyl bromide them is used p-phenylbenzyl bromide.

EXAMPLE 4

2(R,S)-Methyl-4(S)-hydroxy-5(S)-amino-7(S)-ethyl-8-(4-propyloxymethyl-naphth-2-yl)-octanoic acid (N-butyl)amide hydrochloride Analogously to Example 1, the title compound is prepared starting from 51 mg of N-tert-butoxycarbonyl-2(R,S)-methyl-4(S)-hydroxy-5(S)-amino-7(S)-ethyl-8-(4-propyloxymethyl-naphth-2-yl)-octanoic acid (N-butyl) amide and is purified by means of FC (15 g of silica gel, eluant: dichloromethane/methanol=8:2). Title compound: R$_f$(dichloromethane/methanol=8:2)=0.48; FAB-MS (M+H)$^+$=471.

The starting material is obtained analogously to Example 1, step i) being altered as follows:

3-[2(S)-Ethyl-3-(4-propyloxymethyl-naphth-2-yl)-propionyl]-4(R)-benzyl-oxazolidin-2-one 30 ml of tetrahydrofuran and a solution of 2.97 g of 3-butyroyl-4(R)-benzyl-oxazolidin-2-one in 15 ml of tetrahydrofuran are added dropwise in succession to a solution, stirred at −75° C., of 12 ml of 1M lithium hexamethyldisilazide solution. The reaction mixture is stirred for 1 hour at −75° C., a solution of 3.52 g of 4-propoxymethyl-2-bromomethyl-naphthalene in 15 ml of tetrahydrofuran is added dropwise thereto and the mixture is then stirred further for 1 hour at −30° C. and for 3 hours at 0° C. After the dropwise addition at 0° C. of 2.7 ml of saturated ammonium chloride solution, the reaction mixture is concentrated by evaporation and the residue is partitioned between diethyl ether and water. The organic extracts are concentrated by evaporation and the residue is purified by FC (1 kg of silica gel, eluant: dichloromethane/hexane=3:1), yielding the title compound: R$_f$(dichloromethane/hexane=3:1)=0.24; FAB-MS (M+Na)$^+$=482.

EXAMPLE 5

2(R)-Methyl-4(S)-hydroxy-5(S)-amino-7(S)-isopropyl-8-(3-hydroxy-4-tert-butyl-phenyl)-octanoic acid (N-butyl)amide hydrochloride 30 mg of N-tert-butoxycarbonyl-2(R)-methyl-4(S)-hydroxy-5(S)-amino-7(S)-isopropyl-8-(3-hydroxy-4-tert-butyl-phenyl)-octanoic acid (N-butyl)amide are treated with 0.6 ml of 4N hydrochloric acid in dioxane analogously to Example 1 and the product is purified by means of FC (15 g of silica gel, dichloromethane/methanol=9:1). The title compound is obtained: R$_f$(dichloromethane/methanol=9:1)=0.17; R$_t$(I)=28.54 minutes; FAB-MS (M+H)$^+$=435.

The starting materials are prepared as follows:

a) N-Tert-butoxycarbonyl-2(R)-methyl-4(S)-hydroxy-5(S)-amino-7(S)-isopropyl-8-(3-hydroxy-4-tert-butyl-phenyl) octanoic acid (N-butyl)amide 860 mg of N-tert-butoxycarbonyl-2-methylene-4(S)-hydroxy-5(S)-amino-7(S)-isopropyl-8-(3-benzyloxy-4-tert-butyl-phenyl)-octanoic acid (N-butyl)amide are hydrogenated for 3 hours at room temperature and under normal pressure in the presence of 860 mg of 50% Pd/C in 30 ml of methanol. The reaction mixture is filtered and concentrated by evaporation. The residue is purified by means of FC (100 g of silica gel, dichloromethane/ethyl acetate=9:1) with separation of the diastereoisomers. The title compound is obtained: R$_f$(dichloromethane/ethyl acetate=8:2)=0.23.

The unseparated diastereoisomeric mixture N-tert-butoxycarbonyl-2(R,S)-methyl-4(S)-hydroxy-5(S)-amino-7(S)-isopropyl-8-(3-hydroxy-4-tert-butyl-phenyl)-octanoic acid (N-butyl)amide has an R$_f$(ethyl acetate/hexane=1:1) of 0.38.

a') N-tert-butoxycarbonyl-2(R)-methyl-4(S)-hydroxy-5(S)-amino-7(S)-isopropyl-8-(3-hydroxy-4-tert-butyl-phenyl)-octanoic acid (N-butyl)amide can also be prepared as follows:

175 mg of N-tert-butoxycarbonyl-2-methylene-4(S)-hydroxy-5(S)-amino-7(S)-isopropyl-8-(3-benzyloxy-4-tert-butyl-phenyl)-octanoic acid (N-butyl)amide are hydrogenated in the presence of 12 mg of [Ru$_2$Cl$_4$(S-Binap)$_2$]·(NEt$_3$) in 30 ml of methanol for 20 hours at room temperature and under 30 bar. The reaction mixture is filtered, concentrated by evaporation and purified by means of FC (hexane/ethyl acetate=1:1). The title compound so obtained (R$_f$ in hexane/ethyl acetate=1:1)=0.15 is deprotected by hydrogenation with 90 mg of 10% Pd/C in 10 ml of methanol at room temperature and under normal pressure to form N-tert-butoxycarbonyl-2(R)-methyl-4(S)-hydroxy-g(S)-amino-7(S)-isopropyl-8-(3-hydroxy-4-tert-butyl-phenyl)-octanoic acid (N-butyl)amide.

The starting material is prepared analogously to Example 1, steps b) to g), the 2(S)-iso-propyl-3-(3-benzyloxy-4-tert-butyl-phenyl)-propanol used in step g) being prepared as follows:

h) 2(R)-Isopropyl-3-(3-benzyloxy-4-tert-butyl-phenyl)-propanol

At room temperature with stirring, to a solution of 5.65 g of 2(R)-isopropyl-3-(3-hydroxy-4-tert-butyl-phenyl)-propanol in 100 ml of dimethylformamide there are added 11 g of caesium carbonate and, dropwise, a solution of 3.2 ml of benzyl bromide in 20 ml of dimethylformamide. The reaction mixture is stirred at room temperature for a further 16 hours and then concentrated by evaporation, and the residue is partitioned between diethyl ether and water. The organic phases are concentrated by evaporation and the residue is purified by FC (90 g of silica gel, dichloromethane/hexane=9:1), yielding the title compound: R$_f$(dichloromethane/hexane=9:1)=0.44.

i) 2(R)-Isopropyl-3-(3-hydroxy-4-tert-butyl-phenyl)-propanol

To a solution, stirred at 0° C., of 12.3 ml of benzyl mercaptan in 100 ml of tetrahydrofuran there are added dropwise 49 ml of a 1.6M solution of butyllithium in hexane and after a further 15 minutes' stirring at 0° C. a solution of 12.1 g of 3-[2(R)-isopropyl-3-(3-acetoxy-4-tert-butyl-phenyl)-propanoyl]-4(R)-benzyl-oxazolidin-2-one in 100 ml of tetrahydrofuran. The reaction solution is stirred at 0° C. for a further 90 minutes and is then added dropwise at 0° C., with stirring, to a suspension of 4.9 g of LiAlH$_4$ in 100 ml of tetrahydrofuran. The reaction mixture is stirred for a further 150 minutes at 0° C. and then, in succession, 26.8 ml of ethyl acetate, 100 ml of tetrahydrofuran/water=1:1 and 400 ml of 2N H$_2$SO$_4$ are added dropwise thereto. The tetrahydrofuran is removed using a rotary evaporator and the suspension that remains is partitioned between diethyl ether and water. The organic phases are concentrated by evaporation and the residue is purified by FC (300 g of silica gel, dichloromethane/ethyl acetate=9:1 and 200 g of silica gel, ethyl acetate/hexane=1:2), yielding the title compound: R$_f$(ethyl acetate/hexane=1:2)=0.43.

k) 3-[2(R)-Isopropyl-3-(3-acetoxy-4-tert-butyl-phenyl)-propanoyl]-4(R)-benzyl-oxazolidin-2-one Analogously to Example 1i), the title compound is obtained starting from 3-acetoxy-4-tert-butyl-benzyl bromide and by purification using FC (silica gel, dichloromethane/hexane=7:3): R$_f$(dichloromethane/hexane=8:2)=0.29.

l) 3-Acetoxy-4-tert-butyl-benzyl bromide 16.4 g of N-bromosuccinimide, 1 g of α,α'-azoisobutyronitrile and 1 g of dibenzoyl peroxide are added in succession to a solution, stirred at 70° C., of 19 g of 3-acetoxy-4-tert-butyltoluene in 900 ml of CCl$_4$. The reaction mixture is stirred under reflux for 3½ hours under UV irradiation and is filtered, and the filtrate is concentrated by evaporation. The title compound is obtained from the residue by means of FC (900 g of silica gel, hexane/ethyl acetate=95:5): R$_f$(hexane/ethyl acetate=95:5)=0.40.

EXAMPLE 6

2(R,S)-Methyl-4(S)-hydroxy-5(S)-amino-7(S)-isopropyl-8-(2-hydroxy-4-tert-butyl-phenyl)-octanoic acid (N-butyl)amide hydrochloride Analogously to Example 1, the title compound is prepared starting from 20 mg of N-tert-butoxycarbonyl-2(R,S)-methyl-4(S)-hydroxy-5(S)-amino-7(S)-isopropyl-8-(2-hydroxy-4-tert-butyl-phenyl)-octanoic acid (N-butyl)amide by removal of the N-tert-butyloxycarbonyl group using 4N hydrochloric acid in dioxane, and is purified by means of FC (8 g of silica gel, dichloromethane/methanol=9:1). R$_f$(dichloromethane/methanol=8:2)=0.50; R$_t$(I) 28.47, 28.99 minutes; FAB-MS (M+H)$^+$=435.

The starting materials are prepared as follows:

a) N-Tert-butoxycarbonyl-2(R,S)-methyl-4(S)-hydroxy-5(S)-amino-7(S)-isopropyl-8-(2-hydroxy-4-tert-butyl-phenyl)-octanoic acid (N-butyl)amide The title compound is prepared analogously to Example 5a) starting from N-tert-butoxycarbonyl-2-methylene-4(S)-hydroxyl-5(S)-amino-7(S)-isopropyl-8-(2-benzyloxy-4-tert-butyl-phenyl)-octanoic acid (N-butyl)amide and is purified by means of FC (silica gel, hexane/ethyl acetate=2:1, ethyl acetate): R$_f$(hexane/ethyl acetate=1:1)=0.36.

That starting material is obtained analogously to Example 5, the 2-benzyloxy-4-tert-butyl-benzyl bromide to be used in step k) being prepared as follows:

l) 2-Benzyloxy-4-tert-butyl-benzyl bromide 2.9 ml of trimethylsilyl bromide are added to a solution, stirred at room temperature, of 4 g of 2-benzyloxy-4-tert-butyl-benzyl alcohol in 100 ml of chloroform. The reaction mixture is stirred for a further 1 hour and then partitioned between trichloromethane and water. The organic phases are dried with Na$_2$SO$_4$ and concentrated by evaporation, yielding the title compound: R$_f$(dichloromethane/hexane=8:2)= 0.95.

m) 2-Benzyloxy-4-tert-butyl-benzyl alcohol

A solution of 6.44 g of 2-benzyloxy-4-tert-butylbenzoic acid benzyl ester in 10 ml of tetrahydrofuran is slowly added dropwise to a suspension, stirred at room temperature, of 0.47 g of LiAlH$_4$ in 40 ml of tetrahydrofuran. The reaction mixture is stirred for a further 4 hours at room temperature and then, in succession, 0.96 ml of ethyl acetate, 6.4 ml of tetrahydrofuran/water=1:1 and 9.6 ml of 2N H$_2$SO$_4$ are added dropwise thereto. The suspension is partitioned between ethyl acetate and water/saturated sodium chloride solution, the organic phases are concentrated by evaporation and the residue is purified by means of FC (150 g of silica gel, dichloromethane/hexane=6:4). Title compound: R$_f$ (dichloromethane/hexane=8:2)=0.24.

n) 2-Benzyloxy-4-tert-butyl-benzoic acid benzyl ester

A mixture of 5 g of 2-hydroxy-4-tert-butyl-benzoic acid, 9.1 ml of benzyl bromide, 17 g of caesium carbonate, 0.3 g of sodium iodide and 500 ml of acetone is stirred for 20 hours under reflux and then filtered and the filtrate is concentrated by evaporation. The residue is partitioned between diethyl ether and water, the organic phases are concentrated by evaporation and the residue is purified by means of FC (1000 g of silica gel, dichloromethane/hexane= 1:1). Title compound: $R_f$(dichloromethane/hexane=1:1)= 0.47.

EXAMPLE 7

2(R)-Methyl-4(S)-hydroxy-5(S)-amino-7(S)-isopropyl-8-(3-ethoxycarbonylmethoxy-4-tert-butyl-phenyl)-octanoic acid (N-butyl)amide hydrochloride Analogously to Example 1, the title compound is prepared starting from 62 mg of N-tert-butoxy-carbonyl-2(R)-methyl-4(S)-hydroxy-5(S)-amino-7(S)-isopropyl-8-(3-ethoxycarbonylmethoxy-4-tert-butyl-phenyl)-octanoic acid (N-butyl)amide and is purified by means of FC (20 g of silica gel, dichloromethane/methanol=9:1). This yields the title compound: $R_f$(dichloromethane/methanol=9:1)=0.33; $R_t$(I)=34.5 and 34.8 minutes; FAB-MS (M+H)$^+$=521.

The starting materials are obtained as follows:
a) N-tert-butoxycarbonyl-2(R)-methyl-4(S)-hydroxy-5(S)-amino-7(S)-isopropyl-8-(3-ethoxycarbonylmethoxy-4-tert-butyl-phenyl)-octanoic acid (N-butyl)amide A mixture of 52 mg of N-tert-butoxycarbonyl-2(R)-methyl-4(S)-hydroxy-5(S)-amino-7(S)-isopropyl-8-(3-hydroxy-4-tert-butyl-phenyl)-octanoic acid (N-butyl)amide (Example 5a), 47.5 mg of caesium carbonate, 0.012 ml of iodoacetic acid ethyl ester and 5 ml of acetone is stirred for 3 hours under reflux and then concentrated by evaporation. The residue is partitioned between diethyl ether and water. The organic phases are dried and combined and then concentrated by evaporation, yielding the title compound in the form of the crude product: $R_f$(dichloromethane/diethyl ether=8:2)=0.28.

EXAMPLE 8

2(R)-Methyl-4(S)-hydroxy-5(S)-amino-7(S)-isopropyl-8-(3-allyloxy-4-tert-butyl-phenyl)-octanoic acid (N-butyl)amide hydrochloride Analogously to Example 1, the title compound is prepared starting from 45 mg of N-tert-butoxy-carbonyl-2(R)-methyl-4(S)-hydroxy-5(S)-amino-7(S)-isopropyl-8-(3-allyloxy-4-tert-butyl-phenyl)-octanoic acid (N-butyl)amide and is purified by FC (20 g of silica gel, dichloromethane/methanol= 9:1). This yields the title compound: $R_f$(dichloromethane/methanol=9:1)=0.20; FAB-MS (M+H)$^+$=475.

The starting material is prepared analogously to Example 7a) using allyl iodide.

EXAMPLE 9

2(R,S)-Methyl-4(S)-hydroxy-5(S)-amino-7(S)-isopropyl-8-(3-methoxycarbonylallyloxy-4-tert-butyl-phenyl)-octanoic acid (N-butyl)amide hydrochloride Analogously to Example 1, the title compound is prepared starting from 100 mg of N-tert-butoxy-carbonyl-2(R,S)-methyl-4(S)-hydroxy-5(S)-amino-7(S)-isopropyl-8-(3-methoxycarbonylallyloxy-4-tert-butyl-phenyl)-octanoic acid (N-butyl)amide. This yields the title compound in the form of a diastereoisomeric mixture: $R_f$(dichloromethane/methanol=9:1)=0.36; $R_t$(I)=25.32 and 25.8 minutes; FAB-MS (M+H)$^+$=533.

The starting material is prepared analogously to Example 7a) using N-tert-butoxycarbonyl-2(R,S)-methyl-4(S)-hydroxy-5(S)-amino-7(S)-isopropyl-8-(3-hydroxy-4-tert-butyl-phenyl)-octanoic acid (N-butyl)amide and 4-bromo-2-butenoic acid methyl ester.

EXAMPLE 10

2(R,S)-Methyl-4(S)-hydroxy-5(S)-amino-7(S)-isopropyl1-8-(3-methoxycarbonylmethoxy-4-tert-butyl-phenyl)-octanoic acid (N-butyl)amide hydrochloride Analogously to Example 1, the title compound is prepared starting from 91 mg of N-tert-butoxy-carbonyl-2(R,S)-methyl-4(S)-hydroxy-5(S)-amino-7(S)-isopropyl-8-(3-methoxycarbonylmethoxy-4-tert-butyl-phenyl)-octanoic acid (N-butyl)amide and is purified by FC (15 g of silica gel, ethyl acetate/methanol=8:2). This yields the title compound in the form of a diastereoisomeric mixture: $R_f$(ethyl acetate/methanol=8:2)=0.45; $R_t$(I)=32.5 and 33.0 minutes; FAB-MS (M+H)$^+$=507.

The starting material is prepared analogously to Example 7a) using N-tert-butoxy-carbonyl-2(R,S)-methyl-4(S)-hydroxy-5(S)-amino-7(S)-isopropyl-8-(3-hydroxy-4-tert-butyl-phenyl)-octanoic acid (N-butyl)amide and bromoacetic acid methyl ester.

EXAMPLE 11

2(R,S)-Methyl-4(S)-hydroxy-5(S)-amino-7(S)-isopropyl-8-(3-carbamoylmethoxy-4-tert-butyl-phenyl)-octanoic acid (N-butyl)amide Analogously to Example 1, the title compound is prepared starting from 59 mg of N-tert-butoxy-carbonyl-2(R,S)-methyl-4(S)-hydroxy-5(S)-amino-7(S)-isopropyl-8-(3-carboxamidomethoxy-4-tert-butyl-phenyl)-octanoic acid (N-butyl)amide and is purified by FC (20 g of silica gel, dichloromethane/methanol/conc. ammonia=140:10:1). This yields the title compound in the form of a diastereoisomeric mixture: $R_f$ (dichloromethane/methanol/conc. ammonia= 140:10:1)=0.23 and 0.32; $R_t$(I)=25.08 and 25.59 minutes; FAB-MS (M+H)$^+$=492.

The starting material is prepared analogously to Example 7a) using N-tert-butoxy-carbonyl-2(R,S)-methyl-4(S)-hydroxy-5(S)-amino-7(S)-isopropyl-8-(3-hydroxy-4-tert-butyl-phenyl)-octanoic acid (N-butyl)amide and iodoacetamide.

EXAMPLE 12

2(R,S)-Methyl-4(S)-hydroxy-5(S)-amino-7(S)-isopropyl-8-[3-(pyrid-2-yl-methoxy)-4-tert-butyl-phenyl]-octanoic acid (N-butyl)amide hydrochloride Analogously to Example 1, the title compound is prepared starting from 40 mg of N-tert-butoxy-carbonyl-2(R,S)-methyl-4(S)-hydroxy-5(S)-amino-7(S)-isopropyl-8-[3-(pyrid-2-ylmethoxy)-4-tert-butyl-phenyl]-octanoic acid (N-butyl)amide. This yields the title compound in the form of a diastereoisomeric mixture: $R_f$(dichloromethane/methanol=9:1)=0.32; $R_t$(I)=24.52 and 25.19 minutes; FAB-MS (M+H)$^+$=526.

The starting material is prepared analogously to Example 7a) using N-tert-butoxy-carbonyl-2(R,S)-methyl-4(S)-hydroxy-5(S)-amino-7(S)-isopropyl-8-(3-hydroxy-4-tert-butyl-phenyl)-octanoic acid (N-butyl)amide and 2-picolyl chloride hydrochloride.

EXAMPLE 13

2(R,S)-Methyl-4(S)-hydroxy-5(S)-amino-7(S)-isopropyl-8-[3-(pyrid-4-yl-methoxy)-4-tert-butyl-phenyl]-octanoic acid (N-butyl)amide hydrochloride Analogously to Example 1, the title compound is prepared starting from 46 mg of N-tert-butoxy-carbonyl-2(R,S)-methyl-4(S)-hydroxy-5(S)-amino-7(S)-isopropyl-8-[3-(pyrid-4-yl-methoxy)-4-tert-butyl-phenyl]-octanoic acid (N-butyl)amide. This yields the title compound in the form of a diastereoisomeric mixture: $R_f$(dichloromethane/methanol=9:1)=0.17; $R_t$(I)=20.27 and 20.62 minutes; FAB-MS $(M+H)^+$=526.

The starting material is prepared analogously to Example 7a) using N-tert-butoxy-carbonyl-2(R,S)-methyl-4(S)-hydroxy-5(S)-amino-7(S)-isopropyl-8-(3-hydroxy-4-tert-butyl-phenyl)-octanoic acid (N-butyl)amide and 4-picolyl chloride hydrochloride.

EXAMPLE 14

2(R,S)-Methyl-4(S)-hydroxy-5(S)-amino-7(S)-isopropyl-8-[3-(N-oxidopyrid-2-yl-methoxy)-4-tert-butyl-phenyl]-octanoic acid (N-butyl)amide hydrochloride Analogously to Example 1, the title compound is prepared starting from 35 mg of N-tert-butoxy-carbonyl-2(R,S)-methyl-4(S)-hydroxy-5(S)-amino-7(S)-isopropyl-8-[3-(N-oxidopyrid-2-yl-methoxy)-4-tert-butyl-phenyl]-octanoic acid (N-butyl)amide. This yields the title compound in the form of a diastereoisomeric mixture: $R_f$(dichloromethane/methanol=9:1)=0.14; $R_t$(I)=31.06 and 31.6 minutes; FAB-MS $(M+H)^+$=542.

The starting material is prepared analogously to Example 7a) using N-tert-butoxy-carbonyl-2(R,S)-methyl-4(S)-hydroxy-5(S)-amino-7(S)-isopropyl-8-(3-hydroxy-4-tert-butyl-phenyl)-octanoic acid N-(butyl)amide and 2-picolyl chloride N-oxide.

EXAMPLE 15

2(R,S)-Methyl-4(S)-hydroxy-5(S)-amino-7(S)-isopropyl-8-[3-(2-ethoxycarbonylallyloxy)-4-tert-butyl-phenyl]-octanoic acid (N-butyl)amide hydrochloride Analogously to Example 1, the title compound is prepared starting from 30 mg of N-tert-butoxy-carbonyl-2(R,S)-methyl-4(S)-hydroxy-5(S)-amino-7(S)-isopropyl-8-[3-(2-ethoxycarbonylallyloxy)-4-tert-butyl-phenyl]-octanoic acid (N-butyl)amide. This yields the title compound in the form of a diastereoisomeric mixture: $R_f$(dichloromethane/methanol=9:1)=0.28; $R_t$(I)=39.3 and 39.8 minutes FAB-MS $(M+H)^+$=547.

The starting material is prepared analogously to Example 7a) using N-tert-butoxycarbonyl-2(R,S)-methyl-4(S)-hydroxy-5(S)-amino-7(S)-isopropyl-8-(3-hydroxy-4-tert-butyl-phenyl)-octanoic acid (N-butyl)amide and bromomethylacrylic acid ethyl ester.

EXAMPLE 16

2(R,S)-Methyl-4(S)-hydroxy-5(S)-amino-7(S)-isopropyl-8-[3-(2-ethoxycarbonylpropyloxy)-4-tert-butyl-phenyl]-octanoic acid (N-butyl)amide hydrochloride Analogously to Example 1, the title compound is prepared starting from 9 mg of N-tert-butoxy-carbonyl-2(R,S)-methyl-4(S)-hydroxy-5(S)-amino-7(S)-isopropyl-8-[3-(2-ethoxycarbonyl-propyloxy)-4-tert-butyl-phenyl]-octanoic acid (N-butyl)amide. This yields the title compound in the form of a diastereoisomeric mixture: $R_f$(dichloromethane/methanol=9:1)=0.25; $R_t$(I)=38.5; 39.0; 39.6 and 40.2 minutes; FAB-MS $(M+H)^+$=549.

The starting material is prepared by hydrogenating N-tert-butoxycarbonyl-2(R,S)-methyl-4(S)-hydroxy-5(S)-amino-7(S)-isopropyl-8-[3-(2-ethoxycarbonylallyloxy)-4-tert-butyl-phenyl]-octanoic acid (N-butyl)amide (Example 15) with Raney nickel in ethanol at room temperature and under 2 bar $H_2$: $R_f$(ethyl acetate/hexane=1:2)=0.16.

EXAMPLE 17

2(R,S)-Methyl-4(S)-hydroxy-5(S)-amino-7(S)-isopropyl-8-[3-(methylthio-methoxy)-4-tert-butyl-phenyl]-octanoic acid (N-butyl)amide hydrochloride Analogously to Example 1, the title compound is prepared starting from 10 mg of N-tert-butoxycarbonyl-2(R,S)-methyl-4(S)-hydroxy-5(S)-amino-7(S)-isopropyl-8-[3-(methylthiothio-methoxy)-4-tert-butyl-phenyl]-octanoic acid (N-butyl)amide. This yields the title compound in the form of a diastereoisomeric mixture: $R_f$(dichloromethane/methanol=9:1)=0.2; $R_t$(I)=29.32 and 29.56 minutes; FAB-MS $(M+H)^+$=495.

The starting material is prepared as follows:

a) N-Tert-butoxycarbonyl-2(R,S)-methyl-4(S)-hydroxy-5(S)-amino-7(S)-isopropyl-8-[3-(methylthio-methoxy)-4-tert-butyl-phenyl]-octanoic acid (N-butyl)amide A solution of 100 mg of N-tert-butoxycarbonyl-2(R,S)-methyl-4(S)-hydroxy-5(S)-amino-7(S)-isopropyl-8-(3-hydroxy-4-tert-butyl-phenyl)-octanoic acid (N-butyl)amide (Example 5a) in 5 ml of dimethylformamide is added dropwise to a suspension, stirred at room temperature, of 7.6 mg of a 65% NaH dispersion in 3 ml of dimethylformamide. The reaction mixture is stirred for a further 30 minutes at room temperature and then a solution of 0.0 17 ml of chlorodimethyl sulfide in 2 ml of dimethylformamide is added thereto. The reaction mixture is stirred for a further 24 hours and then concentrated by evaporation. The residue is partitioned between ether and water. The organic phases are concentrated by evaporation and the title compound is obtained from the residue by FC (12 g of silica gel, dichloromethane/diethyl ether=2:1): $R_f$(dichloromethane/diethyl ether=2:1)=0.33.

EXAMPLE 18

2(R,S)-Methyl-4(S)-hydroxy-5(S)-amino-7(S)-isopropyl-8-[3-(methylsulfonyl-methoxy)-4-tert-butyl-phenyl]-octanoic acid (N-butyl)amide hydrochloride Analogously to Example 1, the title compound is prepared starting from 15 mg of N-tert-butoxy-carbonyl-2(R,S)-methyl-4(S)-hydroxy-5(S)-amino-7(S)-isopropyl-8-[3-(methylsulfonyl-methoxy)-4-tert-butyl-phenyl]-octanoic acid (N-butyl)amide. This yields the title compound in the form of a diastereoisomeric mixture: $R_f$(dichloromethane/methanol=9:1)=0.75; $R_t$(I)=28.3 and 28.76 minutes; FAB-MS $(M+H)^+$=527.

The starting material is prepared as follows:

a) N-Tert-butoxycarbonyl-2(R,S)-methyl-4(S)-hydroxy-5(S)-amino-7(S)-isopropyl-8-[3-(methylsulfonyl-methoxy)-4-tert-butyl-phenyl]-octanoic acid (N-butyl)amide With stirring at 0° C., a solution of 115 mg of potassium monopersulfate triple salt in 0.5 ml of water is added dropwise to a solution of 74 mg of N-tert-butoxycarbonyl-2(R,S)-methyl-4(S)-hydroxy-5(S)-amino-7(S)-isopropyl-8-[3-(methylthio-methoxy)-4-tert-butyl-phenyl]-octanoic acid (N-butyl)amide in 0.5 ml of methanol and the mixture is then stirred at room temperature for a further 20 hours. The reaction mixture is partitioned between dichloromethane and water. The organic phases are concentrated by evaporation and the title compound is obtained from the residue by FC (11 g of silica gel, ethyl acetate/hexane=1:1): $R_f$(ethyl acetate/hexane=1:1)=0.26; FAB-MS (M+H)$^+$=627.

EXAMPLE 19

2(R,S)-Methyl-4(S)-hydroxy-5(S)-amino-7(S)-isopropyl-8-[3-(carboxymethoxy)-4-tert-butyl-phenyl]-octanoic acid (N-butyl)amide hydrochloride Analogously to Example 1, the title compound is prepared starting from 28 mg of N-tert-butoxy-carbonyl-2(R,S)-methyl-4(S)-hydroxy-5(S)-amino-7(S)-isopropyl-8-[3-(carboxymethoxy)-4-tert-butyl-phenyl]-octanoic acid (N-butyl)amide. This yields the title compound in the form of a diastereoisomeric mixture: $R_f$(dichloromethane/methanol=9:1)=0.26; $R_t$(I)=26.1 and 28.0 minutes; FAB-MS (M+H)$^+$=493.

The starting material is prepared analogously to Example 7a) using N-tert-butoxy-carbonyl-2(R,S)-methyl-4(S)-hydroxy-5(S)-amino-7(S)-isopropyl-8-(3-hydroxy-4-tert-butyl-phenyl)-octanoic acid (N-butyl)amide and bromoacetic acid benzyl ester, with subsequent removal of the benzyl group by hydrolysis (Pd/C-ethanol).

EXAMPLE 20

2(R,S)-Methyl-4(S)-hydroxy-5(S)-amino-7(S)-isopropyl-8-[3-(3,3-dimethyl-2-oxo-butyloxy)-4-tert-butyl-phenyl]-octanoic acid (N-butyl)amide hydrochloride Analogously to Example 1, the title compound is prepared starting from 42 mg of N-tert-butoxy-carbonyl-2(R,S)-methyl-4(S)-hydroxy-5(S)-amino-7(S)-isopropyl-8-[3-(3,3-di-methyl-2-oxo-butyloxy)-4-tert-butyl-phenyl]-octanoic acid (N-butyl)amide. This yields the title compound in the form of a diastereoisomeric mixture: $R_f$(dichloromethane/methanol=9:1)=0.3; $R_t$(I)=37.3 and 37.8 minutes; FAB-MS (M+H)$^+$=533.

The starting material is prepared analogously to Example 17a) using N-tert-butoxy-carbonyl-2(R,S)-methyl-4(S)-hydroxy-5(S)-amino-7(S)-isopropyl-8-(3-hydroxy-4-tert-butyl-phenyl)-octanoic acid (N-butyl)amide and 1-bromopinacolone.

EXAMPLE 21

2(R,S)-Methyl-4(S)-hydroxy-5(S)-amino-7(S)-isopropyl-8-[3-(2-nitrobenzyloxy)-4-tert-butyl-phenyl]-octanoic acid (N-butyl)amide hydrochloride Analogously to Example 1, the title compound is prepared starting from 53 mg of N-tert-butoxy-carbonyl-2(R,S)-methyl-4(S)-hydroxy-5(S)-amino-7(S)-isopropyl-8-[3-(2-nitro-benzyloxy)-4-tert-butyl-phenyl]-octanoic acid (N-butyl)amide. This yields the title compound in the form of a diastereoisomeric mixture: $R_f$(dichloromethane/methanol=9:1)=0.35; $R_t$(I)=52.0 and 52.4 minutes; FAB-MS (M+H)$^+$=570.

The starting material is prepared analogously to Example 7a) using N-tert-butoxy-carbonyl-2(R,S)-methyl-4(S)-hydroxy-5(S)-amino-7(S)-isopropyl-8-(3-hydroxy-4-tert-butyl-phenyl)-octanoic acid (N-butyl)amide and 2-nitrobenzyl chloride.

EXAMPLE 22

2(R,S)-Methyl-4(S)-hydroxy-5(S)-amino-7(S)-isopropyl-8-[3-(2-amino-benzyloxy)-4-tert-butyl-phenyl-]-octanoic acid (N-butyl)amide hydrochloride The title compound is prepared starting from 35 mg of 2(R,S)-methyl-4(S)-hydroxy-5(S)-amino-7(S)-isopropyl-8-[3-(2-nitrobenzyloxy)-4-tert-butyl-phenyl]-octanoic acid (N-butyl)amide (Example 21) by hydrogenation with Pt/C in tetrahydrofuran at room temperature and under normal pressure and is purified by FC (10 g of silica gel, dichloromethane/methanol=9:1). This yields the title compound in the form of a diastereoisomeric mixture: $R_f$(dichloromethane/methanol=9:1)=0.27; $R_t$(I)=30.5 and 31.3 minutes; FAB-MS(M+H)$^+$=539.

EXAMPLE 23

2(R,S)-Methyl-4(S)-hydroxy-5(S)-amino-7(S)-isopropyl-8-[3-(3-chloro-2(R,S)-hydroxy-propyloxy)-4-tert-butyl-phenyl]-octanoic acid (N-butyl)amide hydrochloride Analogously to Example 1, the title compound is prepared starting from 31 mg of N-tert-butoxy-carbonyl-2(R,S)-methyl-4(S)-hydroxy-5(S)-amino-7(S)-isopropyl-8-[3-(2,3epoxypropyloxy)-4-tert-butyl-phenyl]-octanoic acid (N-butyl)amide. This yields the title compound in the form of a diastereoisomeric mixture: $R_f$(dichloromethane/methanol=9:1)=0.18; $R_t$(I)=31.9 and 32.3 minutes; FAB-MS (M+H)$^+$=527.

The starting material is prepared analogously to Example 7a) using N-tert-butoxy-carbonyl-2(R,S)-methyl-4(S)-hydroxy-5(S)-amino-7(S)-isopropyl-8-(3-hydroxy-4-tert-butylphenyl)-octanoic acid (N-butyl)amide and epibromohydrin.

EXAMPLE 24

2(R,S)-Methyl-4(S)-hydroxy-5(S)-amino-7(S)-isopropyl-8-[3-(3-methylthio-2(S,R)-hydroxypropyloxy)-4-tert-butyl-phenyl]-octanoic acid (N-butyl)amide hydrochloride Analogously to Example 1, the title compound is prepared starting from 15 mg of N-tert-butoxy-carbonyl-2(R,S)-methyl-4(S)-hydroxy-5(S)-amino-7(S)-isopropyl-8-[3-(3-methylthio-2(S,R)-hydroxypropyloxy)-4-tert-butyl-phenyl]-octanoic acid (N-butyl)amide. This yields the title compound in the form of a diastereoisomeric mixture: $R_f$ (dichloromethane/methanol=9:1)=0.32; $R_t$(I)=32.6 and 32.9 minutes; FAB-MS(M+H)$^+$=539.

The starting material is prepared as follows:

a) N-tert-butoxycarbonyl-2(R,S)-methyl-4(S)-hydroxy-5(S)-amino7(S)-isopropyl8-[3-(3-methylthio-2(S,R)-hydroxypropyloxy)-4-tert-butyl-phenyl]-octanoic acid (N-butyl)-amide 18 mg of sodium methanethiolate are added to a solution of 150 mg of N-tert-butoxy-carbonyl-2(R,S)-methyl-4(S)-hydroxy-5(S)-amino-7(S)-isopropyl-8-[3-(2,3epoxypropyloxy)-4-tert-butyl-phenyl]-octanoic acid (N-butyl)amide in 10 ml of methanol and the mixture is maintained under reflux for 7 hours. The reaction mixture is concentrated by evaporation and the residue is partitioned between dichloromethane and water. The organic phases are concentrated by evaporation and the title compound is obtained from the residue after purification by means of FC (20 g of silica gel, dichloromethane/diethyl ether=1:1): $R_f$(dichloromethane/diethyl ether=1:1)=0.33; FAB-MS $(M+H)^+$=639.

EXAMPLE 25

2(R,S)-Methyl-4(S)-hydroxy-5(S)-amino-7(S)-isopropyl-8-[3-(3-methylsulfonyl-2(S,R)-hydroxypropyloxy)-4-tert-butyl-phenyl-]-octanoic acid (N-butyl)amide hydrochloride Analogously to Example 1, the title compound is prepared starting from 14 mg of N-tert-butoxy-carbonyl-2(R,S)-methyl-4(S)-hydroxy-5(S)-amino-7(S)-isopropyl-8-[3-(3-methylsulfonyl-2(S,R)-hydroxypropyloxy)-4-tert-butyl-phenyl]-octanoic acid (N-butyl)amide. This yields the title compound in the form of a diastereoisomeric mixture: $R_f$(dichloromethane/methanol=9:1)=0.16; $R_t$(I)=26.3 and 26.8 minutes; FAB-MS$(M+H)^+$=571.

The starting material is prepared analogously to Example 18a) using 62 mg of N-tert-butoxycarbonyl-2(R,S)-methyl-4(S)-hydroxy-5(S)-amino-7(S)-isopropyl-8-[3-(3-methylthio-2(S,R)-hydroxypropyloxy)-4-tert-butyl-phenyl]-octanoic acid (N-butyl)amide: $R_f$(ethyl acetate)=0.60; FAB-MS $(M+H)^+$=671.

EXAMPLE 26

2(R)-Methyl-4(S)-hydroxy-5(S)-amino-7(S)-isopropyl-8-[3-(methylsulfonyl-methoxy)-4-tert-butyl-phenyl]-octanoic acid (N-3-morpholino-propyl)amide hydrochloride Analogously to Example 1, the title compound is prepared starting from 18 mg of N-tert-butoxy-carbonyl-2(R)-methyl-4(S)-hydroxy-5(S)-amino-7(S)-isopropyl-8-(3-methylsulfonyl-methoxy)-4-tert-butyl-phenyl)-octanoic acid (N-3-morpholino-propyl)amide. This yields the title compound: $R_f$(dichloromethane/methanol=8:2)=0.16; $R_t$(I) =17.61 minutes; FAB-MS$(M+H)^+$=598.

The starting material is prepared analogously to Examples 17a) and 18a) using N-tert-butoxycarbonyl-2(R)-methyl-4 (S)-hydroxy-5(S)-amino-7(S)-isopropyl-8-(3-hydroxy-4-tert-butyl-phenyl)-octanoic acid (N-3-morpholino-propyl) amide and chlorodimethyl sulfide.

The N-tert-butoxycarbonyl-2(R)-methyl-4(S)-hydroxy-5 (S)-amino-7(S)-isopropyl-8-(3-hydroxy-4-tert-butyl-phenyl)-octanoic acid (N-3-morpholino-propyl)amide is prepared analogously to Example 5a-1), except that in step 5b) or 1b) methacrylic acid (N-3-morpholino-propyl)amide is used instead of methacrylic acid butylamide.

EXAMPLE 27

2(R)-Methyl-4(S)-hydroxy-5(S)-amino-7(S)-isopropyl-8-(3-methoxycarbonylmethoxy-phenyl)-octanoic acid (N-butyl)amide hydrochloride Analogously to Example 1, the title compound is prepared starting from 12 mg of N-tert-butoxy-carbonyl-2(R)-methyl-4(S)-hydroxy-5(S)-amino-7(S)-isopropyl-8-(3-methoxycarbonyl-methoxy-phenyl)-octanoic acid (N-butyl) amide. This yields the title compound: $R_f$(dichloromethane/ methanol=9:1)=0.18; $R_t$(I)=21.74 minutes; FAB-MS$(M+H)^+$=451.

The starting material is prepared analogously to Example 7a) using N-tert-butoxy-carbonyl-2(R)-methyl-4(S)-hydroxy-5(S)-amino-7(S)-isopropyl-8-(3-hydroxy-phenyl)-octanoic acid (N-butyl)amide and bromoacetic acid methyl ester.

The N-tert-butoxycarbonyl-2(R)-methyl-4(S)-hydroxy-5 (S)-amino-7(S)-isopropyl-8-(3-hydroxyphenyl)-octanoic acid (N-butyl)amide used as starting material is prepared analogously to Example 5a)-51), except that in step k) instead of 3-acetoxy-4-tert-butyl-benzyl bromide there is used 3-benzyloxy-benzyl bromide, so that in step i) 2(R)-isopropyl-3-(3-benzyloxy-phenyl)-propanol, $R_f$(dichloromethane/hexane=1:1)=0.19, is obtained directly.

EXAMPLE 28

2(R)-Methyl-4(S)-hydroxy-5(S)-amino-7(S)-isopropyl-8-[3-(methoxycarbonylmethoxy)-4-methoxy-phenyl]-octanoic acid (N-butyl)amide hydrochloride Analogously to Example 1, the title compound is prepared starting from 15 mg of N-tert-butoxy-carbonyl-2(R)-methyl-4(S)-hydroxy-5(S)-amino-7(S)-isopropyl-8-[3 (methoxycarbonylmethoxy)-4-methoxy-phenyl]-octanoic acid (N-butyl)amide. This yields the title compound: $R_f$(dichloromethane/methanol=9:1)=0.16; $R_t$(I)=19.33 minutes; FAB-MS$(M+H)^+$=481.

The starting material is prepared analogously to Example 7a) using N-tert-butoxy-carbonyl-2(R)-methyl-4(S)-hydroxy-5(S)-amino-7(S)-isopropyl-8-(3-hydroxy-4-methoxy-phenyl)-octanoic acid (N-butyl)amide and bromoacetic acid methyl ester.

The N-tert-butoxycarbonyl-2(R)-methyl-4(S)-hydroxy-5 (S)-amino-7(S)-isopropyl-8-(3-hydroxy-4-methoxy-phenyl) -octanoic acid (N-butyl)amide used as starting material is prepared as follows:

a1) N-tert-butoxycarbonyl-2(R)-methyl-4(S)-hydroxy-5(S)-amino-7(S)-isopropyl-8-(3-benzyloxy-4-methoxy-phenyl)-octanoic acid (N-butyl)amide 3.5 g of N-tert-butoxycarbonyl-2-methylene-4(S)-hydroxy-5(S)-amino-7(S)-isopropyl-8-(3-benzyloxy-4-methoxy-phenyl)-octanoic acid (N-butyl)amide are hydrogenated in 30 ml of absolute methanol in the presence of 20 mg of $[Ru_2Cl_4((S)\text{-Binap})_2] \cdot NEt_3$ at room temperature and 25 bar for 5 hours. The reaction mixture is filtered and the filtrate is concentrated by evaporation. The residue is purified by FC (200 g of silica gel, hexane/ethyl acetate=1:1). Title compound: $R_f$(hexane/ethyl acetate=1:1)=0.16; FAB-MS $(M+H)^+$=599.

a2) N-tert-butoxycarbonyl-2(R)-methyl-4(S)-hydroxy-5(S)-amino-7(S)-isopropyl-8-(3-hydroxy-4-methoxy-phenyl)-octanoic acid (N-butyl)amide 4.7 g of N-tert-butoxycarbonyl-2(R)-methyl-4(S)-hydroxy-5(S)-amino-7(S)-isopropyl-8-(3-benzyloxy-4-methoxy-phenyl)-octanoic acid (N-butyl)amide are hydrogenated in 60 ml of methanol in the presence of 2.35 g of 10% Pd/C at room temperature and under normal pressure for 1 hour. Filtration of the reaction mixture and concentration of the filtrate by evaporation under a high vacuum yield the title compound: $R_f$(hexane/ethyl acetate =1:1)=0.15; FAB-MS $(M+H)^+$=509.

The N-tert-butoxycarbonyl-2-methylene-4(S)-hydroxy-5 (S)-amino-7(S)-isopropyl-8-(3-benzyloxy-4-methoxy-phenyl)-octanoic acid (N-butyl)amide used as starting material is prepared analogously to Example 1b) to i), except that in step i) 3-benzyloxy-4-methoxy-benzyl bromide is used instead of p-tert-butyl benzyl bromide.

EXAMPLE 29

2(R)-Methyl-4(S)-hydroxy-5(S)-amino-7(S)-isopropyl-8-[3-(N-methylcarbamoylmethoxy)-4-methoxy-phenyl]-octanoic acid (N-butyl)amide hydrochloride Analogously to Example 1, the title compound is prepared starting from 18 mg of N-tert-butoxy-carbonyl-2(R)-methyl-4(S)-hydroxy-5(S)-amino-7(S)-isopropyl-8-[3-(N-methylcarbamoylmethoxy)-4-methoxy-phenyl]-octanoic acid (N-butyl)amide. This yields the title compound: $R_f$(dichloromethane/methanol=9:1)=0.21; $R_t$(I)=15.54 minutes; FAB-MS(M+H)$^+$=480.

The starting material is prepared as follows:

A mixture of 29 mg of N-tert-butoxycarbonyl-2(R)-methyl-4(S)=hydroxy-5(S)-amino-7(S)-isopropyl-8-[3-(methoxycarbonylmethoxy)=4-methoxy-phenyl]-octanoic acid (N-butyl)amide (Example 32), 6 ml of dimethylformamide and 1 ml of methylamine is left to stand in a bomb tube at room temperature for 60 hours. Concentration by evaporation and FC (5 g of silica gel, dichloromethane/methanol=9:1) of the residue yield the title compound: $R_f$(dichloromethane/methanol=9:1)=0.55.

EXAMPLE 30

2(R)-Methyl-4(S)-hydroxy-5(S)-amino-7(S)-isopropyl-8-[3-(3-methylsulfonyl-propyloxy)-4-methoxy-phenyl]-octanoic acid (N-butyl)amide hydrochloride Analogously to Example 1, the title compound is prepared starting from 30 mg of N-tert-butoxy-carbonyl-2(R)-methyl-4(S)-hydroxy-5(S)-amino-7(S)-isopropyl-8-[3-(3-methylsulfonyl-propyloxy)-4-methoxy-phenyl]-octanoic acid (N-butyl)amide. This yields the title compound: $R_f$(dichloromethane/methanol=9:1)=0.29; $R_t$(I)=17.83 minutes; FAB-MS(M+H)$^+$=529.

The starting material is prepared analogously to Examples 17a) and 18a) using N-tert-butoxycarbonyl-2(R)-methyl-4(S)-hydroxy-5(S)-amino-7(S)-isopropyl-8-(3-hydroxy-4-methoxy-phenyl)-octanoic acid (N-butyl)amide and 3-methylthiopropyl iodide with subsequent oxidation to the sulfone.

EXAMPLE 31

2(R)-Methyl-4(S)-hydroxy-5(S)-amino-7(S)-isopropyl-8-[3-(methylsulfonyl-methoxy)-4-methoxy-phenyl]-octanoic acid (N-butyl)amide hydrochloride Analogously to Example 1, the title compound is prepared starting from 100 mg of N-tert-butoxy-carbonyl-2(R)-methyl-4(S)-hydroxy-5(S)-amino-7(S)-isopropyl-8-[3-(methylsulfonyl-methoxy)-4-methoxy-phenyl]-octanoic acid (N-butyl)amide. This yields the title compound: $R_f$(dichloromethane/methanol=8:2)=0.5; $R_t$(I)=18.0 minutes; FAB-MS(M+H)$^+$=501.

The starting material is prepared analogously to Examples 17a) and 18a) using N-tert-butoxycarbonyl-2(R)-methyl-4(S)-hydroxy-5(S)-amino-7(S)-isopropyl-8-(3-hydroxy-4-methoxy-phenyl)-octanoic acid (N-butyl)amide and chlorodimethyl sulfide with subsequent oxidation to the sulfone.

EXAMPLE 32

2(R)-Methyl-4(S)-hydroxy-5(S)-amino-7(S)-isopropyl-8-[3-(3-methoxypropyloxy)-4-methoxy-phenyl]-octanoic acid (N-butyl)amide hydrochloride Analogously to Example 1, the title compound is prepared starting from 27 mg of N-tert-butoxy-carbonyl-2(R)-methyl-4(S)-hydroxy-5(S)-amino-7(S)-isopropyl-8-[3-(3methoxypropyloxy)-4-methoxy-phenyl]-octanoic acid (N-butyl)amide and is purified by FC (2 g of silica gel, dichloromethane/methanol=95:5). This yields the title compound: $R_f$(dichloromethane-methanol=9:1)=0.15; $R_t$(I)= 21.9 minutes; FAB-MS(M+H)$^+$=481.

The starting material is prepared analogously to Example 17a) using N-tert-butoxy-carbonyl-2(R)-methyl-4(S)-hydroxy-5(S)-amino-7(S)-isopropyl-8-(3-hydroxy-4-methoxy-phenyl)-octanoic acid (N-butyl)amide and 3-methoxy-propyl iodide.

EXAMPLE 33

2(R)-Methyl-4(S)-hydroxy-5(S)-amino-7(S)-isopropyl-8-[3-(2-methoxy-ethoxy)-4-methoxy-phenyl]-octanoic acid (N-butyl)amide hydrochloride Analogously to Example 1, the title compound is prepared starting from 68 mg of N-tert-butoxy-carbonyl-2(R)-methyl-4(S)-hydroxy-5(S)-amino-7(S)-isopropyl-8-[3-(2-methoxy-ethoxy)-4-methoxy-phenyl]-octanoic acid (N-butyl)amide. This yields the title compound: $R_f$(dichloromethane/methanol=9:1)=0.32; $R_t$(I)=19.84 minutes; FAB-MS(M+H)$^+$=467.

The starting material is prepared analogously to Example 17a) using N-tert-butoxy-carbonyl-2(R)-methyl-4(S)-hydroxy-5(S )-amino-7(S)-isopropyl-8-(3-hydroxy-4-methoxy-phenyl)-octanoic acid (N-butyl)amide and 2-methoxy-ethyl iodide.

EXAMPLE 34

2(R)-Methyl-4(S)-hydroxy-5(S)-amino-7(S)-isopropyl-8-[3-(3-hydroxypropyloxy)-4-methoxy-phenyl]-octanoic acid (N-butyl)amide hydrochloride Analogously to Example 1, the title compound is prepared starting from 93 mg of N-tert-butoxy-carbonyl-2(R)-methyl-4(S)-hydroxy-5(S)-amino-7(S)-isopropyl-8-[3-(3hydroxypropyloxy)-4-methoxy-phenyl]-octanoic acid (N-butyl)amide. This yields the title compound: $R_f$(dichloromethane/methanol=9:1)=0.24; $R_t$(I)=16.13 minutes; FAB-MS(M+H)$^+$=467.

The starting material is prepared analogously to Example 17a) using N-tert-butoxy-carbonyl-2(R)-methyl-4(S)-hydroxy-5(S)-amino-7(S)-isopropyl-8-(3-hydroxy-4-methoxy-phenyl)-octanoic acid (N-butyl)amide and 3-iodopropanol.

EXAMPLE 35

2(R)-Methyl-4(S)-hydroxy-5(S)-amino-7(S)-isopropyl-8-[3-(carbamoyl-methoxy)-4-methoxy-phenyl]-octanoic acid (N-butyl)amide hydrochloride Analogously to Example 1, the title compound is prepared starting from 39 mg of N-tert-butoxy-carbonyl-2(R)-methyl-4(S)-hydroxy-5(S)-amino-7(S)-isopropyl-8-[3-(carbamoyl-methoxy)-4-methoxy-phenyl]-octanoic acid (N-butyl)amide. This yields the title compound: $R_f$(dichloromethane/methanol=8:2)=0.38; $R_t$(I)=13.86 minutes; FAB-MS(M+H)$^+$=466.

The starting material is prepared analogously to Example 7a) using N-tert-butoxy-carbonyl-2(R)-methyl-4(S)-hydroxy-5(S)-amino-7(S)-isopropyl-8-(3-hydroxy-4-methoxy-phenyl)-octanoic acid (N-butyl)amide and iodoacetamide.

EXAMPLE 36

2(R)-Methyl-4(S)-hydroxy-5(S)-amino-7(S)-isopropyl-8-(3-cyanomethoxy-4-methoxy-phenyl)-octanoic acid (N-butyl)amide 1.5 ml of a mixture of trifluoroacetic acid/dichloromethane=1:3 are added at 0° C., with stirring, to a solution of 35 mg of N-tert-butoxycarbonyl-2(R)-methyl-4(S)-hydroxy-5(S)-amino-7(S)-isopropyl-8-(3-cyanomethoxy-4-methoxy-phenyl)-octanoic acid (N-butyl)-amide in 1 ml of dichloromethane, and the mixture is stirred for a further 3 hours at 0° C. and then concentrated by evaporation. The residue is purified by FC (5 g of silica gel, dichloromethane/methanol=9:1). This yields the title compound: $R_f$(dichloromethane/methanol=9:1)=0.19; $R_t$(I)=19.59 minutes; FAB-MS(M+H)$^+$=448.

The starting material is prepared analogously to Example 7a) using N-tert-butoxy-carbonyl-2(R)-methyl-4(S)-hydroxy-5(S)-amino-7(S)-isopropyl-8-(3-hydroxy-4-methoxy-phenyl)-octanoic acid (N-butyl)amide and iodoacetonitrile.

EXAMPLE 37

2(R)-Methyl-4(S)-hydroxy-5(S)-amino-7(S)-isopropyl-8-[3-(4-methoxy-butoxy)-4-methoxy-phenyl]-octanoic acid (N-butyl)amide hydrochloride Analogously to Example 1, the title compound is prepared starting from 24 mg of N-tert-butoxy-carbonyl-2(R)-methyl-4(S)-hydroxy-5(S)-amino-7(S)-isopropyl-8-[3-(4-methoxy-butoxy)-4-methoxy-phenyl]-octanoic acid (N-butyl)amide. This yields the title compound: $R_f$(dichloromethane/methanol=9:1)=0.29; $R_t$(I)=22.51 minutes; FAB-MS(M+H)$^+$=495.

The starting material is prepared analogously to Example 17a) using N-tert-butoxy-carbonyl-2(R)-methyl-4(S)-hydroxy-5(S)-amino-7(S)-isopropyl-8-(3-hydroxy-4-methoxy-phenyl)-octanoic acid (N-butyl)amide and 4-methoxy-propyl iodide.

EXAMPLE 38

2(R)-Methyl-4(S)-hydroxy-5(S)-amino-7(S)-isopropyl-8-f3-(2-ethoxy-ethoxy)-4-methoxy-phenyl]-octanoic acid (N-butyl)amide hydrochloride Analogously to Example 1, the title compound is prepared starting from 24 mg of N-tert-butoxy-carbonyl-2(R)-methyl-4(S)-hydroxy-5(S)-amino-7(S)-isopropyl-8-[3-(2-ethoxy-ethoxy)-4-methoxy-phenyl]-octanoic acid (N-butyl)amide. This yields the title compound: $R_f$(dichloromethane/methanol=9:1)=0.26; $R_t$(I)=21.32 minutes; FAB-MS(M+H)$^+$=481.

The starting material is prepared analogously to Example 17a) using N-tert-butoxy-carbonyl-2(R)-methyl-4(S)-hydroxy-5(S)-amino-7(S)-isopropyl-8-(3-hydroxy-4-methoxy-phenyl)-octanoic acid (N-butyl)amide and 2-iododiethyl ether.

EXAMPLE 39

2(R)-Methyl-4(S)-hydroxy-5(S)-amino-7(S)-isopropyl-8-{3-[2-(2-methoxy-ethoxy)ethoxy]-4-methoxy-phenyl}-octanoic acid (N-butyl)amide hydrochloride Analogously to Example 1, the title compound is prepared starting from 27 mg of N-tert-butoxy-carbonyl-2(R)-methyl-4(S)-hydroxy-5(S)-amino-7(S)-isopropyl-8-{3-[2-(2-methoxy-ethoxy)ethoxy]-4-methoxy-phenyl}-octanoic acid (N-butyl)amide. This yields the tire compound: $R_f$(dichloromethane/methanol=1:1)=0.19; $R_t$(I)=18.93 minutes; FAB-MS(M+H)$^+$=511.

The starting material is prepared analogously to Example 17a) using N-tert-butoxy-carbonyl-2(R)-methyl-4(S)-hydroxy-5(S)-amino-7(S)-isopropyl-8-(3-hydroxy-4-methoxy-phenyl)-octanoic acid (N-butyl)amide and 1-iodo-2-(2-methoxy-ethoxy)-ethane.

EXAMPLE 40

2(R)-Methyl-4(S)-hydroxy-5(S)-amino-7(S)-isopropyl-8-(3-pentyloxy-4-methoxy-phenyl)-octanoic acid (N-butyl)amide hydrochloride Analogously to Example 1, the title compound is prepared starting from 53 mg of N-tert-butoxy-carbonyl-2(R)-methyl-4(S)-hydroxy-5(S)-amino-7(S)-isopropyl-8-(3-pentyloxy-4-methoxy-phenyl)-octanoic acid (N-butyl)amide. This yields the title compound: $R_f$(dichloromethane/methanol=9:1)=0.25; $R_t$(I)=32.01 minutes; FAB-MS(M+H)$^+$=479.

The starting material is prepared analogously to Example 17a) using N-tert-butoxy-carbonyl-2(R)-methyl-4(S)-hydroxy-5(S)-amino-7(S)-isopropyl-8-(3-hydroxy-4-methoxy-phenyl)-octanoic acid (N-butyl)amide and iodo-pentane.

EXAMPLE 41

2(R)-Methyl-4(S)-hydroxy-5(S)-amino-7(S)-isopropyl-8-(3-benzyloxy-4-methoxy-phenyl)-octanoic acid (N-butyl)amide hydrochloride Analogously to Example 1, the title compound is prepared starting from 100 mg of N-tert-butoxy-carbonyl-2(R)-methyl-4(S)-hydroxy-5(S)-amino-7(S)-isopropyl-8-(3-benzyloxy-4-methoxy-phenyl)-octanoic acid (N-butyl)amide. This yields the title compound: $R_f$(dichloromethane/methanol=9:1)=0.31; $R_t$(I)=44.21 minutes; FAB-MS(M+H)$^+$=499.

The starting material is prepared analogously to Example 17a) using N-tert-butoxy-carbonyl-2(R)-methyl-4(S)-hydroxy-5(S)-amino-7(S)-isopropyl-8-(3-hydroxy-4-methoxy-phenyl)-octanoic acid (N-butyl)amide and benzyl bromide.

EXAMPLE 42

2(R)-Methyl-4(S)-hydroxy-5(S)-amino-7(S)-isopropyl-8-[3-(3-ethoxy-propyloxy)-4-methoxy-phenyl]-octanoic acid (N-butyl)amide hydrochloride Analogously to Example 1, the title compound is prepared starting from 113 mg of N-tert-butoxy-carbonyl-2(R)-methyl-4(S)-hydroxy-5(S)-amino-7(S)-isopropyl-8-[3-(3-ethoxypropyloxy)-4-methoxy-phenyl]-octanoic acid (N-butyl)amide. This yields the title compound: $R_f$(dichloromethane/methanol=9:1)=0.30; $R_t$(I)=23.11 minutes; FAB-MS(M+H)$^+$=495.

The starting material is prepared analogously to Example 7a) using N-tert-butoxy-carbonyl-2(R)-methyl-4(S)-hydroxy-5(S)-amino-7(S)-isopropyl-8-(3-hydroxy-4-methoxy-phenyl)-octanoic acid (N-butyl)amide and 1-ethoxy-3-iodopropane.

EXAMPLE 43

2(R)-Methyl-4(S)-hydroxy-5(S)-amino-7(S)-isopropyl-8-[3-(pyrid-4-yl-methoxy)-4-methoxy-phenyl]-octanoic acid (N-butyl)amide hydrochloride Analogously to Example 1, the title compound is prepared starting from 71 mg of N-tert-butoxycarbonyl-2(R)-methyl- 4(S)-hydroxy-5(S)-amino-7(S)-isopropyl-8-[3-(pyrid-4-yl-methoxy)-4-methoxy-phenyl]-octanoic acid (N-butyl) amide. This yields the title compound: $R_f$(dichloromethane/methanol=9:1)=0.19; $R_t$(I)=32.95 minutes; FAB-MS(M+H)$^+$=500.

The starting material is prepared analogously to Example 7a) using N-tert-butoxy-carbonyl-2(R)-methyl-4(S)-hydroxy-5(S)-amino-7(S)-isopropyl-8-(3-hydroxy-4-methoxy-phenyl)-octanoic acid (N-butyl)amide and 4-picolyl chloride.

EXAMPLE 44

2(R,S)-Methyl-4(S)-hydroxy-5(S)-amino-7(S)-isopropyl-8-(2-ethoxycarbonylmethoxy-4-tert-butyl-phenyl)-octanoic acid (N-butyl)amide hydrochloride Analogously to Example 1, the title compound is prepared starting from 67 mg of N-tert-butoxy-carbonyl-2(R,S)-methyl-4(S)-hydroxy-5(S)-amino-7(S)-isopropyl-8-(2-ethoxycarbonylmethoxy-4-tert-butyl-phenyl)-octanoic acid (N-butyl)-amide. This yields the title compound in the form of a diastereoisomeric mixture: $R_f$(dichloromethane/methanol=9:1)=0.19; $R_t$(I)=35.7 and 36.5 minutes; FAB-MS (M+H)$^+$=521.

The starting material is prepared analogously to Example 7a) using N-tert-butoxy-carbonyl-2(R,S)-methyl-4(S)-hydroxy-5(S)-amino-7(S)-isopropyl-8-(2-hydroxy-4-tert-butyl-phenyl)-octanoic acid (N-butyl)amide (Example 6a) and iodoacetic acid ethyl ester.

EXAMPLE 45

2(R,S)-Methyl-4(S)-hydroxy-5(S)-amino-7(S)-isopropyl-8-(2-ethoxy-carbonyl-4-tert-butyl-phenyl)-octanoic acid (N-butyl)amide hydrochloride Analogously to Example 1, the title compound is prepared starting from 80 mg of N-tert-butoxy-carbonyl-2(R,S)-methyl-4(S)-hydroxy-5(S)-amino-7(S)-isopropyl-8-(2-ethoxycarbonylmethoxy-4-tert-butyl-phenyl)-octanoic acid (N-butyl)amide. This yields the title compound in the form of a diastereoisomeric mixture: $R_f$(dichloromethane/methanol=9:1)=0.21; $R_t$(I)=27.8 and 28.39 minutes; FAB-MS(M+H)$^+$=492.

The starting material is prepared analogously to Example 7a) using N-tert-butoxy-carbonyl-2(R,S)-methyl-4(S)-hydroxy-5(S)-amino-7(S)-isopropyl-8-(2-hydroxy-4-tert-butyl-phenyl)-octanoic acid (N-butyl)amide (Example 6a) and iodoacetamide.

EXAMPLE 46

2(R)-Methyl-4(S)-hydroxy-5(S)-amino-7(S)-isopropyl-8-[3-(3-methoxypropyloxy)-4,5-ethylenedioxy-phenyl]-octanoic acid (N-butyl)amide hydrochloride Analogously to Example 1, the title compound is prepared starting from 34 mg of N-tert-butoxycarbonyl-2(R)-methyl-4(S)-hydroxy-5(S)-amino-7(S)-isopropyl-8-[3-(3-methoxypropyloxy)-4,5-ethylenedioxy-phenyl]-octanoic acid (N-butyl)amide. This yields the title compound: $R_f$(dichloromethane/methanol=9:1)=0.16; $R_t$(I)=21.83 minutes; FAB-MS (M+H)$^+$=509.

The starting material is prepared analogously to Example 17a) using N-tert-butoxy-carbonyl-2(R)-methyl-4(S)-hydroxy-5(S)-amino-7(S)-isopropyl-8-(3-hydroxy-4,5-ethylenedioxy-phenyl)-octanoic acid (N-butyl)amide and 3-methoxy-propyl iodide.

The N-tert-butoxycarbonyl-2(R)-methyl-4(S)-hydroxy-5(S)-amino-7(S)-isopropyl-8-(3-hydroxy-4,5-ethylenedioxy-phenyl)-octanoic acid (N-butyl)amide is prepared analogously to Example 28, except that in step i) instead of 3-benzyloxy-4-methoxy-benzyl bromide there is used 3-benzyloxy-4,5-ethylenedioxy-benzyl bromide. That compound is prepared as follows:

a) 5-Hydroxy-1,4-benzodioxane-7-carboxylic acid ethyl ester

A solution of 0.2 ml of 1,2-dibromoethane in 4 ml of dimethylformamide is added dropwise, four times at 2 hour intervals, to a solution, stirred at 100° C., of 2 g of gallic acid ethyl ester and 6.5 g of caesium carbonate in 80 ml of dimethylformamide. After being stirred for a further 2 hours at 100° C. the reaction mixture is concentrated by evaporation and the residue is partitioned between diethyl ether and water. The organic phases are dried over sodium sulfate and concentrated by evaporation. The title compound is obtained from the residue by FC (50 g of silica gel, methylene chloride-methanol=8:2): $R_f$(methylene chloride/methanol=8:2)=0.39.

b) 5-Benzyloxy,1,4-benzodioxane-7-carboxylic acid ethyl ester

The reaction mixture containing 900 ml of acetone, 17.4 g of hydroxy-1,4-benzodioxane-7-carboxylic acid ethyl ester, 37.9 g of caesium carbonate, 11 ml of benzyl bromide and 7.7 g of sodium iodide is stirred under reflux for 3 hours and then concentrated by evaporation. The residue is partitioned between diethyl ether and water. The organic phases are dried over sodium sulfate and concentrated by evaporation. The title compound is obtained from the residue by FC (900 g of silica gel, hexane/ethyl acetate=1:1): $R_f$(hexane/ethyl acetate=2:1)=0.36.

c) 5-Benzyloxy-7-hydroxymethyl-1,4-benzodioxane

A solution of 1.28 g of 5-benzyloxy-1,4-benzodioxane-7-carboxylic acid ethyl ester in 5 ml of tetrahydrofuran is added dropwise at room temperature to a solution of 110 mg of lithium aluminium hydride in 10 ml of tetrahydrofuran and the mixture is stirred at room temperature for a further 30 minutes. Then 0.22 ml of ethyl acetate, 1.5 ml of a mixture (water/tetrahydrofuran=1:1) and finally 2.25 ml of 2N sulfuric acid are added dropwise in succession. The reaction mixture is partitioned between diethyl ether and water. The organic phases are dried over sodium sulfate and concentrated by evaporation. The title compound is obtained from the residue by FC (240 g of silica gel, ethyl acetate/hexane=1:2): $R_f$(ethyl acetate-hexane=1:2)=0.18.

d) 3-Benzyloxy-4,5-ethylenedioxy-benzyl bromide 0.07 ml of trimethylsilyl bromide is added to a solution of 0.1 g of 5-benzyloxy-7-hydroxymethyl-1,4-benzodioxane in 5 ml of chloroform and the mixture is stirred for a further 15 minutes at room temperature and then concentrated by evaporation in a rotary evaporator. The residue is immediately dissolved in a small amount of ethyl acetate; the same volume of hexane is added and the mixture is filtered through 15 g of silica gel, followed by elution with a mixture (hexane/ethyl acetate=4:1). Concentration of the eluates by evaporation yields the title compound: $R_f$(hexane/ethyl acetate=3:1)=0.48.

EXAMPLE 47

In a manner analogous to that described in Examples 1 to 46 or 62 to 180 it is also possible to prepare 5(S)-amino-4(S)-hydroxy-2(S),7(S)-diisopropyl-8-[4-(3-hydroxy-propyloxy)-3-(3-methoxy-propyloxy)-phenyl]-octanoic acid [N-(2-carbamoyl-2,2-di-methyl-ethyl)]-amide hydrochloride.

EXAMPLE 48

In a manner analogous to that described in Examples 1 to 46 or 62 to 180 it is also possible to prepare 5(S)-amino-4 (S)-hydroxy-2(S),7(S)-diisopropyl-8-[4-isopropyl3-(3-methoxypropyloxy)-phenyl]-octanoic acid [N-(2-carbamoyl-2,2-dimethyl-ethyl)]-amide hydrochloride.

EXAMPLE 49

In a manner analogous to that described in Examples 1 to 46 or 62 to 180 it is also possible to prepare 5(S)-amino-4 (S)-hydroxy-2(S),7(S)-diisopropyl-8-[4-tert-butyl-3-(3-methoxy-propyloxy)-phenyl]-octanoic acid [N-(2-carbamoyl-2,2-dimethyl-ethyl)]-amide hydrochloride.

EXAMPLE 50

In a manner analogous to that described in Examples 1 to 46 or 62 to 180, it is also possible to prepare 5(S)-amino-4(S)-hydroxy-2(S),7(S)-diisopropyl-8-[4-(3-methylsulfonyl-propyloxy)-3-(3-methoxy-propyloxy)-phenyl]-octanoic acid (N-2-morpholinoethyl)amide dihydrochloride.

EXAMPLE 51

In a manner analogous to that described in Examples 1 to 46 or 62 to 180 it is also possible to prepare 5(S)-amino-4 (S)-hydroxy-2(S),7(S)-diisopropyl-8-[4-(3-methylsulfonyl-propyloxy)-3-(3-methoxy-propyloxy)-phenyl]-octanoic acid [N-(2-carbamoyl-2,2-dimethyl-ethyl)]-amide hydrochloride.

EXAMPLE 52

In a manner analogous to that described in Examples 1 to 46 or 62 to 180 it is also possible to prepare 5(S)-amino-4 (S)-hydroxy-2(S),7(S)-diisopropyl-8-[3,4-di(3-hydroxypropyloxy)phenyl]-octanoic acid (N-2-morpholinoethyl)amide dihydrochloride.

EXAMPLE 53

In a manner analogous to that described in Examples 1 to 46 or 62 to 180 it is also possible to prepare 5(S)-amino-4 (S)-hydroxy-2(S),7(S)-diisopropyl-8-[3,4-di(3-hydroxypropyloxy)phenyl]-octanoic acid [N-(2-carbamoyl-2,2-dimethyl-ethyl)]-amide hydrochloride.

EXAMPLE 54

In a manner analogous to that described in Examples 1 to 46 or 62 to 180 it is also possible to prepare 5(S)-amino-4 (S)-hydroxy-2(S),7(S)-diisopropyl-8-[4-(3-N-methylcarbamoyl-propyl)-3-(3-methoxy-propyloxy)-phenyl]-octanoic acid (N-2-morpholinoethyl)amide dihydrochloride.

EXAMPLE 55

In a manner analogous to that described in Examples 1 to 46 or 62 to 180 it is also possible to prepare 5(S)-amino-4 (S)-hydroxy-2(S),7(S)-diisopropyl-8-[4-(2-morpholinoethoxy)-3-(3-methoxy-propyloxy)-phenyl]-octanoic acid [N-(2-carbamoyl-2,2-dimethyl-ethyl)]-amide dihydrochloride.

EXAMPLE 56

In a manner analogous to that described in Examples 1 to 46 or 62 to 180 it is also possible to prepare 5(S)-amino-4 (S)-hydroxy-2(S),7(S)-diisopropyl-8-[3-(3-methoxy-propyloxy)-4,5-ethylenedioxy-phenyl]-octanoic acid (N-2-morpholinoethyl)-amide dihydrochloride.

EXAMPLE 57

In a manner analogous to that described in Examples 1 to 46 or 62 to 180 it is also possible to prepare 5(S)-amino-4 (S)-hydroxy-2(S),7(S)-diisopropyl-8-[3-(3-methoxy-propyloxy)-4,5-ethylenedioxy-phenyl]-octanoic acid [N-(2-carbamoyl-2,2-dimethyl-ethyl)]-amide hydrochloride.

EXAMPLE 58

In a manner analogous to that described in Examples 1 to 46 or 62 to 180 it is also possible to prepare 5(S)-amino-4 (S)-hydroxy-2(S),7(S)-diisopropyl-8-[3-(3-methoxy-propyloxy)-4,5-methylenedioxy-phenyl]-octanoic acid (N-2-morpholinoethyl)-amide dihydrochloride.

EXAMPLE 59

In a manner analogous to that described in Examples 1 to 46 or 62 to 180 it is also possible to prepare 5(S)-amino-4 (S)-hydroxy-2(S),7(S)-diisopropyl-8-[3-(3-methoxy-propyloxy)-4,5-methylenedioxy-phenyl]-octanoic acid [N-(2-carbamoyl-2,2-dimethyl-ethyl)]-amide hydrochloride.

EXAMPLE 60

In a manner analogous to that described in Examples 1 to 46 or 62 to 180 it is also possible to prepare 5(S)-amino-4 (S)-hydroxy-2(S),7(S)-diisopropyl-8-[4-methoxy-3-(3-methoxypropyloxy)-phenyl]-octanoic acid [N-(2-carbamoyl-2,2-ethylene-ethyl)]-amide hydrochloride.

EXAMPLE 61

In a manner analogous to that described in Examples 1 to 46 or 62 to 180 it is also possible to prepare 5(S)-amino-4 (S)-hydroxy-2(S),7(S)-diisopropyl-8-[4-methoxy-3-(3-methoxy-propyloxy)-phenyl]-octanoic acid [N-(3(S)-2-oxopyrrolidin-3-yl-methyl)]-amide hydrochloride.

EXAMPLE 62

5(S)-Amino-4(S)-hydroxy-7(S)-isopropyl-2(R)-methyl-8-[4-methoxy-3-(4-methoxy-but-2-enoxy)-phenyl]-octanoic acid (N-butyl)-amide hydrochloride Analogously to Example 1, the title compound is prepared starting from 66 mg of 5(S)-tert-butoxycarbonylamino-4(S)-hydroxy-7(S)isopropyl-2(R)-methyl-8-[4-methoxy-3-(4-methoxy-but-2-enoxy)-phenyl]-octanoic acid (N-butyl)-amide and is purified by FC (30 g of silica gel, dichloromethane/methanol=9:1). This yields the title compound: $R_f$(dichloromethane/methanol=9:1)=0.26; HPLC $R_f(I)$=40.4 minutes; FAB-MS (M+H)$^+$32 493.

The starting material is prepared analogously to Example 17a) using 5(S)-tert-butoxy-carbonylamino-4(S)-hydroxy-7 (S)-isopropyl-2(R)-methyl-8-(3-hydroxy-4-methoxy-phenyl)-octanoic acid (N-butyl)-amide (Example 28) and 4-methoxy-but-2-enyl iodide.

EXAMPLE 63

5(S)-Amino-4(S)-hydroxy-7(S)-isopropyl-2(R)-methyl-8-[4-hydroxy-3-(3-methoxypropyloxy)-phenyl]-octanoic acid (N-butyl)amide hydrochloride Analogously to Example 1, the title compound is prepared starting from 20 mg of 5(S)-tert-butoxycarbonylamino-4(S)

-hydroxy-7(S)-isopropyl-2(R)-methyl-8-[4-hydroxy-3-(3-methoxy-propyloxy)-phenyl]-octanoic acid (N-butyl)-amide. This yields the title compound: $R_f$(dichloromethane/methanol=9:1)=0.05; HPLC $R_t$(I)=36.22 minutes; FAB-MS (M+H)$^+$=467.

The starting material is prepared as follows:

a) 5(S)-Tert-butoxycarbonylamino-4(S)-hydroxy-7(S)-isopropyl-2(R)-methyl-8-[4-hydroxy-3-(3-methoxypropyloxy)-phenyl]-octanoic acid (N-butyl)-amide 1.34 g of 5(S)-tert-butoxycarbonylamino-4(S)-hydroxy-7(S)-isopropyl-2(R)-methyl-8-[4-benzyloxy-3-(3-methoxypropyloxy)-phenyl]-octanoic acid (N-butyl)-amide are hydrogenated in the presence of 400 mg of 5% Pd/C in 50 ml of methanol for 10 minutes at room temperature and under normal pressure. The reaction mixture is filtered and concentrated by evaporation. The residue is purified by means of FC (50 g of silica gel, hexane/ethyl acetate=1:1). The title compound is obtained: $R_f$(hexane/ethyl acetate=1:1)=0.16; HPLC $R_t$=17.42 minutes; FAB-MS:(M+H)$^+$=567.

The 5(S)-tert-butoxycarbonylamino-4(S)-hydroxy-7(S)-isopropyl-2(R)-methyl-8-[4-benzyloxy-3-(3-methoxypropyloxy)-phenyl]-octanoic acid (N-butyl)-amide used as starting material is prepared analogously to Example 28a1) and Examples 1b) to 1g), except that in step g) instead of 2(S)-isopropyl-3-(p-tert-butyl-phenyl)-propanol there is used 2(S)-isopropyl-3-[4-benzyloxy-3-(3-methoxypropyloxy)-phenyl]-propanol. That compound is prepared analogously to Example 124i) to m), except that in step m) instead of 4-methoxy-3-(3-methoxypropyloxy)-benzyl alcohol there is used 4-benzyloxy-3-(3-methoxypropyloxy)-benzyl alcohol.

That compound is prepared as follows:

b) 4-Benzyloxy-3-(3-methoxypropyloxy)-benzaldehyde

A solution of 28.8 g of 4-benzyloxy-3-hydroxy-benzaldehyde in 100 ml of dimethyl-formamide is added dropwise to a suspension of 5.54 g of NaH (60% dispersion in mineral oil) in 150 ml of absolute dimethylformamide. The reaction mixture is stirred at room temperature. After 30 minutes, a solution of 29 g of 3-methoxybromopropane in 120 ml of dimethylformamide is added thereto, and the mixture is stirred at room temperature for a further 4 hours and is then concentrated by evaporation under reduced pressure. The residue is partitioned between diethyl ether and water. The combined organic phases are dried over sodium sulfate and concentrated by evaporation, and the residue is purified by FC (100 g of silica gel, dichloromethane), yielding the title compound, which crystallises spontaneously: $R_f$(dichloromethane/diethyl ether)=0.44.

c) 4-Benzyloxy-3-(3-methoxypropyloxy)-benzyl alcohol

A solution of 31 g of 4-benzyloxy-3-(3-methoxypropyloxy)-benzaldehyde in 530 ml of ethanol/water=8:2 is added dropwise to a suspension, stirred at 0° C., of 11.74 g of sodium boranate in 530 ml of a mixture of ethanol/water=8:2. The reaction mixture is stirred for one hour at 0° C. and is then concentrated by evaporation. The residue is partitioned between diethyl ether and water. The combined organic phases are dried over sodium sulfate and concentrated by evaporation, and the residue is purified by FC (100 g of silica gel, dichloromethane/diethyl ether=1:1), yielding the title compound: $R_f$(dichloromethane/diethyl ether=1:1)=0.43.

EXAMPLE 64

5(S)-Amino-4(S)-hydroxy-7(S)-isopropyl-2(R)-methyl-8-[4-benzyloxy-3-(3-methoxypropyloxy)-phenyl]-octanoic acid (N-butyl)amide hydrochloride Analogously to Example 1, the title compound is prepared starting from 60 mg of 5(S)-tert-butoxycarbonylamino-4(S)-hydroxy-7(S)-isopropyl-2(R)-methyl-8-[4-benzyloxy-3-(3-methoxy-propyloxy)-phenyl]-octanoic acid (N-butyl)amide. This yields the title compound: $R_f$(dichloromethane/methanol=95:5)=0.08; HPLC $R_t$(I)=45.47 minutes; FAB-MS (M+H)$^+$=557.

EXAMPLE 65

5(S)-Amino-4(S)-hydroxy-7(S)-isopropyl-2(R)-methyl-8-[3,4-di(3-methoxy-propyloxy)phenyl]-octanoic acid (N-butyl)amide hydrochloride Analogously to Example 1, the title compound is prepared starting from 66 mg of 5(S)-tert-butoxycarbonylamino-4(S)-hydroxy-7(S)-isopropyl-2(R)-methyl-8-[3,4-di(3-methoxypropyloxy)phenyl]-octanoic acid (N-butyl)amide. This yields the tide compound: $R_f$(dichloromethane/methanol=9:1)=0.21; $R_t$(I)=40.0 minutes; FAB-MS (M+H)$^+$=539.

The starting material is prepared analogously to Example 17a) using 5(S)-tert-butoxy-carbonylamino-4(S)-hydroxy-7(S)-isopropyl-2(R)-methyl-8-[4-hydroxy-3-(3-methoxypropyloxy)-phenyl]-octanoic acid (N-butyl)amide and 3-methoxybromopropane.

EXAMPLE 66

5(S)-Amino-4(S)-hydroxy-7(S)-isopropyl-2(R)-methyl-8-[4-(2,2,2-trifluoroethoxy)-3-(3-methoxypropyloxy)-phenyl]-octanoic acid (N-butyl) amide hydrochloride Analogously to Example 1, the title compound is prepared starting from 14 mg of 5(S)-tert-butoxycarbonylamino-4(S)-hydroxy-7(S)-isopropyl-2(R)-methyl-8-[4-(2,2,2-trifluoroethoxy)-3-(3-methoxypropyloxy)-phenyl]-octanoic acid (N-butyl)amide. This yields the title compound: $R_f$(dichloromethane/methanol=9:1)=0.31; HPLC $R_t$(I)=28.7 minutes; FAB-MS (M+H)$^+$=549.

The starting material is prepared analogously to Example 17a) using 5(S)-tert-butoxy-carbonylamino-4(S)-hydroxy-7(S)-isopropyl-2(R)-methyl-8-[4-hydroxy-3-(3-methoxypropyloxy)-phenyl]-octanoic acid (N-butyl)amide and 2,2,2-trifluoroethyl iodide.

EXAMPLE 67

5(S)-Amino-4(S)-hydroxy-7(S)-isopropyl-2(R)-methyl-8-[4-(3-hydroxypropyloxy)-3-(3-methoxypropyloxy)-phenyl]-octanoic acid (N-butyl) amide hydrochloride Analogously to Example 1, the title compound is prepared starting from 20 mg of 5(S)-tert-butoxycarbonylamino-4(S)-hydroxy-7(S)-isopropyl-2(R)-methyl-8-[4-(3-hydroxy-propyloxy)-3-(3-methoxypropyloxy)-phenyl]-octanoic acid (N-butyl)amide and is purified by FC (2 g of silica gel, dichloromethane/methanol=9:1). This yields the title compound: $R_f$(dichloromethane/methanol=9:1)=0.09; HPLC $R_t$=11.03 minutes; FAB-MS (M+H)$^+$=525.

The starting material is prepared analogously to Example 17a) using 5(S)-tert-butoxy-carbonylamino-4(S)-hydroxy-7(S)-isopropyl-2(R)-methyl-8-[4-hydroxy-3-(3-methoxypropyloxy)-phenyl]-octanoic acid (N-butyl)amide and 3-iodopropanol.

EXAMPLE 68

5(S)-Amino-4(S)-hydroxy-7(S)-isopropyl-2(R)-methyl-8-[4-(2-amino-ethoxy)-3-(3-methoxypropyloxy)-phenyl]-octanoic acid (N-butyl) amide hydrochloride Analogously to Example 1, the title compound is prepared starting from 7.5 mg of 5(S)-tert-butoxycarbonylamino-4(S)

-hydroxy-7(S)-isopropyl-2(R)-methyl-8-[4-(2-aminoethoxy)-3-(3-methoxypropyloxy)-phenyl]-octanoic acid (N-butyl)amide. This yields the title compound: $R_f$(dichloromethane/methanol/conc. ammonia=100:50:1)= 0.28; HPLC $R_f$=6.77 minutes; FAB-MS $(M+H)^+$=510.

The starting material is prepared analogously to Example 17a) using 5(S)-tert-butoxy-carbonylamino-4(S)-hydroxy-7(S)-isopropyl-2(R)-methyl-8-[4-hydroxy-3-(3-methoxypropyloxy)-phenyl]-octanoic acid (N-butyl)amide and iodoacetonitrile, with subsequent reduction of the nitrile function to the amino group with Raney nickel/$H_2$ under normal pressure and at 40° C. in ethanol in the presence of 4% ammonia.

EXAMPLE 69

5(S)-Amino-4(S)-hydroxy-7(S)-isopropyl-2(R)-methyl-8-[4-(5-amino-pentyloxy)-3-(3-methoxypropyloxy)-phenyl]-octanoic acid (N-butyl)amide hydrochloride Analogously to Example 1, the title compound is prepared starting from 22 mg of 5(S)-tert-butoxycarbonylamino-4(S)-hydroxy-7(S)-isopropyl-2(R)-methyl-8-[4-(5-amino-pentyloxy)-3-(3-methoxypropyloxy)-phenyl]-octanoic acid (N-butyl)amide. This yields the title compound: $R_f$(dichloromethane/methanol/conc. ammonia=100:50:1)= 0.11; HPLC $R_f$=7.46 minutes; FAB-MS $(M+H)^+$=552.

The starting material is prepared analogously to Example 17a) using 5(S)-tert-butoxy-carbonylamino-4(S)-hydroxy-7(S)-isopropyl-2(R)-methyl-8-[4-hydroxy-3-(3-methoxypropyloxy)-phenyl]-octanoic acid (N-butyl)amide and 5-iodovaleric acid nitrile, with subsequent reduction of the nitrile function to the amino group with Raney nickel/$H_2$ under normal pressure and at 40° C. in ethanol in the presence of 4% ammonia.

EXAMPLE 70

5(S)-Amino-4(S)-hydroxy-7(S)-isopropyl-2(R)-methyl-8-[4-(4-amino-butyloxy)-3-(3-methoxypropyloxy)-phenyl]-octanoic acid (N-butyl)amide hydrochloride Analogously to Example 1, the title compound is prepared starting from 36 mg of 5(S)-tert-butoxycarbonylamino-4(S)-hydroxy-7(S)-isopropyl-2(R)-methyl-8-[4-(4-aminobutyloxy)-3-(3-methoxypropyloxy)-phenyl]-octanoic acid (N-butyl)amide. This yields the title compound: $R_f$(dichloromethane/methanol/ammonia (conc.)=100:50:1)= 0.15; HPLC $R_f$(I)=33.3 minutes; FAB-MS $(M+H)^+$=538.

The starting material is prepared analogously to Example 17a) using 5(S)-tert-butoxy-carbonylamino-4(S)-hydroxy-7(S)-isopropyl-2(R)-methyl-8-[4-hydroxy-3-(3-methoxypropyloxy)-phenyl]-octanoic acid (N-butyl)amide and 4-iodobutyronitrile, with subsequent reduction of the nitrile function to the amino group with Raney nickel/$H_2$ under normal pressure and at 40° C. in ethanol in the presence of 4% ammonia, to form 5(S)-tert-butoxycarbonylamino-4(S)-hydroxy-7(S)-isopropyl-2(R)-methyl-8-[4-(4-amino-butyloxy)-3-(3-methoxypropyloxy)-phenyl]-octanoic acid (N-butyl)amide, $R_f$(dichloromethane/methanol/conc. ammonia=100:50:1)=0.15, HPLC $R_f$=13.55 minutes.

EXAMPLE 71

5(S)-Amino-4(S)-hydroxy-7(S)-isopropyl-2(R)-methyl-8-[4-(4-N,N-dimethylamino-butyloxy)-3-(3-methoxypropyloxy)-phenyl]-octanoic acid (N-butyl)amide hydrochloride Analogously to Example 1, the title compound is prepared starting from 30 mg of 5(S)-tert-butoxycarbonylamino-4(S)-hydroxy-7(S)-isopropyl-2(R)-methyl-8-[4-(4-N,N-dimethylamino-butyloxy)-3-(3-methoxypropyloxy)-phenyl]-octanoic acid (N-butyl)amide. This yields the title compound:$R_f$(dichloromethane/methanol/ammonia(conc.)= 100:50:1)=0.21; HPLC $R_f$=9.7 minutes; FAB-MS $(M+H)^+$= 566.

The starting material is prepared by hydrogenation of 80 mg of 5(S)-tert-butoxycarbonyl-amino-4(S)-hydroxy-7(S)-isopropyl-2(R)-methyl-8-[4-(4-amino-butyloxy)-3-(3-methoxypropyloxy)-phenyl]-octanoic acid (N-butyl)amide (Example 70), dissolved in 6 ml of methanol and in the presence of 25 ml of 35% formaldehyde solution, with 30 mg of 10% Pd/C for a period of 19 hours at room temperature and under normal pressure, and is purified by FC (5 g of silica gel, dichloromethane/methanol/ammonia (conc.)= 350:50:1). $R_f$(dichloromethane/methanol/conc. ammonia= 350:50:1)=0.21; HPLC $R_f$=14.18 minutes; FAB-MS $(M+H)^+$=666.

EXAMPLE 72

5(S)-Amino-4(S)-hydroxy-7(S)-isopropyl-2(R)-methyl-8-{4-[4-N-(trifluoromethanesulfonylaminobutyloxy)-3-(3-methoxypropyloxy)-phenyl]}-octanoic acid (N-butyl)amide hydrochloride Analogously to Example 1, the title compound is prepared starting from 27 mg of 5(S)-tert-butoxycarbonylamino-4(S)-hydroxy-7(S)-isopropyl-2(R)-methyl-8-{4-[4-N-(trifluoromethanesulfonylaminobutyloxy)-3-(3-methoxypropyloxy)-phenyl]}-octanoic acid (N-butyl)amide. This yields the title compound: $R_f$(dichloromethane/methanol=9:1)=0.27; HPLC $R_f$=14.67 minutes; FAB-MS $(M+H)^+$=670.

The starting material is prepared as follows:
a) 5(S)-Tert-butoxycarbonylamino-4(S)-hydroxy-7(S)-isopropyl-2(R)-methyl-8-[4-(4-N-trifluoromethanesulfonylamido-butyloxy)-3-(3-methoxypropyloxy)-phenyl]-octanoic acid (N-butyl)amide 50 mg of 5(S)-tert-butoxycarbonylamino-4(S)-hydroxy-7(S)-isopropyl-2(R)-methyl-8-[4-(4-aminobutyloxy)-3-(3-methoxypropyloxy)-phenyl]-octanoic acid (N-butyl)-amide are dissolved in 4 ml of dichloromethane, and 23 ml of triethylamine and 13 ml of trifluoromethanesulfonic acid anhydride are added thereto at 0° C. The reaction mixture is stirred for 2 hours at room temperature and is then partitioned between dichloromethane (3x) and saturated $NaHCO_3$ solution (1x). The organic phases are combined, dried over magnesium sulfate and concentrated by evaporation. Purification of the residue by FC (15 g of silica gel, hexane/ethyl acetate=1:1) yields the title compound: $R_f$(hexane/ethyl acetate=1:1)=0.26; HPLC $R_f$=20.02 minutes.

EXAMPLE 73

5(S)-Amino-4(S)-hydroxy-7(S)-isopropyl-2(R)-methyl-8-4-carboxy-methoxy-3-(3-methoxypropyloxy)-phenyl]-octanoic acid (N-butyl)amide hydrochloride Analogously to Example 1, the title compound is prepared starting from 70 mg of 5(S)-tert-butoxycarbonylamino-4(S)-hydroxy-7(S)-isopropyl-2(R)-methyl-8-[4-carboxy-methoxy-3-(3-methoxypropyloxy)-phenyl]-octanoic acid (N-butyl)amide. This yields the title compound: $R_f$(dichloromethane/methanol=7:3)=0.35; HPLC $R_f$(I) =37.18 minutes; FAB-MS (M+H)+=525.

The starting material is prepared analogously to Example 17a) using 5(S)-tert-butoxy-carbonylamino-4(S)-hydroxy-7 (S)-isopropyl-2(R)-methyl-8-[4-hydroxy-3-(3-methoxy-propyloxy)-phenyl]-octanoic acid (N-butyl)amide and bromoacetic acid benzyl ester, with subsequent debenzylation in ethanol with 10% Pd/C at room temperature and under normal pressure.

EXAMPLE 74

5(S)-Amino-4(S)-hydroxy-7(S)-isopropyl-2(R)-methyl-8-[4-(3-ethoxycarbonyl-propyloxy)-3-(3-methoxy-propyloxy)-phenyl]-octanoic acid (N-butyl)-amide hydrochloride Analogously to Example 1, the title compound is prepared starting from 27 mg of 5(S)-tert-butoxycarbonylamino-4(S)-hydroxy-7(S)-isopropyl-2(R)-methyl-8-[4-(3-ethoxy-carbonylpropyloxy)-3-(3-methoxypropyloxy)-phenyl]-octanoic acid (N-butyl)amide. This yields the title compound: $R_f$(dichloromethane/methanol=9:1)=0.24; HPLC $R_f$=18.18 minutes; FAB-MS (M+H)+=581.

The starting material is prepared analogously to Example 17a) using 5(S)-tert-butoxy-carbonylamino-4(S)-hydroxy-7 (S)-isopropyl-2(R)-methyl-8-[4-hydroxy-3-(3-methoxypropyloxy)-phenyl]-octanoic acid (N-butyl)amide and 4-iodobutyric acid ethyl ester.

EXAMPLE 75

5(S)-Amino-4(S)-hydroxy-7(S)-isopropyl-2(R)-methyl-8-[4-(3-carboxypropyloxy)-3-(3-methoxypropyloxy)-phenyl]-octanoic acid (N-butyl) amide hydrochloride Analogously to Example 1, the title compound is prepared starting from 41 mg of 5(S)-tert-butoxycarbonylamino-4(S)-hydroxy-7(S)-isopropyl-2(R)methyl-8-[4-(3-carboxypropyloxy)-3-(3-methoxypropyloxy)-phenyl]-octanoic acid (N-butyl)amide. This yields the title compound: $R_f$(dichloromethane/methanol=9:1)=0.20; HPLC $R_f$(I)=37.65 minutes; FAB-MS (M+H)+=553.

The starting material is prepared from 5(S)-tert-butoxycarbonylamino- 4(S)-hydroxy-7(S)-isopropyl-2(R)-methyl-8-[4-(3methoxycarbonylpropyloxy)-3-(3-methoxypropyloxy)-phenyl]-octanoic acid (N-butyl)amide (Example 74) by hydrolysis of the ester function in methanolic solution with 2 equivalents of 1 N sodium hydroxide, by stirring for 24 hours at room temperature. The reaction mixture is concentrated by evaporation, an aqueous solution of the residue acidified to pH 4 is extracted with ethyl acetate, and the product obtained therefrom is purified by FC (dichloromethane/methanol=9:1). $R_f$(dichloromethane/methanol=95:5)=0.41.

EXAMPLE 76

5(S)-Amino-4(S)-hydroxy-7(S)-isopropyl-2(R)-methyl-8-[4-(4-methoxycarbonylbutyloxy)-3-(3-methoxypropyloxy)-phenyl]-octanoic acid (N-butyl) amide hydrochloride Analogously to Example 1, the title compound is prepared starting from 29 mg of 5(S)-tert-butoxycarbonylamino-4(S)-hydroxy-7(S)-isopropyl-2(R)-methyl-8-[4-(4-methoxycarbonyl-butyloxy)-3-(3-methoxy-propyloxy)-phenyl]-octanoic acid (N-butyl)amide. This yields the title compound: $R_f$(dichloromethane/methanol=9:1)=0.24; HPLC $R_f$(I)=42.55 minutes; FAB-MS (M+H)+=581.

The starting material is prepared analogously to Example 17a) using 5(S)-tert-butoxy-carbonylamino-4(S)-hydroxy-7 (S)-isopropyl-2(R)-methyl-8-[4-hydroxy-3-(3-methoxypropyloxy)-phenyl]-octanoic acid (N-butyl)amide and 5-iodovaleric acid methyl ester.

EXAMPLE 77

5(S)-Amino-4(S)-hydroxy-7(S)-isopropyl-2(R)-methyl-8-[4-(4-carboxybutyloxy)-3-(3-methoxypropyloxy)-phenyl]-octanoic acid (N-butyl) amide hydrochloride Analogously to Example 1, the title compound is prepared starting from 10 mg of 5(S)-tert-butoxycarbonylamino-4(S)-hydroxy-7(S)-isopropyl-2(R)-methyl-8-[4-(4-carboxybutyloxy)-3-(3-methoxypropyloxy)-phenyl]-octanoic acid (N-butyl)amide. This yields the title compound: $R_f$(dichloromethane/methanol=8:2)=0.34; HPLC $R_f$=9.92 minutes; FAB-MS (M+H)+=561.

The starting material is prepared from 5(S)-tert-butoxycarbonylamino-4(S)-hydroxy-7(S)-isopropyl-2(R)-methyl-8-[4-(4-methoxycarbonyl-butyloxy)-3-(3-methoxypropyloxy)-phenyl]-octanoic acid (N-butyl)amide (Example 76) by hydrolysis of the ester function in methanolic solution with 2 equivalents of IN sodium hydroxide, by stirring for 24 hours at room temperature. The reaction mixture is concentrated by evaporation, the residue is dissolved in water, and the solution is acidified to pH 4 and extracted with ethyl acetate. The organic phases are dried over magnesium sulfate and concentrated by evaporation. Purification of the residue by FC (silica gel, dichloromethane/methanol=9:1) yields the title compound: $R_f$(dichloromethane/methanol/conc. ammonia=350:50:1)= 0.14.

EXAMPLE 78

In a manner analogous to that described in Examples 1 to 46 or 62 to 180 it is also possible to prepare 5(S)-amino-4 (S)-hydroxy-2(S),7(S)-diisopropyl-8-[4-methoxy-3-(3-methoxy-propyloxy)-phenyl]-octanoic acid [N-(3(R)-2-oxo-pyrrolidin-3-yl-methyl)]-amide hydrochloride, 5(S)-amino-4(S)-hydroxy-2(S)-7(S)-diisopropyl-8-[4-methoxy-3-(3-methoxy-propyloxy)-phenyl]-octanoic acid [N-(3(S)-2-oxo-piperidin-3-yl-methyl)]-amide hydrochloride, 5(S)-amino-4(S)-hydroxy-2(S)-7(S)-diisopropyl-8-[4-methoxy-3-(3-methoxy-propyloxy)-phenyl]-octanoic acid [N-(3(R)-2-oxo-piperidin-3-yl-methyl)]-amide hydrochloride, 5(S)-amino-4(S)-hydroxy-2(S)-7(S)-diisopropyl-8-[4-methoxy-3-(3-methoxy-propyloxy)-phenyl]-octanoic acid [N-(3-carbamoyl-3,3-dimethyl-propyl)]-amide hydrochloride, 5(S)-amino-4(S)-hydroxy-2(S),7(S)-diisopropyl-8-[4-methoxy-3-(4-methoxy-butyl)-phenyl]-octanoic acid [N-(5 (S)-2-pyrrolidinon-5-yl-methyl)]-amide hydrochloride, 5(S)-amino-4(S)-hydroxy-2(S),7(S)-diisopropyl-8-[4-methoxy-3-(4-methoxy-butyl)-phenyl]-octanoic acid [N-(5 (R)-2-pyrrolidinon-5-yl-methyl)]-amide hydrochloride, 5(S)-amino-4(S)-hydroxy-2(S),7(S)-diisopropyl-8-[4-methoxy-3-(3-methoxy-propyloxy)-phenyl]-octanoic acid [N-(6(S)-2-oxo-piperidin-6-yl-methyl)]-amide hydrochloride, 5(S)-amino-4(S)-hydroxy-2(S),7(S)-diisopropyl-8-[4-methoxy-3-(3-methoxy-propyloxy)-phenyl]-octanoic acid [N-(6(R)-2-oxo-piperidin-6-yl-methyl)]-amide hydrochloride, 5(S)-amino-4(S)-hydroxy-2(S)-7(S)-diisopropyl-8-[4-methoxy-3-(3-methoxy-propyloxy)-phenyl]-octanoic acid [N-(2-thiazol-2-yl-ethyl)]-amide dihydrochloride, 5(S)-amino-4(S)-hydroxy-2(S)-7(S)-diisopropyl-8-[4-methoxy-3-(3-methoxy-propyloxy)-phenyl]-octanoic acid [N-(4(S)-2-oxazolidinon-4-yl-methyl)]-amide hydrochloride, 5(S)-amino-4(S)-hydroxy-2(S)-7(S)-diisopropyl-8-[4-methoxy-3-(3-methoxy-propyloxy)-phenyl]-octanoic acid [N-(4(R)-2-oxazolidinon-4-yl-methyl)]-amide hydrochloride, 5(S)-amino-4(S)-hydroxy-2(S)-7(S)-diisopropyl-8-[4-methoxy-3-(3-methoxy-propyloxy)-phenyl]-octanoic acid [N-(3(S)-2,5-dioxo-pyrrolidin-3-yl-methyl)]-amide hydrochloride, 5(S)-amino-4(S)-hydroxy-2(S)-7(S)-diisopropyl-8-[4-methoxy-3-(3-methoxy-propyloxy)-phenyl]-octanoic acid [N-(3(R)-2,5-dioxo-pyrrolidin-3-yl-methyl)]-amide hydrochloride, 5(S)-amino-4(S)-hydroxy-2(S)-7(S)-diisopropyl-8-[4-methoxy-3-(3-methoxy-propyloxy)-phenyl]-octanoic acid [N-(2,6-dioxo-piperidin-4-yl-methyl)]-amide hydrochloride, or 5(S)-amino-4(S)-hydroxy-2(S)-7(S)-diisopropyl-8-[4-methoxy-3-(3-methoxy-propyloxy)-phenyl]-octanoic acid [N-(4(S)-2-oxothiazolidin-4-yl-methyl)]-amide hydrochloride.

EXAMPLE 79

In a manner analogous to that described in Examples 1 to 46 or 62 to 180 it is also possible to prepare 5(S)-amino-4(S)-hydroxy-2(S)-7(S)-diisopropyl-8-[3-(3-methoxypropoxy)-4,5-ethylene-dioxy-phenyl]-octanoic acid N-(2-carbamoyl-2,2-dimethyl-ethyl)-amide, 5(S)-amino-4(S)-hydroxy-2(S)-7(S)-diisopropyl-8-[4-methoxy-3-(3-methoxy-propyloxy)-phenyl]-octanoic acid [N-(4(R)-2-oxothiazolidin-4-yl-methyl)]-amide hydrochloride, 5(S)-amino-4(S)-hydroxy-2(S)-7(S)-diisopropyl-8-[4-methoxy-3-(3-methoxy-propyloxy)-phenyl]-octanoic acid [N-(tetrahydro-2-pyrimidon-5-yl-methyl)]-amide hydrochloride, 5(S)-amino-4(S)-hydroxy-2(S)-7(S)-diisopropyl-8-[4-methoxy-3-(3-methoxy-propyloxy)-phenyl]-octanoic acid [N-(N-acetyl-2-amino-2-methyl-propyl)]-amide hydrochloride, 5(S)-amino-4(S)-hydroxy-2(S)-7(S)-diisopropyl-8-[4-methoxy-3-(3-methoxy-propyloxy)-phenyl]-octanoic acid [N-(N-formyl-2-amino-2-methyl-propyl)]-amide hydrochloride, 5(S)-amino-4(S)-hydroxy-2(S)-7(S)-diisopropyl-8-[4-methoxy-3-(3-methoxy-propyloxy)-phenyl]-octanoic acid [N-(4-acetyl-piperazinyl-ethyl)]-amide hydrochloride, 5(S)-amino-4(S)-hydroxy-2(S)-7(S)-diisopropyl-8-[4-methoxy-3-(3-methoxy-propyloxy)-phenyl]-octanoic acid [N-(2,4-imidazolinedion-5-yl-methyl)]-amide hydrochloride, 5(S)-amino-4(S)-hydroxy-2(S),7(S)-diisopropyl-8-[4-methoxy-3-(4-methoxy-butyl)-phenyl]-octanoic acid [N-(2-hydroxy-pyridin-6-yl-methyl)]-amide hydrochloride, 5(S)-amino-4(S)-hydroxy-2(S)-7(S)-diisopropyl-8-[4-methoxy-3-(3-methoxy-propyloxy)-phenyl]-octanoic acid [N-(2,2-dimethyl-2-sulfamoyl-ethyl)]-amide hydrochloride, 5(S)-amino-4(S)-hydroxy-2(S)-7(S)-diisopropyl-8-[4-methoxy-3-(3-methoxy-propyloxy)-phenyl]-octanoic acid [N-(2,2-dimethyl-2-(N,N-dimethyl)-sulfamoyl-ethyl)]-amide hydrochloride, 5(S)-amino-4(S)-hydroxy-2(S)-7(S)-diisopropyl-8-[4-methoxy-3-(3-methoxy-propyloxy)-phenyl]-octanoic acid [N-(2-oxo-piperidin-3(R)-yl)]-amide hydrochloride, 5(S)-amino-4(S)-hydroxy-2(S)-7(S)-diisopropyl-8-[4-methoxy-3-(3-methoxy-propyloxy)-phenyl]-octanoic acid [N-(2-oxo-piperidin-3(S)-yl)]-amide hydrochloride, 5(S)-amino-4(S)-hydroxy-2(S)-7(S)-diisopropyl-8-[4-methoxy-3-(3-methoxy-propyloxy)-phenyl]-octanoic acid [N-(2-oxo-piperidin-4-yl)]-amide hydrochloride, 5(S)-amino-4(S)-hydroxy-2(S)-7(S)-diisopropyl-8-[4-methoxy-3-(3-methoxy-propyloxy)-phenyl]-octanoic acid [N-(N-acetyl-piperidin-4-yl)]-amide hydrochloride, or 5(S)-amino-4(S)-hydroxy-2(S)-7(S)-diisopropyl-8-[4-methoxy-3-(4-methoxy-but-1en-yl)-phenyl]-octanoic acid [N-(2-carbamoyl-2,2-dimethyl-ethyl)]-amide hydrochloride.

EXAMPLE 80

5(S)-Amino-4(S)-hydroxy-2(S),7(S)-diisopropyl-8-[4-methoxy-3-(3-methoxypropyloxy)-phenyl]-octanoic acid (N-butyl)amide hydrochloride Analogously to Example 1, the title compound is prepared starting from 82 mg of 5(S)-tert-butoxycarbonylamino-4(S)-hydroxy-2(S)-7(S)-diisopropyl-8-[4-(4-methoxy-3-(3-methoxy-propyloxy)-phenyl]-octanoic acid (N-butyl)amide. This yields the title compound: $R_f$(dichloromethane/methanol=9:1)=0.32; HPLC $R_t(I)$=42.32 minutes; FAB-MS $(M+H)^+$=509.

The starting material is prepared analogously to Examples 206a) and 200b) from 3-tert-butoxycarbonyl-5(S)-[2(S)-carboxy-3-methyl-butyl]-4(S)-{2(S)-isopropyl-3-[4-methoxy-3-(3-methoxypropyloxy)-phenyl]-propyl}-2,2-dimethyl-1,3-oxazolidine (Example 200c) and n-butylamine.

EXAMPLE 81

5(S)-Amino-4(S)-hydroxy-2(S),7(S)-diisopropyl-8-[4-methoxy-3-(2-methoxymethoxyethyl)-phenyl]-octanoic acid (N-butyl)amide 50 mg of 5(S)-azido-4(S)-hydroxy-8(R,S)-isobutyroxy-2(S),7(S)-diisopropyl-8-[4-methoxy-3-(2-methoxymethoxyethyl)-phenyl]-octanoic acid (N-butyl) amide are hydrogenated in 10 ml of methanol in the presence of 50 mg of 10% Pd/C at room temperature and under normal pressure. The reaction mixture is filtered and concentrated by evaporation. The residue is purified by means of FC (2 g of silica gel, dichloromethane/methanol=9:1). The title compound is obtained: $R_f$(dichloromethane/methanol=9:1)=0.19; HPLC $R_t$=13.42 minutes; FAB-MS $(M+H)^+$=509.

The starting material is prepared as follows:

a) 2-(2-Hydroxyethyl)-anisole

To a solution of 10 g of 2-(2-hydroxyphenyl)-ethanol in 200 ml of acetone there are added 35.3 g of $Cs_2CO_3$ and then a solution of 6.5 ml of methyl iodide in 40 ml of acetone. The reaction mixture is stirred for 50 minutes at room temperature, is filtered and is concentrated by evaporation. The residue is partitioned between diethyl ether and water. The organic phases are combined, dried over magnesium sulfate and concentrated by evaporation, and the residue is purified by means of FC (dichloromethane/diethyl ether=

97:3), yielding the title compound: $R_f$(dichloromethane/ diethyl ether=97:3)=0.34; HPLC $R_t$=9.31 minutes.

b) 4-Bromo-2-(2-hydroxyethyl)-anisole 35.72 g of tetrabutylammonium tribromide are added in portions to a solution of 10.7 g of 2-(2-hydroxyethyl)-anisole in 195 ml of dichloromethane and 130 ml of methanol. The reaction mixture is stirred for 150 minutes at room temperature and is then concentrated by evaporation in a rotary evaporator. The residue is partitioned between diethyl ether and water. The organic phases are combined, dried over magnesium sulfate and concentrated by evaporation, and the residue is purified by means of FC (dichloromethane), yielding the title compound: $R_f$(dichloromethane)=0.26; HPLC $R_t$=13.04 minutes.

c) 4-Bromo-2-(2-methoxymethoxy-ethyl)-anisole 1.48 g of N-ethyl-diisopropylamine and 0.49 g of chlorodimethyl ether are added at room temperature to a solution of 948 mg of 4-bromo-2-(2-hydroxyethyl)-anisole in 30 ml of dichloromethane. The reaction mixture is stirred for 200 minutes at room temperature, and then 1 ml of water and 1 ml of 25% ammonium hydroxide solution are added thereto. The two-phase mixture is stirred vigorously for a further 15 minutes and then the organic phase is separated off, dried over sodium sulfate and concentrated by evaporation. Purification of the residue by means of FC (hexane/ dichloromethane=1:1) yields the title compound: $R_f$(dichloromethane)=0.6; HPLC $R_t$=17.33 minutes.

d) 3(S)-Isopropyl-5(S)-{1 (S)-azido-3(S)-isopropyl-4(R,S)-hydroxy-4-[4-methoxy-3-(2-methoxymethoxyethyl)-phenyl]-butyl}-tetrahydrofuran-2-one Several iodine crystals are added to a suspension of 763 mg of magnesium chips in 0.5 ml of tetrahydrofuran, and the mixture is activated in an ultrasound bath for 30 minutes. Then 4 drops of 1,2-dibromoethane and then a solution of 8.64 g of 4-bromo-2-(2-methoxymethoxyethyl)-anisole in 30 ml of tetrahydrofuran are added dropwise in such a manner that the reaction mixture boils under reflux. When the addition is complete, the mixture is maintained under reflux for a further one hour. The reaction mixture is then added dropwise within a period of 45 minutes, with stirring, to a solution, cooled to –75° C., of 2.85 g of 3(S)-isopropyl-5(S)-[1(S)-azido-3(S)-isopropyl-4-oxobutyl]-tetrahydrofuran-2-one in 20 ml of tetrahydrofuran. The reaction mixture is stirred for a further 150 minutes at –75° C., and there are then added thereto, at the same temperature, a solution of 1.4 ml of glacial acetic acid in 1 ml of tetrahydrofuran and then 25 ml of saturated ammonium chloride solution. The reaction mixture is then brought to room temperature, poured onto 60 ml of water and extracted three times with 100 ml of ethyl acetate. The organic phases are washed with 50 ml of saturated sodium chloride solution, combined, dried over magnesium sulfate and concentrated by evaporation. Purification of the residue by means of FC (400 g of silica gel, hexane/ethyl acetate=8:2) yields the title compound: $R_f$(hexane/ethyl acetate=7:3)=0.25; HPLC $R_t$=48.10 and 50.29 minutes (diastereoisomeric mixture).

e) 3(S)-Isopropyl-5 (S)-{1 (S)-azido-3(S)-isopropyl-4(R,S)-isobutyryloxy-4-[4-methoxy-3-(2-methoxymethoxyethyl)-phenyl]-butyl}-tetrahydrofuran-2-one 0.25 ml of pyridine, 0.31 ml of isobutyric acid anhydride and 15 mg of dimethylaminopyridine are added to a solution of 300 mg of 3(S)-isopropyl-5(S)-{1(S)-azido-3(S)-isopropyl-4(R,S)-hydroxy-4-[4-methoxy-3-(2-methoxymethoxyethyl)-phenyl]-butyl}-tetrahydrofuran-2-one in 3.5 ml of dichloromethane, and the mixture is stirred for 80 hours at room temperature. The reaction mixture is then partitioned between dichloromethane (3x), water (1x) and saturated sodium chloride solution (2x). The combined organic phases are dried over magnesium sulfate and concentrated by evaporation, and the residue is purified by FC (30 g of silica gel, hexane/ethyl acetate=8:2), yielding the title compound: $R_f$(hexane/ethyl acetate=8:2)=0.26; HPLC $R_t$=21.38 minutes and 21.76 minutes (diastereoisomeric mixture).

f) 5(S)-Azido-4(S)-hydroxy-2(S),7(S)-diisopropyl-8(R,S)-isobutyryloxy-8-[4-methoxy-3-(2-methoxymethoxyethyl)-phenyl]-octanoic acid (N-butyl)-amide A solution of 170 mg of 3(S)-isopropyl-5(S)-{1(S)-azido-3(S)-isopropyl-4(R,S)-isobutyryloxy-4-[4-methoxy-3-(2-methoxymethoxyethyl)-phenyl]-butyl}-tetrahydrofuran-2-one in 1.4 ml of butylamine is stirred for 16 hours at room temperature and is then concentrated by evaporation. Purification of the residue by means of FC (hexane/ethyl acetate=7:3) yields the title compound: $R_f$(hexane/ethyl acetate=7:3)=0.25; HPLC $R_t$=20.38 and 20.8 minutes (diastereoisomeric mixture).

The 3(S)-isopropyl-5(S)-[1(S)-azido-3(S)-isopropyl-4-oxo-butyl]-tetrahydrofuran-2-one used in step d) is prepared as follows:

g) 2(S),7(S)-Diisopropyl-oct-4-ene-dicarboxylic acid [bis( [4(S)-benzyl-oxazolidin-2-one)]-amide 48 ml of a 1.0M solution of lithium hexamethyldisilazide in tetrahydrofuran are added dropwise, with stirring, at –75° C., within a period of one hour, to a solution of 11.5 g of 4(S)-benzyl-3-isovaleroyl-oxazolidin-2-one in 32 ml of tetrahydrofuran. The mixture is stirred further for 2 hours at –75° C. and for 20 minutes at –20° C., and there are then added thereto 10 ml of 1,3-dimethyl-3,4,5,6-tetrahydro-2-(1H)-pyrimidone (DMPU) and, within a period of 45 minutes, a solution of 4.28 g of 1,4-dibromo-2-butene in 10 ml of tetrahydrofuran. The reaction mixture is stirred for a further 15 hours at –20° C. and is then brought to 0° C. within a period of one hour; 10 ml of saturated ammonium chloride solution are then added thereto at –20° C. and, after 15 minutes, the mixture is brought to room temperature. The reaction mixture is then partitioned between dichloromethane and saturated sodium chloride solution/water= 1:1. The organic phases are combined, dried over sodium sulfate and concentrated by evaporation, and the residue is purified by means of FC (hexane/ethyl acetate=4:1), yielding the title compound: $R_f$(hexane/ethyl acetate=4: 1)=0.30; HPLC $R_t$=21.6 minutes; FAB-MS $(M+H)^+$=575; m.p.= 110°–111° C. (crystallised from ethyl acetate/hexane).

h) 3(S)-Isopropyl-5(S)-{1(R)-bromo-4-methyl-3-(S)-[(4(S)-benzyloxazolidin-2-on-3-yl)-carbonyl]-pentyl}-tetrahydrofuran-2-one 10.5 g of N-bromosuccinimide are added, with stirring, to a solution of 30 g of 2(S),7(S)-diisopropyl-oct-4-ene-dicarboxylic acid [bis(4(S)-benzyl-oxazolidin-2-one)]-amide in 360 ml of tetrahydrofuran and 120 ml of water, the temperature being maintained at room temperature with an ice-bath. The reaction mixture is stirred for a further 2 hours at room temperature, and then the tetrahydrofuran is evaporated off in a rotary evaporator. The aqueous residue is partitioned between diethyl ether (2×200 ml), water (2×50 ml) and saturated sodium chloride solution (1×50 ml). The organic phases are combined, dried over magnesium sulfate and concentrated by evaporation, and the residue is purified by means of FC (90 g of silica gel, hexane/ethyl acetate= 3:1), yielding the title compound in the form of a crude product. Crystallisation from diisopropyl ether yields the pure compound: m.p.=91°–92° C.; $R_f$(hexane/ethyl acetate= 8:2)=0.28; HPLC $R_t$=19.53 minutes; FAB-MS $(M+H)^+$= 494.

i) 3(S)-Isopropyl-5(S)-{1(S)-azido-4-methyl-3(S)-[(4(S)-benzyl-oxazolidin-2-on-3-yl)-carbonyl]-pentyl}-tetrahydrofuran-2-one 13.6 g of freshly dried tetrabutylammonium azide are added to a solution, stirred at room temperature, of 17.8 g of 3(S)-isopropyl-5(S)-{1(R)-bromo-4-methyl-3(S)-[(4(S)-benzyloxazolidin-2-on-3-yl)-carbonyl]-pentyl}-tetrahydrofuran-2-one in 180 ml of toluene, and a further 10 g of the azide are added in the course of 160 hours' stirring at room temperature. The reaction mixture is then partitioned between ethyl acetate and water (2x) and saturated sodium chloride solution (1x). The organic phases are combined, dried over sodium sulfate and concentrated. The title compound is obtained from the evaporation residue by means of FC (hexane/ethyl acetate=8:2) and crystallisation from diethyl ether/hexane: m.p.=102°–103° C.; $R_f$(hexane/ethyl acetate=8:2)=0.2; HPLC $R_f$=18.55 minutes; FAB-MS (M+H)+=457.

k) 3(S)-Isopropyl-5(S)-(1 (S)-azido-3(S)-carboxy-4-methylpentyl)-tetrahydrofuran-2-one 175 ml of water, 74 ml of 30% hydrogen peroxide solution and 5.9 g of lithium hydroxide are slowly added in succession to a solution, stirred at −5° C., of 55.3 g of 3(S)-isopropyl-5(S)-{1(S)-azido-4-methyl-3(S)-[(4(S)-benzyl-oxazolidin-2-on-3-yl)-carbonyl]-pentyl}-tetrahydrofuran-2-one in 500 ml of tetrahydrofuran. The reaction mixture is stirred for one hour at 5° C. and for 150 minutes at room temperature, and then 750 ml of aqueous 1M sodium sulfite solution are added at 3° C. over a period of 30 minutes and the mixture is stirred for a further 30 minutes at room temperature. The reaction mixture is then freed of tetrahydrofuran by concentration, and the aqueous solution is washed three times with 1200 ml of ethyl acetate, the organic phases being back-extracted three times with 100 ml of 0.1N sodium hydroxide. The combined aqueous phases are adjusted to pH 1–2 with approximately 200 ml of 4N hydrochloric acid and are extracted with 3×1200 ml of ethyl acetate. The organic phases are combined, dried over magnesium sulfate and concentrated by evaporation, yielding the crude product which, for the purpose of cyclisation of the opened lactone, is dissolved in 500 ml of toluene and stirred for 2 hours at 50° C. with approximately 1 g of molecular sieve and approximately 1 g of p-toluenesulfonic acid. Filtration, concentration by evaporation and purification of the residue by means of FC (hexane/ethyl acetate/glacial acetic acid=30:60:1) yield the title compound, which crystallises spontaneously: m.p.=56°–58° C.; $R_f$(hexane/ethyl acetate/glacial acetic acid =30:60:1)=0.62; HPLC $R_f$=14.46 minutes; FAB-MS (M+H)+=298.

l) 3(S)-Isopropyl-5(S)-(1(S)-azido-3(S)-isopropyl-4-oxo-butyl)-tetrahydrofuran-2-one 1.45 ml of oxalyl chloride are added dropwise at 0° C., with stirring, within a period of 10 minutes, to a solution of 1.7 g of 3(S)-isopropyl-5(S)-(1(S)-azido-3(S)-carboxy-4-methyl-pentyl)-tetrahydrofuran-2-one in 20 ml of toluene. 0.03 ml of dimethylformamide is then added, and the temperature is then increased to 37° C. within a period of 30 minutes. The reaction mixture is stirred for 2 hours at 37° C. and is then clarified by filtration and concentrated by evaporation under reduced pressure at a bath temperature of 30° C. The residue is twice dissolved in 10 ml of toluene and concentrated by evaporation again in the same manner. The crude acid chloride so obtained is dissolved in 5 ml of tetrahydrofuran, and 16 ml of a 0.34M solution of NaAlH (O-tert-bu)₃in diglyme (H. C. Brown et al., J. Org. Chem. (1992) 58.472) are added thereto at −75° C. within a period of 30 minutes. The reaction mixture is stirred for 70 minutes at −75° C., and then a solution of 0.385 ml of glacial acetic acid in 1 ml of tetrahydrofuran is added dropwise at the same temperature, followed by 2.1 ml of saturated NH₄Cl solution and then 20 ml of diethyl ether. The reaction mixture is brought to room temperature and is partitioned between diethyl ether and water/saturated sodium chloride solution. The organic phases are combined, dried over magnesium sulfate and concentrated by evaporation, and the residue is purified by means of FC (hexane/ethyl acetate=95:5), yielding the title compound: $R_f$(hexane/ethyl acetate=2:1)=0.55; HPLC $R_f$=16.41 minutes.

EXAMPLE 82

5(S)-Amino-4(S)-hydroxy-2(S),7(S)-diisopropyl-8-[4-(3-hydroxy-propyloxy)-3-(3-methoxypropyloxy)-phenyl]-octanoic acid N-(2-morpholinoethyl)amide hydrochloride 30 mg of 5(S)-tert-butoxycarbonylamino-4(S)-hydroxy-2 (S),7(S)-diisopropyl-8-[4-(3-hydroxypropyloxy)-3-(3-methoxypropyloxy)-phenyl]-octanoic acid (N-2-morpholinoethyl)amide are dissolved in 1.5 ml of a 4N solution, cooled to 0° C., of hydrochloric acid in dioxane, and the mixture is then stirred for 10 minutes at 0° C. The reaction mixture is concentrated to dryness by evaporation under reduced pressure and at room temperature. Purification of the residue by means of FC (5 g of silica gel, dichloromethane/methanol=98:2) yields the title compound:$R_f$(dichloromethane/methanol=8:2)=0.20; $R_f$=10.43 minutes; FAB-MS (M+H)+=610.

The starting material is prepared as follows:
a) 2-(3-Methoxypropyloxy)-phenol

A solution of 22 g of pyrocatechol in 80 ml of dimethylformamide is added at room temperature, within a period of 30 minutes, to a suspension of 8.4 g of NaH (60% dispersion in mineral oil) in 300 ml of dimethylformamide, and the mixture is stirred for one hour at room temperature. A solution of 49.3 g of 3-bromopropyl methyl ether in 80 ml of dimethylformamide is then added dropwise. The reaction mixture is stirred for a further 80 hours at room temperature and is then concentrated by evaporation under reduced pressure at a bath temperature of 30° C. The residue is partitioned between diethyl ether and water. The combined organic phases are dried over magnesium sulfate and concentrated by evaporation, and the residue is purified by FC (100 g of silica gel, hexane/dichloromethane=5:95), yielding the title compound: $R_f$(dichloromethane/diethyl ether=96:4) =0.35; HPLC $R_f$=11.2 minutes.

b) 4-Bromo-2-(3-methoxypropyloxy)-phenol 6.9 g of tetrabutylammonium tribromide are added in portions, at room temperature, to a solution of 2.6 g of 2-(3-methoxypropyloxy)-phenol in 60 ml of dichloromethane and 40 ml of methanol, and the mixture is then stirred for 30 minutes. The reaction mixture is concentrated by evaporation and the residue is partitioned between diethyl ether and water. The combined organic phases are dried over magnesium sulfate and concentrated by evaporation, and the residue is purified by FC (700 g of silica gel, dichloromethane/diethyl ether=98:2), yielding the title compound: $R_f$(dichloromethane/diethyl ether=97:3)=0.50; HPLC $R_f$=14.32 minutes; FAB-MS (M+H)+=262.

c) 4-(3-Benzyloxypropyloxy)-3-(3-methoxypropyloxy)-bromobenzene

A mixture of 4 g of 4-bromo-2-(3-methoxypropyloxy)-phenol, 2.3 g of potassium carbonate, 3.8 g of benzyl (3-bromopropyl) ether, a spatula tip of NaI and 15 ml of acetonitrile is stirred under reflux for 30 hours. The reaction mixture is filtered and the filtrate is concentrated by evaporation. The residue is partitioned between ethyl acetate and water. The organic phases are combined, dried over magnesium sulfate and concentrated by evaporation, and the residue is purified by means of FC (hexane/ethyl acetate= 95:5), yielding the title compound: $R_f$(hexane/ethyl acetate= 9:1)=0.15; HPLC $R_t$=20.66 minutes.

d) 3(S)-Isopropyl-5(S)-{1(S)-azido-3(S)-isopropyl-4(R,S)-hydroxy-4-[4-(3-benzyloxypropyloxy)-3-(3-methoxypropyloxy)-phenyl]-butyl}-tetrahydrofuran-2-one 1.3 ml of a 0.9M solution of butyllithium in hexane are slowly added dropwise to a solution, stirred at −75° C., of 500 mg of 4-(3-benzyloxypropyloxy)-3-(3-methoxypropyloxy)-bromobenzene in 2 ml of tetrahydrofuran. The reaction mixture is stirred for 20 minutes at −75° C., and then a suspension of magnesium bromide, freshly prepared from 44.5 mg of magnesium powder and 0.158 ml of 1,2-dibromoethane in 3 ml of tetrahydrofuran at room temperature, is added dropwise. The reaction mixture is stirred for a further 30 minutes at −75° C., and then a solution of 172 mg of 3(S)-isopropyl-5(S)-[1(S)-azido-3(S)-isopropyl-4-oxo-butyl]-tetrahydrofuran-2-one in 2 ml of tetrahydrofuran is added dropwise. The mixture is again stirred for 30 minutes at −75° C., and then 1.2 ml of saturated ammonium chloride solution are added dropwise at the same temperature. The reaction mixture is brought to room temperature and is then extracted three times with ethyl acetate. The organic phases are washed with water (2x) and saturated sodium chloride solution (1x), dried over magnesium sulfate, combined and concentrated by evaporation, and the residue is purified by means of FC (2×30 g of silica gel, hexane/ethyl acetate=6:2), yielding the title compound: $R_f$(hexane/ethyl acetate=2: 1)=0.23; HPLC $R_t$=20.27 and 21.07 minutes (diastereoisomeric mixture); FAB-MS M⁺=611.

e) 3(S)-Isopropyl-5(S)-{1 (S)-azido-3(S)-isopropyl-4(R,S)-acetoxy-4-[4-(3-benzyloxypropyloxy)-3-(3-methoxypropyloxy)-phenyl]-butyl}-tetrahydrofuran-2-one A solution of 144 mg of 3(S)-isopropyl-5(S)-{1(S)-azido-3(S)-isopropyl-4(R,S)-hydroxy-4-[4-(3-benzyloxypropyloxy)-3-(3-methoxypropyloxy)-phenyl]-butyl}-tetrahydrofuran-2-one in 1.8 ml of acetic anhydride and 0.057 ml of pyridine is stirred for 30 hours at room temperature and is then concentrated to dryness by evaporation at room temperature and under reduced pressure. The residue is partitioned between dichloromethane (3x) and water/saturated sodium chloride solution (3x). The organic phases are combined, dried over magnesium sulfate and concentrated by evaporation, and the residue is purified by means of FC (hexane/ethyl acetate=4:1), yielding the title compound: $R_f$(hexane/ethyl acetate=2:1)=0.38 and 0.33; HPLC $R_t$=21.76 and 21.82 minutes (diastereoisomeric mixture); FAB-MS M⁺=653, (M+Na)⁺=676.

f) 3(S)-Isopropyl-5(S)-{1(S)-amino-3(S)-isopropyl-4-[4-(3-hydroxypropyloxy)-3-(3-methoxypropyloxy)-phenyl]-butyl}-tetrahydrofuran-2-one A solution of 15 1 mg of 3(S)-isopropyl-5(S)-{1(S)-azido-3(S)-isopropyl-4(R,S)-acetoxy-4-[4-(3-benzyloxypropyloxy)-3-(3-methoxypropyloxy)-phenyl]-butyl}-tetrahydrofuran-2-one in 10 ml of ethanol is hydrogenated under normal pressure and at room temperature in the presence of 70 mg of PdO for 170 hours. The reaction mixture is faltered and concentrated by evaporation, and the residue is dissolved in 10 ml of ethanol and is again hydrogenated for 24 hours in the presence of 140 mg of PdO under normal pressure and at room temperature. Filtration and concentration by evaporation yield the title compound in the form of a crude product: $R_f$(dichloromethane/methanol) =0.32; HPLC $R_t$=11.72 minutes; FAB-MS (M+H)⁺=480. The compound is used in the next step without being purified.

g) 3(S)-Isopropyl-5(S)-{1 (S)-tert-butoxycarbonylamino-3 (S)-isopropyl-4-[4-(3-hydroxy-propyloxy)-3-(3-methoxypropyloxy)-phenyl]-butyl}-tetrahydrofuran-2-one To a solution, stirred at 0° C., of 106 mg of 3(S)-isopropyl-5(S)-{1(S)-amino-3(S)-isopropyl-4-[4-(3-hydroxy-propyloxy)-3-(3-methoxypropyloxy)-phenyl]-butyl}-tetrahydrofuran-2-one in 4.5 ml of dichloromethane there are added dropwise a solution of 0.07 ml of N-ethyldiisopropylamine in 0.1 ml of dichloromethane and then a solution of 77 mg of di-tert-butyl dicarbonate in 0.4 ml of dichloromethane. The reaction mixture is then brought to room temperature, is stirred at room temperature for 20 hours and is then concentrated to dryness by evaporation. Purification of the residue by means of FC (50 g of silica gel, dichloromethane/methanol=98:2) yields the title compound: $R_f$(dichloromethane/methanol=95:5)=0.34; HPLC $R_t$=19.07 minutes; FAB-MS M⁺=579, (M+Na)⁺=602.

h) 5(S)-Tert-butoxycarbonylamino-4(S)-hydroxy-2(S)-7(S)-diisopropyl-8-[4-(3-hydroxypropyloxy)-3-(3-methoxypropyloxy)-phenyl]-octanoic acid (N-2-morpholinoethyl)amide A mixture of 84 mg of 3(S)-isopropyl-5(S)-{1(S)-tert-butoxycarbonylamino- 3(S)-isopropyl-4-[4-(3-hydroxypropyloxy)-3-(3-methoxypropyloxy)-phenyl]-butyl}-tetrahydrofuran-2-one, 0.6 ml of 4-(2-aminoethyl)-morpholine and 0.025 ml of glacial acetic acid is stirred for 16 hours at room temperature and for 6 hours at 45° C. and is then partitioned between diethyl ether (2x) and saturated NaHCO₃ solution (1x) and water (2x). The organic phases are combined, dried over magnesium sulfate and concentrated by evaporation, and the residue is purified by means of FC (5 g of silica gel, dichloromethane/methanol=98:2), yielding the title compound: $R_f$(dichloromethane/methanol= 95:5)=0.16; HPLC $R_t$=14.49 minutes; FAB-MS (M+H)⁺= 710.

EXAMPLE 83

5(S)-Amino-4(S)-hydroxy-2(S),7(S)-diisopropyl-8-[4-methoxy-3-(3-methoxypropyloxy)-phenyl]-octanoic acid N-(2-carbamoyl-2,2-dimethyl-ethyl)-amide semifumarate 20 g of ice and 12 ml of 2N NaOH are added in succession to a stirred solution of 2.35 g of 5(S)-amino-4(S)-hydroxy-2(S),7(S)-diisopropyl-8-[4-methoxy-3-(3-methoxypropyloxy)-phenyl]-octanoic acid N-(2-carbamoyl-2,2-dimethyl-ethyl)-amide hydrochloride (Example 137) in 20 ml of water, and the mixture is then extracted with 3×50 ml of tertbutyl methyl ether. The combined organic phases are dried With magnesium sulfate and concentrated by evaporation. 0.232 g of fumaric acid is added to the evaporation residue in 25 ml of methanol. The mixture is stirred until a clear solution has formed and is then concentrated by evaporation. The residue is crystallised from 100 ml of acetonitrile/ethanol=95:5. The crystals are filtered off with suction and dried at 60° C. The title compound is obtained in the form of a white powder having a melting point of 95°–104° C.

EXAMPLE 84

5(S)-Amino-2(S),7(S)-diisopropyl-4(S)-hydroxy-8-[4-tert-butyl-3-(3-methoxypropoxyl)-phenyl]-octanoic acid [N-2-(morpholin-4-yl)-ethyl]-amide dihydro-chloride A 4N hydrochloric acid solution in dioxane (20 ml) is added at 0–5° C. to 768 mg of 5(S)-tertbutoxycarbonylamino-4(S)-hydroxy-2(S)-7(S)-diisopropyl-8-[4-tert-butyl-3-(3-methoxypropoxy)-phenyl]-octanoic acid [N-2-(morpholin-4-yl)-ethyl]-amide, and the mixture is then stirred for one hour. The solvent is then removed by lyophilisation under a high vacuum, the residue is dissolved in anhydrous dichloromethane and filtered over cotton wool, and the filtrate is concentrated. A small amount of 4N hydrochloric acid in dioxane is again added to the residue, the resulting solution is lyophilised, and the residue is dried under a high vacuum. The title compound is obtained in the form of a white amorphous solid: $R_f$(dichloromethane/methanol/conc. ammonia=9:1:0.1)=0.23; HPLC $R_t$=14.5 minutes; FAB-MS (M+H)$^+$=592.

The starting materials are prepared as follows:

a) 5(S)-Tert-butoxycarbonylamino-4(S)-hydroxy-2(S)-7(S)-diisopropyl-8-[4-tert-butyl-3-(3-methoxypropoxy)-phenyl]-octanoic acid [N-2-(morpholin-4-yl)-ethyl]-amide A solution of 756 mg of 3(S)-isopropyl-5(S)-{1(S)-tert-butoxycarbonylamino-3(S)-isopropyl-4-[4-tert-butyl-3-(3-methoxypropoxy)-phenyl]-butyl}-tetrahydrofuran-2-one in 4 ml of 4-(2-aminoethyl)-morpholine and 0.23 ml of glacial acetic acid is stirred for 4 hours at 65° C. and is then concentrated by evaporation. The residue is partitioned between diethyl ether (30 ml) and a saturated sodium hydrogen carbonate solution (10 ml), the aqueous phase is extracted with diethyl ether (2×30 ml), and the combined organic phases are dried over magnesium sulfate and concentrated. Purification of the residue by means of FC (70 g of silica gel, dichloromethane/methanol/conc. ammonia=98:2:1 after 96:4:1) yields the title compound in the form of a white foam: $R_f$(dichloromethane/methanol/conc. ammonia=9:1:0.1)=0.43; HPLC $R_t$=19.8 minutes.

b) 3(S)-Isopropyl-5(S)-{1(S)-tert-butoxycarbonylamino-3(S)Isopropyl-4-[4-tert-butyl-3-(3-methoxypropoxy)-phenyl]-butyl}-tetrahydrofuran-2-one A solution of 1.24 g of 3(S)-isopropyl-5(S)-{4(R,S)-acetoxy-1(S)-azido-3(S)-isopropyl-4(R,S)-[4-tert-butyl-3-(3-methoxypropoxy)-phenyl]-butyl}-tetrahydrofuran-2-one in 25 ml of ethanol is hydrogenated for a period of 28 hours in the presence of 2.4 g of 5% PdO/C (Engelhardt) at room temperature and under normal pressure. The reaction mixture is filtered over Celite 545 and washed with ethanol, and the residue obtained after concentration is dried under a high vacuum. The product so obtained (843 mg) is dissolved in 20 ml of dichloromethane, and 0.58 ml of N-diisopropylethylamine and a solution of 638 mg of di-tert-butyl dicarbonate in 5 ml of dichloromethane are added thereto in succession at 0°–5° C. The mixture is stirred at room temperature overnight, and then the solvent is removed in vacuo and the crude product is purified by means of FC (60 g of silica gel, hexane/ethyl acetate/conc. ammonia=80:20:1). The title compound is obtained in the form of a colourless oil: $R_f$(hexane/ethyl acetate/conc. ammonia=50:50:1)=0.90; HPLC $R_t$=26.2 minutes.

c) 3(S)-Isopropyl-5(S)-{4(R,S)-acetoxy-1(S)-azido-3(S)-isopropyl-4(R,S)-[4-tert-butyl-3-(3-methoxypropoxy)-phenyl]-butyl}-tetrahydrofuran-2-one A mixture of 1.15 g of 3(S)-isopropyl-5(S)-{4(R,S)-hydroxy-1(S)-azido-3(S)-isopropyl-4(R,S)-[4-tert-butyl-3-(3-methoxypropoxy)-phenyl]-butyl}-tetrahydrofuran-2-one, 11 ml of acetic anhydride and 0.55 ml of pyridine is stirred overnight at room temperature. The reaction mixture is concentrated and the residue is partitioned between 100 ml of dichloromethane and 20 ml of water. The crude product obtained after working up by extraction is purified by FC (80 g of silica gel, hexane/ethyl acetate=2:1). The title compound is obtained in the form of a yellowish oil: $R_f$(hexane/ethyl acetate=2:1)=0.66.

d) 3(S)-Isopropyl-5(S)-{4(R,S)-hydroxy-1(S)-azido-3(S)-isopropyl-4(R,S)-[4-tert-butyl-3-(3-methoxypropoxy)-phenyl]-butyl}-tetrahydrofuran-2-one In a manner analogous to that described in Example 185c), 4-tert-butyl-3-(3-methoxy-propoxy)-bromobenzene (2.35 g), dissolved in 60 ml of tetrahydrofuran, is reacted with 4.86 ml of a 1N n-butyllithium solution (in hexane) and then with a suspension of magnesium bromide in 20 ml of tetrahydrofuran (prepared from 380 mg of magnesium powder and 1.35 ml of 1,2-dibromoethane in). A solution of 1.46 g of 3(S)-isopropyl-5(S)-[1(S)-azido-3(S)-isopropyl-4-oxobutyl]-tetrahydrofuran-2-one in 6 ml of tetrahydrofuran is added dropwise to the resulting suspension at −70° C. over a period of 20 minutes, and the mixture is then stirred for a further one hour. After working up by extraction, the crude product is purified by FC (300 g of silica gel, hexane/ethyl acetate=5:1 after 3:1). The title compound is obtained in the form of a pale yellow oil: $R_f$(hexane/ethyl acetate=2:1)= 0.57; HPLC $R_t$=22.9 and 24.1 minutes (diastereoisomeric mixture).

e) 4-Tert-butyl-3-(3-methoxypropoxy)-bromobenzene

A suspension of 2.60 g of 5-bromo-2-tert-butyl-phenol, 4.34 g of 3-methoxypropyl bromide and 5.55 g of caesium carbonate in 40 ml of acetone is stirred at 60° C. overnight. After cooling to room temperature, the mixture is filtered and the crude product obtained after concentration of the filtrate is purified by means of FC (80 g of silica gel, hexane/ethyl acetate=98:2). The title compound is obtained in the form of an oil: $R_f$(hexane/ethyl acetate=9:1)=0.56.

EXAMPLE 85

5(S)-Amino-4(S)-hydroxy-7(S)-isopropyl-2(R)-methyl-8-[4-methoxy-3-(3-methoxypropyloxy)-phenyl]-octanoic acid N-[2-(4-hydroxypiperidin-1-yl)ethyl]amide dihydrochloride 100 mg of 5(S)-tert-butoxycarbonylamino-4(S)-hydroxy-7(S)-isopropyl-2(R)-methyl-8-[4-methoxy-3-(3-methoxypropyloxy)-phenyl]-octanoic acid N-[2-(4-hydroxy-piperidin-1-yl)-ethyl]-amide are dissolved in 3 ml of 4N hydrochloric acid in dioxane at 0° C., and the mixture is stirred for 2 hours at 0° C. The reaction mixture is lyophilised and the title compound is obtained: $R_f$(dichloromethane/methanol=8:2)=0.08; HPLC $R_t$=8.85 minutes; FAB-MS (M+H)$^+$=552.

The starting material is prepared as follows:

a) 5(S)-Tert-butoxycarbonylamino-4(S)-hydroxy-7(S)-isopropyl-2(R)-methyl-8-[4-methoxy-3-(3-methoxypropyloxy)-phenyl]-octanoic acid N-[2-(4-hydroxypiperidin-1-yl)-ethyl]-amide 102 mg of 2-{1 (S)-tert-butoxycarbonylamino-3(S)-isopropyl-4-[4-methoxy-3-(3-methoxypropyloxy)-phenyl]-butyl}-4(R)-methyl-tetrahydrofuran-5-one (Example 105e) and 0.5 g of N-(2-aminoethyl)-4-hydroxypiperidine are stirred for 2 hours at 80° C. The reaction mixture is purified by means of FC (60 g of silica gel, dichloromethane/methanol=4:1). The title compound is obtained:$R_f$ (dichloromethane/methanol=4:1)=0.16.

EXAMPLE 86

5(S)-Amino-4(S)-hydroxy-7(S)-isopropyl-2-(R)-methyl-8-[4-methoxy-3-(3-methoxypropyloxy)-phenyl]-octanoic acid N-(2,2-dimethyl-2-morpholino-ethyl)amide dihydrochloride Analogously to Example 85, the title compound is obtained starting from 120 mg of 5(S)-tertbutoxycarbonylamino-4(S)-hydroxy-7(S)-isopropyl-2(R)-methyl-8-[4-methoxy-3-(3-methoxypropyloxy)-phenyl]-octanoic acid N-(2,2-dimethyl-2-morpholino-ethyl)-amide: $R_f$(dichloromethane/methanol=9:1)=0.07; HPLC $R_t$=9.22 minutes; FAB-MS (M+H)$^+$=566.

The starting material is prepared analogously to Example 85a) from 2-{1(S)-tert-butoxy-carbonylamino-3 (S)-isopropyl-4-[4-methoxy-3-(3-methoxypropyloxy)-phenyl]-butyl}-4(R)-methyl-tetrahydrofuran-5-one (Example 105e) and 4-(2-amino-1,1-dimethyl-ethyl)-morpholine.

EXAMPLE 87

5(S)-Amino-4(S)-hydroxy-7(S)-isopropyl-2(R)-methyl-8-[4-methoxy-3-(3-methoxypropyloxy)-phenyl]-octanoic acid N-[2-(trans-2,6-dimethyl-morpholino)-ethyl]amide dihydrochloride Analogously to Example 85, the title compound is obtained starting from 102 mg of 5(S)-tert-butoxycarbonylamino-4(S)-hydroxy-7(S)-isopropyl-2(R)-methyl-8-[4-methoxy-3-(3-methoxypropyloxy)-phenyl]-octanoic acid N-[2-(trans-2,6-dimethyl-morpholino)-ethyl] amide: $R_f$(dichloromethane/methanol=8:2)=0.27; HPLC $R_t$=9.56 minutes; FAB-MS (M+H)$^+$=566.

The starting material is prepared analogously to Example 85a) from 2-{1(S)-tert-butoxy-carbonylamino-3(S)-isopropyl-4-[4-methoxy-3-(3-methoxypropyloxy)-phenyl]-butyl}-4(R)-methyl-tetrahydrofuran-5-one (Example 105e) and 4-(2-aminoethyl)-trans-2,6-dimethyl-morpholine.

a) 4-(2-Amino-ethyl)-2,6-(trans)-dimethyl-morpholine 8.20 g of 4-(2-phthaloylaminoethyl)-trans-2,6-dimethyl-morpholine are stirred under reflux for 2 hours in 250 ml of ethyl alcohol with 2.76 ml of hydrazine hydrate. The reaction mixture is diluted with diethyl ether and then clarified by filtration. The filtrate is concentrated, yielding the crude title compound: $R_f$(dichloromethane/methanol/conc. ammonia=40:10:1)=0.21.

b) 4-(2-Phthaloylaminoethyl)-trans-2,6-dimethyl-morpholine 10.16 g of N-(2-bromoethyl)-phthalimide and 11.50 g of trans-2,6-dimethylmorpholine are stirred for 30 minutes at 130° C. The reaction mixture is then partitioned between ice-water and ethyl acetate. The organic phases are concentrated by evaporation and the residue is purified by means of FC (240 g of silica gel, ethyl acetate/hexane=1:2). The title compound is obtained: $R_f$(ethyl acetate/hexane=1:2)=0.39.

EXAMPLE 88

5(S)-Amino-4(S)-hydroxy-7(S)-isopropyl-2(R)-methyl-8-[4-methoxy-3-(3-methoxypropyloxy)-phenyl]-octanoic acid N-[2-(cis-2,6-dimethyl-morpholino)ethyl]-amide dihydrochloride Analogously to Example 85, the title compound is obtained starting from 97 mg of 5(S)-tert-butoxycarbonylamino-4(S)-hydroxy-7(S)-isopropyl-2(R)-methyl-8-[4-methoxy-3-(3-methoxypropyloxy)-phenyl]-octanoic acid N-[2-(cis-2,6-dimethyl-morpholino)-ethyl] amide: $R_f$(dichloromethane/methanol=8:2)=0.21; HPLC $R_t$=9.38 minutes; FAB-MS (M+H)$^+$=566.

The starting material is prepared analogously to Example 85a) from 2-{1(S)-tert-butoxy-carbonylamino-3(S)-isopropyl-4-[4-methoxy-3-(3-methoxypropyloxy)-phenyl]-butyl}-4(R)-methyl-tetrahydrofuran-5-one (Example 105e) and 4-(2-amino-ethyl)-cis-2,6-dimethyl-morpholine.

The 4-(2-amino-ethyl)-cis-2,6-dimethyl-morpholine is prepared analogously to Examples 87a) and 87 b) from cis-2,6-dimethylmorpholine.

EXAMPLE 89

5(S)-Amino-4(S)-hydroxy-7(S)-isopropyl-2(R)-methyl-8-[4-methoxy-3-(3-methoxypropyloxy)-phenyl]-octanoic acid N-(2-piperidinoethyl)amide dihydrochloride Analogously to Example 85, the title compound is obtained starting from 74 mg of 5(S)-tert-butoxycarbonylamino-4(S)-hydroxy-7(S)-isopropyl-2(R)-methyl-8-[4-methoxy-3-(3-methoxypropyloxy)-phenyl]-octanoic acid N-(2-piperidinoethyl)amide: $R_f$(dichloromethane/methanol=8:2)=0.09; HPLC $R_t$=9.55 minutes; FAB-MS (M+H)$^+$=536.

The starting material is prepared analogously to Example 85a) from 2-{1(S)-tert-butoxy-carbonylamino-3(S)-isopropyl-4-[4-methoxy-3-(3-methoxypropyloxy)-phenyl]-butyl}-4(R)-methyl-tetrahydrofuran-5-one (Example 105e) and N-(2-piperidinoethyl)amine.

EXAMPLE 90

5(S)-Amino-4(S)-hydroxy-7(S)-isopropyl-2(R)-methyl-8-[4-methoxy-3-(3-methoxypropyloxy)-phenyl]-octanoic acid N-[2-(4-methoxypiperidino)-ethyl]-amide dihydrochloride Analogously to Example 85, the title compound is obtained starting from 74 mg of 5(S)-tert-butoxycarbonylamino-4(S)-hydroxy-7(S)-isopropyl-2(R)-methyl-8-[4-methoxy-3-(3-methoxypropyloxy)-phenyl]-octanoic acid N-[2-(4-methoxy-piperidino)ethyl]-amide: $R_f$(dichloromethane/methanol=8:2)=0.12; HPLC $R_t$=9.39 minutes; FAB-MS (M+H)$^+$=566.

The starting material is prepared analogously to Example 85a) from 2-{1(S)-tert-butoxy-carbonylamino-3(S)-isopropyl-4-[4-methoxy-3-(3-methoxypropyloxy)-phenyl]-butyl}-4(R)-methyl-tetrahydrofuran-5-one (Example 105e) and 1-(2-aminoethyl)-4-methoxy-piperidine.

The 1-(2-amino-ethyl)-4-methoxypiperidine is prepared analogously to Examples 87a) and 87 b) from 4-methoxypiperidine.

EXAMPLE 91

5(S)-Amino-4(S)-hydroxy-7(S)-isopropyl-2(R)-methyl-8-[4-methoxy-3-(3-methoxypropyloxy)-phenyl]-octanoic acid N-(2-thiomorpholinoethyl) amide dihydrochloride Analogously to Example 85, the title compound is obtained starting from I 10 mg of 5(S)-tert-butoxycarbonylamino-4(S)-hydroxy-7(S)-isopropyl-2(R)-methyl-8-[4-methoxy-3-(3-methoxypropyloxy)-phenyl]-octanoic acid N-(2-thiomorpholino-ethyl)amide: $R_f$(dichloromethane/methanol=8:2)=0.17; HPLC $R_t$=9.53 minutes; FAB-MS (M+H)$^+$=554.

The starting material is prepared analogously to Example 85a) from 2-{1(S)-tert-butoxy-carbonylamino-3(S)-isopropyl-4-[4-methoxy-3-(3-methoxypropyloxy)-phenyl]-butyl}-4(R)-methyl-tetrahydrofuran-5-one (Example 105e) and 4-(2-aminoethyl)thiomorpholine.

EXAMPLE 92

5(S)-Amino-4(S)-hydroxy-7(S)-isopropyl-2(R)-methyl-8-[4-methoxy-3-(3-methoxypropyloxy)-phenyl]-octanoic acid [N-(3-hydroxypropyl)]amide hydrochloride Analogously to Example 85, the title compound is obtained starting from 110 mg of 5(S)-tertbutoxycarbonylamino-4(S)-hydroxy-7(S)-isopropyl-2(R)-methyl-8-[4-methoxy-3-(3-methoxypropyloxy)-phenyl]-octanoic acid [N-(3-hydroxypropyl)]amide: R$_f$(dichloromethane/methanol=9:1)=0.07; HPLC R$_f$=9.65 minutes; FAB-MS (M+H)$^+$=483.

The starting material is prepared analogously to Example 85a) from 2-{1(S)-tert-butoxy-carbonylamino-3(S)-isopropyl-4-[4-methoxy-3-(3-methoxypropyloxy)-phenyl]-butyl}-4(R)-methyl-tetrahydrofuran-5-one (Example 105e) and 3-amino-1-propanol.

EXAMPLE 93

5(S)-Amino-4(S)-hydroxy-7(S)-isopropyl-2(R)-methyl-8-f4-methoxy-3-(3-methoxypropyloxy)-phenyl]-octanoic acid [N-(4-hydroxybutyl)]amide hydrochloride Analogously to Example 85, the title compound is obtained starting from 112 mg of 5(S)-tert-butoxycarbonylamino-4(S)-hydroxy-7(S)-isopropyl-2(R)-methyl-8-[4-methoxy-3-(3-methoxypropyloxy)-phenyl]-octanoic acid [N-(4-hydroxybutyl)]amide: R$_f$(dichloromethane/methanol=9:1)=0.07; HPLC R$_f$=9.83 minutes; FAB-MS (M+H)$^+$=497.

The starting material is prepared analogously to Example 85a) from 2-{1(S)-tert-butoxy-carbonylamino-3(S)-isopropyl-4-[4-methoxy-3-(3-methoxypropyloxy)-phenyl]-butyl}-4(R)-methyl-tetrahydrofuran-5-one (Example 105e) and 4-amino-1-butanol.

EXAMPLE 94

5(S)-Amino-4(S)-hydroxy-7(S)-isopropyl-7(R)-methyl-8-[4-methoxy-3-(3-methoxypropyloxy)-phenyl]-octanoic acid [N-(4-acetoxybutyl)]amide hydrochloride Analogously to Example 85, the title compound is obtained starting from 27 mg of 5(S)-tert-butoxycarbonylamino-4(S)-hydroxy-7(S)-isopropyl-2(R)-methyl-8-[4-methoxy-3-(3-methoxypropyloxy)-phenyl]-octanoic acid [N-(4-acetoxybutyl)]amide: R$_f$(dichloromethane/methanol=9:1)=0.16; HPLC R$_f$=11.53 minutes; FAB-MS (M+H)$^+$=539.

The starting material is prepared as follows:
a) 5(S)-Tert-butoxycarbonylamino-4(S)-hydroxy-7(S)-isopropyl-2(R)-methyl-8-[4-methoxy-3-(3-methoxypropyloxy)-phenyl]-octanoic acid [N-(4-acetoxybutyl)[amide 30 ml of triethylamine, 2 mg of 4-(N,N'-dimethylamino) pyridine (DMAP) and 20 ml of acetic anhydride are added at 0° C. to 116 mg of 5(S)-tert-butoxycarbonylamino-4(S)-hydroxy-7(S)-isopropyl-2(R)-methyl-8-[4-methoxy-3-(3-methoxypropyloxy)-phenyl]-octanoic acid [N-(4-hydroxybutyl)]amide (Example 93) in 5 ml of tetrahydrofuran. The reaction solution is stirred for 18 hours at room temperature. The reaction mixture is partitioned between diethyl ether and water/saturated sodium chloride solution. The organic phases am concentrated by evaporation and the residue is purified by FC (40 g of silica gel, eluant: dichloromethane/methanol=95:5). The title compound is obtained: R$_f$(dichloromethane/methanol=9:1)= 0.60.

EXAMPLE 95

5(S)-Amino-4(S)-hydroxy-7(S)-isopropyl-2(R)-methyl-8-[4-methoxy-3-(3-methoxypropyloxy)-phenyl]-octanoic acid [N-(3-cyanopropyl)]amide hydrochloride Analogously to Example 85, the title compound is obtained starting from 107 mg of 5(S)-tert-butoxycarbonylamino-4(S)-hydroxy-7(S)-isopropyl-2(R)-methyl-8-[4-methoxy-3-(3-methoxypropyloxy)-phenyl]-octanoic acid [N-(3-cyanopropyl)]amide: R$_f$(dichloromethane/methanol=9:1)=0.07; HPLC R$_f$=10.76 minutes; FAB-MS (M+H)$^+$=492.

The starting material is prepared analogously to Example 85a) from 2-{1(S)-tert-butoxycarbonylamino-3(S)-isopropyl-4-[4-methoxy-3-(3-methoxypropyloxy)-phenyl]-butyl}-4(R)-methyl-tetrahydrofuran-5-one (Example 105e) and 4-amino-butyronitrile.

EXAMPLE 96

5(S)-Amino-4(S)-hydroxy-7(S)-isopropyl-2(R)-methyl-8-[4-methoxy-3-(3-methoxypropyloxy)-phenyl]-octanoic acid [N-(3-methoxypropyl)]amide hydrochloride Analogously to Example 85, the title compound is obtained starting from 107 mg of 5(S)-tert-butoxycarbonylamino-4(S)-hydroxy-7(S)-isopropyl-2(R)-methyl-8-[4-methoxy-3-(3-methoxypropyloxy)-phenyl]-octanoic acid [N-(3-methoxypropyl)]amide: R$_f$(dichloromethane/methanol=8:2)=0.34; HPLC R$_f$=10.70 minutes; FAB-MS (M+H)$^+$=497.

The starting material is prepared analogously to Example 85a) from 2-{1(S)-tert-butoxy-carbonylamino-3(S)-isopropyl-4-[4-methoxy-3-(3-methoxypropyloxy)-phenyl]-butyl}-4(R)-methyl-tetrahydrofuran-5-one (Example 105e) and 3-methoxy-propylamine.

EXAMPLE 97

5(S)-Amino-4(S)-hydroxy-7(S)-isopropyl-2(R)-methyl-8-[4-methoxy-3-(3-methoxypropyloxy)-phenyl]-octanoic acid [N-(2-acetylamino-ethyl)] amide hydrochloride Analogously to Example 85, the title compound is obtained staging from 82 mg of 5(S)-tert-butoxycarbonylamino-4(S)-hydroxy-7(S)-isopropyl-2(R)-methyl-8-[4-methoxy-3-(3-methoxypropyloxy)-phenyl]-octanoic acid [N-(2-acetylamino-ethyl)]amide: R$_f$(dichloromethane/methanol=8:2)=0.17; HPLC R$_f$=9.54 minutes; FAB-MS (M+H)$^+$=510.

The starting material is prepared analogously to Example 85a) from 2-{1(S)-tert-butoxy-carbonylamino-3 (S)-isopropyl-4-[4-methoxy-3-(3-methoxypropyloxy)-phenyl]-butyl}-4(R)-methyl-tetrahydrofuran-5-one (Example 105e) and N-acetyl-ethylenediamine.

EXAMPLE 98

5(S)-Amino-4(S)-hydroxy-7(S)-isopropyl-2(R)-methyl-8-[4-methoxy-3-(3-methoxypropyloxy)-phenyl]-octanoic acid{N-[2-(2-pyridyl)-ethyl]}-amide hydrochloride Analogously to Example 85, the title compound is obtained grafting from 118 mg of 5(S)-tert-butoxycarbonylamino-4(S)-hydroxy-7(S)-isopropyl-2(R)-methyl-8-[4-methoxy-3-(3-methoxypropyloxy)-phenyl]-octanoic acid {N-[2-(2-pyridyl)-ethyl]}-amide: R$_f$(dichloromethane/methanol=9:1)=0.09; HPLC R$_f$=8.88 minutes; FAB-MS (M+H)$^+$=530.

The starting material is prepared analogously to Example 85a) from 2-{1(S)-tert-butoxy-carbonylamino-3(S)-isopropyl-4-[4-methoxy-3-(3-methoxypropyloxy)-phenyl]- butyl}-4(R)-methyl-tetrahydrofuran-5-one (Example 105e) and 2-(2-aminoethyl)-pyridine.

EXAMPLE 99

5(S)-Amino-4(S)-hydroxy-7(S)-isopropyl-2(R)-methyl-8-[4-methoxy-3-(3-methoxypropyloxy)-phenyl]-octanoic acid N-[2-(N'-oxomorpholino) ethyl-amide hydrochloride Analogously to Example 85, the title compound is obtained starting from 82 mg of 5(S)-tert-butoxycarbonylamino-4(S)-hydroxy-7(S)-isopropyl-2(R)-methyl-8-[4-methoxy-3-(3-methoxypropyloxy)-phenyl]-octanoic acid N-[2-(N'-oxomorpholino)ethyl]amide: $R_f$(dichloromethane/methanol=8:2)=0.07; HPLC $R_t$=9.04 minutes; FAB-MS (M+H)$^+$=554.

The starting material is prepared analogously to Example 85a) from 2-{1(S)-tert-butoxy-carbonylamino- 3(S)-isopropyl-4-[4-methoxy-3-(3-methoxypropyloxy)-phenyl]-butyl}-4(R)-methyl-tetrahydrofuran-5-one (Example 105e) and 4-(2-aminoethyl)-N-oxo-morpholine.

The starting material is prepared as follows:
a) 4-(2-Aminoethyl)-N-oxo-morpholine 2.8 g of 4-(2-benzyloxycarbonylaminoethyl)-N-oxo-morpholine are hydrogenated in the presence of 0.30 g of 10% Pd/C in methanol for 10 minutes at room temperature and under normal pressure. The reaction mixture is filtered and concentrated by evaporation. The crude title compound is obtained: $^1$H-NMR (CD$_3$OD), δ(ppm)=4.90 (2H, s), 4.20 (1H, m), 3.87–2.80 (10H, m), 2.50 (1H, m)

b) 4-(2-Benzyloxycarbonylaminoethyl)-N-oxo-morpholine 6 portions, each of 1.48 ml, of 30% hydrogen peroxide are added at 60° C., with stirring, at intervals of 12 hours, to 10.6 g of 4-(2-benzyloxycarbonylaminoethyl)-morpholine in 12 ml of methanol. Saturated sodium sulfite solution is added carefully to the cooled reaction mixture until the excess peroxide has been destroyed. The methanol is evaporated off, and the resulting suspension is taken up in ethyl acetate/methanol 99:1. The mixture is dried with magnesium suEate and is filtered, and the filtrate is concentrated by evaporation. Crystallisation from ethyl acetate yields the title compound: $R_f$(dichloromethane/methanol=8:2)=0.17; m.p. 163° C.

EXAMPLE 100

5(S)-Amino-4(S)-hydroxy-7(S)-isopropyl-2(R)-methyl-8-[4-methoxy-3-(3-methoxypropyloxy)-phenyl]-octanoic acid {N-[3-(tert-butylsulfonyl)-propyl]}-amide hydrochloride Analogously to Example 85, the title compound is obtained starting from 110 mg of 5(S)-tert-butoxycarbonylamino-4(S)-hydroxy-7(S)-isopropyl-2(R)-methyl-8-[4-methoxy-3-(3-methoxypropyloxy)-phenyl]-octanoic acid {N-[3-(tert-butylsulfonyl)-propyl]}-amide: $R_f$(ethyl acetate/methanol/conc. ammonia=80:15:5)=0.45; HPLC $R_t$=11.27 minutes; FAB-MS (M+H)$^+$=587.

The starting material is prepared analogously to Example 85a) from 2-{1(S)-tert-butoxy-carbonylamino-3(S)-isopropyl-4-[4-methoxy-3-(3-methoxypropyloxy)-phenyl]-butyl}-4(R)-methyl-tetrahydrofuran-5-one (Example 105e) and 3-amino-1-(tert-butylsulfonyl)-propane.

The starting material is prepared as follows:
a) 3-Amino-1-(tert-butylsulfonyl)-propane 1.0 g of 3-aminopropyl-(tert-butylsulfonyl)-propane is dissolved at 0° C. in 30 ml of water. 2.14 g of potassium permanganate and 2 ml of 4N hydrochloric acid in 30 ml of water are added in succession, and the mixture is stirred overnight at 0° C. The dark suspension is filtered off and washed with 100 ml of hot water. 50 ml of toluene are added to the filtrate, and the mixture is concentrated. The precipitated white crystals are purified by means of FC (10 g of silica gel, ethyl acetate/methanol/conc. ammonia=80:15:5). The title compound is obtained: $R_f$(ethyl acetate/methanol/conc. ammonia=80:15:5)=0.20.

EXAMPLE 101

5(S)-Amino-4(S)-hydroxy-7(S)-isopropyl-2(R)-methyl-8-[4-methoxy-3-(3-methoxypropyloxy)-phenyl]-octanoic acid {N-[3-(ethylsulfonyl)-propyl]}-amide hydrochloride Analogously to Example 85, the title compound is obtained starting from 44 mg of 5(S)-tert-butoxycarbonylamino-4(S)-hydroxy-7(S)-isopropyl-2(R)-methyl-8-[4-methoxy-3-(3-methoxypropyloxy)-phenyl]-octanoic acid {N-[3-(ethylsulfonyl)-propyl]}-amide: $R_f$(ethyl acetate/methanol/conc. ammonia=80:15:5)=0.26; HPLC $R_t$=10.40 minutes; FAB-MS (M+H)$^+$=559.

The starting material is prepared analogously to Example 85a) from 2-{1(S)-tert-butoxy-carbonylamino-3(S)-isopropyl-4-[4-methoxy-3-(3-methoxypropyloxy)-phenyl]-butyl}-4(R)-methyl-tetrahydrofuran-5-one (Example 105e) and 3-amino-1-(ethylsulfonyl)-propane.

The starting material is prepared as follows:
a) 3-Amino-1-(ethylsulfonyl)-propane 1.0 g of 3-aminopropyl-ethyl sulfide is placed in 35 ml of methanol at 0° C.; 15.5 g of oxone in 35 ml of water are added and the mixture is stirred at 0° C. for 4 hours. 200 ml of water are added and the mixture is extracted with 3×150 ml of dichloromethane. The organic extracts are concentrated by evaporation and purified by FC (10 g of silica gel, ethyl acetate/methanol/conc. ammonia=80:15:5). The title compound is obtained: $R_f$(ethyl acetate/methanol/conc. ammonia=80:15:5)=0.15.

EXAMPLE 102

5(S)-Amino-4(S)-hydroxy-7(S)-isopropyl-2(R)-methyl-8-[4-methoxy-3-(3-methoxypropyloxy)-phenyl]-octanoic acid {N-[2-(ethylsulfonyl)-ethyl]}-amide hydrochloride Analogously to Example 85, the title compound is obtained starting from 90 mg of 5(S)-tert-butoxycarbonylamino-4(S)-hydroxy-7(S)-isopropyl-2(R)-methyl-8-[4-methoxy-3-(3-methoxypropyloxy)-phenyl]-octanoic acid {N-[2-(ethylsulfonyl)-ethyl]}-amide: $R_f$(ethylacetate/methanol/conc. ammonia=80:15:5)=0.39; HPLC $R_t$=10.50 minutes; FAB-MS (M+H)$^+$=545.

The starting material is prepared analogously to Example 85a) from 2-{1(S)-tert-butoxy-carbonylamino-3(S)-isopropyl-4-[4-methoxy-3-(3-methoxypropyloxy)-phenyl]-butyl}-4(R)-methyl-tetrahydrofuran-5-one (Example 105e) and 2-amino-1-(ethylsulfonyl)-ethane.

EXAMPLE 103

5(S)-Amino-4(S)-hydroxy-7(S)-isopropyl-2(R)-methyl-8-[4-methoxy-3-(3-methoxypropyloxy)-phenyl]-octanoic acid {N-[2-(N-butylsulfonyl)-ethyl]}-amide hydrochloride Analogously to Example 85, the title compound is obtained starting from 67 mg of 5(S)-tertbutoxycarbonylamino-4(S)-hydroxy-7(S)-isopropyl-2(R)-methyl-8-[4-methoxy-3-(3-methoxypropyloxy)-phenyl]-octanoic acid {N-[2-(N-butylsulfonyl)-ethyl]}-amide: R$_f$(ethyl acetate/methanol/conc. ammonia=80:15:5)=0.41; HPLC R$_t$=12.52 minutes; FAB-MS (M+H)$^+$=588.

The starting material is prepared analogously to Example 85a) from 2-{1(S)-tert-butoxy-carbonylamino-3(S)-isopropyl-4-[4-methoxy-3-(3-methoxypropyloxy)-phenyl]-butyl}-4(R)-methyl-tetrahydrofuran-5-one (Example 105e) and 2-aminoethyl-(N-butyl)-sulfonamide.

EXAMPLE 104

5(S)-Amino-4(S)-hydroxy-7(S)-isopropyl-2(R)-methyl-8-[4-methoxy-3-(3-methoxypropyloxy)-phenyl]-octanoic acid {N-[2-(N,N-dimethylsulfonyl)-ethyl]}-amide hydrochloride Analogously to Example 85, the title compound is obtained starting from 120 mg of 5(S)-tert-butoxycarbonylamino-4(S)-hydroxy-7(S)-isopropyl-2(R)-methyl-8-[4-methoxy-3-(3-methoxypropyloxy)-phenyl]-octanoic acid {N-[2-(N,N-dimethylsulfonyl)-ethyl]}-amide: R$_f$(ethyl acetate/methanol/conc. ammonia=80:15:5)=0.43; HPLC R$_t$=11.03 minutes; FAB-MS (M+H)$^+$=560.

The starting material is prepared analogously to Example 85a) from 2-{1(S)-tert-butoxy-carbonylamino-3(S)-isopropyl-4-[4-methoxy-3-(3-methoxypropyloxy)-phenyl]-butyl}-4(R)-methyl-tetrahydrofuran-5-one (Example 105e) and 2-aminoethyl-(N,N-dimethyl)-sulfonamide.

EXAMPLE 105

5(S)-Amino-4(S)-hydroxy-7(S)-isopropyl-2(R)-methyl-8-[4-methoxy-3-(3-methoxypropyloxy)-phenyl]-octanoic acid [N-(3-carbamoyl-propyl)]-amide hydrochloride 84 mg of 5(S)-tert-butoxycarbonylamino-4(S)-hydroxy-7(S)-isopropyl-2(R)-methyl-8-[4-methoxy-3-(3-methoxypropyloxy)-phenyl]-octanoic acid [N-(3-carbamoyl-propyl)]-amide are dissolved in 3 ml of 4N hydrochloric acid in dioxane at 0° C. and the mixture is stirred for 2 hours at 0° C. The reaction mixture is lyophilised. The title compound is obtained: R$_f$(dichloromethane/methanol=9:1)=0.04; HPLC R$_t$=9.44 minutes; HR FAB-MS (M+H)$^+$=510.

The starting materials are prepared as follows:

a) 5(S)-Tert-butoxycarbonylamino-4(S)-hydroxy-7(S)-isopropyl-2(R)-methyl-8-[4-methoxy-3-(3-methoxypropyloxy)-phenyl]-octanoic acid [N-(3-carbamoyl-propyl)]-amide 50 mg of tetrabutylammonium fluoride trihydrate are added to 115 mg of 5(S)-tert-butoxy-carbonylamino-4(S)-tert-butyldimethylsilyloxy-7(S)-isopropyl-2(R)-methyl-8-[4-methoxy-3-(3-methoxy-propyloxy)-phenyl]-octanoic acid [N-(3-carbamoyl-propyl)]-amide in 4 ml of dimethyl-formamide at 0° C. The reaction mixture is stirred for a further 5 hours at room temperature and then concentrated by evaporation. 20 ml of saturated sodium hydrogen carbonate solution are added to the evaporation residue and the mixture is extracted repeatedly with ethyl acetate. The organic phases are washed with saturated sodium chloride solution and concentrated by evaporation. The residue is purified by means of FC (18 g of silica gel, dichloromethane/methanol=9:1). The title compound is obtained:R$_f$ (dichloromethane/methanol=9:1)=0.24.

b) 5(S)-Tert-butoxycarbonylamino-4(S)-tert-butyldimethylsilyloxy-7(S)-isopropyl-2(R)-methyl-8-[4-methoxy-3-(3-methoxypropyloxy)-phenyl]-octanoic acid [N-(3-carbamoylpropyl)]-amide 67 μl of triethylamine, 34 mg of 4-aminobutyric acid amide hydrochloride and 38 μl of cyanophosphonic acid diethyl ester are added in succession to 128 mg of 5(S)-tert-butoxy-carbonylamino-4(S)-tert-butyldimethylsilyloxy-7(S)-isopropyl-2(R)-methyl-8-[4-methoxy-3-(3-methoxy-propyloxy)-phenyl]-octanoic acid in 8 ml of dimethylformamide at 0° C. The reaction mixture is stirred for a further 18 hours at room temperature. The reaction mixture is concentrated by evaporation and 20 ml of 10% citric acid solution and ice are added to the residue. The mixture is extracted repeatedly with ethyl acetate and the organic phases am then washed with saturated sodium hydrogen carbonate solution and saturated sodium chloride solution. After concentration by evaporation, the residue is purified by means of FC (70 g of silica gel, dichloromethane/methanol=9:1). The title compound is obtained: R$_f$(dichloromethane/methanol=9:1)=0.38.

c) 5(S)-tert-butoxycarbonylamino-4(S)-tert-butyldimethylsilyloxy-7(S)-isopropyl-2(R)-methyl-8-[4-methoxy-3-(3-methoxypropyloxy)-phenyl]-octanoic acid 4.45 g of 5(S)-tert-butoxycarbonylamino-4(S)-hydroxy-7(S)-isopropyl-2(R)-methyl-8-[4-methoxy-3-(3-methoxypropyloxy)-phenyl]-octanoic acid (crude) are stirred in 45 ml of dimethylformamide with 2.36 g of tert-butyldimethylsilyl chloride and 2.03 g of imidazole for 6 days at room temperature. The mixture is concentrated by evaporation and the residue is partitioned between 10% citric acid solution and ethyl acetate. The organic phase is concentrated and stirred in 20 ml of tetrahydrofuran, 8 ml of water and 20 ml of acetic acid at room temperature for 16 hours. After concentration by evaporation, ice/water is added to the residue and the mixture is then extracted with ethyl acetate. The title compound is obtained from the organic phase after FC (260 g of silica gel, ethyl acetate/hexane=1:1): R$_f$(ethyl acetate/hexane=1:1)=0.32.

d) 5(S)-Tert-butoxycarbonylamino-4(S)-hydroxy-7(S)-isopropyl-2(R)-methyl-8-[4-methoxy-3-(3-methoxypropyloxy)-phenyl]-octanoic acid 28.5 ml of 1N lithium hydroxide solution are added to 3.6 g of 2-{1(S)-tert-butoxy-carbonylamino-3(S)-isopropyl-4-[4-methoxy-3-(3-methoxy-propyloxy)-phenyl]-butyl}-4(R)-methyl-tetrahydrofuran-5-one in 210 ml of 1,2-dimethoxyethane/water (2:1) at room temperature. The reaction mixture is stirred at room temperature for a further 1 hour and then concentrated by evaporation. Ice and 10% aqueous citric acid solution are added to the residue. Repeated extraction with chloroform yields the crude title compound: R$_f$(ethyl acetate/hexane=1:1)=0.05; HPLC R$_t$=16.41 minutes.

e) 2-{1 (S)-tert-butoxycarbonylamino-3(S)-isopropyl-4-[4-methoxy-3-(3-methoxy-propyl-oxy)-phenyl]-butyl}-4(R)-methyl-tetrahydrofuran-5-one 2.02 g of p-toluenesulfonic acid (monohydrate) are added to 5.6 g of 5(S)-tert-butoxy-carbonylamino-4(S)-hydroxy-7(S)-isopropyl-2(R)-methyl-8-[4-methoxy- 3-(3-methoxy-propyloxy)-phenyl]-octanoic acid (N-butyl)-amide (Example 32) in 240 ml of chloroform at room temperature and the mixture is stirred at room temperature for a further 18 hours. The reaction mixture is concentrated by evaporation and the residue is partitioned between diethyl ether and 0.1N hydrochloric acid. The organic phases are concentrated by evaporation and the title compound is obtained from the residue after FC (160 g of silica gel, eluant: ethyl acetate/hexane 1:1): R$_f$(ethyl acetate/hexane=2:1)=0.47; m.p. 86°–87° C.

EXAMPLE 106

5(S)-Amino-4(S)-hydroxy-7(S)-isopropyl-2(R)-methyl-8-[4-methoxy-3-(3-methoxypropyloxy)-phenyl]-octanoic acid {N-[3-(1H-tetrazol-5-yl)-propyl]}-amide hydrochloride Analogously to Example 105, the title compound is obtained starting from 47 mg of 5(S)-tert-butoxycarbonylamino-4(S)-hydroxy-7(S)-isopropyl-2(R)-methyl-8-[4-methoxy-3-(3-methoxypropyloxy)-phenyl]-octanoic acid {N-[3-(1H-tetrazol-5-yl)-propyl]}-amide and after lyophilisation: $R_f$(dichloromethane/methanol=8:2)= 0.46; HPLC $R_t$=9.97 minutes; FAB-MS $(M+H)^+$=535.

The starting material is prepared analogously to Example 105a) and 105b) from 5(S)-tert-butoxycarbonylamino-4(S)-tert-butyldimethyl-silyloxy-7(S)-isopropyl-2(R)-methyl-8-[4-methoxy-3-(3-methoxypropyloxy)-phenyl]-octanoic acid (Example 105c) and 3-(1H-tetrazol-5-yl)-propylamine.

EXAMPLE 107

5(S)-Amino-4(S)-hydroxy-7(S)-isopropyl-2(R)-methyl-8-[4-methoxy-3-(3-methoxypropyloxy)-phenyl]-octanoic acid {N-J3-(1H-imidazol-5-yl)-propyl]}-amide hydrochloride Analogously to Example 105, the title compound is obtained starting from 43 mg of 5(S)-tert-butoxycarbonylamino-4(S)-hydroxy-7(S)-isopropyl-2(R)-methyl-8-[4-methoxy-3-(3-methoxypropyloxy)-phenyl]-octanoic acid {N-[3-(1H-imidazol-5-yl)-propyl]}-amide and after lyophilisation: $R_f$(dichloromethane/methanol=8:2)= 0.13; HPLC $R_t$=8.83 minutes; FAB-MS $(M+H)^+$=533.

The starting material is prepared analogously to Example 105a) and 105b) from 5(S)-tert-butoxycarbonylamino-4(S)-tert-butyldimethyl-silyloxy-7(S)-isopropyl-2(R)-methyl-8-[4-methoxy-3-(3-methoxypropyloxy)-phenyl]-octanoic acid (Example 105c) and 3-(1H-imidazol-5-yl)-propylamine.

EXAMPLE 108

5(S)-Amino-4(S)-hydroxy-7(S)-isopropyl-2(R)-methyl-8-[4-methoxy-3-(3-methoxypropyloxy)-phenyl]-octanoic acid {N-[3-(3-methyl-1,2,4-oxadiazol-5-yl)-propyl]}-amide hydrochloride Analogously to Example 105, the title compound is obtained starting from 140 mg of 5(S)-tert-butoxycarbonylamino-4(S)-hydroxy-7(S)-isopropyl-2(R)-methyl-8-[4-methoxy-3-(3-methoxypropyloxy)-phenyl]-octanoic acid {N-[3-(3-methyl-1,2,4-oxadiazol-5-yl)-propyl]}-amide and after lyophilisation:$R_f$(dichloromethane/methanol=9:1)=0.12; HPLC $R_t$=11.05 minutes; FAB-MS $(M+H)^+$=549.

The starting material is prepared analogously to Example 105a) and 105b) from 5(S)-tert-butoxycarbonylamino-4(S)-tert-butyldimethyl-silyloxy-7(S)-isopropyl-2(R)-methyl-8-[4-methoxy-3-(3-methoxypropyloxy)-phenyl]-octanoic acid (Example 105c) and 3-(3-methyl-1,2,4-oxadiazol-5-yl)-propylamine.

a) 3-(3-Methyl-1,2,4-oxadiazol-5-yl)-propylamine 272 mg of 3-methyl-5-[3-(N-phthaloylamino)propyl]-1,2,4-oxadiazole in 10 ml of ethyl alcohol are stirred for 2 hours under reflux with 146 ml of hydrazine hydrate. The reaction mixture is diluted with diethyl ether and then clarified by filtration. The filtrate is concentrated by evaporation and yields the crude title compound: $R_f$(dichloromethane/methyl alcohol/conc. ammonia=40:10:1)=0.37.

b) 3-Methyl-5-[3-(N-phthaloylamino)propyl]-1,2,4-oxadiazole 0.84 g of sodium hydride dispersion (80%) is added to 2.08 g of acetamidoxime in 200 ml of tetrahydrofuran at room temperature and the mixture is stirred at 60° C. for 2 hours. A solution of 2.47 g of 4-(N-phthaloylamino) butyric acid methyl ester in 30 ml of tetrahydrofuran is then added and stirring is continued at 60° C. for a further 3 hours. The reaction mixture is poured onto 1N hydrochloric acid/ice and extracted repeatedly with ethyl acetate. The dried organic phases are concentrated by evaporation and the residue is boiled in 60 ml of xylene for 3 hours on a water-separator. The solvent is evaporated off and the title compound is obtained from the residue after FC (40 g of silica gel, ethyl acetate/hexane=1:1): $R_f$(ethyl acetate/hexane=1:1)=0.26.

EXAMPLE 109

5(S)-Amino-4(S)-hydroxy-7(S)-isopropyl-2(R)-methyl-8-[4-methoxy-3-(3-methoxypropyloxy)-phenyl]-octanoic acid [N-(3-aminopropyl)]-amide dihydrochloride Analogously to Example 105, the title compound is obtained starting from 125 mg of 5(S)-tert-butoxycarbonylamino-4(S)-hydroxy-7(S)-isopropyl-2(R)-methyl-8-[4-methoxy-3-(3-methoxypropyloxy)-phenyl]-octanoic acid [N-(3-tert-butoxycarbonylamino-propyl)]-amide and after lyophilisation: $R_f$(dichloromethane/methanol/conc. ammonia=40:10:1)=0.08; HPLC $R_t$=6.48 minutes; FAB-MS $(M+H)^+$=482.

The starting material is prepared analogously to Example 105a) and 105b) from 5(S)-tert-butoxycarbonylamino-4(S)-tert-butyldimethylsilyloxy-7(S)-isopropyl-2(R)-methyl-8-[4-methoxy-3-(3-methoxypropyloxy)-phenyl]-octanoic acid (Example 105c) and 3-tert-butoxycarbonylamino-propylamine.

EXAMPLE 110

5(S)-Amino-4(S)-hydroxy-7(S)-isopropyl-2(R)-methyl-8-[4-methoxy-3-(3-methoxypropyloxy)-phenyl]-octanoic acid [N-(2-dimethylamino-ethyl)]-amide dihydrochloride Analogously to Example 105, the title compound is obtained starting from 38 mg of 5(S)-tert-butoxycarbonylamino-4(S)-hydroxy-7 (S)-isopropyl-2(R)-methyl-8-[4-methoxy-3-(3-methoxypropyloxy)-phenyl]-octanoic acid [N-(2-dimethylamino-ethyl)]-amide and after lyophilisation: $R_f$(dichloromethane/methanol/conc. ammonia=350:50:1)=0.03; HPLC $R_t$=8.61 minutes; FAB-MS $(M+H)^+$=496.

The starting material is prepared analogously to Example 105a) and 105b) from 5(S)-tert-butoxycarbonylamino-4(S)-tert-butyldimethyl-silyloxy-7(S)-isopropyl-2(R)-methyl-8-[4-methoxy-3-(3-methoxypropyloxy)-phenyl]-octanoic acid (Example 105c) and 2-dimethylaminoethylamine.

EXAMPLE 111

5(S)-Amino-4(S)-hydroxy-7(S)-isopropyl-2(R)-methyl-8-[4-methoxy-3-(3-methoxypropyloxy)-phenyl]-octanoic acid N-(2-morpholinoethyl)amide dihydrochloride Analogously to Example 105, the title compound is obtained starting from 70 mg of 5(S)-tert-butoxycarbonylamino-4(S)-hydroxy-7(S)-isopropyl-2(R)- methyl-8-[4-methoxy-3-(3-methoxypropyloxy)-phenyl]-octanoic acid N-(2-morpholinoethyl)amide and after lyophilisation: R$_f$(dichloromethane/methanol/conc. ammonia=350:50:1)=0.15; HPLC R$_t$=8.74 minutes; FAB-MS (M+H)$^+$=538.

The starting material is prepared analogously to Example 105a) and 105b) from 5(S)-tert-butoxycarbonylamino-4(S)-tert-butyldimethyl-silyloxy-7(S)-isopropyl-2(R)-methyl-8-[4-methoxy-3-(3-methoxypropyloxy)-phenyl]-octanoic acid (Example 105c) and 4-(2-aminoethyl)-morpholine.

EXAMPLE 112

5(S)-Amino-4(S)-hydroxy-7(S)-isopropyl-2(R)-methyl-8-14-methoxy-3-(3-methoxypropyloxy)-phenyl]-octanoic acid N-(3-morpholinopropyl) amide dihydrochloride Analogously to Example 105, the title compound is obtained starting from 37 mg of 5(S)-tert-butoxycarbonylamino-4(S)-hydroxy-7(S)-isopropyl-2(R)-methyl-8-[4-methoxy-3-(3-methoxypropyloxy)-phenyl]-octanoic acid N-(3-morpholinopropyl)amide and after lyophilisation: R$_f$(dichloromethane/methanol/conc. ammonia=350:50:1)=0.11; HPLC R$_t$=8.68 minutes; FAB-MS (M+H)$^+$=552.

The starting material is prepared analogously to Example 105a) and 105b) from 5(S)-tert-butoxycarbonylamino-4(S)-tert-butyldimethyl-silyloxy-7(S)-isopropyl-2(R)-methyl-8-[4-methoxy-3-(3-methoxypropyloxy)-phenyl]-octanoic acid (Example 105c) and 4-(3-aminopropyl)-morpholine.

EXAMPLE 113

5(S)-Amino-4(S)-hydroxy-7(S)-isopropyl-2(R)-methyl-8-[4-methoxy-3-(3-methoxypropyloxy)-phenyl]-octanoic acid N-[2-(1,1-dioxothiomorpholino)ethyl]amide dihydrochloride Analogously to Example 105, the title compound is obtained starting from 100 mg of 5(S)-tert-butoxycarbonylamino-4(S)-hydroxy-7(S)-isopropyl-2(R)-methyl-8-[4-methoxy-3-(3-methoxypropyloxy)-phenyl]-octanoic acid N-[2-(1,1-dioxothiomorpholino)ethyl]-amide and after lyophilisation: R$_f$(dichloromethane/methanol=8:2)=0.30; HPLC R$_t$=9.29 minutes; FAB-MS (M+H)$^+$=586.

The starting material is prepared analogously to Example 105a) and 105b) from 5(S)-tert-butoxycarbonylamino-4(S)-tert-butyldimethyl-silyloxy-7(S)-isopropyl-2(R)-methyl-8-[4-methoxy-3-(3-methoxypropyloxy)-phenyl]-octanoic acid (Example 105c) and 2-(1,1-dioxothiomorpholino)-ethylamine.

EXAMPLE 114

5(S)-Amino-4(S)-hydroxy-7(S)-isopropyl-2(R)-methyl-8-[4-methoxy-3-3-methoxypropyloxy)-phenyl]-octanoic acid N-(2-ethoxycarbonylethyl) amide hydrochloride Analogously to Example 105, the title compound is obtained starting from 32 mg of 5(S)-tert-butoxycarbonylamino-4(S)-hydroxy-7(S)-isopropyl-2(R)-methyl-8-[4-methoxy-3-(3-methoxypropyloxy)-phenyl]-octanoic acid [N-(2-ethoxycarbonyl-ethyl)]-amide and after lyophilisation: R$_f$(dichloromethane/methanol=9:1)=0.17; HPLC R$_t$=11.31 minutes; FAB-MS (M+H)$^+$=525.

The starting material is prepared analogously to Example 105a) and 105b) from 5(S)-tert-butoxycarbonylamino-4(S)-tert-butyldimethyl-silyloxy-7(S)-isopropyl-2(R)-methyl-8-[4-methoxy-3-(3-methoxypropyloxy)-phenyl]-octanoic acid (Example 105c) and β-alanine ethyl ester hydrochloride.

EXAMPLE 115

5(S)-Amino-4(S)-hydroxy-7(S)-isopropyl-2(R)-methyl-8-4-methoxy-3-(3-methoxypropyloxy)-phenyl]-octanoic acid [N-(2-carboxy-ethyl)]-amide hydrochloride Analogously to Example 105, the title compound is obtained starting from 60 mg of 5(S)-tert-butoxycarbonylamino-4(S)-hydroxy-7(S)-isopropyl-2(R)-methyl-yl-[4-methoxy-3-(3-methoxypropyloxy)-phenyl]-octanoic acid [N-(2-carboxy-ethyl)]-amide and after lyophilisation: R$_f$(dichloromethane/methanol=8:2)=0.28; HPLC R$_t$=9.74 minutes; FAB-MS (M+H)$^+$=497.

The starting material is prepared as follows:

a) 5(S)-Tert-butoxycarbonylamino-4(S)-hydroxy-7(S)-isopropyl-2(R)-methyl-8-[4-methoxy-3-(3-methoxypropyloxy)-phenyl]-octanoic acid [N-(2-carboxyethyl)]-amide 70 mg of 5(S)-tert-butoxyamino-4(S)-hydroxy-7(S)-isopropyl-2(R)-methyl-8-[4-methoxy-3-(3-methoxypropyloxy)-phenyl]-octanoic acid [N-(2-ethyloxycarbonylethyl)]-amide (Example 114) are stirred in 2 ml of methanol with 224 μl of 1N sodium hydroxide at room temperature for 18 hours. After evaporation of the methanol, 250 μl of 1N hydrochloric acid are added and the product is extracted with ethyl acetate. The organic phase is concentrated by evaporation and the residue is purified by means of FC (10 g of silica gel, eluant: dichloromethane/methanol= 8:2). The title compound is obtained: R$_f$(dichloromethane/methanol=9:1)=0.12.

EXAMPLE 116

5(S)-Amino-4(S)-hydroxy-7(S)-isopropyl-2(R)-methyl-8-[4-methoxy-3-(3-methoxypropyloxy)-phenyl]-octanoic acid [N-(3-methoxycarbonyl-ethyl)]-amide hydrochloride Analogously to Example 105, the title compound is obtained starting from 90 mg of 5(S)-tert-butoxycarbonylamino-4(S)-hydroxy-7(S)-isopropyl-2(R)-methyl-8-[4-methoxy-3-(3-methoxypropyloxy)-phenyl]-octanoic acid [N-(3-methoxycarbonyl-ethyl)]-amide and after lyophilisation: R$_f$(dichloromethane/methanol=9:1)= 0.13; HPLC R$_t$=10.80 minutes; FAB-MS (M+H)$^+$=525.

The starting material is prepared analogously to Example 105a) and 105b) from 5(S)-tert-butoxycarbonylamino-4(S)-tert-butyldimethyl-silyloxy-7(S)-isopropyl-2(R)-methyl-8-[4-methoxy-3-(3-methoxypropyloxy)-phenyl]-octanoic acid (Example 105c) and 4-aminobutyric acid methyl ester hydrochloride.

EXAMPLE 117

(S)-Amino-4(S)-hydroxy-7(S)-isopropyl-2(R)-methyl-8-[4-methoxy-3-(3-methoxypropyloxy)-phenyl]-octanoic acid [N-(3-carboxypropyl)]-amide hydrochloride Analogously to Example 105, the title compound is obtained starting from 38 mg of 5(S)-tert-butoxycarbonylamino-4(S)-hydroxy-7(S)-isopropyl-2(R)-methyl-8-[4-methoxy-3-(3-methoxypropyloxy)-phenyl]-octanoic acid [N-(3-carboxypropyl)]-amide and after lyophilisation: R*f*(dichloromethane/methanol=8:2)=0.55; HPLC R*t*=9.85 minutes; FAB-MS (M+H)⁺=511.

The starting material is prepared as follows:
5(S)-Tert-butoxycarbonylamino-4(S)-hydroxy-7(S)-isopropyl-2(R)-methyl-8-[4-methoxy-3-(3-methoxypropyloxy)-phenyl]-octanoic acid [N-(3-carboxypropyl)]-amide Analogously to Example 115a), the title compound is prepared from 5(S)-tert-butoxy-carbonyl-amino-4(S)-hydroxy-7(S)-isopropyl-2(R)-methyl-8-[4-methoxy-3-(3-methoxy-propyloxy)-phenyl]-octanoic acid [N-(3-methyloxycarbonylpropyl)]-amide (Example 116).

EXAMPLE 118

5(S)-Amino-4(S)-hydroxy-7(S)-isopropyl-2(R)-methyl-8-[4-methoxy-3-(3-methoxypropyloxy)-phenyl]-octanoic acid [N-(2-carbamoylethyl)]-amide hydrochloride Analogously to Example 105, the title compound is obtained starting from 93 mg of 5(S)-tert-butoxycarbonylamino-4(S)-hydroxy-7(S)-isopropyl-2(R)-methyl-8-[4-methoxy-3-(3-methoxypropyloxy)-phenyl]-octanoic acid [N-(2-carbamoylethyl)]-amide and after lyophilisation: R*f*(dichloromethane/methanol=8:2)=0.15; HPLC R*t*=9.33 minutes; FAB-MS (M+H)⁺=496.

The starting material is prepared analogously to Example 105a) and 105b) from 5(S)-tert-butoxycarbonylamino-4(S)-tert-butyldimethyl-silyloxy-7(S)-isopropyl-2(R)-methyl-8-[4-methoxy-3-(3-methoxypropyloxy)-phenyl]-octanoic acid (Example 105c) and 3-aminopropionic acid amide hydrochloride.

EXAMPLE 119

5(S)-Amino-4(S)-hydroxy-7(S)-isopropyl-2(R)-methyl-8-[4-methoxy-3-(3-methoxypropyloxy)-phenyl]-octanoic acid [N-(4-carbamoylbutyl)]-amide hydrochloride Analogously to Example 105, the title compound is obtained starting from 85 mg of 5(S)-tert-butoxycarbonylamino-4(S)-hydroxy-7(S)-isopropyl-2(R)-methyl-8-[4-methoxy-3-(3-methoxypropyloxy)-phenyl]-octanoic acid [N-(4-carbamoylbutyl)]-amide and after lyophilisation: R*f*(dichloromethane/methanol=8:2)=0.20; HPLC R*t*=9.72 minutes; FAB-MS (M+H)⁺=524.

The starting material is prepared analogously to Example 105a) and 105b) from 5(S)-tert-butoxycarbonylamino-4(S)-tert-butyldimethyl-silyloxy-7(S)-isopropyl-2(R)-methyl-8-[4-methoxy-3-(3-methoxypropyloxy)-phenyl]-octanoic acid (Example 105c) and 5-aminopentanoic acid amide hydrochloride.

EXAMPLE 120

5(S)-Amino-4(S)-hydroxy-7(S)-isopropyl-2(R)-methyl-8-[4-methoxy-3-(3-methoxypropyloxy)-phenyl]-octanoic acid N-[3(N-methylcarbamoyl)propyl]amide hydrochloride Analogously to Example 105, the title compound is obtained starting from 89 mg of 5(S)-tert-butoxycarbonylamino-4(S)-hydroxy-7(S)-isopropyl-2(R)-methyl-8-[4-methoxy-3-(3-methoxypropyloxy)-phenyl]-octanoic acid N-[3-(N-methylcarbamoyl)propyl]amide and after lyophilisation: R*f*(dichloromethane/methanol=9:1)= 0.04; HPLC R*t*=9.74 minutes; FAB-MS (M+H)⁺=524.

The starting material is prepared analogously to Example 105a) and 105b) from 5(S)-tert-butoxycarbonylamino-4(S)-tert-butyldimethyl-silyloxy-7(S)-isopropyl-2(R)-methyl-8-[4-methoxy-3-(3-methoxypropyloxy)-phenyl]-octanoic acid (Example 105c) and 4-amino-N-methyl-butyric acid amide hydrochloride.

EXAMPLE 121

5(S)-Amino-4(S)-hydroxy-7(S)-isopropyl-2(R)-methyl-8-[4-methoxy-3-(3-methoxypropyloxy)-phenyl]-octanoic acid N-{3-[N-(2-methoxyethyl)-carbamoyl]propyl}-amide hydrochloride Analogously to Example 105, the title compound is obtained starting from 92 mg of 5(S)-tert-butoxycarbonylamino-4(S)-hydroxy-7(S)-isopropyl-2(R)-methyl-8-[4-methoxy-3-(3-methoxypropyloxy)-phenyl]-octanoic acid N-{3-[N-(2-methoxyethyl)carbamoyl]propyl}-amide and after lyophilisation: R*f*(dichloromethane/methanol=8:2)=0.28; HPLC R*t*=10.14 minutes; FAB-MS (M+H)⁺=568.

The starting material is prepared analogously to Example 105a) and 105b) from 5(S)-tert-butoxycarbonylamino-4(S)-tert-butyldimethyl-silyloxy-7(S)-isopropyl-2(R)-methyl-8-[4-methoxy-3-(3-methoxypropyloxy)-phenyl]-octanoic acid (Example 105c) and 4-aminobutyric acid N-(2-methoxyethyl)amide hydrochloride.

The starting material is prepared as follows:
4-Aminobutyric acid N-(2-methoxyethyl)amide hydrochloride 2.95 g of 4-benzyloxycarbonylaminobutyric acid N-(2-methoxyethyl)amide are hydrogenated in the presence of 0.24 g of 10% Pd/C in 150 ml of methanol and 100 ml of 0.1N hydrochloric acid for 2 hours at room temperature and under normal pressure. The reaction mixture is filtered and concentrated by evaporation. The crude title compound is obtained: ¹H NMR (CD₃OD), δ(ppm)=4.92 (4H, s), 3.53–3.20 (4H, m), 3.34 (3H, s), 2.96 (2H, t, J=12 Hz), 2.37 (2H, t, J=12 Hz), 1.93 (2H, m).

b) 4-Benzyloxycarbonylaminobutyric acid N-(2-methoxyethyl)amide 5.02 g of 4-benzyloxycarbonylaminobutyric acid methyl ester are stirred under reflux in 35 ml of ethanol with 15 ml of 2-methoxyethylamine for 5 days. The reaction mixture is concentrated by evaporation and the residue is purified by means of FC (240 g of silica gel, dichloromethane/methanol=95:5). The title compound is obtained: R*f*(dichloromethane/methanol=95:5)=0.33.

EXAMPLE 122

5(S)-Amino-4(S)-hydroxy-7(S)-isopropyl-2(R)-methyl-8-[4-methoxy-3-(3-methoxypropyloxy)-phenyl]-octanoic acid N-(4-morpholino-4-oxo-butyl)amide hydrochloride Analogously to Example 105, the title compound is obtained starting from 110 mg of 5(S)-tert-butoxycarbonylamino-4(S)-hydroxy-7(S)-isopropyl-2(R)-methyl-8-[4-methoxy-3-(3-methoxypropyloxy)-phenyl]-octanoic acid N-(4-morpholino-4-oxo-butyl)amide and after lyophilisation: R*f*(dichloromethane/methanol=9:1)=0.06; HPLC R*t*=10.17 minutes; FAB-MS (M+H)⁺=580.

The starting material is prepared analogously to Example 105a) and 105b) from 5(S)-tert-butoxycarbonylamino-4(S)-tert-butyldimethyl-silyloxy-7(S)-isopropyl-2(R)-methyl-8-[4-methoxy-3-(3-methoxypropyloxy)-phenyl]-octanoic acid (Example 105c) and 4-aminobutyric acid N'-(4-morpholino) amide hydrochloride.

EXAMPLE 123

5(S)-Amino-4(S)-hydroxy-7(S)-isopropyl-2(R)-methyl-8-[4-methoxy-3-(3-methoxypropyloxy)-phenyl]-octanoic acid [N-(2-carbamoyl-2,2-dimethyl-ethyl)]-amide hydrochloride Analogously to Example 105, the title compound is obtained starting from 66 mg of 5(S)-tert-butoxycarbonylamino-4(S)-hydroxy-7(S)-isopropyl-2(R)-methyl-8-[4-methoxy-3-(3-methoxypropyloxy)-phenyl]-octanoic acid [N-(2-carbamoyl-2,2-dimethyl-ethyl)]-amide and after lyophilisation: $R_f$(dichloromethane/methanol=8:2) =0.27; HPLC $R_t$=12.10 minutes; FAB-MS $(M+H)^+$=524.

The starting material is prepared analogously to Example 105a) and 105b) from 5(S)-tert-butoxycarbonylamino-4(S)-tert-butyldimethylsilyloxy-7 (S)-isopropyl-2(R)-methyl-8-[4-methoxy-3-(3-methoxypropyloxy)-phenyl]-octanoic acid (Example 105c) and 3-amino-2,2-dimethyl-propionic acid amide hydrochloride.

EXAMPLE 124

5(S)-Amino-4(S)-hydroxy-2(S),7(S)-diisopropyl-8-[4-methoxy-3-(3-methoxypropyloxy)-phenyl]-octanoic acid N-(2-morpholinoethyl)amide dihydrochloride 3.09 g of 5(S)-tert-butoxycarbonylamino-4(S)-hydroxy-2(S),7(S)-diisopropyl-8-[4-methoxy-3-(3-methoxypropyloxy)-phenyl]-octanoic acid N-(2-morpholinoethyl)amide are dissolved in 40 ml of 4N hydrochloric acid in dioxane at 0° C. and the solution is stirred at 0° C. for 2 hours. The reaction mixture is lyophilised and the title compound is obtained: $R_f$(dichloromethane/methanol=8:2)=0.27; HPLC $R_t$=9.52 minutes; HR FAB-MS $(M+H)^+$=566.

The starting materials are prepared as follows:
a) 5(S)-Tert-butoxycarbonylamino-4(S)-hydroxy-2(S),7(S)-diisopropyl-8-[4-methoxy-3-(3-methoxypropyloxy)-phenyl]-octanoic acid N-(2-morpholino-ethyl)amide 1.30 g of p-toluenesulfonic acid (monohydrate) are added to 4.18 g of 3-tert-butoxy-carbonyl-5(S)-{2(S)-[N-(2-morpholino-ethyl)carbamoyl]-2(S)-isopropyl-ethyl}-4(S)-{2(S)-isopropyl-3-[4-methoxy-3-(3-methoxypropyloxy)-phenyl]-propyl}-2,2-dimethyl-1,3-oxazolidine in 160 ml of methanol at 0° C. The reaction solution is stirred at room temperature for a further 18 hours. After evaporation of the solvent, 200 ml of 0.1N sodium hydroxide are added to the residue and extraction is carried out with dichloromethane. The organic extracts are concentrated by evaporation and purified by FC (230 g of silica gel, dichloromethane/methanol=95:5). The title compound is obtained: $R_f$(dichloromethane/methanol=9:1)=0.55.

b) 3-Tert-butoxycarbonyl-5(S)-{2(S)-[N-(2-morpholino-ethyl)-carbamoyl]-2(S)-iso-propyl-ethyl}-4(S)-{2(S)-isopropyl-3-[4-methoxy-3-(3-methoxypropyloxy)-phenyl]-propyl}-2,2-dimethyl-1,3-oxazolidine 1.09 ml of triethylamine, 1.02 ml of 4-(2-aminoethyl)-morpholine and 1.19 ml of cyanophosphonic acid diethyl ester are added in succession to 3.88 g of 3-tert-butoxycarbonyl-5(S)-[2(S)-carboxy-3-methyl-butyl]-4(S)-{2(S)-isopropyl-3-[4-methoxy-3-(3propyloxy)-phenyl]-propyl}-2,2-dimethyl-1,3-oxazolidine in 190 ml of dimethylformamide at 0° C. The reaction mixture is stirred at room temperature for a further 18 hours. The reaction mixture is concentrated by evaporation and the residue is partitioned between diethyl ether and saturated sodium hydrogen carbonate solution. The organic phases are washed with saturated sodium chloride solution and concentrated by evaporation. The residue is purified by FC (230 g of silica gel, dichloromethane/methanol=95:5). The title compound is obtained: $R_f$(dichloromethane/methanol=95:5)=0.25.

c) 3-Tert-butoxycarbonyl-5(S)-(2(S)-carboxy-3-methyl-butyl)-4(S)-{2(S)-isopropyl-3-methoxy-3-(3-methoxypropyloxy)-phenyl]-propyl}-2,2-dimethyl-1,3-oxazolidine 53 g of 3-tert-butoxycarbonyl-5(S)-(2(S)-formyl-3-methyl-butyl)-4(S)-{2(S)-isopropyl-3-[4-methoxy-3-(3-methoxypropyloxy)-phenyl]-propyl}-2,2-dimethyl-1,3-oxazolidine are dissolved in 470 ml of toluene, and, at 0° C., 470 ml of water, 79.1 g of potassium permanganate and 9.7 g of tetrabutylammonium bromide are added in succession thereto. The reaction mixture is stirred for a further 48 hours at 0°–5° C., and then, at 10° C., 1.2 litres of 10% sodium sulfite solution are added. After a further 30 minutes, 1.95 litres of 10% citric acid solution and 1.2 litres of water are added. The product is extracted by repeated extraction with ethyl acetate. The extracts are concentrated by evaporation and purified by FC (2.3 kg of silica gel, ethyl acetate/hexane=3:7). The title compound is obtained: $R_f$(ethyl acetate/hexane=1:2)=0.21.

d) 3-Tert-butoxycarbonyl-5(S)-(2(S)-formyl-3-methyl-butyl)-4(S)-{2(S)-isopropyl-3-[4-methoxy-3-(3-methoxypropyloxy)-phenyl]-propyl}-2,2-dimethyl-1,3-oxazolidine 100 g of molecular sieve (0.3 nm) and 16.6 g of N-methylmorpholine-N-oxide are added to 53 g of 3-tert-butoxycarbonyl-5(S)-(3-hydroxy-2(S)-isopropyl-propyl)-4(S)-{2(S)-isopropyl-3-[4-methoxy-3-(3-methoxypropyloxy)-phenyl]-propyl}-2,2-dimethyl-1,3-oxazolidine in 1.8 litres of dichloromethane at room temperature. The reaction mixture is stirred for 10 minutes and then 1.60 g of tetrapropylammonium perrutherate are added. The reaction mixture is stirred for a further 30 minutes and then filtered. The filtrate is diluted with dichloromethane and then washed in succession with 2M sodium sulfite solution, saturated sodium chloride solution and 1M copper(II) sulfate. The organic phase is concentrated by evaporation and the crude title compound is obtained: $R_f$(ethyl acetate/hexane=1:2)=0.43.

e) 3-Tert-butoxycarbonyl-5(S)-(3-hydroxy-2(S)-isopropyl-propyl)-4(S)-{2(S)-isopropyl-3-[4-methoxy-3-(3-methoxypropyloxy)-phenyl]-propyl}-2,2-dimethyl-1,3-oxazolidine 3.7 g of 3-tert-butoxycarbonyl-5(S)-(3-benzyloxy-2(S)-isopropyl-propyl)-4(S)-{2(S)-iso-propyl-3-[4-methoxy-3-(3-methoxypropyloxy)-phenyl]-propyl}-2,2-dimethyl-1,3-oxazolidine are hydrogenated in the presence of 1.0 g of 5% Pd/C in 50 ml of tetrahydrofuran for 15 minutes at room temperature and under normal pressure. The reaction mixture is filtered and concentrated by evaporation. The residue is purified by means of FC (140 g of silica gel, ethyl acetate/hexane=1:2). The title compound is obtained: $R_f$(ethyl acetate/hexane=1:2)=0.28.

f) 3-Tert-butoxycarbonyl-5 (S)-(3-benzyloxy-2(S)-isopropyl-propyl)-4(S)-{2(S)-iso-propyl-3-[4-methoxy-3-(3-methoxypropyloxy)-phenyl]-propyl}-2,2-dimethyl-1,3-oxazolidine (A)
and
3-tert-butoxycarbonyl-5(R)-(3-benzyloxy-2(S)-isopropyl-propyl)-4(S)-{2(S)-isopropyl-3-[4-methoxy-3-(3-methoxypropyloxy)-phenyl]-propyl}-2,2-dimethyl-1,3-oxazolidine (B)

10.9 ml of 2,2-dimethoxypropane and 10 mg of p-toluenesulfonic acid (monohydrate) are added to 7.0 g of 5(S)-tert-butoxycarbonylamino-4(R,S)-hydroxy-2(S),7(S)-diisopropyl-8-[4-methoxy-3-(3-methoxypropyloxy)-phenyl]-octyl-benzyl ether in 1.86 litres of dichloromethane at room temperature. The reaction mixture is stirred at room temperature for a further 24 hours. After concentration by evaporation, the residue is purified by FC (1 kg of silica gel and dichloromethane/diethyl ether=96:4). The title compounds are obtained:

A) R$_f$(dichloromethane/tert-butyl methyl ether)=0.36
B) R$_f$(dichloromethane/tert-butyl methyl ether)=0.44 g) 5(S)-Tert-butoxycarbonylamino-4(R,S)-hydroxy-2(S),7(S)-diisopropyl-8-[4-methoxy-3-(3-methoxypropyloxy)-phenyl]-octyl-benzyl ether 51.1 g of magnesium chips are placed in 1.4 litres of tetrahydrofuran at 55° C. A solution of 380 g of 2(S)-bromomethyl-3-methyl-butyl-benzyl ether, 30.2 ml of 1,2-dibromoethane in 0.8 litre of tetrahydrofuran at 55° C. is added dropwise over a period of 30 minutes. The reaction mixture is stirred for a further 20 minutes at 55° C. and then cooled to 5° C. A solution of 190 g of 2(S)-tert-butoxycarbonylamino-4(S)-isopropyl-5-[4-methoxy-3-(3-methoxypropyloxy)-phenyl]-pentanal in 0.7 litre of tetrahydrofuran is then added dropwise. The reaction mixture is stirred for a further 3 hours at room temperature, and then, at 5° C., saturated ammonium chloride solution is added and extraction is carried out with diethyl ether. The extracts are concentrated by evaporation and purified by FC (4 kg of silica gel, ethyl acetate/hexane=1:3). The title compound is obtained in the form of a diastereoisomeric mixture: R$_f$(ethyl acetate/hexane=1:2)=0.26; HPLC R$_t$=22.67 and 22.81 (40:60).

h) 2(S)-Tert-butoxycarbonylamino-4(S)-isopropyl-5-[4-methoxy-3-(3-methoxy-propyloxy)-phenyl]-pentanal The title compound is prepared analogously to Example 1c) to 1 g), except that in step 1 g) instead of 2(S)-isopropyl-3-(p-tert-butyl-phenyl)-propanol there is used 2(R)-isopropyl-3-[4-methoxy-3-(3-methoxypropyloxy)-phenyl]-propanol. That compound is prepared as follows:

i) 2(R)-Isopropyl-3-[4-methoxy-3-(3-methoxypropyloxy)-phenyl]-propanol 186 g of 2(R)-isopropyl-3-[4-methoxy-3-(3-methoxypropyloxy)-phenyl]-propionic acid in 0.5 litre of tetrahydrofuran are added dropwise at room temperature to a stirred mixture of 27.2 g of sodium borohydride in 1.5 litres of tetrahydrofuran. After 45 minutes a solution of 76.2 g of iodine in 1 litre of tetrahydrofuran is added dropwise. The reaction mixture is stirred for 4 days and then 1 litre of methanol is carefully added dropwise. After evaporation of the solvent the residue is taken up in 2 litres of 2N hydrochloric acid and extracted repeatedly with ethyl acetate. The organic extracts are washed in succession with water, saturated sodium thiosulfate solution, water/saturated sodium chloride solution (1:1), 0.1N sodium hydroxide solution and saturated sodium chloride solution. The organic extracts are concentrated by evaporation and purified by FC (2.4 kg of silica gel, ethyl acetate/hexane=1:4). The title compound is obtained: R$_f$(ethyl acetate/hexane=1:1)=0.28.

k) 2(R)-Isopropyl-3-[4-methoxy-3-(3-methoxypropyloxy)-phenyl]-propionic acid 0.434 litre of 30% hydrogen peroxide is slowly added to 300 g of 4(R)-benzyl-3-{2(S)-isopropyl-3-[4-methoxy-3-(3-methoxypropyloxy)-phenyl]-propionyl}-oxazolidin-2-one in 4.8 litres of tetrahydrofuran/water (3:1) at 0° C. After the addition of 31.2 g of lithium hydroxide, the mixture is stirred for 3 hours at 0°-20° C. 2.55 litres of 1.5M sodium sulfite solution are then added to the reaction mixture at 0°-15° C. and stirring is continued for a further 30 minutes. 1 litre of saturated sodium hydrogen carbonate solution is added and the tetrahydrofuran is evaporated off. The aqueous solution is washed repeatedly with dichloromethane and then acidified with 2N hydrochloric acid (pH 3.0). Extraction with dichloromethane and subsequent evaporation of the solvent yield the title compound: R$_f$(ethyl acetate/hexane=2:1)=0.30; m.p. 43.5°-44° C.

1) 4(R)-Benzyl-3-{2(R)-isopropyl-3-[4-methoxy-3-(3-methoxypropyloxy)-phenyl]-propionyl}-oxazolidin-2-one 600 ml of tetrahydrofuran are added to a solution of 600 ml of 1M lithium hexamethyldisilazide and the mixture is stirred at –70° C. Then a solution of 156.6 g of 4(R)-benzyl-3-isovaleroyl-oxazolidin-2-one in 500 ml of tetrahydrofuran is added dropwise and the reaction mixture is stirred for a further 75 minutes at –70° C. Then a solution of 145 g of 4-methoxy-3-(3-methoxypropyloxy)-benzyl bromide in 500 ml of tetrahydrofuran is added dropwise. The temperature of the reaction mixture is allowed to rise from –70° to 0° C. over a period of 2 hours. The reaction mixture is left to stand for a further 18 hours at 4° C. and then, with stirring, 250 ml of saturated ammonium chloride solution are added. The tetrahydrofuran is evaporated off and the residue is extracted with ethyl acetate. The title compound is obtained from the residue of the extracts by purification by means of FC (2.4 kg of silica gel, ethyl acetate/hexane=1:1):R$_f$(ethyl acetate/hexane=1:2)=0.30; m.p. 55°-56° C.

m) 4-Methoxy-3-(3-methoxypropyloxy)-benzyl bromide 97 ml of trimethylbromosilane are added, with stirring at room temperature, to 113.1 g of 4-methoxy-3-(3-methoxypropyloxy)-benzyl alcohol in 1.31 litres of chloroform. After 10 minutes the solvent is evaporated off and the residue is immediately purified by means of FC (900 g of silica gel, eluant: ethyl acetate/hexane 1:3). The title compound is obtained: R$_f$(ethyl acetate/hexane=1:2)=0.34; m.p. 50°-51° C.

n) 4-Methoxy-3-(3-methoxypropyloxy)-benzyl alcohol 7.7 g of 3-hydroxy-4-methoxy-benzyl alcohol, 10.35 g of potassium carbonate and 12.1 g of 1-bromo-3-methoxypropane are stirred under reflux in 150 ml of acetone for 3 days. After evaporation of the solvent, water is added to the residue and extraction is carried out with ethyl acetate. After evaporation of the solvent the title compound is obtained from the organic extracts by means of FC (240 g of silica gel, dichloromethane/methanol=96:4): R$_f$(ethyl acetate/hexane=2:1)=0.31.

EXAMPLE 125

5(S)-Amino-4(S)-hydroxy-2(S),7(S)-diisopropyl-8-[4-methoxy-3-(3-methoxylpropyloxy)-phenyl]-octanoic acid N-(3-morpholinopropyl)amide dihydrochloride Analogously to Example 124, the title compound is obtained starting from 120 mg of 5(S)-tert-butoxycarbonylamino-4(S)-hydroxy-2(S)-7(S)-diisopropyl-8-[4-methoxy-3-(3-methoxy-propyloxy)-phenyl]-octanoic acid N-(3-morpholinopropyl)amide: R$_f$(dichloromethane/methanol/conc. ammonia=350:50:1)=0.12; HPLC R$_t$=9.64 minutes; FAB-MS (M+H)$^+$=580.

The starting material is prepared analogously to Example 124a) and 124b) from 3-tert-butoxycarbonyl-5(S)-(2(S)-carboxy-3-methyl-butyl)-4(S)-{2(S)-isopropyl-3-[4-methoxy-3-(3-methoxypropyloxy)-phenyl]-propyl}-2,2-dimethyl-1,3-oxazolidine (Example 124c) and 4-(3-aminopropyl)morpholine.

EXAMPLE 126

5(S)-Amino-4(S)-hydroxy-2(S),7(S)-diisopropyl-8-[4-methoxy-3-(3-methoxypropyloxy)-phenyl]-octanoic acid N-(2,2-dimethyl-2-morpholino-ethyl) amide dihydrochloride Analogously to Example 124, the title compound is obtained starting from 110 mg of 5(S)-tertbutoxycarbonylamino-4(S)-hydroxy-2(S)-7(S)-diisopropyl-8-[4-methoxy-3-(3-methoxy-propyloxy)-phenyl]-octanoic acid N-(2,2-dimethyl-2-morpholino-ethyl)amide: $R_f$(dichloromethane/methanol=9:1)=0.05; HPLC $R_t$=10.35 minutes; FAB-MS (M+H)$^+$=594.

The starting material is prepared analogously to Example 124a) and 124b) from 3-tert-butoxycarbonyl-5(S)-(2(S)-carboxy-3-methyl-butyl)-4(S)-{2(S)-isopropyl-3-[4-methoxy-3-(3-methoxypropyloxy)-phenyl]-propyl}-2,2-dimethyl-1,3-oxazolidine (Example 124c) and 4-(2-amino-1,1-dimethyl-ethyl)-morpholine.

a) 4-(2-Amino-1,1-dimethyl-ethyl)-morpholine

A solution of 8.33 g of 2-methyl-2-morpholino-propionic acid amide in 50 ml of tetrahydrofuran is slowly added at room temperature to 3.33 g of lithium aluminium hydride in 85 ml of tetrahydrofuran. The reaction mixture is then stirred for a further 2 hours under reflux. The reaction mixture is cooled and then 5 ml of water, 6.67 ml of 2N sodium hydroxide and a further 5 ml of water are added in succession. The suspension is clarified by filtration and the crude title compound is obtained from the concentrated filtrate: $^1$H NMR (CDCl$_3$), δ(ppm)=3.67 (4H, m), 2.52 (2H, s), 2.48 (4H, m), 1.37 (2H, bs),0.92 (6H, s).

b) 2-Methyl-2-morpholino-propionic acid amide 272 ml of concentrated sulfuric acid are slowly added, with stirring, to 57.9 g of 2-methyl-2-morpholino-propionitrile (exothermic reaction). After the addition of 43 ml of water, the mixture is stirred for 2 hours at 100°–110° C. The reaction mixture is cooled to 50° C. and added dropwise at 0° C. to a solution of 846 ml of 20% ammonia in 242 ml of water. The mixture is then extracted repeatedly with dichloromethane. The organic phases are washed with saturated sodium chloride solution and with sodium sulfate. The crude title compound is obtained from the concentrated filtrate: $^1$H NMR (CDCl$_3$), δ(ppm) =7.08 (1 H, bs), 5.38 (1H, bs), 3.72 (4H, m), 2.53 (4H, m), 1.22 (6H, s)

EXAMPLE 127

5(S)-Amino-4(S)-hydroxy-2(S),7(S)-diisopropyl-8-[4-methoxy-3-(3-methoxypropyloxy)-phenyl]-octanoic acid N-(2-thiomorpholinoethyl)amide dihydrochloride Analogously to Example 124, the title compound is obtained starting from 110 mg of 5(S)-tert-butoxycarbonylamino-4(S)-hydroxy-2(S)-7(S)-diisopropyl-8-[4-methoxy-3-(3-methoxy-propyloxy)-phenyl]-octanoic acid N-(2-thiomorpholinoethyl)amide: $R_f$(dichloromethane/methanol=8:2)=0.33; HPLC $R_t$=10.39 minutes; FAB-MS (M+H)$^+$=582.

The starting material is prepared analogously to Example 124a) and 124b) from 3-tert-butoxycarbonyl-5(S)-(2(S)-carboxy-3-methyl-butyl)-4(S)-{2(S)-isopropyl-3-[4-methoxy-3-(3-methoxypropyloxy)-phenyl]-propyl )-2,2-dimethyl-1,3-oxazolidine (Example 124c) and 4-(2-aminoethyl)thiomorpholine.

EXAMPLE 128

5(S)-Amino-4(S)-hydroxy-2(S),7(S)-diisopropyl-8-[4-methoxy-3-(3-methoxypropyloxy)-phenyl]-octanoic acid N-(1,1-dimethyl-2-morpholino-ethyl) amide dihydrochloride Analogously to Example 124, the title compound is obtained starting from 95 mg of 5(S)-tert-butoxycarbonylamino-4(S)-hydroxy-2(S),7(S)-diisopropyl-8-[4-methoxy-3-( 3-methoxy-propyloxy)-phenyl]-octanoic acid N-(1,1-dimethyl-2-morpholino-ethyl)amide: $R_f$(dichloromethane/methanol=8:2)=0.42; HPLC $R_t$=10.37 minutes; FAB-MS (M+H)$^+$=594.

The starting material is prepared analogously to Example 124a) and 130b) from 3-tert-butoxycarbonyl-5(S)-(2(S)-carboxy-3-methyl-butyl)-4(S)-{2(S)-isopropyl-3-[4-methoxy-3-(3-methoxypropyloxy)-phenyl]-propyl}-2,2-dimethyl-1,3-oxazolidine (Example 124c) and 4-(2-amino-2,2-dimethyl-ethyl)-morpholine.

EXAMPLE 129

5(S)-Amino-4(S)-hydroxy-2(S),7(S)-diisopropyl-8-[4-methoxy-3-(3-methoxypropyloxy)-phenyl]-octanoic acid N-[1 (R,S)-methyl-2-morpholino-ethyl]amide dihydrochloride Analogously to Example 124, the title compound is obtained starting from 73 mg of 5(S)-tert-butoxycarbonylamino-4(S)-hydroxy-2(S),7(S)-diisopropyl-8-[4-methoxy-3-(3-methoxy-propyloxy)-phenyl]-octanoic acid N-[1(R,S)-methyl-2-morpholino-ethyl]amide: $R_f$(dichloromethane/methanol=8:2)=0.43; HPLC $R_t$=9.98/ 10.58 minutes; FAB-MS (M+H)$^+$=580.

The starting material is prepared analogously to Example 124a) and 124b) from 3-tert-butoxycarbonyl-5(S)-(2(S)-carboxy-3-methyl-butyl)-4(S)-{2(S)-isopropyl-3-[4-methoxy-3-(3-methoxypropyloxy)-phenyl]-propyl}-2,2-dimethyl-1,3-oxazolidine (Example 124c) and 4-(2-amino-2(R,S)-methyl-ethyl)-morpholine.

EXAMPLE 130

5(S)-Amino-4(S)-hydroxy-2(S),7(S)-diisopropyl-8-[4-methoxy-3-(3-methoxypropyloxy)-phenyl]-octanoic acid [N-(1-carbamoyl-1-methyl-ethyl)]-amide hydrochloride 1.5 ml of trifluoroacetic acid are added to 56 mg of 5(S)-tert-butoxycarbonylamino-4(S)-hydroxy-2(S),7(S)-diisopropyl-8-[4-methoxy-3-(3-methoxypropyloxy)-phenyl]-octanoic acid [N-(1-carbamoyl-1-methyl-ethyl)]-amide in 1.5 ml of dichloromethane at 0° C. The mixture is stirred for a further 30 minutes at 0° C. The reaction mixture is poured onto cooled 1N sodium hydroxide and the product is extracted repeatedly with dichloromethane. The organic phases are dried, and ethereal hydrochloric acid is added. Concentration by evaporation yields the title compound: $R_f$(dichloromethane/methanol=8:2)=0.30; HPLC $R_t$=11.25; FAB-MS (M+H)$^+$=538.

The starting materials are prepared as follows:

a) 5(S)-Tert-butoxycarbonylamino-4(S)-hydroxy-2(S),7(S)-diisopropyl-8-[4-methoxy-3-(3-methoxypropyloxy)-phenyl]-octanoic acid [N-(1-carbamoyl-1-methyl-ethyl)]-amide 5 mg of p-toluenesulfonic acid (monohydrate) are added to 82 mg of 3-tert-butoxycarbonyl-5(S)-{2-[N-(1-carbamoyl-1-methyl-ethyl)-carbamoyl]-2(S)-isopropyl-ethyl}-4(S)-{2(S)-isopropyl-3-[4-methoxy-3-(3-methoxypropyloxy)-phenyl]-propyl}-2,2-dimethyl-1,3-oxazolidine in 5 ml of methanol at 0° C. The reaction solution is stirred for a further 18 hours at room temperature. After evaporation of the solvent, 20 ml of saturated sodium hydrogen carbonate solution are added to the residue and extraction is carried out repeatedly with ethyl acetate. The organic extracts are concentrated by evaporation and purified by means of FC (35 g of silica gel, dichloromethane/ methanol=9:1). The title compound is obtained: R_f (dichloromethane/methanol=9:1)=0.47.

b) 3-Tert-butoxycarbonyl-5(S)-{2-[N-(1-carbamyl-1-methyl-ethyl)-carbamoyl]-2(S)-isopropyl-ethyl}-4(S)-{2(S)-isopropyl-3-[4-methoxy-3-(3-methoxypropyloxy)-phenyl]-propyl}-2,2-dimethyl-1,3-oxazolidine 106 μl of 4-methyl-morpholine, 66 mg of 2-aminoisobutyric acid amide hydrochloride and 91 mg of O-benzotriazol-1-yl-N,N,N',N'-tetramethyluronium hexafluorophosphate (HBTU) are added in succession to 119 mg of 3-tert-butoxycarbonyl-5(S)-(2(S)-carboxy-3-methyl-butyl)-4(S)-{2(S)-isopropyl-3-[4-methoxy-3-(3-methoxypropyloxy)-phenyl]-propyl}-2,2-dimethyl-1,3-oxazolidine (Example 124c) in 8 ml of dimethylformamide. The reaction mixture is stirred for 8 days at 40° C. The mixture is concentrated by evaporation and the residue is partitioned between ethyl acetate and saturated sodium chloride solution. The organic phases are concentrated by evaporation and the residue is purified by means of FC (60 g of silica gel, dichloromethane/methanol=95:5). The title compound is obtained: R_f(dichloromethane/methanol= 95:5)=0.30.

EXAMPLE 131

5(S)-Amino-4(S)-hydroxy-2(S),7(S)-diisopropyl-8-[4-methoxy-3-(3-methoxypropyloxy)-phenyl]-octanoic acid {N-[3-(N-methylcarbamoyl)-propyl]}-amide hydrochloride The title compound is obtained analogously to Example 124 starting from 101 mg of 5(S)-tert-butoxycarbonylamino-4(S)-hydroxy-2(S)-7(S)-diisopropyl-8-[4-methoxy-3-(3-methoxypropyloxy)-phenyl]-octanoic acid {N-[3-(N-methylcarbamoyl)-propyl]}-amide: R_f(dichloromethane/methanol=8:2)=0.32; HPLC R_t=10.11 minutes; FAB-MS (M+H)⁺=552.

The starting material is prepared analogously to Examples 130a) and 124b) from 3-tert-butoxycarbonyl-5(S)-(2(S)-carboxy-3-methyl-butyl)-4(S)-{2(S)-isopropyl-3-[4-methoxy-3-(3-methoxypropyloxy)-phenyl]-propyl}-2,2-dimethyl-1,3-oxazolidine (Example 124c) and 4-amino-N-methylbutyric acid amide hydrochloride.

EXAMPLE 132

5(S)-Amino-4(S)-hydroxy-2(S),7(S)-diisopropyl-8-[4-methoxy-3-(3-methoxypropyloxy)-phenyl]-octanoic acid {N-[3-(N,N-dimethylcarbamoyl)-propyl}-amide hydrochloride The title compound is obtained analogously to Example 124 starting from 91 mg of 5(S)-tert-butoxycarbonylamino-4(S)-hydroxy-2(S),7(S)-diisopropyl-8-[4-methoxy-3-(3-methoxypropyloxy)-phenyl]-octanoic acid {N-[3-(N,N-dimethylcarbamoyl)-propyl]}-amide: R_f(dichloromethane/methanol=8:2)=0.36; HPLC R_t=10.38 minutes; FAB-MS (M+H)⁺=566.

The starting material is prepared analogously to Examples 130a) and 124b) from 3-tert-butoxycarbonyl-5(S)-(2(S)-carboxy-3-methyl-butyl)-4(S)-{2(S)-isopropyl-3-[4-methoxy-3-(3-methoxypropyloxy)-phenyl]-propyl}-2,2-dimethyl-1,3-oxazolidine (Example 124c) and 4-amino-N,N-dimethylbutyric acid amide hydrochloride.

EXAMPLE 133

5(S)-Amino-4(S)-hydroxy-2(S),7(S)-diisopropyl-8-[4-methoxy-3-(3-methoxypropyloxy)-phenyl]-octanoic acid N-[2-(N,N-dimethylcarbamoyl)ethyl] amide hydrochloride The title compound is obtained analogously to Example 124 starting from 87 mg of 5(S)-tert-butoxycarbonylamino-4(S)-hydroxy-2(S),7(S)-diisopropyl-8-[4-methoxy-3-(3-methoxypropyloxy)-phenyl]-octanoic acid N-[2-(N,N-dimethylcarbamoyl)ethyl]-amide: R_f(dichloromethane/methanol=8:2)=0.38; HPLC R_t=10.31 minutes; FAB-MS (M+H)⁺=552.

The starting material is prepared analogously to Examples 130a) and 124b) from 3-tert-butoxycarbonyl-5(S)-(2(S)-carboxy-3-methyl-butyl)-4(S)-{2(S)-isopropyl-3-[4-methoxy-3-(3-methoxypropyloxy)-phenyl]-propyl}-2,2-dimethyl-1,3-oxazolidine (Example 124c) and 3-amino-N,N-dimethylpropionic acid amide hydrochloride.

EXAMPLE 134

5(S)-Amino-4(S)-hydroxy-2(S),7(S)-diisopropyl-8-[4-methoxy-3-(3-methoxypropyloxy)-phenyl]-octanoic acid [N-(1-carbamoylmethyl)]-amide hydrochloride The title compound is obtained analogously to Example 124 starting from 84 mg of 5(S)-tert-butoxycarbonylamino-4(S)-hydroxy-2(S),7(S)-diisopropyl-8-[4-methoxy-3-(3-methoxypropyloxy)-phenyl]-octanoic acid [N-(1-carbamoylmethyl)]-amide: R_f(dichloromethane/methanol=8:2)=0.20; HPLC R_t=9.73 minutes; FAB-MS (M+H)⁺=510.

The starting material is prepared analogously to Examples 130a) and 124b) from 3-tert-butoxycarbonyl-5(S)-(2(S)-carboxy-3-methyl-butyl)-4(S)-{2(S)-isopropyl-3-[4-methoxy-3-(3-methoxypropyloxy)-phenyl]-propyl}-2,2-dimethyl-1,3-oxazolidine (Example 124c) and glycinamide hydrochloride.

EXAMPLE 135

5(S)-Amino-4(S)-hydroxy-2(S),7(S)-diisopropyl-8-[4-methoxy-3-(3-methoxypropyloxy)-phenyl]-octanoic acid [N-(2-carbamoylethyl)]-amide hydrochloride The title compound is obtained analogously to Example 124 starting from 78 mg of 5(S)-tert-butoxycarbonylamino-4(S)-hydroxy-2(S),7(S)-diisopropyl-8-[4-methoxy-3-(3-methoxypropyloxy)-phenyl]-octanoic acid N-(2-carbamoylethyl)amide: R_f(dichloromethane/methanol=8:2)=0.24; HPLC R_t=9.87 minutes; FAB-MS (M+H)⁺=524.

The starting material is prepared analogously to Examples 130a) and 124b) from 3-tert-butoxycarbonyl-5(S)-[2(S)-carboxy-3-methyl-butyl]-4(S)-{2(S)-isopropyl-3-[4-methoxy-3-(3-methoxypropyloxy)-phenyl]-propyl}-2,2-dimethyl-1,3-oxazolidine (Example 124c) and 3-aminopropionic acid amide hydrochloride.

EXAMPLE 136

5(S)-Amino-4(S)-hydroxy-2(S),7(S)-diisopropyl-8-[4-methoxy-3-(3-methoxypropyloxy)-phenyl]-octanoic acid N-(3-carbamoylpropyl)amide hydrochloride The title compound is obtained analogously to Example 124 starting from 74 mg of 5(S)-tert-butoxycarbonylamino-4(S)-hydroxy-2(S),7(S)-diisopropyl-8-[4-methoxy-3-(3-methoxypropyloxy)-phenyl]-octanoic acid N-(3-carbamoylpropyl)amide: R_f(dichloromethane/methanol=9:1)=0.06; HPLC R_t=10.27 minutes; FAB-MS (M+H)⁺=538.

The starting material is prepared analogously to Examples 130a) and 124b) from 3-tert-butoxycarbonyl-5(S)-(2(S)- carboxy-3-methyl-butyl)-4(S)-{2(S)-isopropyl-3-[4-methoxy-3-(3-methoxypropyloxy)-phenyl]-propyl}-2,2-dimethyl-1,3-oxazolidine (Example 124c) and 4-aminobutyric acid amide hydrochloride.

EXAMPLE 137

5(S)-Amino-4(S)-hydroxy-2(S),7(S)-diisopropyl-8-[4-methoxy-3-(3-methoxypropyloxy)-phenyl]-octanoic acid N-(2-carbamoyl-2,2-dimethyl-ethyl) amide hydrochloride The title compound is obtained analogously to Example 124 starting from 94 mg of 5(S)-tert-butoxycarbonylamino-4(S)-hydroxy-2(S),7(S)-diisopropyl-8-[4-methoxy-3-(3-methoxypropyloxy)-phenyl]-octanoic acid N-(2-carbamoyl-2,2-dimethyl-ethyl)amide: $R_f$(dichloromethane/methanol=8:2)=0.33; HPLC $R_t$=11.26 minutes; FAB-MS $(M+H)^+$=552.

The starting material is prepared analogously to Examples 130a) and 124b) from 3-tert-butoxycarbonyl-5(S)-(2(S)-carboxy-3-methyl-butyl)-4(S)-{2(S)-isopropyl-3-[4-methoxy-3-(3-methoxypropyloxy)-phenyl]-propyl}-2,2-dimethyl-1,3-oxazolidine (Example 124c) and 3-amino-2,2-dimethylpropionic acid amide hydrochloride.

EXAMPLE 138

5(S)-Amino-4(S)-hydroxy-2(S),7(S)-diisopropyl-8-[4-methoxy-3-(3-methoxypropyloxy)-phenyl]-octanoic acid N-[2,2-dimethyl-2-(N-methylcarbamoyl)-ethyl]amide hydrochloride The title compound is obtained analogously to Example 124 starting from 87 mg of 5(S)-tert-butoxycarbonylamino-4(S)-hydroxy-2(S),7(S)-diisopropyl-8-[4-methoxy-3-(3-methoxypropyloxy)-phenyl]-octanoic acid {N-[2,2-dimethyl-2-(N-methylcarbamoyl)-ethyl]}-amide: $R_f$(dichloromethane/methanol=8:2)=0.40; HPLC $R_t$=11.69 minutes; FAB-MS $(M+H)^+$=566.

The starting material is prepared analogously to Examples 130a) and 124b) from 3-tert-butoxycarbonyl-5(S)-(2(S)-carboxy-3-methyl-butyl)-4(S)-{2(S)-isopropyl-3-[4-methoxy-3-(3-methoxypropyloxy)-phenyl]-propyl}-2,2-dimethyl-1,3-oxazolidine (Example 124c) and 3-amino-2,2-dimethyl-N-methylpropionic acid amide hydrochloride.

a) 3-Amino-2,2-dimethyl-N-methylpropionic acid amide hydrochloride

Analogously to Example 121a) from 3-benzyloxycarbonylamino-2,2-dimethyl-N-methylpropionic acid amide.

b) 3-Benzyloxycarbonylamino-2,2-dimethyl-N-methylpropionic acid amide 4.19 g of 3-benzyloxycarbonylamino-2,2-dimethylpropionic acid ethyl ester and 50 ml of 33% methylamine (in ethanol) are stirred for 8 days at 60° C. in a bomb tube. The reaction mixture is concentrated by evaporation and the residue is purified by FC (220 g of silica gel, dichloromethane/methanol=95:5). The title compound is obtained: $R_f$(dichloromethane/methanol=9:1)=0.51.

c) 3-Benzyloxycarbonylamino-2,2-dimethylpropionic acid ethyl ester 31 ml of 90% chloroformic acid benzyl ester are slowly added, at 0°–5° C., to 29.04 g of 3-amino-2,2-dimethylpropionic acid ethyl ester in 500 ml of ethyl acetate and 250 ml of 1M sodium hydrogen carbonate solution. The reaction mixture is stirred for 2 hours at 0°–5° C. and extracted with ethyl acetate. The organic phases are washed with saturated sodium chloride solution and then concentrated. The evaporation residue is purified by FC (1 kg of silica gel; eluant: ethyl acetate/hexane=1:3). The title compound is obtained: $R_f$(ethyl acetate/hexane=1:3)=0.28.

EXAMPLE 139

5(S)-Amino-4(S)-hydroxy-2(S),7(S)-diisopropyl-8-[4-methoxy-3-(3-methoxypropyloxy)-phenyl]-octanoic acid N-[2-(N-methylcarbamoyl)ethyl] amide hydrochloride The title compound is obtained analogously to Example 124 starting from 92 mg of 5(S)-tert-butoxycarbonylamino-4(S)-hydroxy-2(S),7(S)-diisopropyl-8-[4-methoxy-3-(3-methoxypropyloxy)-phenyl]-octanoic acid N-[2-(N-methylcarbamoyl)-ethyl]amide: $R_f$(dichloromethane/methanol=8:2)=0.24; HPLC $R_t$=10.40 minutes; FAB-MS $(M+H)^+$=538.

The starting material is prepared analogously to Examples 130a) and 124b) from 3-tert-butoxycarbonyl-5(S)-(2(S)-carboxy-3-methyl-butyl)-4(S)-{2(S)-isopropyl-3-[4-methoxy-3-(3-methoxypropyloxy)-phenyl]-propyl}-2,2-dimethyl-1,3-oxazolidine (Example 124c) and 3-amino-N-methylpropionic acid amide hydrochloride.

EXAMPLE 140

5(S)-Amino-4(S)-hydroxy-2(S),7(S)-diisopropyl-8-[4-methoxy-3-(3-methoxypropyloxy)-phenyl]-octanoic acid N-(3-morpholino-3-oxopropyl)amide hydrochloride The title compound is obtained analogously to Example 124 starting from 99 mg of 5(S)-tert-butoxycarbonylamino-4(S)-hydroxy-2(S),7(S)-diisopropyl-8-[4-methoxy-3-(3-methoxypropyloxy)-phenyl]-octanoic acid N-(3-morpholino-3-oxopropyl)amide: $R_f$(dichloromethane/methanol=8:2)=0.51; HPLC $R_t$=11.35 minutes; FAB-MS $(M+H)^+$=594.

The starting material is prepared analogously to Examples 130a) and 124b) from 3-tert-butoxycarbonyl-5(S)-(2(S)-carboxy-3-methyl-butyl)-4(S)-{2(S)-isopropyl-3-[4-methoxy-3-(3-methoxypropyloxy)-phenyl]-propyl}-2,2-dimethyl-1,3-oxazolidine (Example 124c) and 3-aminopropionic acid morpholide hydrochloride.

EXAMPLE 141

5(S)-Amino-4(S)-hydroxy-2(S),7(S)-diisopropyl-8-[4-methoxy-3-(3-methoxypropyloxy)-phenyl]-octanoic acid N-(2-carbamoyl-1(R,S)-methyl-ethyl) amide hydrochloride The title compound is obtained analogously to Example 124 starting from 86 mg of 5(S)-tert-butoxycarbonylamino-4(S)-hydroxy-2(S),7(S)-diisopropyl-8-[4-methoxy-3-(3-methoxypropyloxy)-phenyl]-octanoic acid [N-(2-carbamoyl-1(R,S)-methyl-ethyl)]-amide: $R_f$(dichloromethane/methanol=8:2)=0.24; HPLC $R_t$=10.43/11.16 minutes; FAB-MS $(M+H)^+$=538.

The starting material is prepared analogously to Examples 130a) and 124b) from 3-tert-butoxycarbonyl-5 (S)-(2(S)-carboxy-3-methyl-butyl)-4(S)-{2(S)-isopropyl-3-[4-methoxy-3-(3-methoxypropyloxy)-phenyl]-propyl}-2,2-dimethyl-1,3-oxazolidine (Example 124c) and 3(R,S)-aminobutyric acid amide hydrochloride.

EXAMPLE 142

5(S)-Amino-4(S)-hydroxy-2(S),7(S)-diisopropyl-8-[4-methoxy-3-(3-methoxypropyloxy)-phenyl]-octanoic acid {N-[2-(N-methylcarbamoyl)-1(R,S)-methyl-ethyl]}-amide hydrochloride The title compound is obtained analogously to Example 124 starting from 95 mg of 5(S)-tert-butoxycarbonylamino- 4(S)-hydroxy-2(S),7(S)-diisopropyl-8-[4-methoxy-3-(3-methoxypropyloxy)-phenyl]-octanoic acid {N-[2-(N-methylcarbamoyl)-1(R,S)-methyl-ethyl]}-amide: R$_f$(dichloromethane/methanol=8:2)=0.33; HPLC R$_f$=10.78/11.45 minutes; FAB-MS (M+H)$^+$552.

The starting material is prepared analogously to Examples 130a) and 124b) from 3-tert-butoxycarbonyl-5(S)-(2(S)-carboxy-3-methyl-butyl)-4(S)-{2(S)-isopropyl-3-[4-methoxy-3-(3-methoxypropyloxy)-phenyl]-propyl}-2,2-dimethyl-1,3-oxazolidine (Example 124c) and 3(R,S)-amino-N-methylbutyric acid amide hydrochloride.

EXAMPLE 143

5(S)-Amino-4(S)-hydroxy-2(S),7(S)-diisopropyl-8-[4-methoxy-3-(3-methoxypropyloxy)-phenyl]-octanoic acid {N-[2-(N,N-dimethylcarbamoyl)-1(R, S)-methyl-ethyl]}-amide hydrochloride The title compound is obtained analogously to Example 124 starting from 95 mg of 5(S)-tert-butoxycarbonylamino-4(S)-hydroxy-2(S), 7(S)-diisopropyl-8-[4-methoxy-3-(3-methoxypropyloxy)-phenyl]-octanoic acid {N-[2-(N,N-dimethylcarbamoyl)-1(R,S)-methyl-ethyl]}-amide: R$_f$(dichloromethane/methanol=8:2)=0.39; HPLC R$_f$=11.44/12.04 minutes; FAB-MS (M+H)$^+$=566. The starting material is prepared analogously to Examples 130a) and 124b) from 3-tert-butoxycarbonyl-5(S)-(2(S)-carboxy-3-methyl-butyl)-4(S)-{2(S)-isopropyl-3-[4-methoxy-3-(3-methoxypropyloxy)-phenyl]-propyl}-2,2-dimethyl-1,3-oxazolidine (Example 124c) and 3(R,S)-amino-N,N-dimethylbutyric acid amide hydrochloride.

EXAMPLE 144

5-(S)-Amino4(S)-hydroxy-2(S), 7(S)-diisopropyl-8-[4-methoxy-3-(3-methoxypropyloxy)-phenyl]-octanoic acid [N-(2-carbamoyl-1(R)-isopropyl-ethyl)]-amide hydrochloride The title compound is obtained analogously to Example 124 starting from 71 mg of 5(S)-tert-butoxycarbonylamino-4(S)-hydroxy-2(S),7(S)-diisopropyl-8-[4-methoxy-3-(3-methoxypropyloxy)-phenyl]-octanoic acid [N-(2-carbamoyl-1(R)-isopropyl-ethyl)]-amide: R$_f$(dichloromethane/methanol=8:2)=0.27; HPLC R$_f$=10.64 minutes; FAB-MS (M+H)$^+$=566.

The starting material is prepared analogously to Examples 130a) and 124b) from 3-tert-butoxycarbonyl-5(S)-(2(S)-carboxy-3-methyl-butyl)-4(S)-{2(S)-isopropyl-3-[4-methoxy-3-(3-methoxypropyloxy)-phenyl]-propyl}-2,2-dimethyl-1,3-oxazolidine (Example 124c) and 3(S)-amino-4-methyl-pentanoic acid amide hydrochloride.

a) 3(S)-Amino-4-methylpentanoic acid amide hydrochloride is prepared analogously to Example 121a from 3(R)-benzyloxycarbonylamino-4-methyl-pentanoic acid amide.

b) 3(S)-Benzyloxycarbonylamino-4-methylpentanoic acid amide 2.23 g of 3(S)-benzyloxycarbonylamino-4-methylpentanoic acid ethyl ester and 50 ml of 6N ammonia (in methanol) are stirred for 6 days at 75° C. in a bomb tube. The reaction mixture is concentrated by evaporation and the residue is crystallised from ethyl acetate. The title compound is obtained: R$_f$(dichloromethane/methanol=95:5)=0.20; m.p. 171°–172° C.

EXAMPLE 145

5(S)-Amino-4(S)-hydroxy-2(S),7(S)-diisopropyl-8-[4-methoxy-3-(3-methoxypropyloxy)-phenyl]-octanoic acid {N-[2-(N-methylcarbamoyl)-1(R)-isopropyl-ethyl]}-amide hydrochloride The title compound is obtained analogously to Example 124 starting from 81 mg of 5(S)-tert-butoxycarbonylamino-4(S)-hydroxy-2(S),7(S)-diisopropyl-8-[4-methoxy-3-(3-methoxypropyloxy)-phenyl]-octanoic acid N-[2-(N-methylcarbamoyl)-1(R)-isopropyl-ethyl]amide: R$_f$(dichloromethane/methanol=8:2)=0.37; HPLC R$_f$=10.96 minutes; FAB-MS (M+H)$^+$=580.

The starting material is prepared analogously to Examples 130a) and 124b) from 3-tert-butoxycarbonyl-5(S)-(2(S)-carboxy-3-methyl-butyl)-4(S)-{2(S)-isopropyl-3-[4-methoxy-3-(3-methoxypropyloxy)-phenyl]-propyl}-2,2-dimethyl-1,3-oxazolidine (Example 124c) and 3(R)-amino-4-methyl-pentanoic acid N-(methyl)amide hydrochloride.

a) 3(R)-Amino-4-methylpentanoic acid N-(methyl)amide hydrochloride is prepared analogously to Example 121a) from 3(R)-benzyloxycarbonylamino-4-methyl-pentanoic acid N-(methyl)amide.

b) 3(R)-Benzyloxycarbonylamino-4-methylpentanoic acid N-(methyl)amide 2.23 g of 3(R)-benzyloxycarbonylamino-4-methylpentanoic acid ethyl ester and 50 ml of 33% methylamine (in ethanol) are left to stand for 48 hours at room temperature. The reaction mixture is concentrated by evaporation and the residue is crystallised from ethyl acetate. The title compound is obtained: R$_f$(dichloromethane/methanol=95:5)=0.24; m.p. 190–191° C.

EXAMPLE 146

5(S)-Amino-4(S)-hydroxy-2(S),7(S)-diisopropyl-8-[4-methoxy-3-(3-methoxypropyloxy)-phenyl]-octanoic acid {N-[2-(N,N-dimethylcarbamoyl)-1(R)-isopropyl-ethyl]}-amide hydrochloride The title compound is obtained analogously to Example 124 starting from 72 mg of 5(S)-tert-butoxycarbonylamino-4(S)-hydroxy-2(S),7(S)-diisopropyl-8-[4-methoxy-3-(3-methoxypropyloxy)-phenyl]-octanoic acid {N-[2-(N,N-dimethylcarbamoyl)-1(R)-isopropyl-ethyl]}-amide: R$_f$(dichloromethane/methanol=8:2)=0.45; HPLC R$_f$=11.76 minutes; FAB-MS (M+H)$^+$=594.

The starting material is prepared analogously to Examples 130a) and 124b) from 3-tert-butoxycarbonyl-5(S)-(2(S)-carboxy-3-methyl-butyl)-4(S)-{2 (S)-isopropyl-3-[4-methoxy-3-(3-methoxypropyloxy)-phenyl]-propyl}-2,2-dimethyl-1, 3-oxazolidine (Example 124c) and 3(R)-amino-4-methyl-pentanoic acid N,N-dimethylamide hydrochloride.

a) 3(R)-Amino-4-methylpentanoic acid N,N-dimethylamide hydrochloride is prepared analogously to Example 12 1a) from 3(R)-benzyloxycarbonylamino-4-methyl-pentanoic acid N,N-dimethylamide.

b) 3(R)-Benzyloxycarbonylamino-4-methylpentanoic acid N,N-dimethylamide 2.23 g of 3(R)-benzyloxycarbonylamino-4-methylpentanoic acid ethyl ester and 50 ml of 30% dimethylamine (in methanol) are stirred for 6 days at 75° C. in a bomb tube. The reaction mixture is concentrated by evaporation and the residue is purified by FC (dichloromethane/methanol=97:3). The title compound is obtained: R$_f$ (dichloro-methane/methanol=95:5)=0.40.

EXAMPLE 147

5(S)-Amino-4(S)-hydroxy-2(S),7(S)-diisopropyl-8-[4-methoxy-3-(3-methoxypropyloxy)-phenyl]-octanoic acid [N-(1(S)-carbamoyl-2-hydroxy-ethyl)]-amide hydrochloride The title compound is obtained analogously to Example 130 starting from 82 mg of 5(S)-tert-butoxycarbonylamino- 4(S)-hydroxy-2(S),7(S)-diisopropyl-8-[4-methoxy-3-(3-methoxypropyloxy)-phenyl]-octanoic acid [N-(1(S)-carbamoyl-2-hydroxy-ethyl)]-amide: R_f(dichloromethane/methanol=8:2)=0.16; HPLC R_f=10.09 minutes; FAB-MS (M+H)⁺=540.

The starting material is prepared analogously to Examples 130a) and 124b) from 3-tert-butoxycarbonyl-5(S)-(2(S)-carboxy-3-methyl-butyl)-4(S)-{2(S)-isopropyl-3-[4-methoxy-3-(3-methoxypropyloxy)-phenyl]-propyl}-2,2-dimethyl-1,3-oxazolidine (Example 124c) and L-serine amide hydrochloride.

EXAMPLE 148

5(S)-Amino-4(S)-hydroxy-2(S),7(S)-diisopropyl-8-[4-methoxy-3-(3-methoxypropyloxy)-phenyl]-octanoic acid [N-(1(S),2-dicarbamoyl-ethyl)]-amide hydrochloride The title compound is obtained analogously to Example 130 starting from 68 mg of 5(S)-tert-butoxycarbonylamino-4(S)-hydroxy-2(S),7(S)-diisopropyl-8-[4-methoxy-3-(3-methoxypropyloxy)-phenyl]-octanoic acid [N-(1(S),2-dicarbamoyl-ethyl)]-amide: R_f(dichloromethane/methanol=8:2)=0.12; HPLC R_f=9.54 minutes; FAB-MS (M+H)⁺=567.

The starting material is prepared analogously to Examples 130a) and 124b) from 3-tert-butoxycarbonyl-5(S)-(2(S)-carboxy-3-methyl-butyl)-4(S)-{2(S)-isopropyl-3-[4-methoxy-3-(3-methoxypropyloxy)-phenyl]-propyl}-2,2-dimethyl-1,3-oxazolidine (Example 124c) and L-aspartic acid diamide hydrochloride.

EXAMPLE 149

5(S)-Amino-4(S)-hydroxy-2(S),7(S)-diisopropyl-8-[4-methoxy-3-(3-methoxypropyloxy)-phenyl]-octanoic acid [N-(1(S),3-dicarbamoylpropyl)]-amide hydrochloride The title compound is obtained analogously to Example 130 starting from 83 mg of 5(S)-tert-butoxycarbonylamino-4(S)-hydroxy-2(S),7(S)-diisopropyl-8-[4-methoxy-3-(3-methoxypropyloxy)-phenyl]-octanoic acid [N-(1(S),3-dicarbamoylpropyl)]-amide: R_f(dichloromethane/methanol=8:2)=0.13; HPLC R_f=9.50 minutes; FAB-MS (M+H)⁺=581.

The starting material is prepared analogously to Examples 130a) and 124b) from 3-tert-butoxycarbonyl-5(S)-(2(S)-carboxy-3-methyl-butyl)-4(S)-{2(S)-isopropyl-3-[4-methoxy-3-(3-methoxypropyloxy)-phenyl]-propyl}-2,2-dimethyl-1,3-oxazolidine (Example 124c) and L-glutaric acid diamide hydrochloride.

EXAMPLE 150

5(S)-Amino-4(S)-hydroxy-2(S),7(S)-diisopropyl-8-[4-methoxy-3-(3-methoxypropyloxy)-phenyl]-octanoic acid [N-(1(S)-carbamoylpropyl)]-amide hydrochloride The title compound is obtained analogously to Example 130 starting from 90 mg of 5(S)-tert-butoxycarbonylamino-4(S)-hydroxy-2(S),7(S)-diisopropyl-8-[4-methoxy-3-(3-methoxypropyloxy)-phenyl]-octanoic acid [N-(1(S)-carbamoylpropyl)]-amide: R_f(dichloromethane/methanol=8:2)=0.30; HPLC R_f=10.73 minutes; FAB-MS (M+H)⁺=538.

The starting material is prepared analogously to Examples 130a) and 124b) from 3-tert-butoxycarbonyl-5(S)-(2(S)-carboxy-3-methyl-butyl)-4(S)-{2(S)-isopropyl-3-[4-methoxy-3-(3-methoxypropyloxy)-phenyl]-propyl}-2,2-dimethyl-1,3-oxazolidine (Example 124c) and 2(S)-aminobutyric acid amide hydrochloride.

EXAMPLE 151

5(S)-Amino-4(S)-hydroxy-2(S),7(S)-diisopropyl-8-[4-methoxy-3-(3-methoxypropyloxy)-phenyl]-octanoic acid [N-(1(S)-carbamoyl-2(S)-methyl-butyl)]-amide hydrochloride The title compound is obtained analogously to Example 130 starting from 73 mg of 5(S)-tert-butoxycarbonylamino-4(S)-hydroxy-2(S),7(S)-diisopropyl-8-[4-methoxy-3-(3-methoxypropyloxy)-phenyl]-octanoic acid [N-(1(S)-carbamoyl-2(S)-methyl-butyl)]-amide: R_f(dichloromethane/methanol=8:2)=0.36; HPLC R_f=11.59 minutes; FAB-MS (M+H)⁺=566.

The starting material is prepared analogously to Examples 130a) and 124b) from 3-tert-butoxycarbonyl-5(S)-(2(S)-carboxy-3-methyl-butyl)-4(S)-{2(S)-isopropyl-3-[4-methoxy-3-(3-methoxypropyloxy)-phenyl]-propyl}-2,2-dimethyl-1,3-oxazolidine (Example 124c) and L-isoleucine amide hydrochloride.

EXAMPLE 152

5(S)-Amino-4(S)-hydroxy-2(S),7(S)-diisopropyl-8-[4-methoxy-3-(3-methoxypropyloxy)-phenyl]-octanoic acid N-[2(R,S)-carbamoyl-2(R,S)-methyl-ethyl]-amide hydrochloride The title compound is obtained analogously to Example 124 starting from 93 mg of 5(S)-tert-butoxycarbonylamino-4(S)-hydroxy-2(S),7(S)-diisopropyl-8-[4-methoxy-3-(3-methoxypropyloxy)-phenyl]-octanoic acid N-[2(R,S)-carbamoyl-2(R,S)-methyl-ethyl]-amide: R_f(dichloromethane/methanol=8:2)=0.28; HPLC R_f=10.19/10.31 minutes; FAB-MS (M+H)⁺=538.

The starting material is prepared analogously to Examples 130a) and 124b) from 3-tert-butoxycarbonyl-5(S)-(2(S)-carboxy-3-methyl-butyl)-4(S)-{2(S)-isopropyl-3-[4-methoxy-3-(3-methoxypropyloxy)-phenyl]-propyl}-2,2-dimethyl-1,3-oxazolidine (Example 124c) and 3-amino-2(R,S)-methylpropionic acid amide hydrochloride.

EXAMPLE 153

5(S)-Amino-4(S)-hydroxy-2(S),7(S)-diisopropyl-8-[4-methoxy-3-(3-methoxypropyloxy)-phenyl]-octanoic acid N-[2(R,S)-(N-methylcarbamoyl)-2(R,S)-methyl-ethyl]-amide hydrochloride The title compound is obtained analogously to Example 124 starting from 93 mg of 5(S)-tert-butoxycarbonylamino-4(S)-hydroxy-2(S),7(S)-diisopropyl-8-[4-methoxy-3-(3-methoxypropyloxy)-phenyl]-octanoic acid N-[2(R,S)-(N-methylcarbamoyl)-2(R,S)-methyl-ethyl]amide: R_f(dichloromethane/methanol=8:2)=0.31; HPLC R_f=10.76/10.85 minutes; FAB-MS (M+H)⁺=552.

The starting material is prepared analogously to Examples 130a) and 124b) from 3-tert-butoxycarbonyl-5(S)-(2(S)-carboxy-3-methyl-butyl)-4(S)-{2(S)-isopropyl-3-[4-methoxy-3-(3-methoxypropyloxy)-phenyl]-propyl}-2,2-dimethyl-1,3-oxazolidine (Example 124c) and 3-amino-2(R,S)-methylpropionic acid N-methylamide hydrochloride.

a) 3-Amino-2(R,S)-methylpropionic acid N-methylamide hydrochloride is prepared analogously to Example 121a)

from 3-benzyloxycarbonylamino-2(R,S)-methylpropionic acid N-methylamide.

b) 3-Benzyloxycarbonylamino-2(R,S)-methylpropionic acid N-methylamide 2.52 g of 3-benzyloxycarbonylamino-2(R,S)-methylpropionic acid methyl ester and 50 ml of 33% methylamine (in ethanol) are stirred at room temperature for 48 hours. The reaction mixture is concentrated by evaporation and the title compound is obtained from the residue by crystallisation from ethyl acetate: $R_f$(dichloromethane/methanol=95:5)=0.42; m.p. 128°–129° C.

c) 3-Benzyloxycarbonylamino-2(R,S)-methylpropionic acid methyl ester 22.6 g of 3-benzyloxycarbonylamino-2(R,S)-methylpropionic acid are left to stand for 24 hours in 230 ml of methanol with a few drops of concentrated sulfuric acid. The reaction mixture is concentrated by evaporation and the residue is purified by FC (220 g of silica gel, dichloromethane). The title compound is obtained: $R_f$(dichloromethane/methanol=95:5)=0.60.

d) 3-Benzyloxycarbonylamino-2(R,S)-methylpropionic acid

A solution of 41.7 ml of chloroformic acid benzyl ester (90%) in toluene is added to 25 g of 3-amino-2(R,S)-methylpropionic acid in 533 ml of 1N sodium hydroxide at 0° C. The reaction mixture is then stirred for 30 minutes at 0° C. After the addition of 400 ml of diethyl ether, the aqueous phase is removed and 140 ml of 4N hydrochloric acid are added. The crude title compound is obtained from the organic phase by extraction with diethyl ether: $R_f$(dichloromethane/methanol=8:2)=0.41.

EXAMPLE 154

5(S)-Amino-4(S)-hydroxy-2(S), 7(S)-diisopropyl-8-[4-methoxy-3-(3-methoxypropyloxy)-phenyl]-octanoic acid [N-(2-carbamoyl-1(S)-methyl-ethyl)]-amide hydrochloride The title compound is obtained analogously to Example 124 starting from 445 mg of 5(S)-tert-butoxycarbonylamino-4(S)-hydroxy-2(S), 7(S)-diisopropyl-8-[4-methoxy-3-(3-methoxypropyloxy)-phenyl]-octanoic acid [N-(2-carbamoyl-1(S)-methyl-ethyl)]-amide: $R_f$(dichloromethane/methanol=8:2)=0.24; HPLC $R_t$=10.27 minutes; FAB-MS (M+H)$^+$=538.

The starting material is prepared analogously to Examples 130a) and 124b) from 3-tert-butoxycarbonyl-5(S)-(2(S)-carboxy-3-methyl-butyl)-4(S)-{2(S)-isopropyl-3-[4-methoxy-3-(3-methoxypropyloxy)-phenyl]-propyl}-2,2-dimethyl-1,3-oxazolidine (Example 124c) and 3(S)-aminobutyric acid amide hydrochloride.

EXAMPLE 155

5(S)-Amino-4(S)-hydroxy-2(S),7(S)-diisopropyl-8-[4-methoxy-3-(3-methoxypropyloxy)-phenyl]-octanoic acid [N-(2-carbamoyl-1(R)-methyl-ethyl)]-amide hydrochloride The title compound is obtained analogously to Example 124 starting from 10 mg of 5(S)-tert-butoxycarbonylamino-4(S)-hydroxy-2(S),7(S)-diisopropyl-8-[4-methoxy-3-(3-methoxypropyloxy)-phenyl]-octanoic acid [N-(2-carbamoyl-1(R)-methyl-ethyl)]-amide: $R_f$(dichloromethane/methanol=8:2)=0.24; HPLC $R_t$=10.92 minutes; FAB-MS (M+H)$^+$=538.

The starting material is prepared analogously to Examples 130a) and 124b) from 3-tert-butoxycarbonyl-5(S)-(2(S)-carboxy-3-methyl-butyl)-4(S)-{2(S)-isopropyl-3-[4-methoxy-3-(3-methoxypropyloxy)-phenyl]-propyl}-2,2-dimethyl-1,3-oxazolidine (Example 124c) and 3(R)-aminobutyric acid amide hydrochloride.

EXAMPLE 156

5(S)-Amino-4(S)-hydroxy-2(S),7(S)-diisopropyl-8-[4-methoxy-3-(3-methoxypropyloxy)-phenyl]-octanoic acid N-[2(S)-carbamoyl-2(S)-methyl-ethyl]-amide hydrochloride The title compound is obtained analogously to Example 124 starting from 350 mg of 5(S)-tert-butoxycarbonylamino-4(S)-hydroxy-2(S),7(S)-diisopropyl-8-[4-methoxy-3-(3-methoxypropyloxy)-phenyl]-octanoic acid N-[2(S)-carbamoyl-2(S)-methyl-ethyl]-amide (diastereoisomer A): $R_f$(dichloromethane/methanol=8:2)= 0.19; HPLC $R_t$=10.50 minutes; FAB-MS (M+H)$^+$=538.

The starting material is prepared as follows: 5(S)-Tert-butoxycarbonylamino-4(S)-hydroxy-2(S),7(S)-diisopropyl-8-[4-methoxy-3-(3-methoxypropyloxy)-phenyl]-octanoic acid N-[2(S)-carbamoyl-2(S)-methyl-ethyl]-amide (diastereoisomer A) and 5(S)-tert-butoxycarbonylamino-4(S)-hydroxy-2(S),7(S)-diisopropyl-8-[4-methoxy-3-(3-methoxypropyloxy)-phenyl]-octanoic acid [N-[2(S)-carbamoyl-2(R)-methyl-ethyl]-amide (diastereoisomer B)

40 mg of p-toluenesulfonic acid (monohydrate) are added to 1.29 g of 3-tert-butoxy-carbonyl-5(S)-{2-[N-(2-carbamoyl-2(R,S)-methyl-ethyl)-carbamoyl]-2(S)-isopropyl-ethyl}-4(S)-{2(S)-isopropyl-3-[4-methoxy-3-(3-methoxypropyloxy)-phenyl]-propyl }-2,2-dimethyl-1,3-oxazolidine in 50 ml of methanol at 0° C. The reaction solution is stirred for 18 hours at room temperature. After removal of the solvent by evaporation, 100 ml of saturated sodium hydrogen carbonate solution are added to the residue and extraction is carried out repeatedly with ethyl acetate. The organic extracts are concentrated by evaporation and purified by FC (5 times with 60 g of silica gel, dichloromethane/methanol=9:1). The title compounds are obtained:

Diastereoisomer A: $R_f$(dichloromethane/methanol=95:5) =0.19.

Diastereoisomer B: $R_f$(dichloromethane/methanol=95:5) =0.14.

The starting material is prepared analogously to Example 124b) from 3-tert-butoxy-carbonyl-5(S)-(2(S)-carboxy-3-methyl-butyl)-4(S)-{2(S)-isopropyl-3-[4-methoxy-3-(3-methoxypropyloxy)-phenyl]-propyl}-2,2-dimethyl-1,3-oxazolidine (Example 124c) and 3-amino-2(R,S)-methylpropionic acid amide hydrochloride.

EXAMPLE 157

5(S)-Amino-4(S)-hydroxy-2(S),7(S)-diisopropyl-8-[4-methoxy-3-(3-methoxypropyloxy)-phenyl]-octanoic acid N-[2(R)-carbamoyl-2(R)-methyl-ethyl]-amide hydrochloride The title compound is obtained analogously to Example 124 starting from 370 mg of 5(S)-tert-butoxycarbonylamino-4(S)-hydroxy-2(S),7(S)-diisopropyl-8-[4-methoxy-3-(3-methoxypropyloxy)-phenyl]-octanoic acid N-[2(R)-carbamoyl-2(R)-methyl-ethyl]-amide diastereoisomer B (Example 156a)): $R_f$(dichloromethane/methanol= 8:2)=0.19; HPLC $R_t$=10.39 minutes; FAB-MS (M+H)$^+$= 538.

EXAMPLE 158

5(S)-Amino-4(S)-hydroxy-2(S),7(S)-diisopropyl-8-
[4-methoxy-3-(3-methoxypropyloxy)-phenyl]-
octanoic acid {N-[2(R)-(N-methylcarbamoyl)-2(R)-
methyl-ethyl]}-amide hydrochloride The title compound is obtained analogously to Example 124 starting from 60 mg of 5(S)-tert-butoxycarbonylamino-4(S)-hydroxy-2(S),7(S)-diisopropyl-8-[4-methoxy-3-(3-methoxypropyloxy)-phenyl]-octanoic acid N-[2(R)-(N-methylcarbamoyl)-2(R)-methyl-ethyl]-amide: $R_f$(dichloromethane/methanol=8:2)=0.31; HPLC $R_f$=10.33 minutes; FAB-MS (M+H)$^+$=552.

The starting material is prepared analogously to Example 130a) from 3-tert-butoxy-carbonyl-5(S)-{2-[N-(2(R)-(N-methylcarbamoyl)-2(R)-methyl-ethyl)-carbamoyl]-2(S)-isopropyl-ethyl}-4(S)-{2(S)-isopropyl-3-[4-methoxy-3-(3-methoxypropyloxy)-phenyl]-propyl}-2,2-dimethyl-1,3-oxazolidine.

a) 3-Tert-butoxycarbonyl-5(S)-{2(S)-[N-(2(R)-(N-methylcarbamoyl)-2(R)-methyl-ethyl-carbamoyl]-2(S)-isopropyl-ethyl}-4(S)-{2(S)-isopropyl-3-{4-methoxy-3-(3-methoxy-propyloxy)-phenyl]-propyl}-2,2-dimethyl-1,3-oxazolidine 120 mg of 3-tert-butoxycarbonyl-5(S)-{2(S)-[N-(2(R)-methoxycarbonyl)-2(R)-methyl-ethyl)-carbamoyl]-2(S)-isopropyl-ethyl}-4(S)-{2(S)-isopropyl-3-[4-methoxy-3-(3-methoxypropyloxy)-phenyl]-propyl}-2,2-dimethyl-1,3-oxazolidine are left to stand for 48 hours at room temperature in 5 ml of 33% methylamine solution (in ethanol). The reaction mixture is concentrated by evaporation and the residue is purified by FC (30 g of silica gel, dichloromethane/methanol=95:5). The title compound is obtained: $R_f$(dichloromethane/methanol=95:5)=0.30.

b) 3-Tert-butoxycarbonyl-5(S)-{2(S)-[N-(2(R)-methoxycarbonyl)-2(R)-methyl-ethyl)-carbamoyl]-2(S)-isopropyl-ethyl}-4(S)-{2(S)-isopropyl-3-[4-methoxy-3-(3-methoxy-propyloxy)-phenyl]-propyl}-2,2-dimethyl-1,3-oxazolidine The title compound is prepared analogously to Example 124b) from 3-tert-butoxy-carbonyl-5(S)-(2(S)-carboxy-3-methyl-butyl)-4(S)-{2(S)-isopropyl-3-[4-methoxy-3-(3-methoxypropyloxy)-phenyl]-propyl}-2,2-dimethyl-1,3-oxazolidine (Example 124c) and 3-amino-2(R)-methylpropionic acid methyl ester hydrochloride.

c) 3-Amino-2(R)-methylpropionic acid methyl ester hydrochloride 2.7 g of 3-azido-2(R)-methylpropionic acid methyl ester are hydrogenated in the presence of 1.4 g of 10% Pd/C in 50 ml of tetrahydrofuran for 4 hours at room temperature at pH 6.0(pH-stat; 2N hydrochloric acid). The reaction mixture is filtered and concentrated by evaporation. The title compound is obtained by crystallisation from isopropanol/diethyl ether: $^1$H NMR (DMSO-d$_6$), δ (ppm)=7.95(3H, bs), 3.65(3H, s), 3.12–2.78(3H, m), 1.15 (3H, d); m.p. 122°–125° C.

EXAMPLE 159

5(S)-Amino-4(S)-hydroxy-2(S),7(S)-diisopropyl-8-
[4-methoxy-3-(3-methoxypropyloxy)-phenyl]-
octanoic acid {N-[2(S)-(N-methylcarbamoyl)-2(S)-
methyl-ethyl]}-amide hydrochloride The title compound is obtained analogously to Example 124 starting from 81 mg of 5(S)-tert-butoxycarbonylamino-4(S)-hydroxy-2(S),7(S)-diisopropyl-8-[4-methoxy-3-(3-methoxypropyloxy)-phenyl]-octanoic acid {N-[2(S)-(N-methylcarbamoyl)-2(S)-methyl-ethyl]}-amide: $R_f$(dichloromethane/methanol=8:2)=0.3; HPLC $R_f$=10.50 minutes; FAB-MS (M+H)$^+$=552.

The starting material is prepared analogously to Example 158a) to c) from 3-tert-butoxy-carbonyl-5(S)-{(2(S)-carboxy-3-methyl-butyl)-4(S)-{2(S)-isopropyl-3-[4-methoxy-3-(3-methoxypropyloxy)-phenyl]-propyl}-2,2-dimethyl-1,3-oxazolidine (Example 124c) and 3-amino-2(S)-methylpropionic acid methyl ester hydrochloride.

EXAMPLE 160

5(S)-Amino-4(S)-hydroxy-2(S), 7(S)-diisopropyl-8-
[4-methoxy-3-(3-methoxypropyloxy)-phenyl]-
octanoic acid [N-(2-carboxy-2,2-dimethyl-ethyl)]-
amide hydrochloride The title compound is obtained analogously to Example 124 starting from 71 mg of 5(S)-tert-butoxycarbonylamino-4(S)-hydroxy-2(S), 7(S)-diisopropyl-8-[4-methoxy-3-(3-methoxypropyloxy)-phenyl]-octanoic acid [N-(2-carboxy-2,2-dimethyl-ethyl)]-amide: $R_f$(dichloromethane/methanol=8:2)=0.52; HPLC $R_f$=10.95 minutes; FAB-MS (M+H)$^+$=553.

The starting material is prepared analogously to Example 130a) from 3-tert-butoxy-carbonyl-5(S)-{2(S)-[N-(2-carboxy-2,2-dimethyl-ethyl)-carbamoyl]-2(S)-isopropyl-ethyl}-4(S)-{2(S)-isopropyl-3-[4-methoxy-3-(3-methoxypropyloxy)-phenyl]-propyl}-2,2-dimethyl-1,3-oxazolidine.

a) 3-Tert-butoxycarbonyl-5(S)-{2(S)-[N-(2-carboxy-2,2-dimethyl-ethyl)-carbamoyl]-2(S)-isopropyl-ethyl}-4(S)-{2(S)-isopropyl-3-[4-methoxy-3-(3-methoxypropyloxy-phenyl]-propyl}-2,2-dimethyl-1,3-oxazolidine 36 mg of 3-tert-butoxycarbonyl-5(S)-{2(S)-[N-(2-ethyloxycarbonyl-2,2-dimethyl-ethyl)-carbamoyl]-2(S)-isopropyl-ethyl}-4(S)-{2(S)-isopropyl-3-[4-methoxy-3-(3-methoxy-propyloxy)-phenyl]-propyl}-2,2-dimethyl-1,3-oxazolidine are stirred for 24 hours at room temperature in 1 ml of ethanol and 0.1 ml of 2N potassium hydroxide. The reaction mixture is concentrated by evaporation and, after the addition of 0.1 ml of 2N hydrochloric acid, extracted repeatedly with diethyl ether. The extracts are concentrated by evaporation and purified by FC (18 g of silica gel, dichloromethane/methanol=9:1). The title compound is obtained: $R_f$(dichloromethane/methanol=9:1)=0.45.

The starting material is prepared analogously to Example 124b) from 3-tert-butoxy-carbonyl-5(S)-(2(S)-carboxy-3-methyl-butyl)-4(S)-{2(S)-isopropyl-3-[4-methoxy-3-(3-methoxypropyloxy)-phenyl]-propyl}-2,2-dimethyl-1,3-oxazolidine (Example 124c) and 3-amino-2,2-dimethylpropionic acid ethyl ester.

EXAMPLE 161

5(S)-Amino-4(S)-hydroxy-2(S),7(S)-diisopropyl-8-
[4-methoxy-3-(3-methoxypropyloxy)-phenyl]-
octanoic acid [N-(2-carboxy-2,2-diethyl-ethyl)]-
amide hydrochloride The title compound is obtained analogously to Example 124 starting from 136 mg of 5(S)-tert-butoxycarbonylamino-4(S)-hydroxy-2(S),7(S)-diisopropyl-8-[4-methoxy-3-(3-methoxypropyloxy)-phenyl]-octanoic acid [N-(2-carboxy-2,2-diethyl-ethyl)]-amide: $R_f$(dichloromethane/methanol=8:2)=0.26; HPLC $R_f$=12.53 minutes; FAB-MS (M+H)$^+$=581.

The starting material is prepared analogously to Example 130a) from 3-tert-butoxy-carbonyl-5(S)-{2(S)-[N-(2-carboxy-2,2-diethyl-ethyl)-carbamoyl]-2(S)-isopropyl-ethyl}-4(S)-{2(S)-isopropyl-3-[4-methoxy-3-(3-methoxypropyloxy)-phenyl]-propyl}-2,2-dimethyl-1,3-oxazolidine.

a) 3-Tert-butoxycarbonyl-5(S)-{2-[N-(2-carboxy-2,2-diethyl-ethyl)-carbamoyl]-2(S)-isopropyl-ethyl}-4(S)-{2(S)-isopropyl-3-[4-methoxy-3-(3-methoxypropyloxy-phenyl]-propyl}-2,2-dimethyl-1,3-oxazolidine 258 mg of 3-tert-butoxycarbonyl-5(S)-{2-[N-(2-(2-ethyloxycarbonyl-2,2-diethyl-ethyl)-carbamoyl]-2(S)-isopropyl-ethyl}-4(S)-{2(S)-isopropyl-3-[4-methoxy-3-(3-methoxy-propyloxy)-phenyl]-propyl}- 2,2-dimethyl-1,3-oxazolidine are stirred for 24 hours at 80° C. in 6 ml of ethanol and 0.69 ml of 2N potassium hydroxide. The reaction mixture is concentrated by evaporation and, after the addition of 0.69 ml of 2N hydrochloric acid, extracted repeatedly with diethyl ether. The extracts are concentrated by evaporation and purified by FC (35 g of silica gel, dichloromethane/methanol=9:1). The title compound is obtained: $R_f$(dichloromethane/methanol=9:1)=0.50.

The starting material is prepared analogously to Example 124b) from 3-tert-butoxy-carbonyl-5(S)-(2(S)-carboxy-3-methyl-butyl)-4(S)-{2(S)-isopropyl-3-[4-methoxy-3-(3-methoxypropyloxy)-phenyl]-propyl}-2, 2-dimethyl-1,3-oxazolidine (Example 124c) and 3-amino-2,2-diethylpropionic acid ethyl ester.

EXAMPLE 162

5(S)-Amino-4(S)-hydroxy-2(S),7(S)-diisopropyl-8-[4-methoxy-3-(3-methoxypropyloxy)-phenyl]-octanoic acid N-[(1-carboxy-cyclopentyl)-methyl]-amide hydrochloride The title compound is obtained analogously to Example 124 starting from 142 mg of 5(S)-tert-butoxycarbonylamino-4(S)-hydroxy-2(S),7(S)-diisopropyl-8-[4-methoxy-3-(3-methoxypropyloxy)-phenyl]-octanoic acid N-[(1-carboxy-cyclopentyl)-methyl]-amide: $R_f$(dichloromethane/methanol=8:2)=0.26; HPLC $R_f$=12.18 minutes; FAB-MS (M+H)$^+$=579.

The starting material is prepared analogously to Examples 130a), 161a)and 124b) from 3-tert-butoxycarbonyl-5(S)-(2(S)-carboxy-3-methyl-butyl)-4(S)-{2(S)-isopropyl-3-[4-methoxy-3-(3-methoxypropyloxy)-phenyl]-propyl}-2,2-dimethyl-1,3-oxazolidine (Example 124c) and 1-(aminomethyl)cyclopentane-1-carboxylic acid ethyl ester.

EXAMPLE 163

5(S)-Amino-4(S)-hydroxy-2(S),7(S)-diisopropyl-8-[4-methoxy-3-(3-methoxypropyloxy)-phenyl]-octanoic acid {N-[2-(1H-tetrazol-5-yl)-ethyl]}-amide hydrochloride The title compound is obtained analogously to Example 124 starting from 100 mg of 5(S)-tert-butoxycarbonylamino-4(S)-hydroxy-2(S),7(S)-diisopropyl-8-[4-methoxy-3-(3-methoxypropyloxy)-phenyl]-octanoic acid {N-[2-(1H-tetrazol-5-yl)-ethyl]}-amide: $R_f$(dichloromethane/methanol=8:2)=0.19; HPLC $R_f$=12.30 minutes; FAB-MS (M+H)$^+$=549.

The starting material is prepared analogously to Examples 130a) and 124b) from 3-tert-butoxycarbonyl-5 (S)-(2(S)-carboxy-3-methyl-butyl)-4(S)-{2(S)-isopropyl-3-[4-methoxy-3-(3-methoxypropyloxy)-phenyl]-propyl}-2,2-dimethyl-1,3-oxazolidine (Example 124c) and 2-(1H-tetrazol-5-yl)-ethylamine.

EXAMPLE 164

5(S)-Amino-4(S)-hydroxy-2(S),7(S)-diisopropyl-8-[4-methoxy-3-(3-methoxypropyloxy)-phenyl]-octanoic acid N-[1(S)-(5-oxopyrrolidin-2-yl)methyl]-amide hydrochloride The title compound is obtained analogously to Example 124 starting from 100 mg of 5(S)-tert-butoxycarbonylamino-4(S)-hydroxy-2(S),7(S)-diisopropyl-8-[4-methoxy-3-(3-methoxypropyloxy)-phenyl]-octanoic acid N-[(1-carboxy-cyclopentyl)-methyl]-amide: $R_f$(dichloromethane/methanol=8:2)=0.27; HPLC $R_f$=12.55 minutes; FAB-MS (M+H)$^+$=550.

The starting material is prepared analogously to Examples 130a) and 124b) from 3-tert-butoxycarbonyl-5(S)-(2(S)-carboxy-3-methyl-butyl)-4(S)-{2(S)-isopropyl-3-[4-methoxy-3-(3-methoxypropyloxy)-phenyl]-propyl}-2,2-dimethyl-1,3-oxazolidine (Example 124c) and 5(S)-(aminomethyl)-2-pyrrolidone.

EXAMPLE 165

5(S)-Amino-4(S)-hydroxy-2(S),7(S)-diisopropyl-8-[4-methoxy-3-(3-methoxypropyloxy)-phenyl]-octanoic acid N-[1(R)-(5-oxopyrrolidin-2-yl)methyl]-amide hydrochloride The title compound is obtained analogously to Example 124 starting from 95 mg of 5(S)-tert-butoxycarbonylamino-4(S)-hydroxy-2(S),7(S)-diisopropyl-8-[4-methoxy-3-(3-methoxypropyloxy)-phenyl]-octanoic acid N-[1(R)-(5-oxopyrrolidin-2-yl)methyl]-amide: $R_f$(dichloromethane/methanol=8:2)=0.31; HPLC $R_f$=12.24 minutes; FAB-MS (M+H)$^+$=550.

The starting material is prepared analogously to Examples 130a) and 124b) from 3-tert-butoxycarbonyl-5(S)-(2(S)-carboxy-3-methyl-butyl)-4(S)-{2(S)-isopropyl-3-[4-methoxy-3-(3-methoxypropyloxy)-phenyl]-propyl}-2,2-dimethyl-1,3-oxazolidine (Example 124c) and 5(R)-(aminomethyl)-2-pyrrolidone.

EXAMPLE 166

5(S)-Amino-4(S)-hydroxy-2(S),7(S)-diisopropyl-8-[4-methoxy-3-(3-methoxypropyloxy)-phenyl]-octanoic acid {N-[(N,N-dimethyl)-carbamoylmethyl]}-amide hydrochloride The title compound is obtained analogously to Example 130 starting from 56 mg of 5(S)-tert-butoxycarbonylamino-4(S)-hydroxy-2(S), 7(S)-diisopropyl-8-[4-methoxy-3-(3-methoxypropyloxy)-phenyl]-octanoic acid {N-[(N,N-dimethyl)-carbamoylmethyl]}-amide and after lyophilisation: $R_f$(ethyl acetate/methanol/conc. ammonia= 80:15:5)=0.42; HPLC $R_f$=11.82 minutes; FAB-MS (M+H)$^+$=538.

The starting material is prepared analogously to Examples 130a) and 124b) from 3-tert-butoxycarbonyl-5(S)-(2(S)-carboxy-3-methyl-butyl)-4(S)-{2(S)-isopropyl-3-[4-methoxy-3-(3-methoxypropyloxy)-phenyl]-propyl}-2,2-dimethyl-1,3-oxazolidine (Example 124c) and 2(S)-aminoacetic acid (N,N-dimethyl)-amide hydrochloride.

EXAMPLE 167

5(S)-Amino-4(S)-hydroxy-2(S),7(S)-diisopropyl-8-[4-methoxy-3-(3-methoxypropyloxy)-phenyl]-octanoic acid N-[N-(morpholin-4-yl) carbamoylmethyl]amide hydrochloride The title compound is obtained analogously to Example 130 starting from 76 mg of 5(S)-tert-butoxycarbonylamino- 4(S)-hydroxy-2(S),7(S)-diisopropyl-8-[4-methoxy-3-(3-methoxypropyloxy)-phenyl]-octanoic acid N-[N-(morpholin-4-yl)carbamoylmethyl]-amide and after lyophilisation: R$_f$(ethyl acetate/methanol/conc. ammonia=80:15:5)=0.43; HPLC R$_f$=10.66 minutes; FAB-MS (M+H)$^+$=580.

The starting material is prepared analogously to Examples 130a) and 124b) from 3-tert-butoxycarbonyl-5(S)-(2(S)-carboxy-3-methyl-butyl)-4(S)-{2(S)-isopropyl-3-[4-methoxy-3-(3-methoxypropyloxy)-phenyl]-propyl}-2,2-dimethyl-1,3-oxazolidine (Example 124c) and 2-aminoacetic acid N-(morpholin-4-yl)amide hydrochloride.

EXAMPLE 168

5(S)-Amino-4(S)-hydroxy-2(S),7(S)-diisopropyl-8-[4-methoxy-3-(3-methoxypropyloxy)-phenyl]-octanoic acid [N-(1(S)-carbamoyl-ethyl)]-amide hydrochloride The title compound is obtained analogously to Example 130 starting from 64 mg of 5(S)-tert-butoxycarbonylamino-4(S)-hydroxy-2(S),7(S)-diisopropyl-8-[4-methoxy-3-(3-methoxypropyloxy)-phenyl]-octanoic acid [N-(1(S)-carbamoylethyl)]-amide and after lyophilisation: R$_f$(ethyl acetate/methanol/conc. ammonia=80:15:5)=0.42; HPLC R$_f$-10.48 minutes; FAB-MS (M+H)$^+$=524.

The starting material is prepared analogously to Examples 130a) and 130b) from 3-tert-butoxycarbonyl-5(S)-(2(S)-carboxy-3-methyl-butyl)-4(S)-{2(S)-isopropyl-3-[4-methoxy-3-(3-methoxypropyloxy)-phenyl]-propyl}-2,2-dimethyl-1,3-oxazolidine (Example 124c) and 2(S)-aminopropionic acid amide hydrochloride.

EXAMPLE 169

5(S)-Amino-4(S)-hydroxy-2(S),7(S)-diisopropyl-8-[4-methoxy-3-(3-methoxypropyloxy)-phenyl]-octanoic acid N-{1(S)-[(N-methyl)-carbamoyl]-ethyl}-amide hydrochloride The title compound is obtained analogously to Example 130 starting from 31 mg of 5(S)-tert-butoxycarbonylamino-4(S)-hydroxy-2(S),7(S)-diisopropyl-8-[4-methoxy-3-(3-methoxypropyloxy)-phenyl]-octanoic acid N-{1(S)-[(N-methyl)-carbamoyl]-ethyl}-amide and after lyophilisation: R$_f$(ethyl acetate/methanol/conc. ammonia=80:15:5) =0.38; HPLC R$_f$=11.08 minutes; FAB-MS (M+H)$^+$=538.

The starting material is prepared analogously to Examples 130a) and 124b) from 3-tert-butoxycarbonyl-5(S)-(2(S)-carboxy-3-methyl-butyl)-4(S)-{2(S)-isopropyl-3-[4-methoxy-3-(3-methoxypropyloxy)-phenyl]-propyl}-2,2-dimethyl-1,3-oxazolidine (Example 124c) and 2(S)-aminopropionic acid (N-methyl)-amide hydrochloride.

EXAMPLE 170

5(S)-Amino-4(S)-hydroxy-2(S),7(S)-diisopropyl-8-[4-methoxy-3-(3-methoxypropyloxy)-phenyl]-octanoic acid N-{1(S)-[(N,N-dimethyl)-carbamoyl]-ethyl}-amide hydrochloride The title compound is obtained analogously to Example 130 starting from 86 mg of 5(S)-tert-butoxycarbonylamino-4(S)-hydroxy-2(S),7(S)-diisopropyl-8-[4-methoxy-3-(3-methoxypropyloxy)-phenyl]-octanoic acid N-{1(S)-[(N,N-dimethyl)-carbamoyl]-ethyl}-amide and after lyophilisation: R$_f$(ethyl acetate/methanol/conc. ammonia=80:15:5)=0.50; HPLC R$_f$=11.53 minutes; FAB-MS (M+H)$^+$=552.

The starting material is prepared analogously to Examples 130a) and 124b) from 3-tert-butoxycarbonyl-5(S)-(2(S)-carboxy-3-methyl-butyl)-4(S)-{2(S)-isopropyl-3-[4-methoxy-3-(3-methoxypropyloxy)-phenyl]-propyl}-2,2-dimethyl-1,3-oxazolidine (Example 124c) and 2(S)-aminopropionic acid (N,N-dimethyl)-amide hydrochloride.

EXAMPLE 171

5(S)-Amino-4(S)-hydroxy-2(S),7(S)-diisopropyl-8-[4-methoxy-3-(3-methoxypropyloxy)-phenyl]-octanoic acid N-{1(S)-N-[(morpholin-4-yl)-carbamoyl]-ethyl}amide hydrochloride The title compound is obtained analogously to Example 130 starting from 51 mg of 5(S)-tert-butoxycarbonylamino-4(S)-hydroxy-2(S),7(S)-diisopropyl-8-[4-methoxy-3-(3-methoxypropyloxy)-phenyl]-octanoic acid N-{1(S)-N-[(morpholin-4-yl)-carbamoyl]-ethyl}amide and after lyophilisation: R$_f$(ethyl acetate/methanol/conc. ammonia=80:15:5)=0.51; HPLC R$_f$=11.29 minutes; FAB-MS (M+H)$^+$=594.

The starting material is prepared analogously to Examples 130a) and 124b) from 3-tert-butoxycarbonyl-5(S)-(2(S)-carboxy-3-methyl-butyl)-4(S)-{2(S)-isopropyl-3-[4-methoxy-3-(3-methoxypropyloxy)-phenyl]-propyl}-2,2-dimethyl-1,3-oxazolidine (Example 124c) and 2(S)-aminopropionic acid N-(morpholin-4-yl)amide hydrochloride.

EXAMPLE 172

5(S)-Amino-4(S)-hydroxy-2(S),7(S)-diisopropyl-8-[4-methoxy-3-(3-methoxypropyloxy)-phenyl]-octanoic acid N-[1(S)-carbamoyl-butyl]amide hydrochloride The title compound is obtained analogously to Example 130 starting from 49 mg of 5(S)-tert-butoxycarbonylamino-4(S)-hydroxy-2(S), 7(S)-diisopropyl-8-[4-methoxy-3-(3-methoxypropyloxy)-phenyl]-octanoic acid N-[1(S)-carbamoylbutyl]amide and after lyophilisation: R$_f$(ethyl acetate)=0.38; HPLC R$_f$=10.67 minutes; FAB-MS (M+H)$^+$=552.

The starting material is prepared analogously to Example 130a) and 130b) from 3-tert-butoxycarbonyl-5(S)-(2(S)-carboxy-3-methyl-butyl)-4(S)-{2(S)-isopropyl-3-[4-methoxy-3-(3-methoxypropyloxy)- phenyl]-propyl}-2,2-dimethyl-1,3-oxazolidine (Example 124c) and 2(S)-aminopentanoic acid amide hydrochloride.

EXAMPLE 173

5(S)-Amino4(S)-hydroxy-2(S),7(S)-diisopropyl-8-[4-methoxy-3-(3-methoxypropyloxy)-phenyl]-octanoic acid N-[1(S)-carbamoyl-2-methyl-propyl]-amide hydrochloride The title compound is obtained analogously to Example 130 starting from 65 mg of 5(S)-tert-butoxycarbonylamino-4(S)-hydroxy-2(S),7(S)-diisopropyl-8-[4-methoxy-3-(3-methoxypropyloxy)-phenyl]-octanoic acid N-[1(S)-carbamoyl-2-methyl-propyl]-amide and after lyophilisation: R$_f$(ethyl acetate/methanol/conc. ammonia=80:15:5)=0.47; HPLC R$_f$=11.22 minutes; FAB-MS (M+H)$^+$=552.

The starting material is prepared analogously to Example 130a) and 130b) from 3-tert-butoxycarbonyl-5(S)-(2(S)-carboxy-3-methyl-butyl)-4(S)-{2(S)-isopropyl-3-[4-methoxy-3-(3-methoxypropyloxy)-phenyl]-propyl}-2,2-

EXAMPLE 174

5(S)-Amino-4(S)-hydroxy-2(S),7(S)-diisopropyl-8-
[4-methoxy-3-(3-methoxypropyloxy)-phenyl]-
octanoic acid N-[1(S)-(N-methylcarbamoyl)-2-
methyl-propyl]amide hydrochloride The title compound is obtained analogously to Example 130 starting from 58 mg of 5(S)-tert-butoxycarbonylamino-4(S)-hydroxy-2(S),7(S)-diisopropyl-8-[4-methoxy-3-(3-methoxypropyloxy)-phenyl]-octanoic acid N-[1(S)-(N-methylcarbamoyl)-2-methyl-propyl]amide and after lyophilisation: $R_f$(ethyl acetate/methanol/conc. ammonia=80:15:5)=0.51; HPLC $R_t$=11.87 minutes; FAB-MS $(M+H)^+$=566.

The starting material is prepared analogously to Examples 130a) and 124b) from 3-tert-butoxycarbonyl-5(S)-(2(S)-carboxy-3-methyl-butyl)-4(S)-{2(S)-isopropyl-3-[4-methoxy-3-(3-methoxypropyloxy)-phenyl]-propyl}-2,2-dimethyl-1,3-oxazolidine (Example 124c) and 2(S)-amino-3-methylbutyric acid (N-methyl)amide hydrochloride.

EXAMPLE 175

5(S)-Amino-4(S)-hydroxy-2(S),7(S)-diisopropyl-8-
[4-methoxy-3-(3-methoxypropyloxy)-phenyl]-
octanoic acid N-[1(S)-(N,N-dimethylcarbamoyl)-2-
methyl-propyl]amide hydrochloride The title compound is obtained analogously to Example 130 starting from 80 mg of 5(S)-tert-butoxycarbonylamino-4(S)-hydroxy-2(S),7(S)-diisopropyl-8-[4-methoxy-3-(3-methoxypropyloxy)-phenyl]-octanoic acid N-[1(S)-(N,N-dimethylcarbamoyl)-2-methyl-propyl]amide and after lyophilisation: $R_f$(ethyl acetate/methanol/conc. ammonia=80:15:5)=0.62; HPLC $R_t$=12.36 minutes; FAB-MS $(M+H)^+$=580.

The starting material is prepared analogously to Examples 130a) and 124b) from 3-tert-butoxycarbonyl-5(S)-(2(S)-carboxy-3-methyl-butyl)-4(S)-{2(S)-isopropyl-3-[4-methoxy-3-(3-methoxypropyloxy)-phenyl]-propyl}-2,2-dimethyl-1,3-oxazolidine (Example 124c) and 2(S)-amino-3-methylbutyric acid (N,N-dimethyl)amide hydrochloride.

The starting material is prepared as follows:
a) 2(S)-Amino-3-methylbutyric acid (N,N-dimethyl)amide hydrochloride 0.85 g of 2(S)-tert-butoxycarbonylamino-3-methylbutanoic acid (N,N-dimethyl)amide is dissolved in 10 ml of 4N hydrochloric acid in dioxane at 0° C. and stirred for 7 hours at 0° C. The reaction mixture is lyophilised and the title compound is obtained: $R_f$(ethyl acetate/methanol/conc. ammonia=80:15:5)=0.23.

EXAMPLE 176

5(S)-Amino-4(S)-hydroxy-2(S),7(S)-diisopropyl-8-
[4-methoxy-3-(3-methoxypropyloxy)-phenyl-
octanoic acid N-{1(S)-[N-(morpholin-4-yl)
carbamoyl]-2-methyl-propyl}amide hydrochloride The title compound is obtained analogously to Example 130 starting from 74 mg of 5(S)-tert-butoxycarbonylamino-4(S)-hydroxy-2(S),7(S)-diisopropyl-8-[4-methoxy-3-(3-methoxypropyloxy)-phenyl]-octanoic acid N-{1(S)-[N-(morpholin-4-yl)carbamoyl]-2-methyl-propyl}amide and after lyophilisation: $R_f$(ethyl acetate/methanol/conc. ammonia=80:15:5)=0.59; HPLC $R_t$=11.81 minutes; FAB-MS $(M+H)^+$=622.

The starting material is prepared analogously to Examples 130a) and 124b) from 3-tert-butoxycarbonyl-5(S)-(2(S)-carboxy-3-methyl-butyl)-4(S)-{2(S)-isopropyl-3-[4-methoxy-3-(3-methoxypropyloxy)-phenyl]-propyl}-2,2-dimethyl-1,3-oxazolidine (Example 124c) and 2(S)-amino-3-methylbutanoic acid N-(morpholin-4-yl)amide hydrochloride.

EXAMPLE 177

5(S)-Amino-4(S)-hydroxy-2(S),7(S)-diisopropyl-8-
[4-methoxy-3-(3-methoxypropyloxy)-phenyl]-
octanoic acid N-[2-(N-methylsulfonyl)ethyl]amide
hydrochloride The title compound is obtained analogously to Example 124 starting from 90 mg of 5(S)-tert-butoxycarbonylamino-4(S)-hydroxy-2(S),7(S)-diisopropyl-g-[4-methoxy-3-(3-methoxypropyloxy)-phenyl]-octanoic acid N-[2-(N-methylsulfonyl)ethyl]amide and after lyophilisation: $R_f$(ethyl acetate/methanol/conc. ammonia=80:15:5)=0.52; HPLC $R_t$=11.50 minutes; FAB-MS $(M+H)^+$=574.

The starting material is prepared analogously to Examples 130a) and 124b) from 3-tert-butoxycarbonyl-5(S)-(2(S)-carboxy-3-methyl-butyl)-4(S)-{2(S)-isopropyl-3-[4-methoxy-3-(3-methoxypropyloxy)-phenyl]-propyl}-2,2-dimethyl-1,3-oxazolidine (Example 124c) and 2-aminoethyl-(N-methyl)-sulfonamide.

EXAMPLE 178

5(S)-Amino-4(S)-hydroxy-2(S),7(S)-diisopropyl-8-
[4-methoxy-3-(3-methoxypropyloxy)-phenyl]-
octanoic acid N-{2-[N-(morpholin-4-1-yl)-sulfonyl]
ethyl}-amide hydrochloride The title compound is obtained analogously to Example 130 starting from 98 mg of 5(S)-tert-butoxycarbonylamino-4(S)-hydroxy-2(S),7(S)-diisopropyl-8-[4-methoxy-3-(3-methoxypropyloxy)-phenyl]-octanoic acid N-{2-[N-(morpholin-4-yl)-sulfonyl]ethyl}-amide and after lyophilisation: $R_f$(ethyl acetate/methanol/conc. ammonia=80:15:5)=0.53; HPLC $R_t$=11.63 minutes; FAB-MS $(M+H)^+$=630.

The starting material is prepared analogously to Examples 130a) and 124b) from 3-tert-butoxycarbonyl-5(S)-(2(S)-carboxy-3-methyl-butyl)-4(S)-{2(S)-isopropyl-3-[4-methoxy-3-(3-methoxypropyloxy)-phenyl]-propyl}-2,2-dimethyl-1,3-oxazolidine (Example 124c) and 2-aminoethyl-N-(morpholin-4-yl)-sulfonamide.

The starting material is prepared as follows:
a) 2-Aminoethyl-N-(morpholin-4-yl)-sulfonamide 3.0 g of 2-phthaloylaminoethyl-N-(morpholin-4-yl)-sulfonamide in 20 ml of methanol are stirred for 2 hours under reflux with 20 ml of hydrazine hydrate. The reaction mixture is cooled and 1.0 ml of concentrated hydrochloric acid and 15 ml of methanol are added. The reaction mixture is filtered and the filtrate is concentrated. After the addition of 10 ml of 10% potassium hydroxide solution the title compound is obtained by extraction with dichloromethane: $R_f$(ethyl acetate/methanol/conc. ammonia=80:15:5)=0.26.

b) 2-Phthaloylaminoethyl-N-(morpholin-4-yl)-sulfonamide 4.77 ml of morpholine are added to 5.0 g of 2-phthaloylaminoethylsulfonyl chloride in 40 ml of dichloromethane at −12° C. The reaction mixture is stirred for 30 minutes at 0° and washed with water. The organic phase is dried over sodium sulfate and concentrated. The title compound is obtained: R$_f$(ethyl acetate/methanol/conc. ammonia=80:15:5)=0.68.

EXAMPLE 179

5(S)-Amino-4(S)-hydroxy-2(S),7(S)-diisopropyl-8-[4-methoxy-3-(3-methoxypropyloxy)-phenyl]-octanoic acid N-[2-(N-acetyl)-piperidin-4-yl)ethyl] amide hydrochloride The title compound is obtained analogously to Example 124 starting from 42 mg of 5(S)-tert-butoxycarbonylamino-4(S)-hydroxy-2(S),7(S)-diisopropyl-8-[4-methoxy-3-(3-methoxypropyloxy)-phenyl]-octanoic acid N-[2-(N-acetyl)-piperidin-4-yl)ethyl]amide and after lyophilisation: R$_f$(ethyl acetate/methanol/conc. ammonia=80:15:5)=0.51; HPLC R$_t$=12.06 minutes; FAB-MS (M+H)$^+$=606.

The starting material is prepared analogously to Examples 130a) and 124b) from 3-tert-butoxycarbonyl-5(S)-(2(S)-carboxy-3-methyl-butyl)-4(S)-{2(S)-isopropyl-3-[4-methoxy-3-(3-methoxypropyloxy)-phenyl]-propyl}-2,2-dimethyl-1,3-oxazolidine (Example 124c) and 4-(2-aminoethyl)-(N-acetyl)-piperidine hydrochloride.

The starting material is prepared as follows:
a) 4-(2-Aminoethyl)-(N-acetyl)-piperidine hydrochloride is prepared analogously to Example 175a) from 4-(2-tert-butoxycarbonylaminoethyl)-(N-acetyl)-piperidine.
b) N-Acetyl-4-(2-tert-butoxycarbonylaminoethyl)-piperidine 0.5 g of 4-(2-tert-butoxycarbonylaminoethyl)-piperidine and 0.61 ml of triethylamine are dissolved in 5 ml of dichloromethane and, at 0° C., 0.22 ml of acetyl chloride is added. The reaction mixture is stirred at room temperature for 7 hours and then washed with water. The organic phase is concentrated by evaporation and purified by FC (10 g of silica gel, ethyl acetate/methanol=9:1). The title compound is obtained: R$_f$(ethyl acetate/methanol=9:1)=0.39.

EXAMPLE 180

5(S)-Amino-4(S)-hydroxy-2(S),7(S)-diisopropyl-8-[4-methoxy-3-(3-methoxypropyloxy)-phenyl]-octanoic acid N-[(N-acetyl-piperidin-4-yl)methyl] amide hydrochloride The title compound is obtained analogously to Example 130 starting from 71 mg of 5(S)-tert-butoxycarbonylamino-4(S)-hydroxy-2(S),7(S)-diisopropyl-8-[4-methoxy-3-(3-methoxypropyloxy)-phenyl]-octanoic acid N-[(N-acetylpiperidin-4-yl)methyl]amide and after lyophilisation: R$_f$(ethyl acetate/methanol/conc. ammonia=80:15:5)=0.44; HPLC R$_t$=12.83 minutes; FAB-MS (M+H)$^+$=629.

The starting material is prepared analogously to Examples 130a) and 130b) from 3-tert-butoxycarbonyl-5(S)-(2(S)-carboxy-3-methyl-butyl)-4(S)-{2(S)-isopropyl-3-[4-methoxy-3-(3-methoxypropyloxy)-phenyl]-propyl}-2,2-dimethyl-1,3-oxazolidine (Example 124c) and 4-aminomethyl-(N-acetyl)-piperidine hydrochloride.

EXAMPLE 181

5(S)-Amino-4(S)-hydroxy-2(S),7(S)-diisopropyl-8-[4-methoxy-3-(4-methoxybutyl)-phenyl]-octanoic acid N-(2-carbamoyl-2,2-dimethyl-ethyl)amide hydrochloride The title compound is obtained analogously to Example 105 starting from 25 mg of 5(S)-tert-butoxycarbonylamino-4(S)-hydroxy-2(S),7(S)-diisopropyl-8-[4-methoxy-3-(4-methoxybutyl)-phenyl]-octanoic acid N-(2-carbamoyl-2,2-dimethyl-ethyl)amide: R$_f$(dichloromethane/methanol/conc. ammonia=350:50:1)=0.30; HPLC R$_t$=13.31 minutes; FAB-MS (M+H)$^+$=550.

The starting material is prepared analogously to Example 82d), 82e), Example 83d), Example 83 and Example 105, except that there is used instead of 4-(3-benzyloxy-propyloxy)-3-(3-methoxypropyloxy)-bromobenzene in Example 82d), 4-methoxy-3-(4-methoxy-butyl)-bromobenzene, which is prepared as follows:
a) 4-Methoxy-3-(4-methoxybutyl)-bromobenzene A solution of 50 g of 4-methoxy-3-(4-methoxy-2-butenyl)-bromobenzene in 700 ml of tetrahydrofuran is hydrogenated for 2 hours under normal pressure and at room temperature in the presence of 2.5 g of 5% Pt/C. The reaction mixture is filtered. The filtrate is concentrated by evaporation. The evaporation residue obtained from the filtrate is purified by FC (1.6 kg of silica gel, hexane/ethyl acetate= 20:1). Distillation under a high vacuum yields the title compound: R$_f$(hexane/ethyl acetate=10:1)=0.38; HPLC R$_t$=19.92 minutes; FAB-MS (M+H)$^+$=273.
b) 4-Methoxy-3-(4-methoxy-2-butenyl)-bromobenzene 251.1 g of 3-methoxypropyltriphenylphosphonium bromide are added to a solution, stirred at 5°, of 110.8 g of sodium bis(trimethylsilyl)amide in 1200 ml of tetrahydrofuran. The reaction mixture is further stirred for 45 minutes at 0° and then a solution of 100 g of 5-bromo-o-anisaldehyde in 1000 ml of tetrahydrofuran is added dropwise thereto. The reaction mixture is stirred for a further 1 hour at 0°. Then, at 0° C., 1 litre of a saturated ammonium chloride solution is added dropwise. After concentration, the residue is extracted 4 times with ethyl acetate. The organic phases are washed with water and saturated sodium chloride solution and concentrated by evaporation. The residue is purified by FC (500 g of silica gel, hexane/ethyl acetate=5:1). Distillation under a high vacuum yields the title compound: R$_f$(hexane/ethyl acetate=4:1)=0.61.

EXAMPLE 182

5(S)-Amino-4(S)-hydroxy-2(S),7(S)-diisopropyl-8-[4-methoxy-3-(3-methoxypropyloxy)-phenyl]-octanoic acid N-[2-(N,N-dimethylcarbamoyl)ethyl]-amide sodium dihydrogen citrate 768 mg of 5(S)-amino-4(S)-hydroxy-2(S),7(S)-diisopropyl-8-[4-methoxy-3-(3-methoxy-propyloxy)-phenyl]-octanoic acid N-[2-(N,N-dimethylcarbamoyl)ethyl] amide hydrochloride (Example 134) are stirred in 50 ml of 1.0N sodium hydroxide and extracted repeatedly with dichloromethane. The extracts are concentrated and the residue is dissolved in 50 ml of ethanol. 274 mg of citric acid monohydrate, 50 ml of water and 1.30 ml of 1N sodium hydroxide are added in succession to the stirred solution. The solution is then concentrated to dryness by evaporation and the residue is taken up in 100 ml of water and lyophilised. The lyophilisate is dissolved in methanol and clarified by filtration; the filtrate is concentrated and the residue is dried at room temperature under a high vacuum. The title compound is obtained in the form of a white amorphous solid having a melting point of 80° C.

EXAMPLE 183

5(S)-Amino-4(S)-hydroxy-2(S),7(S)-diisopropyl-8-[4-methoxy-3-(4-methoxybutyl)-phenyl]-octanoic acid N-(2-morpholinoethyl)amide dihydrochloride The title compound is obtained analogously to Example 124 starting from 100 mg of 5(S)-tertbutoxycarbonylamino-4(S)-hydroxy-2(S),7(S)-diisopropyl-8-[4-methoxy-3-(4-methoxybutyl)-phenyl]-octanoic acid N-[2-(4-morpholino)ethyl]-amide: R$_f$(dichloro-methane/methanol=10:1)=0.21; HPLC R$_f$=12.69 minutes; FAB-MS (M+H)$^+$=564.

The starting material is prepared as follows:

a) 5(S)-Tert-butoxycarbonylamino-4(S)-hydroxy-2(S),7(S)-diisopropyl-8-[4-methoxy-3-(4-methoxybutyl)-phenyl]-octanoic acid N-[2-(4-morpholino)-ethyl]-amide 10 ml of acetic acid are added to a solution of 100 mg of 3(S)-isopropyl-5(S)-{1(S)-tert-butoxycarbonylamino-3(S)-isopropyl-4-[4-methoxy-3-(4-methoxybutyl)-phenyl]-butyl}-tetrahydrofuran-2-one (for preparation see Example 181) in 2 ml of 4-(2-aminoethyl)-morpholine. The reaction mixture is stirred for 39 hours at 80° C. and then concentrated by evaporation in a rotary evaporator. Purification of the residue by FC (dichloromethane/methanol=10:1) yields the title compound in the form of a crude product. Crystallisation from diethyl ether/hexane yields the title compound: m.p.=94°–96° C., R$_f$ (dichloromethane/methanol=10:1)= 0.35; HPLC R$_f$=17.42 minutes; FAB-MS (M+H)$^+$=664.

EXAMPLE 184

5(S)-Amino-4(S),8(R,S)-dihydroxy-2(S),7(S)-diisopropyl-8-[4-methoxy-3-(2-methoxymethoxyethyl)-phenyl]-octanoic acid (N-butyl)-amide 40 mg of 5(S)-azido-4(S),8(R,S)-dihydroxy-2(S),7(S)-diisopropyl-8-[4-methoxy-3-(2-methoxymethoxyethyl)-phenyl]-octanoic acid (N-butyl)-amide are hydrogenated in 10 ml of methanol/acetic acid (9:1) in the presence of 20 mg of 10% Pd/C at room temperature and under normal pressure. The reaction mixture is filtered and concentrated by evaporation. The residue is purified by FC (2.4 g of silica gel, dichloromethane/methanol=9:1). The title compound is obtained: R$_f$(dichloromethane/methanol=9:1)=0.17; HPLC R$_f$=11.44 and 12.63 minutes (diastereoisomeric mixture); FAB-MS (M+H)$^+$=525.

a) 5(S)-Azido-4(S),8(R,S)-dihydroxy-2(S),7(S)-diisopropyl-8-[4-methoxy-3-(2-methoxy-methoxyethyl)-phenyl]-octanoic acid (N-butyl)-amide A solution of 400 mg of 3(S)-isopropyl-5(S)-{1(S)-azido-4(R,S)-hydroxy-3(S)-isopropyl-4-[4-methoxy-3-(2-methoxymethoxyethyl)-phenyl]-butyl}-tetrahydrofuran-2-one (Example 8d) and 3.8 ml of n-butylamine is stirred for 16 hours at 50° C. and then concentrated by evaporation. Purification of the residue by FC (50 g of silica gel, hexane/ethyl acetate=1:1) yields the title compound: R$_f$(hexane/ethyl acetate=1:1)=0.44; HPLC R$_f$=16.13 and 17.03 minutes (diastereoisomeric mixture).

EXAMPLE 185

5(S)-Amino-4(S),8(S or R)-dihydroxy-2(S),7(S)-diisopropyl-8-[4-methoxy-3-(3-methoxypropyloxy)-phenyl]-octanoic acid N-(2-carbamoyl-2,2-dimethyl-ethyl)-amide hydrochloride 60 mg of 5(S)-azido-4(S),8(S or R)-dihydroxy-2(S),7(S)-diisopropyl-8-[4-methoxy-3-(3-methoxypropyloxy)-phenyl]-octanoic acid N-(2-carbamoyl-2,2-dimethyl-ethyl)-amide and 6 ml of ethanolamine are hydrogenated in 8 ml of ethanol in the presence of 120 mg of 5% PdO/C for 2 hours at room temperature and under normal pressure. The reaction mixture is filtered and concentrated by evaporation. The residue is dissolved in 0.5 ml of dioxane and 23 ul of 4N hydrochloric acid in dioxane are added. The title compound is obtained after lyophilisation: HPLC R$_f$=10.74; FAB-MS (M+H)$^+$=568.

The starting materials are prepared as follows:

a) 5(S)-Azido-4(S),8(S or R)-dihydroxy-2(S),S)-dihydroxy-7(S)-diisopropyl-8-[4-methoxy-3-(3-methoxypropyloxy)-phenyl]-octanoic acid N-(2-carbamoyl-2,2-dimethyl-ethyl)-amide 150 mg of 3(S)-isopropyl-5(S)-{1(S)-azido-4(S or R)-hydroxy-3(S)-isopropyl-4-[4-methoxy-3-(3-methoxypropyloxy)-phenyl]-butyl}-tetrahydrofuran-2-one (Example 185b) diastereoisomer B) and 109 m g of 3-amino-2,2-dimethylpropionic acid amide are stirred in 3 ml of triethylamine with 30 mg of 2-hydroxypyridine for 24 hours under reflux temperature. After removal of the solvent by evaporation, the residue, in diethyl ether, is washed repeatedly with water. The organic extracts are concentrated by evaporation and purified by FC (10 g of silica gel, dichloromethane/methanol=95:5). The title compound is obtained: R$_f$(dichloromethane/methanol=95:5)=0.22; HPLC R$_f$=14.88 minutes.

b) 3(S)-Isopropyl-5(S)-{1(S)-azido-4(S or R)-hydroxy-3(S)-isopropyl-4-[4-methoxy-3-(3-methoxypropyloxy)-phenyl]-butyl}-tetrahydrofuran-2-one (A) and 3(S)-isopropyl-5(S)-{1(S)-azido-4(S or R)-hydroxy-3(S)-isopropyl-4-[4-methoxy-3-(3-methoxypropyloxy)-phenyl]-butyl}-tetrahydrofuran-2-one (B)

Separation of 0.5 g of 3(S)-isopropyl-5(S)-{1(S)-azido-4 (R,S)-hydroxy-3(S)-isopropyl-4-[4-methoxy-3-(3-methoxypropyloxy)-phenyl]-butyl}-tetrahydrofuran-2-one (diastereoisomeric mixture) by means of preparative HPLC on Kromasil 7 C18(EKA-Nobel, A. B. Sweden); mobile phase: A) water B) acetonitrile, gradient: 20–80% B in 40 minutes. The two pure diastereoisomers A and B are obtained (isomer A is eluted first). After concentration of the eluate fractions by evaporation, the aqueous residue is extracted with ethyl acetate. The organic extracts are dried over magnesium sulfate and concentrated. The title compounds are obtained: diastereoisomer A) HPLC R$_f$=18.53 minutes and B) HPLC R$_f$=19.49 minutes.

c) 3(S)-Isopropyl-5(S)-{1(S)-azido-4(R,S)-hydroxy-3(S)-isopropyl-4-[4-methoxy-3-(3-methoxypropyloxy)-phenyl]-butyl}-tetrahydrofuran-2-one 45.1 ml of a 1N n-butyllithium solution (in hexane) are added dropwise at −75° C. to a mixture of 12 g of 4-methoxy-3-(3-methoxypropyloxy)-bromobenzene and 9.7 ml of 4-methylmorpholine in 75 ml of tetrahydrofuran. The reaction mixture is stirred for a further 20 minutes at −75° C. and then, at from −75° C. to −60° C., a suspension of magnesium bromide in tetrahydrofuran (freshly prepared from 1.6 g of magnesium powder and 5.7 ml of 1,2-dibromoethane in 150 ml of tetrahydrofuran) is added. The reaction mixture is stirred for a further 30 minutes and then, at −75° C., a solution of 8.84 g of 3(S)-isopropyl-5(S)-[1 (S)-azido-3(S)-isopropyl-4-oxobutyl]-tetrahydrofuran-2-one in 75 ml of tetrahydrofuran is added. The reaction mixture is then stirred for 15 minutes at −75° C. and subsequently 70 ml of saturated ammonium chloride solution are added. The reaction mixture is then poured into 180 ml of saturated sodium chloride solution:water (1:1) and extracted with ethyl acetate (2×360 ml). The organic phases are dried over magnesium sulfate and concentrated by evaporation. The title compound is obtained by purifying the residue by FC (240 g of silica gel, ethyl acetate/hexane=1:2): R$_f$(ethyl acetate/hexane =1:2)=0.16; HPLC R$_f$=18.53 and 19.49 minutes (diastereoisomeric mixture).

d) 4-Methoxy-3-(3-methoxypropyloxy)-bromobenzene 66.0 g of potassium carbonate and 3-methoxy-1-bromopropane are added at room temperature to a solution of 64.6 g of 5-bromo-2-methoxyphenol in 350 ml of acetonitrile. The reaction mixture is stirred under reflux for 14 hours. After removal of the solvent by evaporation, 1200 ml of ice/water are added to the residue and extraction is carried out with ether. The organic extracts are washed with saturated sodium chloride solution, dried over magnesium sulfate and concentrated by evaporation. Distillation under a high vacuum yields the title compound: $R_f$(hexane/ethyl acetate=4:1)=0.33; b.p.=126°–129° C./1.4 mbar; HPLC $R_t$=16.38 minutes; MS (M$^+$)=274, 276.

EXAMPLE 186

5(S)-Amino-4(S),8(R or S)-dihydroxy-2(S),S)-dihydroxy-7(S)-diisopropyl-8-[4-methoxy-3-(3-methoxypropyloxy)-phenyl]-octanoic acid N-(2-carbamoyl-2,2-dimethyl-ethyl)-amide hydrochloride The title compound is obtained analogously to Example 185 starting from 5(S)-azido-4(S),8(R or S)-dihydroxy-2(S),S)-dihydroxy-7(S)-diisopropyl-8-[4-methoxy-3-(3-methoxypropyloxy)-phenyl]-octanoic acid N-(2-carbamoyl-2,2-dimethyl-ethyl)-amide: HPLC $R_t$=10.68; FAB-MS (M+H)$^+$=568.

The starting material is prepared analogously to Example 185a) from 3(S)-isopropyl-5(S)-{1(S)-azido-4(R or S)-hydroxy-3(S)-isopropyl-4-[4-methoxy-3-(3-methoxypropyloxy)-phenyl]-butyl}-tetrahydrofuran-2-one (Example 185b) diastereoisomer A).

EXAMPLE 187

Gelatin Solution

A sterile-filtered aqueous solution, containing 20% cyclodextrins as solubiliser, of one of the compounds of formula I mentioned in the preceding Examples as active ingredient, is so mixed, with the application of heat and under aseptic conditions, with a sterile gelatin solution containing phenol as preservative, that 1.0 ml of solution has the following composition:

| | |
|---|---|
| active ingredient | 3 mg |
| gelatin | 150.0 mg |
| phenol | 4.7 mg |
| dist. water containing 20% cyclodextrins as solubiliser | 1.0 ml |

EXAMPLE 188

Sterile Dry Substance for Injection 5 mg of one of the compounds of formula I mentioned in the preceding Examples as active ingredient are dissolved in 1 ml of an aqueous solution containing 20 mg of mannitol and 20% cyclodextrins as solubiliser. The solution is sterile-filtered and, under aseptic conditions, introduced into a 2 ml ampoule, deep-frozen and lyophilised. Before being used, the lyophilisate is dissolved in 1 ml of distilled water or 1 ml of physiological saline. The solution is administered intramuscularly or intravenously. The formulation can also be filled into double-chamber disposable syringes.

EXAMPLE 189

Nasal Spray 500 mg of finely ground (<5.0 µm) powder of one of the compounds of formula I mentioned in the preceding Examples are suspended as active ingredient in a mixture of 3.5 ml of "Myglyol 812" and 0.08 g of benzyl alcohol. The suspension is introduced into a container having a metering valve. 5.0 g of "Freon 12" are introduced under pressure through the valve into the container. The "Freon" is dissolved in the Myglyol/benzyl alcohol mixture by shaking. The spray container contains approximately 100 single doses which can be administered individually.

EXAMPLE 190

Film-Coated Tablets

The following constituents are processed for the preparation of 10 000 tablets each containing 100 mg of active ingredient:

| | |
|---|---|
| active ingredient | 1000 g |
| corn starch | 680 g |
| colloidal silicic acid | 200 g |
| magnesium stearate | 20 g |
| stearic acid | 50 g |
| sodium carboxymethyl starch | 250 g |
| water | quantum satis |

A mixture of one of the compounds of formula I mentioned in the preceding Examples as active ingredient, 50 g of corn starch and the colloidal silicic acid is processed into a moist mass with starch paste prepared from 250 g of corn starch and 2.2 kg of demineralised water. The mass is forced through a sieve having a mesh size of 3 mm and dried at 45° for 30 minutes in a fluidised bed drier. The dried granules are pressed through a sieve having a mesh size of 1 mm, mixed with a previously sieved mixture (1 mm sieve) of 330 g of corn starch, the magnesium stearate, the stearic acid and the sodium carboxymethyl starch, and compressed to form slightly biconvex tablets.

What is claimed is:

1. An δ-amino-γ-hydroxy-ω-aryl-alkanoic acid amide of formula I

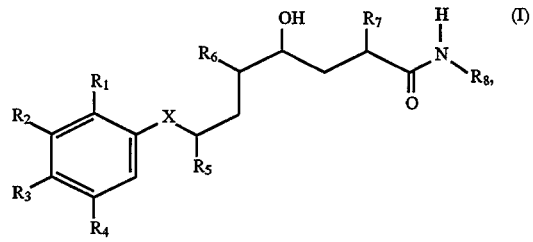

wherein $R_1$ is hydrogen, hydroxy, lower alkoxy, cycloalkoxy, lower alkoxy-lower alkoxy or free or esterified or amidated carboxy-lower alkoxy, $R_2$ is hydrogen, lower alkyl, cycloalkyl, lower alkoxy-lower alkyl, lower alkoxy-lower alkoxy-lower alkyl, cycloalkoxy-lower alkyl, hydroxy, optionally lower alkanoylated, halogenated or sulfonylated hydroxy-lower alkoxy; amino-lower alkyl that is unsubstituted or substituted by lower alkyl, by lower alkanoyl and/or by lower alkoxycarbonyl; optionally hydrogenated heteroaryl-lower alkyl; amino-lower alkoxy that is substituted by lower alkyl, by lower alkanoyl and/or by lower alkoxycarbonyl; oxo-lower alkoxy, lower alkoxy, cycloalkoxy, lower alkenyloxy, cycloalkoxy-lower alkoxy, lower alkoxy-lower alkoxy, lower alkoxy-lower alkenyl, lower alkenyloxy-lower alkoxy, lower alkoxy-lower alkenyloxy, lower alkenyloxy-lower alkyl, lower alkanoyl-lower alkoxy, optionally S-oxidised lower alkylthio-lower alkoxy, lower alkylthio-(hydroxy)-lower alkoxy, aryl-lower alkoxy, optionally hydrogenated heteroaryl-lower alkoxy, cyano-lower alkoxy, free or esterified or amidated carboxy-lower alkoxy or free or esterified or amidated carboxy-lower alkyl, $R_3$ together with $R_4$ is lower alkylenedioxy or a fused-on benzo or cyclohexane ring, X is methylene or hydroxymethylene, $R_5$ is lower alkyl or cycloalkyl, $R_6$ is unsubstituted or N-mono- or N,N-di-lower alkylated or N-lower alkanoylated amino, $R_7$ is lower alkyl, lower alkenyl, cycloalkyl or aryl-lower alkyl, and is lower alkyl, cycloalkyl, free or aliphatically esterified or etherified $R_6$ hydroxy-lower alkyl; amino-lower alkyl that is unsubstituted or N-lower alkanoylated or N-mono- or N,N-di-lower alkylated or N,N-disubstituted by lower alkylene, by hydroxy-, lower alkoxy- or lower alkanoyloxy-lower alkylene, by unsubstituted or N'-lower alkanoylated or N'-lower alkylated aza-lower alkylene, by oxa-lower alkylene or by optionally S-oxidised thia-lower alkylene; free or esterified or amidated carboxy-lower alkyl, free or esterified or amidated dicarboxy-lower alkyl, free or esterified or amidated carboxy-(hydroxy)-lower alkyl, free or esterified or amidated carboxycycloalkyl-lower alkyl, cyano-lower alkyl, lower alkanesulfonyl-lower alkyl, unsubstituted or N-mono- or N,N-di-lower alkylated thiocarbamoyl-lower alkyl, unsubstituted or N-mono- or N,N-di-lower alkylated sulfamoyl-lower alkyl, or a heteroaryl radical bonded via a carbon atom and optionally hydrogenated and/or oxo-substituted, or lower alkyl substituted by a heteroaryl radical bonded via a carbon atom and optionally hydrogenated and/or oxo-substituted, or a salt thereof.

2. A compound according to claim 1 of formula I wherein $R_1$ is hydrogen, hydroxy, lower alkoxy, cycloalkoxy, lower alkoxy-lower alkoxy, carboxy-lower alkoxy, lower alkoxycarbonyl-lower alkoxy, carbamoyl-lower alkoxy or N-mono- or N,N-di-lower alkylcarbamoyl-lower alkoxy, $R_2$ is hydrogen, lower alkyl, cycloalkyl, lower alkoxy-lower alkyl, lower alkoxy-lower alkoxy-lower alkyl, cycloalkoxy-lower alkyl, hydroxy, lower alkanoyloxy-lower alkyl, hydroxy-lower alkoxy, halo-(hydroxy)-lower alkoxy, lower alkane-sulfonyl-(hydroxy)-lower alkoxy, amino-lower alkyl, lower alkylamino-lower alkyl, di-lower alkylamino-lower alkyl, lower alkanoylamino-lower alkyl, lower alkoxycarbonylamino-lower alkyl, amino-lower alkoxy, lower alkylamino-lower alkoxy, di-lower alkylamino-lower alkoxy, lower alkanoylamino-lower alkoxy, lower alkoxycarbonylamino-lower alkoxy, oxo-lower alkoxy, lower alkoxy, cycloalkoxy, lower alkenyloxy, cycloalkoxy-lower alkoxy, lower alkoxy-lower alkoxy, lower alkoxy-lower alkenyl, lower alkenyloxy-lower alkoxy, lower alkoxy-lower alkenyloxy, lower alkenyloxy-lower alkyl, lower alkanoyl-lower alkoxy, lower alkylthio-lower alkoxy, lower alkanesulfonyl-lower alkoxy, lower alkylthio-(hydroxy)-lower alkoxy, aryl-lower alkoxy, thiazolylthio-lower alkoxy or thiazolinylthio-lower alkoxy, imidazolylthio-lower alkoxy, optionally N-oxidised pyridylthio-lower alkoxy, pyrimidinylthio-lower alkoxy, cyano-lower alkoxy, lower alkoxycarbonyl-lower alkoxy, carbamoyl-lower alkoxy, N-mono- or N,N-di-lower alkylcarbamoyl-lower alkoxy, carboxy-lower alkyl, lower alkoxycarbonyl-lower alkyl, carbamoyl-lower alkyl or N-mono- or N,N-di-lower alkylcarbamoyl-lower alkyl, $R_3$ together with $R_4$ is lower alkylenedioxy or a fused-on benzo or cyclohexeno ring, X is methylene or hydroxymethylene, $R_5$ is lower alkyl or cycloalkyl, $R_6$ is amino, lower alkylamino, di-lower alkylamino or lower alkanoylamino, $R_7$ is lower alkyl, lower alkenyl, cycloalkyl, or phenyl- or naphthyl-lower alkyl that is unsubstituted or mono-, di- or tri-substituted by lower alkyl, lower alkoxy, hydroxy, lower alkylamino, di-lower alkylamino, halogen and/or by trifluoromethyl, and $R_8$ is lower alkyl, cycloalkyl, hydroxy-lower alkyl, lower alkanoyloxy-lower alkyl, lower alkoxy-lower alkyl or lower alkenyloxy-lower alkyl, amino-lower alkyl, lower alkanoylamino-lower alkyl, N-mono- or N,N-di-lower alkylamino-lower alkyl, optionally hydroxylated or lower alkoxylated piperidino-lower alkyl, such as piperidino-lower alkyl, hydroxypiperidino-lower alkyl or lower alkoxypiperidino-lower alkyl, piperazino-, N'-lower alkylpiperazino- or N'-lower alkanoylpiperazino-lower alkyl, unsubstituted or lower alkylated morpholino-lower alkyl, such as morpholino-lower alkyl or dimethylmorpholino-lower, alkyl or optionally S-oxidised thiomorpholino-lower alkyl, such as thiomorpholino-lower alkyl, S,S-dioxothiomorpholino-lower alkyl, carboxy-lower alkyl, lower alkoxycarbonyl-lower alkyl, carbamoyl-lower alkyl, N-mono- or N,N-di-lower alkylcarbamoyl-lower alkyl, dicarboxy-lower alkyl, di-lower alkoxycarbonyl-lower alkyl, dicarbamoyl-lower alkyl, di-(N-mono- or N,N-di-lower alkylcarbamoyl)-lower alkyl, carboxy-(hydroxy)-lower alkyl, lower alkoxycarbonyl-(hydroxy)-lower alkyl or carbamoyl-(hydroxy)-lower alkyl, cyano-lower alkyl, lower alkanesulfonyl-lower alkyl, sulfamoyl-lower alkyl, lower alkylsulfamoyl-lower alkyl, di-lower alkylsulfamoyl-lower alkyl thiocarbamoyl-lower alkyl, lower alkylthiocarbamoyl-lower alkyl, di-lower alkylthiocarbamoyl-lower alkyl, pyrrolidinyl, imidazolyl, benzimidazolyl, oxadiazolyl, pyridyl, oxopiperidinyl, quinolinyl, unsubstituted or N-lower alkanoylated piperidyl or pyrrolidinyl, imidazolyl-lower alkyl, benzimidazolyl-lower alkyl, oxadiazolyl-lower alkyl, pyridyl-lower alkyl, unsubstituted or N-lower alkanoylated piperidyl-lower alkyl or pyrrolidinyl-lower alkyl, oxopiperidinyl-lower alkyl, quinolinyl-lower alkyl, morpholinocarbonyl-lower alkyl or unsubstituted or N-lower alkanoylated piperidyl-lower alkyl, or a salt thereof.

3. A compound according to claim 1 of formula I wherein $R_1$ is hydrogen, $R_2$ is lower alkyl, lower alkoxy-lower alkyl, lower alkoxy-lower alkoxy, lower alkoxy-lower alkoxy-lower alkyl; phenyl-lower alkoxy that is unsubstituted or substituted by lower alkyl, lower alkoxy, hydroxy, halogen, nitro and/or by amino; optionally N-oxidised pyridyl-lower alkoxy, lower alkylthio-lower alkoxy, lower alkanesulfonyl-lower alkoxy, lower alkanoyl-lower alkoxy, optionally N-oxidised pyridyl-lower alkoxy, cyano-lower alkoxy, carboxy-lower alkoxy, lower alkoxycarbonyl-lower alkoxy, carbamoyl-lower alkoxy, lower alkylcarbamoyl-lower alkoxy or di-lower alkylcarbamoyl-lower alkoxy, $R_3$ together with $R_4$ is lower alkylenedioxy, X is methylene or hydroxymethylene, $R_5$ is lower alkyl or cycloalkyl, $R_6$ is amino, lower alkylamino, di-lower alkylamino or lower alkanoylamino, $R_7$ is lower alkyl, and $R_8$ is lower alkyl, hydroxy-lower alkyl, lower alkanoyl-lower alkyl, lower alkoxy-lower alkyl, lower alkenyloxy-lower alkyl, amino-lower alkyl, lower alkanoyl-amino-lower alkyl, such as 2-($C_1$-$C_4$alkanoylamino)-2-methyl-propyl, such as 2-acetylamino-2-methyl-propyl or 2-formylamino-2-methyl-propyl, N-mono- or N,N-di-lower alkylamino-lower alkyl, piperidino-lower alkyl, hydroxypiperidino-lower alkyl, lower alkoxypiperidino-lower alkyl, morpholino-lower alkyl, dimethylmorpholino-lower alkyl, thiomorpholino-lower alkyl, S,S-dioxothiomorpholino-lower alkyl, carboxy-lower alkyl, lower alkoxycarbonyl-lower alkyl, carbamoyl-lower alkyl, N-mono- or N,N-di-lower alkylcarbamoyl-lower alkyl, carboxy-(hydroxy)-lower alkyl, lower alkoxycarbonyl-(hydroxy)-lower alkyl, carbamoyl-(hydroxy)-lower alkyl, 5- or 6-membered carboxycycloalkyl-lower alkyl, 5- or 6-membered lower alkoxycarbonylcycloalkyl-lower alkyl, 5- or 6-membered carbamoylcycloalkyl-lower alkyl, 5- or 6-membered N-mono- or N,N-di-lower alkylcarbamoylcycloalkyl-lower alkyl, cyano-lower alkyl, lower alkanesulfonyl-lower alkyl, sulfamoyl-lower alkyl, lower alkylsulfamoyl-lower alkyl or di-lower alkylsulfamoyl-lower alkyl, imidazolyl-lower alkyl, oxopyrrolidinyl-lower alkyl, benzimidazolyl-lower alkyl, oxadiazolyl-lower alkyl, pyridyl-lower alkyl, oxopiperidinyl-lower alkyl or quinolinyl-lower alkyl, piperidin-4-yl-lower alkyl or 1-$C_1$-$C_4$-lower alkanoylpiperidin-4-yl-lower alkyl, or a salt thereof.

4. A compound according to claim 1 of formula I wherein $R_1$ and $R_4$ are hydrogen, $R_2$ is $C_1$-$C_4$alkoxy-$C_1$-$C_4$alkoxy or $C_1$-$C_4$alkoxy-$C_1$-$C_4$alkyl, $R_3$ is $C_1$-$C_4$alkyl or $C_1$-$C_4$alkoxy, $R_6$ is amino, X is methylene or hydroxymethylene, $R_5$ and $R_7$ are branched $C_1$-$C_4$alkyl, and $R_8$ is carbamoyl-$C_1$-$C_4$alkyl, N-$C_1$-$C_4$alkylcarbamoyl-$C_1$-$C_4$alkyl, N, N-di-$C_1$-$C_4$alkyl-carbamoyl-$C_1$-$C_4$alkyl, morpholino-$C_1$-$C_4$alkyl, thiomorpholino-$C_1$-$C_4$alkyl, 4-(1-$C_1$-$C_4$alkanoylpiperidyl)-$C_1$-$C_4$alkyl or 2-oxopyrrolidinyl-$C_1$-$C_4$alkyl, or a salt thereof.

5. A compound according to claim 1 of formula I wherein at least one asymmetric carbon atom of the main chain has the stereochemical configuration shown in formula Ia

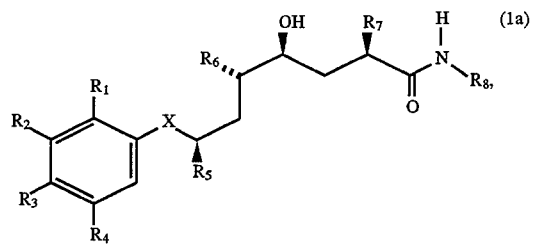

each of the variables being as defined in claim 1, or a pharmaceutically acceptable salt thereof.

6. A compound according to claim 1 of formula I wherein X is methylene, or a pharmaceutically acceptable salt thereof.

7. A compound according to claim 1 selected from the group consisting of 2(R)-methyl-4(S)-hydroxy-5(S)-amino-7(S)-isopropyl-8-[3-(3-methoxy-propyloxy)-4,5-ethylenedioxy-phenyl]-octanoic acid (N-butyl)amide;

5(S)-amino-4(S)-hydroxy-2(S),7(S)-diisopropyl-8-[3-(3-methoxypropyloxy)-4,5-ethylenedioxy-phenyl]-octanoic acid (N-2-morpholinoethyl)amide;

5(S)-amino-4(S)-hydroxy-2(S),7(S)-diisopropyl-8-[3-(3-methoxypropyloxy)-4,5-ethylenedioxy-phenyl]-octanoic acid [N-(2-carbamoyl-2,2-dimethyl-ethyl)]-amide;

5(S)-amino-4(S)-hydroxy-2(S),7(S)-diisopropyl-8-[3-(3-methoxy-propyloxy)-4,5-methylenedioxy-phenyl]-octanoic acid (N-2-morpholinoethyl)amide;

5(S)-amino-4(S)-hydroxy-2(S),7(S)-diisopropyl-8-[3-(3-methoxypropyloxy)-4,5-methylenedioxy-phenyl]-octanoic acid [N-(2-carbamoyl-2,2-dimethyl-ethyl)] amide;

and in each case a salt thereof.

8. A compound according to claim 1 which is selected from the group consisting of 5(S)-amino-4(S)-hydroxy-2(S), 7(S)-diisopropyl-8-[3-(3-methoxypropoxy)-4,5-ethylenedioxy-phenyl]-octanoic acid N-(2-carbamoyl-2,2-dimethyl-ethyl)-amide;

5(S)-amino-4(S)-hydroxy-2(S),7(S)-diisopropyl-8-[4-methoxy-3-(4-methoxy-but-1-en-yl)-phenyl]-octanoic acid [N-(2-carbamoyl-2,2-dimethyl-ethyl)]-amide and in each case a salt thereof.

9. A method of treating hypertension, congestive heart failure, cardiac hypertrophy, cardiac fibrosis, cardiomyopathy postinfarction, nephropathy, vasculopathy, neuropathy, restenosis following angioplasty, raised intra-ocular pressure, glaucoma, abnormal vascular growth, hyperaldosteronism or anxiety states, characterized in that a therapeutically effective amount of a compound according to claim 1 in the free form or in the form of a pharmaceutically acceptable salt is administered to a warm-blooded organism in need of such treatment.

10. A pharmaceutical composition comprising as pharmaceutical active ingredient a compound according to claim 1 in free form or in pharmaceutically acceptable salt form, together with one or more customary pharmaceutical excipient(s).

* * * * *

UNITED STATES PATENT AND TRADEMARK OFFICE
CERTIFICATE OF CORRECTION

PATENT NO. : 5,646,143
DATED : July 8, 1997
INVENTOR(S) : Richard Goschke

It is certified that error appears in the above-identified patent and that said Letters Patent is hereby corrected as shown below:

Column 131,
Line 44, delete claim 4 in its entirety.

Signed and Sealed this

Third Day of January, 2006

JON W. DUDAS
*Director of the United States Patent and Trademark Office*